United States Patent
Vath et al.

(10) Patent No.: US 9,682,965 B2
(45) Date of Patent: Jun. 20, 2017

(54) FUMAGILLOL HETEROCYCLIC COMPOUNDS AND METHODS OF MAKING AND USING SAME

(71) Applicant: Zafgen, Inc., Boston, MA (US)

(72) Inventors: James E. Vath, Lynnfield, MA (US); Robert Zahler, Pennington, NJ (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 15/354,834

(22) Filed: Nov. 17, 2016

(65) Prior Publication Data

US 2017/0066749 A1 Mar. 9, 2017

Related U.S. Application Data

(63) Continuation of application No. PCT/US2016/046511, filed on Aug. 11, 2016.

(60) Provisional application No. 62/203,742, filed on Aug. 11, 2015.

(51) Int. Cl.
| | |
|---|---|
| *C07D 405/12* | (2006.01) |
| *C07D 405/14* | (2006.01) |
| *C07D 401/14* | (2006.01) |
| *A61K 31/397* | (2006.01) |
| *A61K 31/4025* | (2006.01) |
| *A61K 31/4523* | (2006.01) |
| *C07D 413/08* | (2006.01) |
| *C07D 491/048* | (2006.01) |
| *C07D 491/107* | (2006.01) |
| *A61K 9/00* | (2006.01) |
| *A61K 31/403* | (2006.01) |
| *A61K 31/4155* | (2006.01) |
| *A61K 31/4427* | (2006.01) |
| *A61K 31/496* | (2006.01) |
| *A61K 31/5377* | (2006.01) |
| *A61K 31/5383* | (2006.01) |
| *A61K 31/541* | (2006.01) |
| *C07D 417/14* | (2006.01) |
| *C07D 487/08* | (2006.01) |
| *C07D 491/08* | (2006.01) |
| *A61P 3/10* | (2006.01) |

(52) U.S. Cl.
CPC .......... *C07D 405/12* (2013.01); *A61K 9/0019* (2013.01); *A61K 31/397* (2013.01); *A61K 31/403* (2013.01); *A61K 31/4025* (2013.01); *A61K 31/4155* (2013.01); *A61K 31/4427* (2013.01); *A61K 31/4523* (2013.01); *A61K 31/496* (2013.01); *A61K 31/5377* (2013.01); *A61K 31/5383* (2013.01); *A61K 31/541* (2013.01); *C07D 401/14* (2013.01); *C07D 405/14* (2013.01); *C07D 413/08* (2013.01); *C07D 417/14* (2013.01); *C07D 487/08* (2013.01); *C07D 491/048* (2013.01); *C07D 491/08* (2013.01); *C07D 491/107* (2013.01)

(58) Field of Classification Search
CPC combination set(s) only.
See application file for complete search history.

(56) References Cited

U.S. PATENT DOCUMENTS

| | | | |
|---|---|---|---|
| 5,164,410 | A | 11/1992 | Kishimoto et al. |
| 5,166,172 | A | 11/1992 | Kishimoto et al. |
| 5,180,735 | A | 1/1993 | Kishimoto et al. |
| 5,180,738 | A | 1/1993 | Kishimoto et al. |
| 5,196,406 | A | 3/1993 | Kamei et al. |
| 5,204,345 | A | 4/1993 | Kishimoto et al. |
| 5,288,722 | A | 2/1994 | Kishimoto et al. |
| 5,290,807 | A | 3/1994 | Folkman et al. |
| 5,422,363 | A | 6/1995 | Yanai et al. |
| 5,536,623 | A | 7/1996 | Ohmachi et al. |
| 5,698,586 | A | 12/1997 | Kishimoto et al. |
| 5,767,293 | A | 6/1998 | Oku et al. |
| 5,846,562 | A | 12/1998 | Yanai et al. |
| 5,900,431 | A | 5/1999 | Molina et al. |
| 6,017,949 | A | 1/2000 | D'Amato et al. |
| 6,017,954 | A | 1/2000 | Folkman et al. |
| 6,040,337 | A | 3/2000 | Hong, II et al. |
| 6,063,812 | A | 5/2000 | Hong et al. |
| 6,180,626 | B1 | 1/2001 | Shimomura et al. |
| 6,207,704 | B1 | 3/2001 | Liu et al. |
| 6,242,494 | B1 | 6/2001 | Craig et al. |
| 6,277,391 | B1 | 8/2001 | Seo et al. |
| 6,306,819 | B1 | 10/2001 | Rupnick et al. |
| 6,323,228 | B1 | 11/2001 | BaMaung et al. |
| 6,383,471 | B1 | 5/2002 | Chen et al. |

(Continued)

FOREIGN PATENT DOCUMENTS

| | | |
|---|---|---|
| EP | 0354787 A1 | 2/1990 |
| EP | 0682020 A1 | 11/1995 |

(Continued)

OTHER PUBLICATIONS

Anderson, "The Use of Fumagillin in Amoebiasis," Annals of the New York Academy of Sciences, 55:1118-1124, 1952.

(Continued)

*Primary Examiner* — Michael Barker
*Assistant Examiner* — Amanda L Aguirre
(74) *Attorney, Agent, or Firm* — Goodwin Procter LLP

(57) ABSTRACT

Disclosed herein, in part, are fumagillol compounds and methods of use in treating medical disorders, such as obesity. Pharmaceutical compositions and methods of making fumagillol compounds are provided. The compounds are contemplated to have activity against methionyl aminopeptidase 2.

9 Claims, No Drawings

(56) References Cited

U.S. PATENT DOCUMENTS

| | | |
|---|---|---|
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,877,863 B2 | 4/2005 | Wood et al. |
| 6,989,392 B2 | 1/2006 | Collins et al. |
| 7,030,262 B2 | 4/2006 | BaMaung et al. |
| 7,037,890 B2 | 5/2006 | Olson et al. |
| 7,084,108 B2 | 8/2006 | Olson et al. |
| 7,268,111 B2 | 9/2007 | Olson et al. |
| 7,304,082 B2 | 12/2007 | Marino, Jr. et al. |
| 7,718,695 B2 | 5/2010 | Kim et al. |
| 8,299,067 B2 * | 10/2012 | Yang ............... C07D 303/16 514/231.5 |
| 8,367,721 B2 | 2/2013 | Hughes et al. |
| 8,642,650 B2 | 2/2014 | Hughes et al. |
| 8,980,946 B2 | 3/2015 | Hughes |
| 9,000,035 B2 | 4/2015 | Hughes |
| 9,173,865 B2 | 11/2015 | Hughes |
| 9,328,082 B2 | 5/2016 | Vath et al. |
| 9,573,918 B2 * | 2/2017 | Zahler ............... C07D 405/12 |
| 2003/0220371 A1 | 11/2003 | Kallander et al. |
| 2004/0067266 A1 | 4/2004 | Toppo |
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2012/0322867 A1 | 12/2012 | Hughes et al. |
| 2013/0316994 A1 | 11/2013 | Hughes |
| 2014/0011870 A1 | 1/2014 | Hughes |
| 2014/0045934 A1 | 2/2014 | Hughes |
| 2014/0045935 A1 | 2/2014 | Hughes |
| 2014/0051752 A1 | 2/2014 | Hughes |
| 2014/0336251 A1 | 11/2014 | Hughes et al. |
| 2015/0126489 A1 | 5/2015 | Zahler et al. |
| 2015/0150840 A1 | 6/2015 | Vath |
| 2015/0150857 A1 | 6/2015 | Vath |
| 2015/0209320 A1 | 7/2015 | Hughes et al. |
| 2015/0209321 A1 | 7/2015 | Hughes |
| 2015/0335608 A1 | 11/2015 | Hughes et al. |
| 2015/0361061 A1 | 12/2015 | Vath |
| 2016/0038453 A1 | 2/2016 | Hughes et al. |
| 2016/0243073 A1 | 8/2016 | Hughes |

FOREIGN PATENT DOCUMENTS

| | | |
|---|---|---|
| WO | WO-98/56372 A1 | 12/1998 |
| WO | WO-99/39702 A2 | 8/1999 |
| WO | WO-99/57097 A2 | 11/1999 |
| WO | WO-99/59986 A1 | 11/1999 |
| WO | WO-99/59987 A1 | 11/1999 |
| WO | WO-00/64876 A1 | 11/2000 |
| WO | WO-02/26782 A2 | 4/2002 |
| WO | WO-02/42295 A2 | 5/2002 |
| WO | WO-02/083065 A2 | 10/2002 |
| WO | WO-03/027104 A1 | 4/2003 |
| WO | WO-03/082845 A1 | 10/2003 |
| WO | WO-2004/033419 A1 | 4/2004 |
| WO | WO-2005/066197 A2 | 7/2005 |
| WO | WO-2005/082349 A1 | 9/2005 |
| WO | WO-2006/010498 A2 | 2/2006 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 A1 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 A2 | 4/2013 |
| WO | WO-2013/109735 A1 | 7/2013 |
| WO | WO-2013/109739 A1 | 7/2013 |
| WO | WO-2013/169727 A1 | 11/2013 |
| WO | WO-2013/169860 A1 | 11/2013 |
| WO | WO 2013169860 A1 * | 11/2013 ........... C07D 405/12 |

OTHER PUBLICATIONS

Benny et al., "An Orally Delivered Small-Molecule Formulation with Antiangiogenic and Anticancer Activity," Nat Biotechnol. Jul. 2008;26(7):799-807.

Bernier et al.,"Fumagillin class inhibitors of methionine aminopeptidase-2," Drugs of the Future 30(5):497-500, 2005.

Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.

Braunwald et al., "Obesity" in Harrison's Principles of Internal Medicine, 15th Ed., McGraw Hill (New York) pp. 479-486, 2001.

Butler et al., "Clinical Findings and Natural History of Prader-Willi Syndrome," Chapter 1; Clinical Findings and Natural History of PWS, pp. 3-48 (2006).

Cassidy et al., "Prader-Willi syndrome," European Journal of Human Genetics 17:3-13 (2009).

Cassidy et al., "Prader-Willi syndrome," Genetics in Medicine, vol. 14(1) pp. 10-26 (2012).

Cataletto et al., "Prader-Willi syndrome: A primer for clinicians," International Journal of Pediatric Endocrinology, vol. 12:1-13 (2011).

Chun et al., "Novel inhibitors targeted to methionine aminopeptidase 2 (MetAP2) strongly inhibit the growth of cancers in xenografted nude model," Int J Cancer. Mar. 10, 2005;114(1):124-30.

Didier et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo et al.,"Studies on the Carcinolytic Activity of Fumagillin and Some of its Derivatives," Antibiot Annu.1958-1959;6:541-6.

Drevs et al.,"Antiangiogenic Potency of FK866/K22.175, a New Inhibitor of Intracellular NAD Biosynthesis, In Murine Renal Cell Carcinoma," Anticancer Res. Nov.-Dec. 2003;23(6C):4853-4858.

Dumas et al., "Synthesis and Structure Activity Relationships of Novel Small Molecule Cathepsin D Inhibitors" Bioorg Med Chem Lett. Sep. 6, 1999;9(17):2531-6.

Dykens et al., "Assessment of Hyperphagia in Prader-Willi Syndrome," Obesity 15:7 (2007).

(56) References Cited

OTHER PUBLICATIONS

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.").
Edgar et al., "Body composition in Prader-Willi syndrome compared with nonsyndromal obesity: Relationship to physical activity and growth homrone function," The Journal of Pediatrics 139:5, 708-714 (2001).
Einfield et al., "Mortality in Prader-Willi Syndrome," Am. J. Ment. Retard. 111(3):193-198 (2006).
European Communication for EP Application No. 12 798 444.1, dated Aug. 28, 2015 (8 pages).
European Search Report for EP 09798793 dated Oct. 11, 2011, 9 pages.
Evdokimov et al., "Serendipitous discovery of novel bacterial methionine aminopeptidase inhibitors," Proteins Feb. 15; 66(3):538-546 (2007).
Everhart, "Contributions of Obesity and Weight Loss to Gallstone Disease" Ann Intern Med. Nov. 15, 1993;119(10)1029-35.
Garrabrant et al.,"Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.
Garrison et al., "A metabolic basis for fibromyalgia and its related disorders: the possible role of resistance to thyroid hormone," Med. Hypotheses. Aug;61(2):182-189 (2003).
Han et al., "Design and Synthesis of Highly Potent Fumagillin Analogues from Homology Modeling for a Human MetAP-2," Bioorg Med Chem Lett. Jan. 3, 2000;10(1):39-43.
Holland et al., "The paradoc of Prader-Willi syndrome: a genetic model of starvation," The Lancet 362, 989-991 (2003).
Huang et al., "Inhibition of Monometalated Methionine Aminopeptidase: Inhibitor Discovery and Crystallographic Analysis," J. Med. Chem., Nov. 15;50(23):5735-5742 (2007).
Ingber et al., "Synthetic Analogues of Fumagillin that Inhibit Angiogenesis and Suppress Tumour Growth," Nature, 348(6301):555-557 (1990).
International Search Report for International Application No. PCT/US2011/020515, International Filing Date Jul. 1, 2011, 4 pages.
International Search Report for International Application No. PCT/US2011/020866, mailed Jul. 22, 2011, 8 pages.
International Search Report for International Application No. PCT/US2011/060127, mailed Jan. 2, 2012, 2 pages.
International Search Report for International Application No. PCT/US2011/062320, mailed Feb. 17, 2012, 3 pages.
International Search Report for International Application No. PCT/US2011/062421, mailed Feb. 17, 2012, 3 pages.
International Search Report for International Application No. PCT/US2011/38352, International Filing Date May 27, 2011,3 pages.
International Search Report for International Application No. PCT/US2012/000461, mailed May 2, 2013, 7 pages.
International Search Report for International Application PCT/US2010/052050, dated Mar. 25, 2011, 3 pages.
Jauregi et al., "Behavioral profile of adults with Prader-Willi syndrome: correlations with individual and environmental variables," Journal of Neurodevelopmental Disorders 5:18, 1-10 (2013).
Jeong et al, "Total synthesis and antiangiogenic activity of cyclopentane analogues of fumagillol" Bioorg Med Chem Lett. Aug. 1, 2005;15(15):3580-3.
Kawai et al., "Development of Sulfonamide Compounds as Potent Methionine Aminopeptidase Type II Inhibitors with Antiproliferative Properties", Bioorg. Med. Chem. Lett. Jul. 1;16(13):3574-3577 (2006).
Kim et al. "Assessment of the Anti-Obesity Effects of the TNP-470 Analog, CKD-732" J Mol Endocrinol. Apr. 2007;38(4):455-65.
Kim et al. "Development of parenteral formulation for a novel angiogenesis inhibitor, CKD-732 through complexation with hydroxypropyl-beta-cyclodextrin" Int J Pharm. Mar. 19, 2004;272(1-2):79-89.
Kim et al. "General pharmacology of CKD-732, a new anticancer agent: effects on central nervous, cardiovascular, and respiratory system" Biol Pharm Bull. Feb. 2005;28(2):217-23.
Kim et al., "Depletion of Methionine Aminopeptidase 2 does not Alter Cell Response to Fumagillin or Bengamides," Cancer Res., May 1;64(9):2984-2987 (2004).
Kruger, "TNP-470: An Angiogenesis Inhibitor in Clinical Development for Cancer" Expert Opin Investig Drugs. Jun. 2000;9(6):1383-96.
Lee et al. "Absorption, distribution, metabolism, and excretion of CKD-732, a novel antiangiogenic fumagillin derivative, in rats, mice, and dogs" Arch Pharm Res. Feb. 2004;27(2):265-72.
Lee et al. "Design, Synthesis, and Antiangiogenic Effects of a Series of Potent Novel Fumagillin Analogues" Chem Pharm Bull (Tokyo). Jul. 2007;55(7):1024-9.
Lee et al. "Selective N-demethylation of tertiary aminofumagillols with selenium dioxide via a non-classical Polonovski type reaction" Heterocycles 68(5):915-932, 2006.
Lijnen et al. "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Luo et al., "Discovery and Structural Modification of Inhibitors of Methionine Aminopeptidases from *Escherichia coli* and *Saccharomyces cerevisiae*," J. Med. Chem. Jun. 19;46(13):2631-2640 (2003).
Ma et al., "Structural Analysis of Inhibition of *E. coli* Methionine Aminopeptidase: Implication of Loop Adaptability in Selective Inhibition of Bacterial Enzymes," BMC Struct Biol., Dec. 19;7:84 (2007).
Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951;113(2930):202-3.
Milkowski et al., "TNP-470" Antiangiogenic Agents in Cancer Therapy, Chapter 22 pp. 385-398, 1999.
Miller et al., "Nutritional Phases in Prader-Willi Syndrome," Am. J. Med. Genet. A. 155A(5): 1040-1049 (2011).
Molina et al. "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al. "Fumagillin Treatment of Intestinal Microsporidiosis" N Engl J Med. Jun. 20, 2002;346(25)1963-9.
Molina, et al. "Trial of Oral Fumagillin for the Treatment of Intestinal Microsporidiosis in Patients with HIV Infection" AIDS. Jul. 7, 2000;14(10):1341-8.
Mosteller, R.D., "Simplified Calculation of Body-surface Area," N. Engl .J. Med., 317(17):1098 (Oct. 22, 1987).
Myung et al. "The identification of in vitro metabolites of CKD-732 by liquid chromatography/tandem mass spectrometry" Rapid Commun Mass Spectrom. 2002;16(21):2048-53.
Naganuma et al. "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA Aug. 25, 1993;270(8):967-74.
Noel et al. "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.
Pagliarulo et al.,"Gallstone disease and related risk factors in a large cohort of diabetic patients" Dig. Liver Dis., Feb;36(2):130-134 (2004).
Picoul et al., "Progress in fumagillin synthesis," Pure Appl. Chem. 75(2-3): 235-249 (2003).

(56) References Cited

OTHER PUBLICATIONS

Rhee et al., "Angiogenesis inhibitor attenuates parathyroid hormone-induced anabolic effect" Biomed Pharmacother. Jan;63(1):63-68 (2009).

Rupnick et al., "Adipose Tissue Mass Can be Regulated Through the Vasculature," Proc. Natl. Acad. Sci. U.S.A. Aug. 6;99(16)1 0730-10735 (2002).

Seneca et al., "Amebiasis: a review. II. Laboratory diagnosis, differential diagnosis and therapy," Am. J. Dig. Dis. Jul;1(7):310-322 (1956).

Sheppard et al., "3-Amino-2-Hydroxyamides and Related Compounds as Inhibitors of Methionine Aminopeptidase-2", Bioorg. Med. Chem Lett., Feb. 23;14(4):865-868 (2004).

Shin et al., "A Phase I Pharmacokinetic and Pharmacodynamic Study of CKD-732, an Antiangiogenic Agent, in Patients with Refractory Solid Cancer," Invest New Drugs Oct;28(5):650-658 (2010).

Shin et al., "A Phase Ib pharmacokinetic study of the anti-angiogenic agent CKD-732 used in combination with capecitabine and oxaliplatin (XELOX) in metastatic colorectal cancer patients who progressed on irinotecan-based chemotherapy," Invest. New Drugs, Apr;30(2):672-680 (2012).

Srikumar et al., "Structural insights on Brugia malayi transglutaminase with cinnamoyl derivatives—a molecular docking approach," International Journal of Pharma and Bio Sciences 3(3):998-1006 (2012).

Towbin et al., "Proteomics-based target identification: bengamides as a new class of methionine aminopeptidase inhibitors," J. Biol. Chem. 278(52):52964-52971 (2003).

Vedantham et al., "Studies towards the synthesis of methionine aminopeptidase inhibitors: diversification utilizing a ROMP-derived coupling reagent", J Comb Chem. Mar-Apr;10(2):195-203 (2008).

Wang et al. "Lead optimization of methionine aminopeptidase-2 (MetAP2) inhibitors containing sulfonamides of 5,6-disubstituted anthranilic acids", Bioorg Med Chem Lett. May 15, 2007;17(10):2817-22. Epub Feb. 25, 2007.

Wang et al. "Tumor Suppression by a Rationally Designed Reversible Inhibitor of Methionine Aminopeptidase-2", Cancer Res. 63:7861-7869, 2003.

Wang et al., "Discovery of inhibitors of *Escherichia coli* methionine aminopeptidase with the Fe(II)-form selectivity and antibacterial activity", J Med Chem. Oct. 9, 2008;51(19):6110-20.

Weinsier et al., "Gallstone Formation and Weight Loss" Obes Res. Jan;1(1):51-56 (1993).

Weinsier et al., "Medically Safe Rate of Weight Loss for the Treatment of Obesity: A Guideline Based on Risk of Gallstone Formation" Am. J. Med. Feb;98(2):115-117 (1995).

Winter et al., "Endothelial anb3 Integrin-Targeted Fumagillin Nanoparticles Inhibit Angiogenesis in Atherosclerosis," Arterioscler Thromb Vasc. Biol., Sep;26(9):2103-2109 (2006).

Written Opinion for International Application No. PCT/US2009/066816, mailed Apr. 8, 2010, 3 pages.

Written Opinion for International Application No. PCT/US2011/060127, mailed May 10, 2013, 4 pages.

Written Opinion for International Application No. PCT/US2011/062320, mailed May 29, 2013, 5 pages.

Yanai et al., "Antitumor Activity of a Medium-chain Triglyceride Solution of the Angiogenesis Inhibitor TNP-470 (AGM-1470) when Administered via the Hepatic Artery to Rats Bearing Walker 256 Carcinosarcoma in the Liver," J. Pharmacol. Exp. Ther. Dec;271(3):1267-1273 (1994).

Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res., May;12(5):653-657 (1995).

Zhang et al., "Angiogenesis Inhibitors Specific for Methionine Aminopeptidase 2 as Drugs for Malaria and Leishmaniasis," J. Biomed. Sci., 9(1):34-40 (Jan.-Feb. 2002).

Arico-Muendel et al., "Carbamate Analogs of Fumagillin as Potent, Targeted Inhibitors of Methionine Aminopeptidase-2," J. Med. Chem., 52:8047-8056 (2009).

International Search Report and Written Opinion for International Application No. PCT/US2016/046511, mailed Oct. 21, 2016, 12 pages.

\* cited by examiner

FUMAGILLOL HETEROCYCLIC COMPOUNDS AND METHODS OF MAKING AND USING SAME

CROSS REFERENCE TO RELATED APPLICATIONS

This application is a continuation of PCT/US2016/046511, filed Aug. 11, 2016, which claims the benefit of and priority to U.S. Provisional Patent Application Number 62/203,742, filed Aug. 11, 2015, the contents of each of which are hereby incorporated by reference in their entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitors, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) J. Proteome Res. 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc. Natl. Acad. Sci. USA 99:10730).

Such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The present disclosure provides, for example, compounds which may be modulators of MetAP2, and their use as medicinal agents, processes for their preparation, and pharmaceutical compositions containing them as an active ingredient both alone or in combination with other agents, as well as provides for their use as medicaments and/or in the manufacture of medicaments for the inhibition of MetAP2 activity in warm-blooded animals such as humans. In particular this disclosure relates to compounds useful for the treatment of obesity, type 2 diabetes, and other obesity-associated conditions. Also provided are pharmaceutical compositions comprising at least one disclosed compound and a pharmaceutically acceptable carrier.

For example, the disclosure is directed in part to compounds represented by:

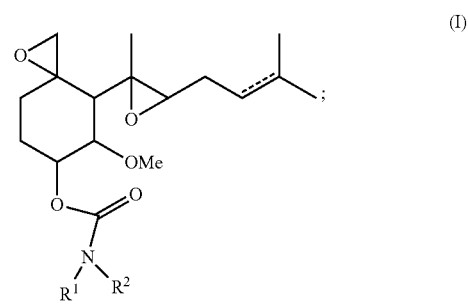

(I)

wherein ⌒ is a single or double bond;

$R^1$ and $R^2$, together with the nitrogen to which they are attached, form a 4-6 membered heterocyclic ring A which may have an additional heteroatom selected from the group consisting of O, $S(O)_w$ (wherein w is 0, 1, or 2), and $NR^a$; wherein heterocyclic ring A is substituted on an available carbon by a substituent represented by L-B; and wherein heterocyclic ring A is additionally and optionally substituted by one or two substituents each independently selected from the group consisting of halogen, hydroxyl, $C_{1-3}$alkyl and $C_{1-3}$alkoxy; wherein $C_{1-3}$alkyl and $C_{1-3}$alkoxy may optionally be substituted by one or more fluorine atoms or a substituent selected from the group consisting of cyano, hydroxyl, and $N(R^aR^b)$; wherein L, B, $R^a$ and $R^b$ are described herein, and pharmaceutically acceptable salts, stereoisomers, esters, and prodrugs thereof.

Also provided herein is a pharmaceutically acceptable composition comprising a disclosed compound (e.g., of Formula I) and a pharmaceutically acceptable excipient.

Methods of treating and/or controlling obesity are contemplated herein, comprising administering to a patient in need thereof an effective amount of a disclosed compound (e.g., of Formula I). In an embodiment, a method of inducing weight loss in a patient in need thereof is provided, comprising administering to said patient an effective amount of a disclosed compound (e.g., of Formula I). In another embodiment, a method of substantially preventing weight gain in a patient in need thereof is provided comprising administering to said patient an effective amount of a disclosed compound (e.g., of Formula I).

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to e.g. saturated or partially unsaturated, 4-10 membered monocyclic or bicyclic ring structures, or e.g. 4-9 or 4-6 membered saturated ring structures, including bridged, fused or spirocyclic rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the present disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the present disclosure is desirably a mammal in which treatment of obesity or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the present disclosure are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis,* Wiley-VCH: Weinheim, 2009.

The compounds disclosed herein can exist in solvated as well as unsolvated forms with pharmaceutically acceptable solvents such as water, ethanol, and the like, and it is intended that the present disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The present disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the present disclosure or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a disclosed compound contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-($C_{1-6}$)alkylcarbonyloxy)ethyl ($C_{1-6}$)alkoxycarbonyloxymethyl, N-($C_{1-6}$)alkoxycarbonylaminomethyl, succinoyl, ($C_{1-6}$)alkylcarbonyl, α-amino ($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

If a compound of the present disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

I. Fumagillol Compounds

In one aspect, the present disclosure provides compounds of Formula I:

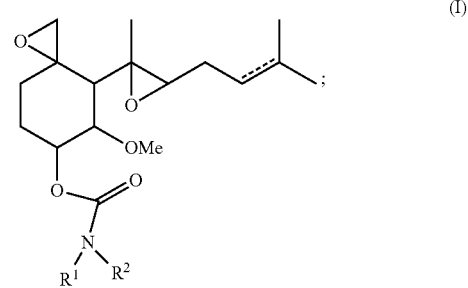

wherein:
 is a single or double bond;
$R^1$ and $R^2$, together with the nitrogen to which they are attached, form a 4-6 membered saturated heterocyclic ring A which may have an additional heteroatom selected from the group consisting of O, S(O)$_w$ (wherein w is 0, 1, or 2), and NR$^a$;

heterocyclic ring A is substituted on an available carbon by a substituent represented by L-B; and wherein heterocyclic ring A is additionally and optionally substituted by one or two substituents each independently selected from the group consisting of halogen, hydroxyl, $C_{1-3}$alkyl and $C_{1-3}$alkoxy; wherein $C_{1-3}$alkyl and $C_{1-3}$alkoxy may optionally be substituted by one or more fluorine atoms or a substituent selected from the group consisting of cyano, hydroxyl, and N(R$^a$R$^b$);

L is selected from the group consisting of $C_{1-6}$alkylene and $C_{1-6}$alkenylene; wherein $C_{1-6}$alkylene and $C_{1-6}$alkenylene may optionally be substituted by one or two substituents each independently selected from the group consisting of halogen and hydroxyl; and wherein one or two methylene units of L may optionally and independently be replaced by a moiety selected from the group consisting of a bond, —O—, —C(O)—, —O—C(O)—, —C(O)—O—, —NR$^a$—, —C(O)—NR$^a$—, —NR$^a$—C(O)—, —O—C(O)—NR$^a$—, —NR$^a$—C(O)—O—, —S(O)$_w$— (wherein w is 0, 1, or 2), —S(O)$_w$—NR$^a$—, and —NR$^a$—S(O)$_w$—;

B is selected from the group consisting of hydrogen, R$^i$R$^j$N—, heterocyclyl, heterocyclyloxy, heteroaryl, and heterocyclyl-(NR$^a$)—; wherein said heteroaryl may optionally be substituted with one or more substituents selected from R$^f$; and wherein said heterocyclyl is bound to L through a ring carbon and may optionally be substituted by one or more substituents selected from R$^g$; and wherein if said heterocyclyl contains a —NH moiety that nitrogen may optionally be substituted by R$^h$;

R$^i$ and R$^j$ are selected independently for each occurrence from the group consisting of hydrogen, C$_{1-6}$alkyl, C$_{2-6}$alkenyl, C$_{3-6}$cycloalkyl, heterocyclyl and heterocyclylcarbonyl; wherein C$_{1-6}$alkyl, C$_{2-6}$alkenyl and C$_{3-6}$cycloalkyl may be optionally substituted by one or more substituents independently selected from the group consisting of fluorine, hydroxyl, cyano, R$^a$R$^b$N—, R$^a$R$^b$N-carbonyl- and C$_{1-3}$alkoxy; and wherein heterocyclyl and heterocyclylcarbonyl may be optionally substituted by one or more substituents independently selected from the group consisting of C$_{1-6}$alkyl, C$_{2-6}$alkenyl, C$_{2-6}$alkynyl, C$_{3-6}$cycloalkyl, C$_{1-6}$alkoxy, halo-C$_{1-6}$-alkyl, hydroxyl-C$_{1-6}$-alkyl, R$^a$R$^b$N—C$_{1-6}$alkyl- and C$_{1-6}$-alkoxy-C$_{1-6}$-alkyl group; and wherein if said heterocyclyl or heterocyclylcarbonyl contains a —NH moiety that nitrogen may optionally be substituted by one or more groups independently selected from the group consisting of C$_{1-6}$alkyl, C$_{3-6}$alkenyl, C$_{3-6}$alkynyl, C$_{3-6}$cycloalkyl, C$_{1-6}$alkyl-S(O)$_2$— and C$_{1-6}$-alkylcarbonyl;

or R$^i$ and R$^j$ taken together with the nitrogen to which they are attached form a 4-9 membered monocyclic, bridged bicyclic, fused bicyclic or spirocyclic heterocyclic ring, which may have an additional heteroatom selected from the group consisting of N, O, and S(O)$_w$ (wherein w is 0, 1 or 2); wherein the 4-9 membered monocyclic, bridged bicyclic, fused bicyclic or spirocyclic heterocyclic ring may be optionally substituted on carbon by one, two, or more substituents selected from the group consisting of halogen, hydroxyl, oxo, cyano, C$_{1-6}$alkyl, C$_{1-6}$alkoxy, R$^a$R$^b$N—, R$^a$R$^b$N—SO$_2$— and R$^a$R$^b$N-carbonyl-; wherein said C$_{1-6}$alkyl or C$_{1-6}$alkoxy may optionally be substituted by the group consisting of fluorine, hydroxyl, and cyano; and wherein if said 4-9 membered monocyclic, bridged bicyclic, fused bicyclic or spirocyclic heterocyclic ring contains a —NH moiety that nitrogen may be optionally substituted by a substituent selected from the group consisting of hydrogen, C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, C$_{1-6}$alkoxycarbonyl-, R$^i$R$^j$N-carbonyl- and R$^i$R$^j$N—SO$_2$—; wherein C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, and C$_{1-6}$alkoxycarbonyl- may optionally be substituted by one or more substituents selected from the group consisting of fluorine, hydroxyl, and cyano;

R$^a$ and R$^b$ are independently selected, for each occurrence, from the group consisting of hydrogen and C$_{1-3}$alkyl; wherein C$_{1-3}$alkyl may optionally be substituted by one or more substituents selected from halogen, cyano, oxo and hydroxyl;

R$^f$ is independently selected, for each occurrence, from the group consisting of R$^P$, hydrogen, C$_{1-6}$alkyl, C$_{3-6}$cycloalkyl, C$_{2-6}$alkenyl, C$_{2-6}$alkynyl, C$_{1-6}$alkoxy, C$_{1-6}$alkyl-S(O)$_w$—, (wherein wherein w is 0, 1 or 2), C$_{1-6}$alkylcarbonyl-N(R$^a$)— and C$_{1-6}$alkoxycarbonyl-N(R$^a$)—; wherein C$_{1-6}$alkyl, C$_{3-6}$cycloalkyl, C$_{2-6}$alkenyl, C$_{2-6}$alkynyl, C$_{1-6}$alkoxy, C$_{1-6}$alkyl-S(O)$_w$—, C$_{1-6}$alkylcarbonyl-N(R$^a$)—, C$_{1-6}$alkoxycarbonyl-N(R$^a$)— may be optionally substituted by one or more substituents selected from R$^P$;

R$^g$ is independently selected for each occurrence from the group consisting of R$^P$, hydrogen, oxo, C$_{1-6}$alkyl, C$_{2-6}$alkenyl, C$_{2-6}$alkynyl, C$_{3-6}$cycloalkyl, C$_{1-6}$alkoxy, C$_{1-6}$alkyl-S(O)$_w$— (wherein w is 0, 1 or 2), C$_{1-6}$alkylcarbonyl-N(R$^a$)— and C$_{1-6}$alkoxycarbonyl-N(R$^a$)—; wherein C$_{1-6}$alkyl, C$_{2-6}$alkenyl, C$_{2-6}$alkynyl, C$_{3-6}$cycloalkyl, C$_{1-6}$alkoxy, C$_{1-6}$alkyl-S(O)$_w$—, C$_{1-6}$alkylcarbonyl-N(R$^a$)—, and C$_{1-6}$alkoxycarbonyl-N(R$^a$)— may be optionally substituted by one or more substituents selected from R$^P$;

R$^h$ is independently selected for each occurrence from the group consisting of hydrogen, C$_{1-6}$alkyl, C$_{3-6}$alkenyl, C$_{3-6}$alkynyl, C$_{3-6}$cycloalkyl, C$_{1-6}$alkyl-S(O)$_2$—, C$_{1-6}$alkylcarbonyl-, C$_{1-6}$alkoxycarbonyl-, R$^i$R$^j$N-carbonyl- and R$^i$R$^j$N—SO$_2$—; wherein C$_{1-6}$alkyl, C$_{3-6}$alkenyl, C$_{3-6}$alkynyl, C$_{3-6}$cycloalkyl, C$_{1-6}$alkyl-S(O)$_2$-, C$_{1-6}$alkylcarbonyl-, and C$_{1-6}$alkoxycarbonyl- may optionally be substituted by one or more substituents selected from R$^P$; and R$^P$ is independently selected, for each occurrence, from the group consisting of halogen, hydroxyl, cyano, C$_{1-6}$alkoxy, R$^i$R$^j$N-carbonyl-, R$^i$R$^j$N—SO$_2$—, and R$^i$R$^j$N-carbonyl-N(R$^a$)-;

and pharmaceutically acceptable salts, stereoisomers, esters and prodrugs thereof.

In certain embodiments, heterocyclic ring A may be selected from the group consisting of:

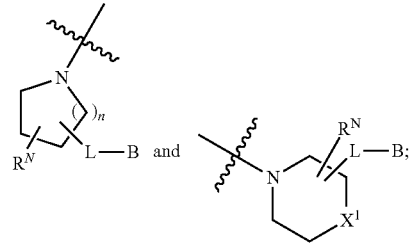

wherein:

R$^N$ is selected from the group consisting of hydrogen, halogen, hydroxyl, C$_{1-3}$alkyl and C$_{1-3}$alkoxy;

n is 0, 1, or 2; and

X$^1$ is O, S(O)$_w$, CH$_2$ or NR$^a$, wherein w is 0, 1, or 2.

For example, heterocyclic ring A may be selected from the group consisting of:

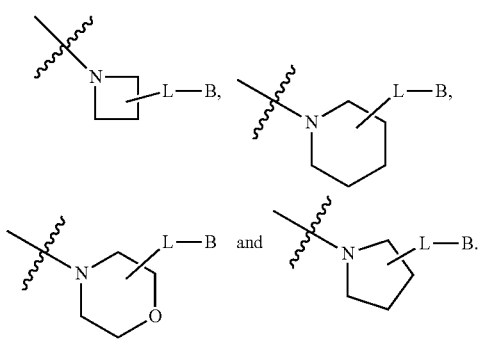

In certain embodiments, a disclosed compound may be represented by:

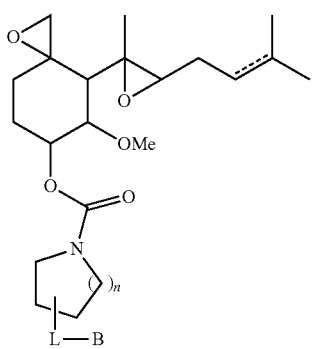

wherein n is 0, 1, or 2.

In certain embodiments, n may be 1. For example, a disclosed compound may be selected from the group consisting of:

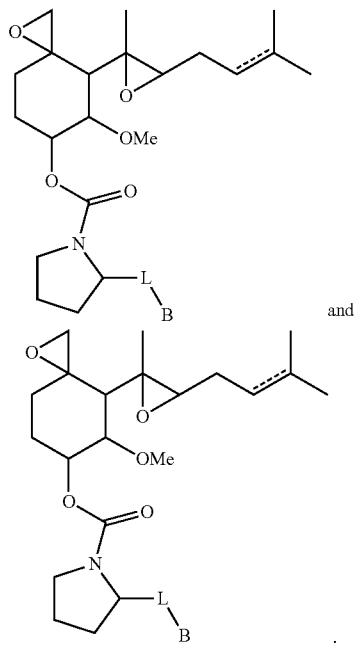

In certain embodiments, n may be 0. For example, a disclosed compound may be selected from the group consisting of:

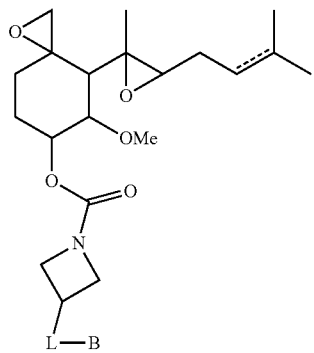
and

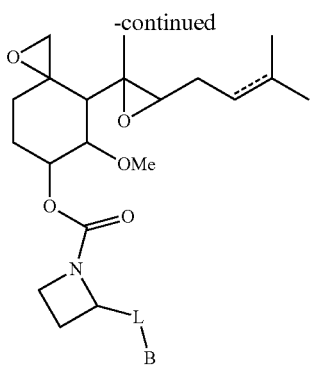

In certain embodiments, L may be selected from the group consisting of: —CH$_2$CH$_2$—, —CH$_2$—, —CH$_2$CH$_2$CH$_2$—, —CH$_2$—C(O)—, —CH$_2$—CH$_2$—C(O)—, —CH$_2$—O—C(O)—, —O—C(O)—, —O—CH$_2$—O—C(O)—, —NH—C(O)—, —NH—C(O)—CH$_2$—CH$_2$—, —NH—C(O)—O—CH$_2$—, —(=CH)—CH$_2$—, —(=CH)—, NH—, —NMe-, —O—, and —C(O)—. For example, L may be —CH$_2$—, —CH$_2$CH$_2$—, or —CH$_2$CH$_2$CH$_2$—.

In certain embodiments, a disclosed compound may be represented by:

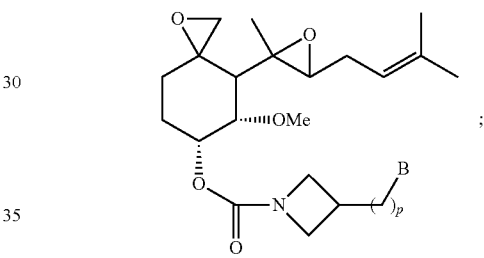

wherein p is 1, 2, or 3.

For example, in certain embodiments p may be 2.

In certain embodiments, B may be hydrogen. In other embodiments, B may be R$^i$R$^j$N—; wherein R$^i$ and R$^j$ are independently selected from the group consisting of hydrogen and C$_{1-6}$alkyl, and wherein C$_{1-6}$alkyl may optionally be substituted by one or more substituents independently selected from the group consisting of fluorine and hydroxyl.

For example, B may be selected from the group consisting of:

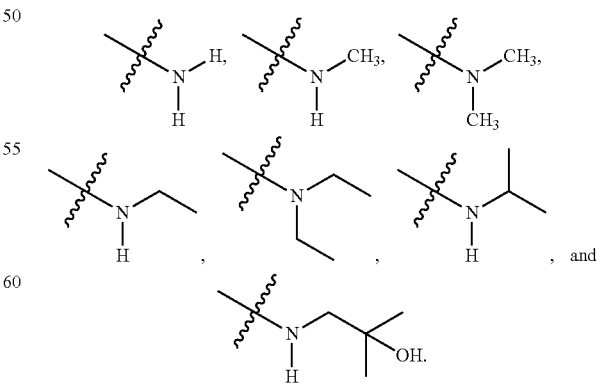

In certain embodiments, B may be R$^i$R$^j$N—; wherein R$^i$ and R$^j$ taken together with the nitrogen to which they are attached form a 4-9 membered monocyclic, bridged bicyclic, fused bicyclic or spirocyclic heterocyclic ring, which may have an additional heteroatom selected from the group consisting of N, O, and S(O)$_w$ (wherein w is 0, 1 or 2); wherein the 4-9 membered monocyclic, bridged bicyclic, fused bicyclic or spirocyclic heterocyclic ring may be optionally substituted on carbon by one, two, or more substituents selected from the group consisting of halogen, hydroxyl, oxo, cyano, $C_{1-6}$alkyl, $C_{1-6}$alkoxy, and $R^aR^bN$-carbonyl-; wherein said $C_{1-6}$alkyl may optionally be substituted by one, two, or more substituents selected from the group consisting of fluorine and hydroxyl; and wherein if said 4-9 membered monocyclic, bridged bicyclic, fused bicyclic or spirocyclic heterocyclic ring contains a —NH moiety that nitrogen may be optionally substituted by a substituent selected from the group consisting of $C_{1-6}$alkyl and $C_{1-6}$alkyl-S(O)$_2$—; wherein $C_{1-6}$alkyl and $C_{1-6}$alkyl-S(O)$_2$— may optionally be substituted by one or more fluorines.

For example, B may be selected from the group consisting of:

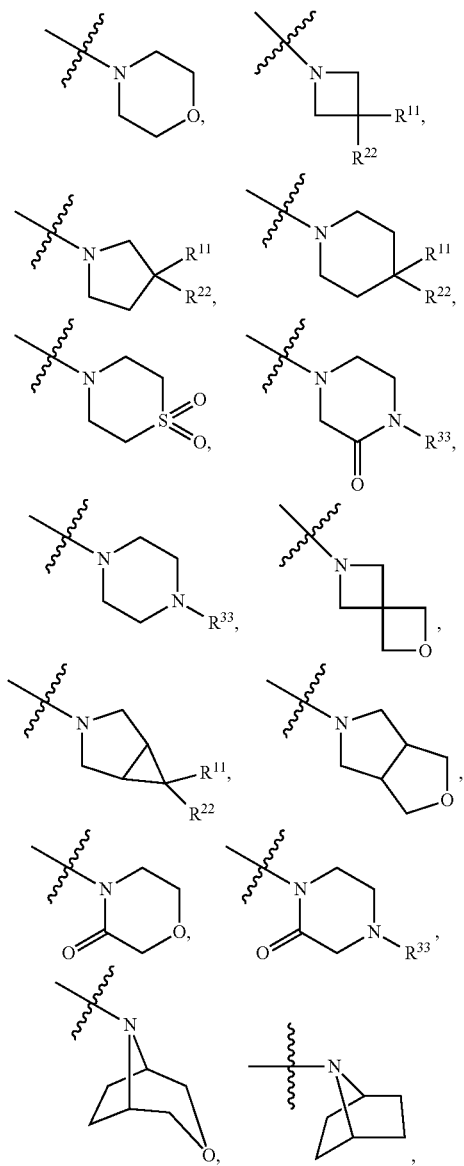

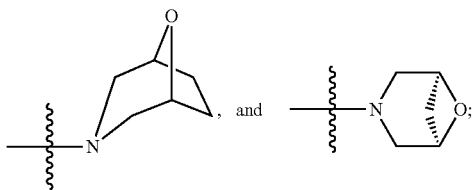

wherein $R^{11}$ and $R^{22}$ are independently selected from the group consisting of hydrogen, fluorine, hydroxyl, cyano, —C(O)—NR$^a$R$^b$, $C_{1-3}$alkyl, and $C_{1-3}$alkoxy; wherein $C_{1-3}$alkyl may optionally be substituted by one, two, or three fluorine atoms;

$R^{33}$ is selected from the group consisting of hydrogen, $C_{1-3}$alkyl, and —SO$_2$—$C_{1-3}$alkyl; wherein $C_{1-3}$alkyl and —SO$_2$—$C_{1-3}$alkyl may optionally be substituted by one, two, or three fluorine atoms; and $R^a$ and $R^b$ are independently selected from the group consisting of hydrogen and $C_{1-3}$alkyl.

In certain embodiments, for example, B may be selected from the group consisting of:

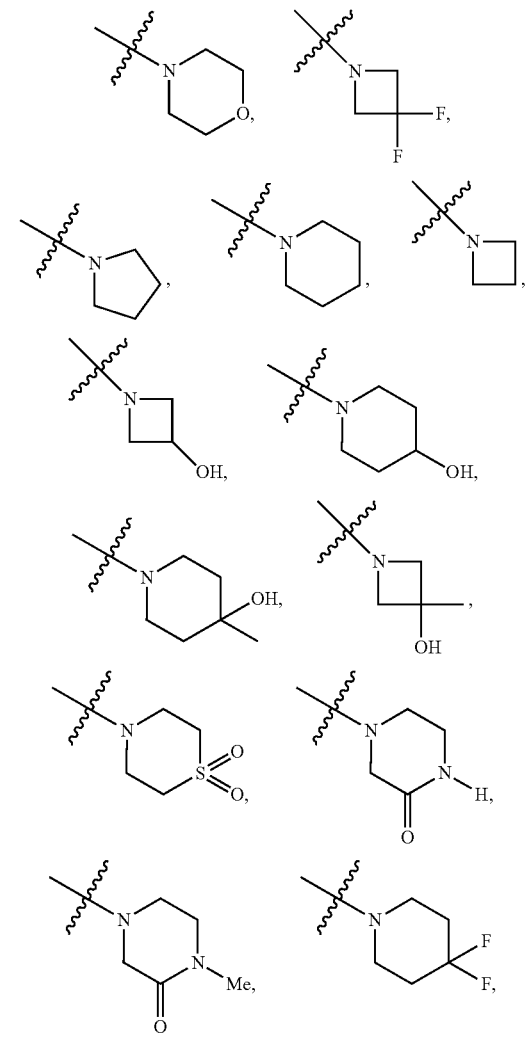

-continued

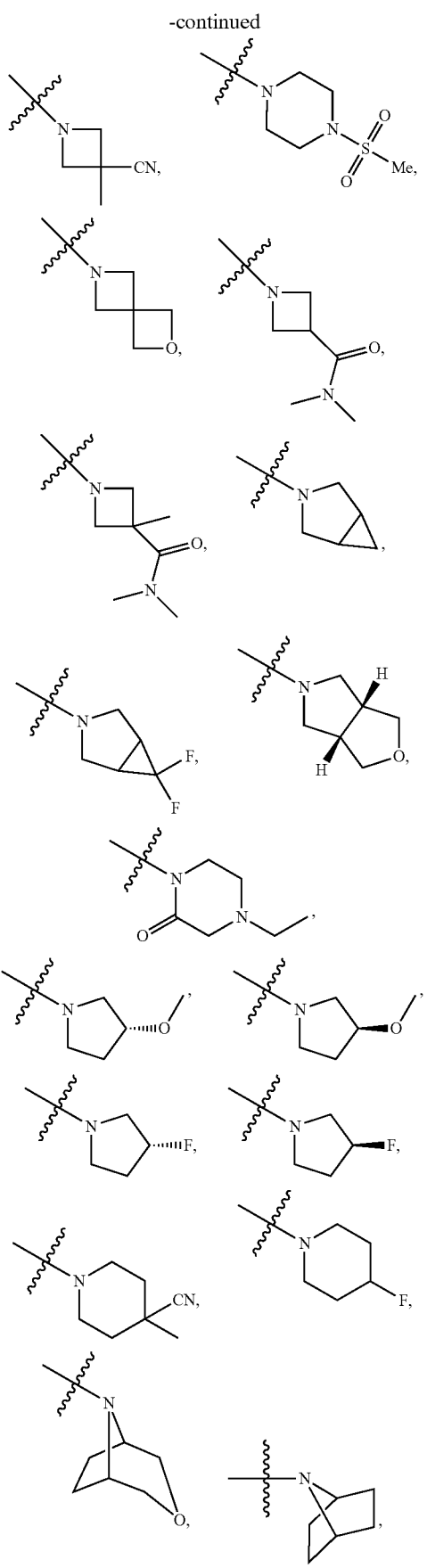

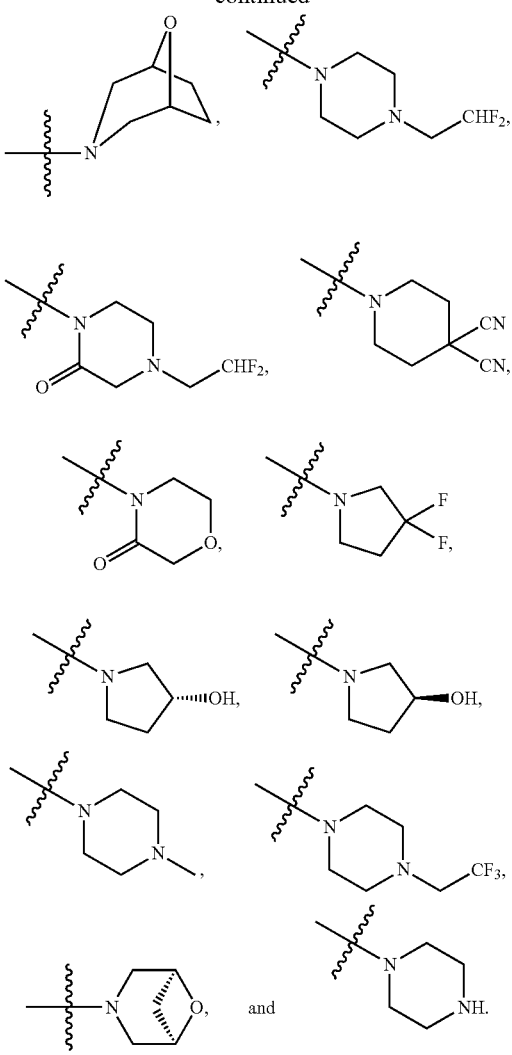

In certain embodiments, B may be heterocyclyl, wherein if said heterocyclyl contains a —NH moiety that nitrogen may optionally be substituted by a substituent selected from the group consisting of $C_{1-6}$alkyl and $C_{1-6}$alkyl-$S(O)_2$—, and wherein $C_{1-6}$alkyl and $C_{1-6}$alkyl-$S(O)_2$— may optionally be substituted by one or more fluorine atoms.

For example, B may be selected from the group consisting of:

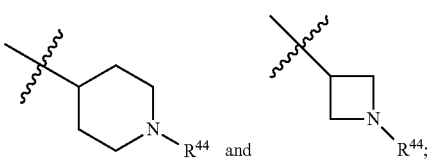

wherein $R^{44}$ is selected from the group consisting of hydrogen, $C_{1-3}$alkyl, and —$SO_2$—$C_{1-3}$alkyl; wherein $C_{1-3}$alkyl and —$SO_2$—$C_{1-3}$alkyl may optionally be substituted by one, two, or three fluorine atoms.

For example, B may be selected from the group consisting of:

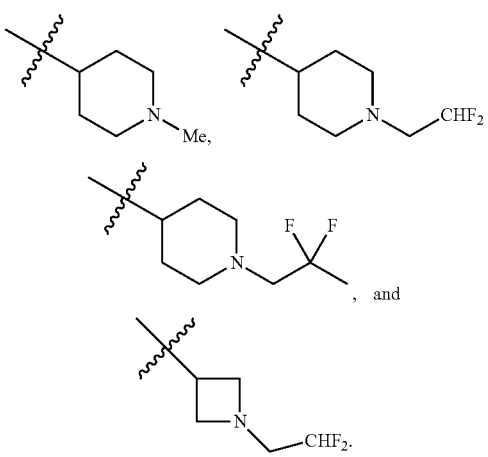

In certain embodiments, B may be heteroaryl. For example, B may be selected from the group consisting of:

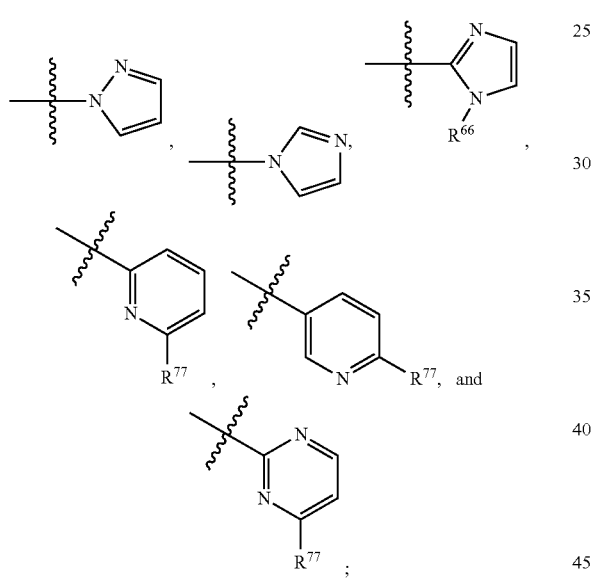

wherein $R^{66}$ is selected from the group consisting of hydrogen, $C_{1-3}$alkyl, and $C_{1-3}$alkyl-S(O)$_2$—; and wherein $R^{77}$ is selected from the group consisting of hydrogen, $C_{1-3}$alkyl, $C_{1-3}$alkoxy, and —NR$^a$R$^b$; wherein $R^a$ and $R^b$ are independently selected from the group consisting of hydrogen and $C_{1-3}$alkyl.

In certain embodiments, $R^{66}$ may be hydrogen. In other embodiments, $R^{77}$ is selected from the group of hydrogen, methyl, methoxy, and

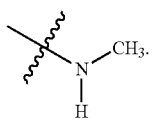

For example, B may be selected from the group consisting of:

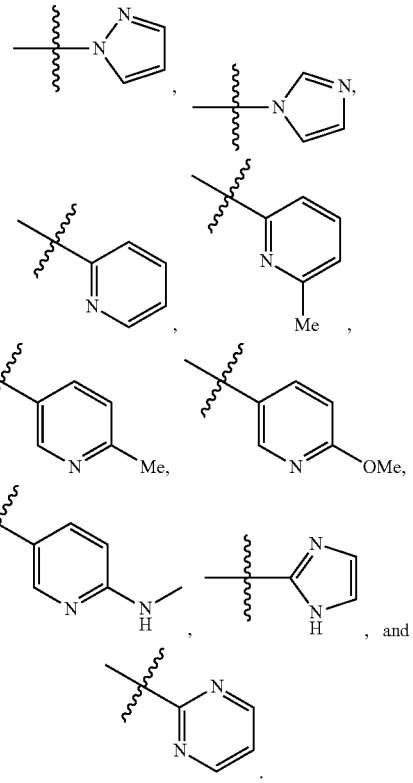

Also provided herein are compounds that may be selected from the group consisting of: (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholinoethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3,3-difluoroazetidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(pyrrolidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(piperidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(azetidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-hydroxyazetidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-hydroxypiperidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-hydroxy-4-methylpiperidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-hydroxy-3-methylazetidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-thiomorpholinoethyl)azetidine 2,2-dioxide-1-carboxylate; (3R,4S,5S,6R)-5-methoxy-4-((2R,3R)-2-methyl-3-(3-methylbut-2-enyl)oxiran-2-yl)-1-oxaspiro[2.5]

octan-6-yl 3-(2-(4-methyl-3-oxopiperazin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-oxopiperazin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4,4-difluoropiperidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-cyano-3-methylazetidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-(methylsulfonyl)piperazin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(2-oxa-6-azaspiro[3.3]heptan-6-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1H-pyrazol-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1H-imidazol-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-(dimethylcarbamoyl)azetidin-1-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-(dimethylcarbamoyl)-3-methylazetidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(3-azabicyclo[3.1.0]hexan-3-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(6,6-difluoro-3-azabicyclo[3.1.0]hexan-3-yl)ethyl)azetidine-1-carboxylate; (3R,4S,5S,6R)-5-methoxy-4-(2R,3R)-2-methyl-3-(3-methylbut-2-en-1-yl)oxiran-2-yl)-1-oxaspiro[2.5]octan-6-yl 3-(2-((3aR,6aS)-tetrahydro-1H-furo[3,4-c]pyrrol-5(3H)-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-ethyl-2-oxopiperazin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((S)-3-methoxypyrrolidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((R)-3-methoxypyrrolidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((R)-3-fluoropyrrolidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((S)-3-fluoropyrrolidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-cyano-4-methylpiperidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-fluoropiperidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((1R,5S)-3-oxa-8-azabicyclo[3.2.1]octan-8-yl)ethyl)azetidine-1-carboxylate; (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((1S,4S)-7-azabicyclo[2.2.1]heptan-7-yl)ethyl)azetidine-1-carboxylate; (4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(8-oxa-3-azabicyclo[3.2.1]octan-3-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-(2,2-difluoroethyl)piperazin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-(2,2-difluoroethyl)-2-oxopiperazin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4,4-dicyanopiperidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-3-(morpholinomethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-3-((diethylamino)methyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(3-oxomorpholino)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-2-((diethylamino)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-2-(pyrrolidin-1-ylmethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-2-(pyrrolidin-1-ylmethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-2-((diethylamino)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-((diethylamino)methyl)morpholine-4-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(3,3-difluoropyrrolidin-1-yl)ethyl)azetidine-1-carboxylate; (3R,4S,5S,6R)-5-methoxy-4-(2R,3R)-2-methyl-3-(3-methylbut-2-en-1-yl)oxiran-2-yl)-1-oxaspiro[2.5]octan-6-yl 3-(2-((S)-3-hydroxypyrrolidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((R)-3-hydroxypyrrolidin-1-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-2-((diethylamino)methyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(diethylamino)ethyl)-3-hydroxyazetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-2-(2-(diethylamino)ethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-2-(2-(diethylamino)ethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(diethylamino)ethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-3-(2-(diethylamino)ethyl)pyrrolidine-1-carboxylate; (3R,4S,5S,6R)-5-methoxy-4-((2R,3R)-2-methyl-3-(3-methylbut-2- en-1-yl)oxiran-2-yl)-1-oxaspiro[2.5]octan-6-yl (S)-3-(2-morpholinoethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-3-(2-morpholinoethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-3-(2-(diethylamino)ethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-3-(2-(3,3-difluoroazetidin-1-yl)ethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-3-(2-(3,3-difluoroazetidin-1-yl)ethyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-(pyrrolidin-1-yl)propyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-2-((diethylamino)methyl)pyrrolidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-(diethylamino)propyl)-3-hydroxyazetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-morpholino-2-oxoethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(methylamino)-2-oxoethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(dimethylamino)-2-oxoethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-amino-2-oxoethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((2-(diethylamino)ethyl)amino)-2-oxoethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-((2-morpholinoethyl)amino)-3-oxopropyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((((2-(diethylamino)ethyl)carbamoyl)oxy)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(((methylcarbamoyl)oxy)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(((dimethylcarbamoyl)oxy)methyl)azetidine-1-carboxylate; 1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl morpholine-4-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(carbamoyloxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(((2-(diethylamino)ethyl)carbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((methylcarbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((ethylcarbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((isopropylcarbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((dimethylcarbamoyl)oxy)azetidine-1-carboxylate; 1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl 4-methylpiperazine-1-carboxylate; 1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl thiomorpholine-4-carboxylate 1,1-dioxide; 1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl 4-(2,2-difluoroethyl)piperazine-1-carboxylate; 1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl 4-(2,2,2-trifluoroethyl)piperazine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(((2-hydroxy-2-methylpropyl)carbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(methylamino)-2-oxoethoxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-methylureido)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3,3-dimethylureido)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-propionamidoazetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((methoxycarbonyl)amino)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-((2-(diethylamino)ethyl)amino)-3-oxopropyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-((2-morpholinoethyl)amino)-3-oxopropyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(1-methylpiperidin-4-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(1-(2,2-difluoroethyl)piperidin-4-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(1-(2,2-difluoroethyl)azetidin-3-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 4-(2-(1-(2,2-difluoroethyl)azetidin-3-yl)ethyl)piperidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((1-(2,2-difluoroethyl)piperidin-4-yl)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(morpholinomethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-morpholinoethylidene)azetidine-1-carboxylate; (3R,4S,5S,6R)-5-methoxy-4-((2R,3R)-2-methyl-3-(3-methylbut-2-en-1-yl)

oxiran-2-yl)-1-oxaspiro[2.5]octan-6-yl 3-(2-(4-(2,2-difluoroethyl)piperazin-1-yl)ethylidene)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(pyridin-2-ylamino)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(pyridin-2-yloxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(pyridin-2-ylmethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((6-methylpyridin-3-yl)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(pyridin-2-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(diethylamino)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-(diethylamino)propyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-((diethylamino)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 2-(2-(diethylamino)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((6-methylpyridin-3-yl)methylene)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-((1R,5S)-6-oxa-3-azabicyclo[3.1.1]heptan-3-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((dimethylcarbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((ethylcarbamoyl)oxy)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(1-(2,2-difluoropropyl)piperidin-4-yl)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(methyl(pyridin-2-yl)amino)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((6-methylpyridin-2-yl)amino)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((6-methoxypyridin-3-yl)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((1H-imidazol-2-yl)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((6-(methylamino)pyridin-3-yl)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(ethylcarbamoyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(azetidine-1-carbonyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(dimethylcarbamoyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(pyrimidin-2-ylamino)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(ethylamino)ethyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (S)-2-((ethylamino)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl (R)-2-((ethylamino)methyl)azetidine-1-carboxylate; (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(3-(ethylamino)propyl)azetidine-1-carboxylate; 1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl piperazine-1-carboxylate; (3R,4S,5S,6R)-4-((2R,3R)-3-isopentyl-2-methyloxiran-2-yl)-5-methoxy-1-oxaspiro[2.5]octan-6-yl 3-(2-(3,3-difluoroazetidin-1-yl)ethyl)azetidine-1-carboxylate; (3R,4S,5S,6R)-4-((2R,3R)-3-isopentyl-2-methyloxiran-2-yl)-5-methoxy-1-oxaspiro[2.5]octan-6-yl 3-(2-morpholinoethyl)azetidine-1-carboxylate; (3R,4S,5S,6R)-4-((2R,3R)-3-isopentyl-2-methyloxiran-2-yl)-5-methoxy-1-oxaspiro[2.5]octan-6-yl 3-(2-(1-(2,2-difluoroethyl)piperidin-4-yl)ethyl)azetidine-1-carboxylate; and a pharmaceutically acceptable salt or stereoisomer thereof.

Procedures for making compounds described herein are provided below in the working examples and may be supplemented or substituted by procedures known to those of skill in the art. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 2nd Ed. (1999)). The deprotection step may be the final step in the synthesis such that the removal of protecting groups affords compounds of Formula I, as disclosed herein. Starting materials used in the working examples can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of Formula I, or any of the intermediates described herein, can be further derivatised by using one or more standard synthetic methods known to those skilled in the art. Such methods can involve substitution, oxidation or reduction reactions. These methods can also be used to obtain or modify compounds of Formula I or any preceding intermediates by modifying, introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride) followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl sulfonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyl lithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis(triphenylphosphine)palladium(0), palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as tetrahydrofuran or DMF), under appropriate conditions (such as heating to, for example, 50-120° C.). In another example, a Sonogashira reaction can be used to couple such a ring system to an alkyne (which may, or may not be further substituted) by treatment with a palladium complex (such as tetrakis(triphenylphosphine)palladium(0)) and a halide salt of copper (I) (such as copper (I) iodide), in the presence of a base (such as a potassium carbonate or a tertiary amine, for example, triethylamine), in an appropriate solvent (such as tetrahydrofuran or dimethylformamide), under appropriate conditions (such as heating to, for example, 50-120° C.). In another example, a Stille reaction can be used to couple such a ring system to an alkene, by treatment with an organotin compound (such as an alkynyltin or alkenyltin reagent, for example an alkenyltributylstannane) in the presence of a palladium complex (such as tetrakis(triphenylphosphine)palladium(0)), with, or without the presence of a salt (such as a copper (I) halide), in an appropriate solvent (such as dioxane or dimethylformamide), under appropriate conditions (such as heating to, for example, 50-120° C.).

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine) Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, $CH_2OH$ groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of Formula I can be prepared by the reaction of a compound of Formula I with an appropriate acid or base in a suitable solvent, or mixture of solvents (such as an ether, for example, diethyl ether, or an alcohol, for example ethanol, or an aqueous solvent) using conventional procedures. Salts of compound of Formula I can be exchanged for other salts by treatment using conventional ion-exchange chromatography procedures.

Where it is desired to obtain a particular enantiomer of a compound of Formula I, this may be produced from a corresponding mixture of enantiomers by employing any suitable conventional procedure for resolving enantiomers. For example, diastereomeric derivatives (such as salts) can be produced by reaction of a mixture of enantiomers of a compound of Formula I (such a racemate) and an appropriate chiral compound (such as a chiral base). The diastereomers can then be separated by any conventional means such as crystallisation, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Steroselective Biocatalysts, Marcel Decker; New York 2000).

In another resolution process a racemate of compounds of Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the present disclosure.

II. Methods

Another aspect of the present disclosure provides methods of modulating the activity of MetAP2. Such methods comprise exposing said receptor to a compound described herein. In some embodiments, the compound utilized by one or more of the foregoing methods is one of the generic, subgeneric, or specific compounds described herein, such as a compound of Formula I. The ability of compounds described herein to modulate or inhibit MetAP2 can be evaluated by procedures known in the art and/or described herein. Another aspect of the present disclosure provides methods of treating a disease associated with expression or activity of MetAP2 in a patient.

In certain embodiments, the present disclosure provides a method of treating and/or controlling obesity, comprising administering to a patient in need thereof an effective amount of a disclosed compound.

In certain embodiments, the present disclosure provides a method of inducing weight loss in a patient in need thereof, comprising administering to said patient an effective amount of a disclosed compound.

In certain embodiments, the present disclosure provides a method of substantially preventing weight gain in a patient in need thereof, comprising administering to said patient an effective amount of a disclosed compound.

In certain embodiments, the patient is a human.

In certain embodiments, the patient is a cat or dog.

In certain embodiments, the patient has a body mass index greater than or equal to about 30 kg/m$^2$ before the administration.

In certain embodiments, administering a disclosed compound may comprise subcutaneous administration. In certain embodiments, administering a disclosed compound may comprise intravenous administration.

Provided methods of treatment may include administering a disclosed compound once, twice, or three times daily; about every other day (e.g. every 2 days); twice weekly (e.g. every 3 days, every 4 days, every 5 days, every 6 days, or e.g. administered with an interval of about 2 to about 3 days between doses); once weekly; three times weekly; every other week; twice monthly; once a month; every other month; or even less often.

In certain embodiments, a method disclosed herein further comprises administering said compound in an amount sufficient to establish inhibition of intracellular MetAP2 effective to increase thioredoxin production in the patient and to induce multi organ stimulation of anti-obesity processes in the subject.

In certain embodiments, the method comprises administering said compound in an amount insufficient to reduce angiogenesis in the patient.

Other contemplated methods of treatment include method of treating or ameliorating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the present disclosure provides a method of treating one or more of the above medical indications comprising administering to a subject in need thereof a therapeutically effective amount of a compound described herein, such as a compound of Formula I.

Obesity or reference to "overweight" refers to an excess of fat in proportion to lean body mass. Excess fat accumulation is associated with increase in size (hypertrophy) as well as number (hyperplasia) of adipose tissue cells. Obesity is variously measured in terms of absolute weight, weight: height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$ (m$^2$) (SI) or 703×weight (lb)/height$^2$ (in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds of the present disclosure also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the present disclosure provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of Formula I.

The compounds of the present disclosure may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this present disclosure may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. a lower dose sufficient to prevent weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

Another aspect of the present disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this disclosure may be used in the form of a pharmaceutical preparation, for example, in solid, semisolid or liquid form, which contains one or more disclosed compounds, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the present disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the present disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the present disclosure also provides kits for use by e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497): 1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (*Chest* (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the present disclosure provides methods for facilitating and maintaining weight loss in a subject involving administering to the subject an amount of a disclosed compound effective to result in weight loss in the subject; and optionally administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the present disclosure.

Example A

General Procedures

All reagents were purchased from commercial suppliers (Sigma-Aldrich, Alfa, Across etc.) and used without further purification unless otherwise stated. THF was continuously refluxed and freshly distilled from sodium and benzophenone under nitrogen, and dichloromethane was continuously refluxed and freshly distilled from $CaH_2$ under nitrogen.

Reactions were monitored by TLC on silica gel 60 HSGF254 percolated plates (0.15-0.2 mm $SiO_2$) and visualized using UV light (254 nm or 365 nm) and/or staining with phosphomolybdic acid ethanol solution (10 g in 100 mL ethanol) and subsequent heating or monitored by LCMS.

LCMS were performed on SHIMADZU LCMS-2010EV (Chromolith SpeedROD, RP-18e, 50×4.6 mm, mobile phase: Solvent A: $CH_3CN/H_2O/HCOOH$=10/90/0.05, Solvent B: $CH_3CN/H_2O/$ HCOOH=90/10/0.05, 0.8 min@10% B, 2.7 min gradient (10-95% B), then 0.8 min@95% B, Flow rate: 3 mL/min, temperature: 40° C.).

Preparative HPLC were performed either on Method A: SHIMADZU LC-8A (Column: YMC Pack ODS-A (150*30 mm, 10 μm)) or Method B: LC-6AD (Column: Shim=Pack PREP-ODS-H (250*20 mm, 10 μm)) with UV detection which were controlled by LC solution Chemstation software. $H_2O$ (0.1% HCOOH) and MeOH (MeCN) as mobile phase at the indicated flow rate.

Analytical HPLC were performed on SHIMADZU LC-2010A (Chromolith SpeedROD, RP-18e, 50×4.6 mm, mobile phase: Solvent A: $CH_3CN/H_2O/HCOOH$=10/90/0.05, Solvent B: $CH_3CN/H_2O$ /HCOOH=90/10/0.05, 0.8 min@10% B, 2.7 min gradient (10-95% B), then 0.8 min@95% B, Flow rate: 3 mL/min, temperature: 40° C.).

Chiral HPLC were performed on SHIMADZU LC-2010A (Chiral column, mobile phase: Solvent A: hexane (or containing 0.1% diethylamine), Solvent B: Ethanol or Isopropanol; Flow rate: 0.8 mL/min, temperature: 30° C.).

$^1$H spectra were recorded on Bruker Avance II 400 MHz, Chemical shifts (δ) are reported in ppm relative to tetramethylsilane (δ=0.000 ppm), and the spectra were calibrated to the residual solvent signal of chloroform (δ=7.26), Dimethyl sulfoxide (δ=2.50), or methanol (δ=3.30). Data for $^1$H-NMR spectra are reported as follows: chemical shift (multiplicity, number of hydrogens). Abbreviations are as follows: s (singlet), d (doublet), t (triplet), q (quartet), quint (quintet), m (multiple), br (broad). Abbreviations:

| | |
|---|---|
| Ac | Acetyl |
| AcOH; HOAc | acetic acid |
| aq. | Aqueous |
| Bs | Benzenesulfonyl |
| Cbz | Benzyloxycarbonyl |
| CDI | Carbonyldimidazole |

-continued

| | |
|---|---|
| DCM | Dichloromethane |
| DEAD | Diethyl azodicarboxylate |
| DIPEA | Ethyldiisopropylamine |
| DMA | Dimethyl acetamide |
| DMF | Dimethyl formamide |
| EDCl/EDC | 3-(ethyliminomethyleneamino)-N,N-dimethylpropan-1-amine |
| EtOH | Ethanol |
| eq(s). | equivalent(s) |
| EtOAc | ethyl acetate |
| Et | Ethyl |
| FA | Formic acid |
| Et$_3$N | Triethylamine |
| hr | hour(s) |
| HATU | (Dimethylamino)-N,N-dimethyl(3H-[1,2,3]triazolo[4,5-b]pyridin-3-yloxy)methaniminium hexafluorophosphate |
| HOBt | 1-Hydroxybenzotriazole |
| HPLC | High pressure liquid chromatography |
| LAH | Lithium Aluminum Hydride |
| LCMS; LC-MS | liquid chromatography mass spectrometry |
| m-CPBA | m-Chloroperoxybenzoic acid |
| MeOH | Methanol |
| mg | milligram(s) |
| min | Minute(s) |
| mL; ml | milliliter(s) |
| NCS | N-Chlorosuccinimide |
| NMe | N-methyl |
| NMO | N-methylmorpholine-N-oxide |
| NMP | N-methylpyrrolidinone |
| NMR | Nuclear magnetic resonance |
| Pd(dppf)Cl$_2$ | (1,1'-bis(diphenylphosphino)ferrocene) palladium (II) dichloride |
| PE | Petroleum Ether |
| Ph | Phenyl |
| PTSA | p-Toluenesulfonic acid |
| r.t./RT | Room temperature |
| S. | Saturated |
| SEMCl | 2-(Trimethylsilyl)ethoxymethyl chloride |
| TBAF | Tetrabutylammonium fluoride |
| TEA | Triethylamine |
| THF | Tetrahydrofuran |
| THP | Tetrahydropyran |
| TFA | Trifluoroacetic acid |
| TMSCN | Trimethylsilyl cyanide |
| TMS OTf | Trimethylsilyl Triflate |
| THF | Tetrahydrofuran |
| TLC | Thin layer chromatography |
| Ts | Tosyl (4-methylbenzene-1-sulfonyl) |

Preparation of Intermediates

Intermediate 1

(3R,4S,5S,6R)-5-methoxy-4-((2R,3R)-2-methyl-3-(3-methylbut-2-en-1-yl)oxiran-2-yl)-1-oxaspiro[2.5]octan-6-yl(4-nitrophenyl)carbonate

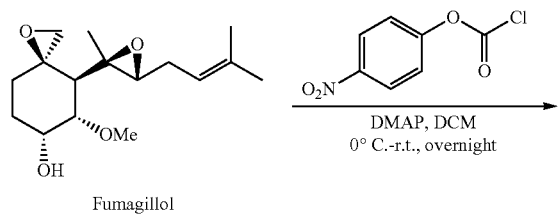

Fumagillol

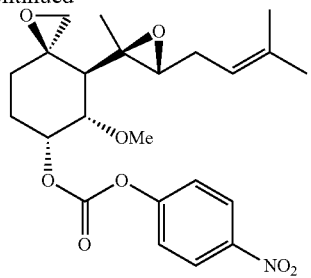

Intermediate 1

Fumagillol (40 g, 0.142 mol) and DMAP (34.6 g, 0.283 mol) were dissolved in anhydrous DCM (480 mL) with stirring at 0° C. A solution of p-nitrophenyl chloroformate (48.65 g, 0.241 mol) in DCM (250 mL) was added dropwise to the mixture above for 1 hr, and the temperature was kept below 0° C. After addition was complete, the mixture was stirred at room temperature for 16 hrs. The mixture was diluted with DCM (500 mL), washed sequentially with a 10% aq. solution of citric acid, saturated aq. K$_2$CO$_3$ and brine. The organic layer was dried, concentrated and purified by silica gel chromatography (PE:EtOAc=20:1 to PE:EtOAc:DCM=5:1:1). The crude product was washed with PE/EtOAc (100 mL/30 mL) twice, hot EtOH (200 mL, ~70° C.), dried under vacuum at r.t. to give (3R,4S,5S,6R)-5-methoxy-4-((2R,3R)-2-methyl-3-(3-methylbut-2-en-1-yl)oxiran-2-yl)-1-oxaspiro[2.5]octan-6-yl (4-nitrophenyl) carbonate as a white solid (47.9 g, 75.4% yield). LC-MS: m/z=448 [M+H]$^+$. $^1$H NMR (400 MHz, CDCl$_3$) δ 8.39-8.23 (m, 2H), 7.53-7.34 (m, 2H), 5.63 (d, J=2.8 Hz, 1H), 5.23 (t, J=7.4 Hz, 1H), 3.74 (dd, J=11.3, 2.6 Hz, 1H), 3.03 (d, J=4.2 Hz, 1H), 2.69-2.53 (m, 2H), 2.50-2.33 (m, 1H), 2.27-1.90 (m, 5H), 1.77 (s, 3H), 1.68 (s, 3H), 1.37-1.06 (m, 4H).

Procedures for the preparation of additional intermediates and compounds of the present disclosure are described in the following examples.

Intermediate 2

4-(2-(azetidin-3-yl)ethyl)morpholine, Trifluoroacetate

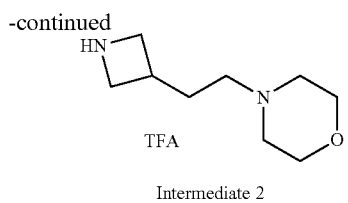

Intermediate 2

Step 1: Preparation of tert-butyl 3-(2-hydroxyethyl)azetidine-1-carboxylate

To a solution of 2-(1-(tert-butoxycarbonyl)azetidin-3-yl)acetic acid (12.2 g, 56.74 mmol) in THF (anhydrous, 100 mL) was added a solution of $BH_3$-THF (153 mL, 153.20 mmol, 1M in THF) drop-wise at −20° C. for 30 min. The reaction was stirred at r.t. overnight. The resulting mixture was cooled to 0-5° C., MeOH (50 mL) was added drop-wise below 10° C., and the mixture was stirred at r.t. for 20 min. The mixture was concentrated to give a residue, which was purified by silica gel chromatography (DCM:MeOH=50:1) to give tert-butyl 3-(2-hydroxyethyl)azetidine-1-carboxylate (10.5 g, 92.1% yield) as a colorless oil. LC-MS: m/z=146 [M+H−56]$^+$.

Step 2: tert-butyl 3-(2-(tosyloxy)ethyl)azetidine-1-carboxylate

To a solution of tert-butyl 3-(2-hydroxyethyl)azetidine-1-carboxylate (10.5 g, 52.24 mmol) in DCM (80 mL) was added triethylamine (21.7 mL, 156.72 mmol) at 0° C. followed by drop-wise addition of a solution of 4-methylbenzene-1-sulfonyl chloride (12.9 g, 67.91 mmol) in DCM (50 mL) for 40 min. The resulting mixture was stirred at 25° C. overnight. The mixture was washed with water (30 mL), brine (50 mL), dried over anhydrous $Na_2SO_4$ and concentrated. The residue was purified by silica gel chromatography (DCM:MeOH=100:0~70:1) to give tert-butyl 3-(2-(tosyloxy)ethyl)azetidine-1-carboxylate (16.8 g, 100% yield) as a pale-yellow oil. LC-MS: m/z=300 [M+H−56]$^+$.

Step 3: tert-butyl 3-(2-morpholinoethyl)azetidine-1-carboxylate

To a solution of tert-butyl 3-(2-(tosyloxy)ethyl)azetidine-1-carboxylate (15.6 g, 43.94 mmol) in MeCN (100 mL) was added morpholine (11.5 mL, 131.82 mmol), $K_2CO_3$ (12.1 g, 87.88 mmol) and NaI (1.63 g, 8.79 mmol). The resulting mixture was stirred at reflux overnight under a $N_2$ atmosphere. The mixture was concentrated to dryness, and the residue was dissolved in ethyl acetate (80 mL), washed with water (30 mL), brine (50 mL), dried over anhydrous $Na_2SO_4$ and concentrated to give a crude product, which was purified by silica gel chromatography (DCM:MeOH=200:1~50:1) to give tert-butyl 3-(2-morpholinoethyl)azetidine-1-carboxylate (10.2 g, 86% yield) as pale yellow solid. LC-MS: m/z=271 [M+H]$^+$. Retention Time: 0.747 min. $^1$H-NMR (400 MHz, $CDCl_3$) δ 4.05-4.01 (m, 2 H), 3.74-3.72 (m, 4 H), 3.60-3.56 (m, 2 H), 2.58-2.45 (m, 5 H), 2.31-2.74 (m, 2 H), 1.82-1.77 (m, 2 H), 1.45 (s, 9 H).

Step 4: 4-(2-(azetidin-3-yl)ethyl)morpholine, Trifluoroacetate

To a solution of tert-butyl 3-(2-morpholinoethyl)azetidine-1-carboxylate (10 g, 0.037 mol) in DCM (80 mL) was added was added TFA (25 mL) drop-wise at 0° C. After addition was complete, the mixture was stirred at room temperature overnight. The mixture was concentrated under reduce pressure, and the residue was azeotroped with toluene three times to give 4-(2-(azetidin-3-yl)ethyl)morpholine TFA salt (23.3 g, containing 4.03 mol of TFA), which was directly used in the next reaction without purification. LC-MS: m/z=171 [M+H]$^+$.

The following intermediates were prepared according to procedures similar to that described for Intermediate 2 by using the corresponding amines

| Intermediate # | Structure | LC-MS |
|---|---|---|
| 3 | (azetidine-CH$_2$CH$_2$-N-azetidine with 2F) TFA | 177 [M + H]$^+$ |
| 4 | (azetidine-CH$_2$CH$_2$-pyrrolidine) TFA | 155 [M + H]$^+$ |
| 5 | (azetidine-CH$_2$CH$_2$-piperidine) TFA | 169 [M + H]$^+$ |
| 6 | (azetidine-CH$_2$CH$_2$-azetidine) TFA | 141 [M + H]$^+$ |
| 7 | (azetidine-CH$_2$CH$_2$-N-azetidine-OH) TFA | 157 [M + H]$^+$ |
| 8 | (azetidine-CH$_2$CH$_2$-N-azetidine-OH with Me) TFA | 185 [M + H]$^+$ |
| 9 | (azetidine-CH$_2$CH$_2$-piperidine-OH-Me) TFA | 199 [M + H]$^+$ |
| 10 | (azetidine-CH$_2$CH$_2$-N-azetidine-OH-diMe) TFA | 171 [M + H]$^+$ |

| Intermediate # | Structure | LC-MS |
|---|---|---|
| 11 | azetidine-CH2CH2-thiomorpholine-1,1-dioxide, TFA | 219 [M + H]+ |
| 12 | azetidine-CH2CH2-(4-methyl-3-oxopiperazin-1-yl), TFA | 198 [M + H]+ |
| 13 | azetidine-CH2CH2-(3-oxopiperazin-1-yl), TFA | 184 [M + H]+ |
| 14 | azetidine-CH2CH2-(4,4-difluoropiperidin-1-yl), TFA | 205 [M + H]+ |
| 15 | azetidine-CH2CH2-(3-cyano-3-methylazetidin-1-yl), TFA | 180 [M + H]+ |
| 16 | azetidine-CH2CH2-(4-methylsulfonylpiperazin-1-yl), TFA | 248 [M + H]+ |
| 17 | azetidine-CH2CH2-(2-oxa-6-azaspiro[3.3]heptan-6-yl), TFA | 183 [M + H]+ |
| 18 | azetidine-CH2CH2-(1H-pyrazol-1-yl), TFA | 152 [M + H]+ |
| 19 | azetidine-CH2CH2-(1H-imidazol-1-yl), TFA | 152 [M + H]+ |
| 20 | azetidine-CH2CH2-(N,N-dimethylazetidine-3-carboxamide), TFA | 212 [M + H]+ |
| 21 | azetidine-CH2CH2-(N,N,3-trimethylazetidine-3-carboxamide), TFA | 226 [M + H]+ |
| 22 | azetidine-CH2CH2-(3-azabicyclo[3.1.0]hexan-3-yl), TFA | 167 [M + H]+ |
| 23 | azetidine-CH2CH2-(6,6-difluoro-3-azabicyclo[3.1.0]hexan-3-yl), TFA | 203 [M + H]+ |
| 24 | azetidine-CH2CH2-(cis-hexahydrofuro[3,4-c]pyrrol-5-yl), TFA | 197 [M + H]+ |
| 25 | azetidine-CH2CH2-(4-ethyl-3-oxopiperazin-1-yl), TFA | 212 [M + H]+ |
| 26 | azetidine-CH2CH2-((R)-3-methoxypyrrolidin-1-yl), TFA | 185 [M + H]+ |
| 27 | azetidine-CH2CH2-((S)-3-methoxypyrrolidin-1-yl), TFA | 185 [M + H]+ |

-continued

| Intermediate # | Structure | LC-MS |
|---|---|---|
| 28 | (azetidine-CH2CH2-pyrrolidine-F) TFA | 173 [M + H]+ |
| 29 | (azetidine-CH2CH2-pyrrolidine-F, other stereo) TFA | 173 [M + H]+ |
| 30 | (azetidine-CH2CH2-piperidine-CN,Me) TFA | 208 [M + H]+ |
| 31 | (azetidine-CH2CH2-piperidine-F) TFA | 187 [M + H]+ |
| 32 | (azetidine-CH2CH2-8-oxa-bicyclic amine) TFA | 197 [M + H]+ |
| 33 | (azetidine-CH2CH2-bicyclic amine) TFA | 181 [M + H]+ |
| 34 | (azetidine-CH2CH2-oxa-bicyclic amine) TFA | 197 [M + H]+ |

Intermediate 35

1-(2-(azetidin-3-yl)ethyl)-4-(2,2-difluoroethyl)piperazine, Trifluoroacetate

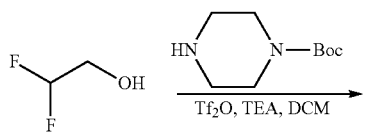

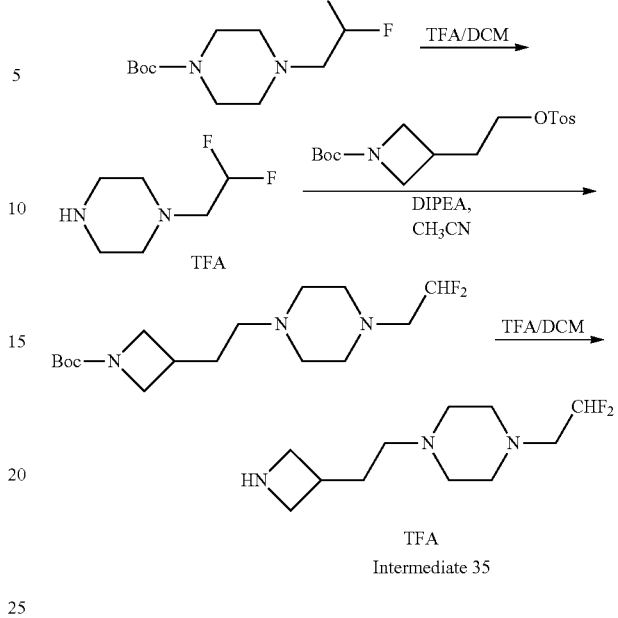

Intermediate 35

Step 1: tert-butyl 4-(2,2-difluoroethyl)piperazine-1-carboxylate

To a solution of (1.35 mL, 9.6 mmol) anhydrous triethylamine and (1.27 mL, 7.52 mmol) of trifluoromethanesulfonic acid anhydride in dichloromethane (10 mL) were added a solution of (0.40 mL, 6.4 mmol) of 2,2-difluoroethanol in dichloromethane (10 mL) at 0° C. After the resulting mixture was stirred at 0° C. for 30 min, a solution of tert-butyl piperazine-1-carboxylate (1.0 g, 5.3 mmol) in DCM (10 mL) was added. The reaction mixture was then allowed to warm to room temperature and stirred for 16 hrs. The reaction mixture was poured into ice water and extracted with ethyl acetate. The organic layer was dried over Na$_2$SO$_4$, filtered and concentrated. The residue was purified by silica gel column chromatography (petroleum ether:ethyl acetate=10:1 to 4:1) to give tert-butyl 4-(2,2-difluoroethyl)piperazine-1-carboxylate (750 mg, 55.8% yield) as a white solid. LC-MS: m/z 250 [M+H]+.

Step 2: 1-(2,2-difluoroethyl)piperazine Trifluoroacetate

To a solution of tert-butyl 4-(2,2-difluoroethyl)piperazine-1-carboxylate (750 mg, 3.0 mmol) in dichloromethane (9 mL) was added TFA (3 mL) dropwise at 0° C. The mixture was then stirred at 25° C. for 3 hrs. The resulting mixture was concentrated under vacuum to give a residue, which was azeotroped with toluene to give 1-(2,2-difluoroethyl)piperazine trifluoroacetate (1.6 g, 100% yield) as a brown oil, which was directly used to the next reaction without purification. LC-MS: m/z 151 [M+H]+.

Step 3: tert-butyl 3-(2-(4-(2,2-difluoroethyl)piperazin-1-yl)ethyl)azetidine-1-carboxylate To a mixture of 1-(2,2-difluoroethyl)piperazine trifluoroacetate (1.6 g, 3.0 mmol) and tert-butyl 3-(2-(tosyloxy)ethyl)azetidine-1-carboxylate (1.28 g, 3 6 mmol) in CH$_3$CN (10 mL) was added DIPEA (3.04 g, 18.0 mmol) at 0° C. After the resulting mixture was stirred at 80° C. overnight, solvent was removed and the residue was partitioned between water and EtOAc. The aqueous layer were extracted with EtOAc. The combined organic layers were dried over Na$_2$SO$_4$ and concentrated. The residue was purified by silica gel column chromatography (DCM: MeOH=150:1~50:1) to give tert-butyl 3-(2-(4-(2,2-difluoroethyl)piperazin-1-yl)ethyl)azetidine-1-carboxylate (610 mg, 63.3% yield) as a light yellow oil LC-MS: m/z 334 [M+H]$^+$.

Step 4: 1-(2-(azetidin-3-yl)ethyl)-4-(2,2-difluoroethyl)piperazine Trifluoroacetate To a solution of tert-butyl 3-(2-(4-(2,2-difluoroethyl)piperazin-1-yl)ethyl)azetidine-1-carboxylate (610 mg, 1.9 mmol) in DCM (6 mL) was added TFA (2 mL) dropwise at 0° C. The mixture was then stirred at 25° C. for 3 hrs. The resulting mixture was concentrated under vacuum to give a residue, which was azeotroped with toluene to give 1-(2-(azetidin-3-yl)ethyl)-4-(2,2-difluoroethyl)piperazine trfluoroacetate (1.3 g, 100% yield) as a brown oil, which was directly used to the next reaction without purification. LC-MS: m/z 234 [M+H]$^+$.

The following intermediate were prepared according to procedures similar to that described for Intermediate 35 by using the corresponding amine.

| Intermediate # | Structure | LC-MS |
|---|---|---|
| 36 | 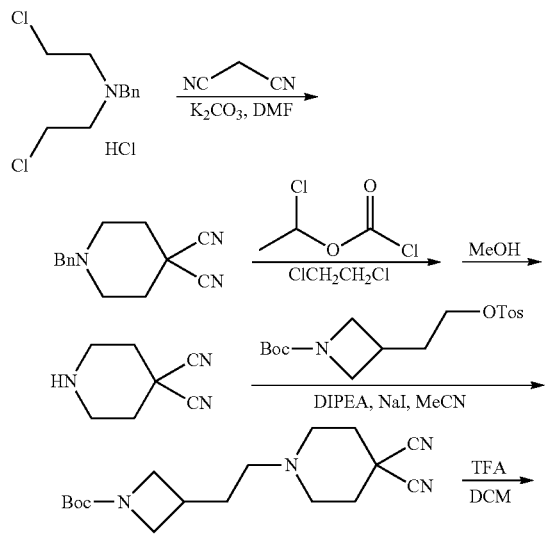 | 248 [M + H]$^+$ |

Intermediate 37

1-(2-(azetidin-3-yl)ethyl)piperidine-4,4-dicarbonitrile Trifluoroacetate

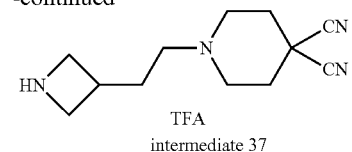

Step 1: 1-benzylpiperidine-4,4-dicarbonitrile

To a solution of malononitrile (491.9 mg, 7.45 mmol) in DMF (10 mL) was added K$_2$CO$_3$ (2.26 g, 16.38 mmol). After the mixture was stirred at 65° C. for 2 hrs, a solution of N-benzyl-2-chloro-N-(2-chloroethyl)ethanamine hydrochloride (2.0 g, 7.45 mmol) in DMF (5 mL) was added. The reaction mixture was then stirred at 65° C. overnight. The reaction was quenched with ice water and extracted with EtOAc (50 mL×2). The combined organic layers were dried over anhydrous Na$_2$SO$_4$, filtered and concentrated. The residue was purified by silica gel column chromatography (petroleum ether:EtOAc=20:1 to 3:1) to give 1-benzylpiperidine-4,4-dicarbonitrile (1.4 g, 83.3% yield) as a colorless oil. LC-MS m/z: 226 [M+H]$^+$.

Step 2: piperidine-4,4-dicarbonitrile

To a solution of 1-benzylpiperidine-4,4-dicarbonitrile (1.2 g, 5.33 mmol) in 1,2-dichloroethane (10 mL) was added 1-chloroethyl chloroformate (0.69 mL, 6.39 mmol) dropwise at 0° C. The reaction was stirred at reflux overnight. The mixture was concentrated under reduced pressure and to the residue was added MeOH (10 mL). The resulting solution was stirred at reflux for 2 hrs. The reaction mixture was concentrated under reduced pressure to give piperidine-4,4-dicarbonitrile (700 mg, 97.2% yield) as a yellow oil, which was directly used to the next reaction without purification. LC-MS m/z: 136 [M+H]$^+$.

Step 3: tert-butyl 3-(2-(4,4-dicyanopiperidin-1-yl)ethyl)azetidine-1-carboxylate To a solution of tert-butyl 3-(2-(tosyloxy)ethyl)azetidine-1-carboxylate (1.0 g, 2.81 mmol) in acetonitrile (30 mL) was added piperidine-4,4-dicarbonitrile (700 mg, 5.18 mmol), DIPEA (0.97 mL, 5.63 mmol) and NaI (100 mg, 0.67 mmol). The resulting mixture was stirred at reflux overnight. The mixture was then concentrated and the residue was partitioned between EtOAc (50 mL) and water (50 mL). The organic layer was dried and concentrated and the residue was purified by silica gel column chromatography (DCM: MeOH=100:1 to 80:1) to give tert-butyl 3-(2-(4,4-dicyanopiperidin-1-yl)ethyl)azetidine-1-carboxylate (350 mg, 39.0% yield) as a brown oil. LC-MS m/z: 319 [M+H]$^+$.

Step 4: 1-(2-(azetidin-3-yl)ethyl)piperidine-4,4-dicarbonitrile Trifluoroacetate To a mixture of tert-butyl 3-(2-(4,4-dicyanopiperidin-1-yl)ethyl)azetidine-1-carboxylate (350 mg, 1.10 mmol) in DCM (2 mL) was added TFA (2 mL) dropwise at 0° C. The reaction was stirred at room temperature for 1 hr. The mixture was concentrated under reduced pressure to give 1-(2-(azetidin-3-yl)ethyl)piperidine-4,4-dicarbonitrile trifluoroacetate (230 mg, 95.8% yield) as a yellow syrup, which was directly used to the next reaction without purification. LC-MS m/z: 219 [M+H]+.

Intermediate 38

(R)-4-(pyrrolidin-3-ylmethyl)morpholine, Trifluoroacetate

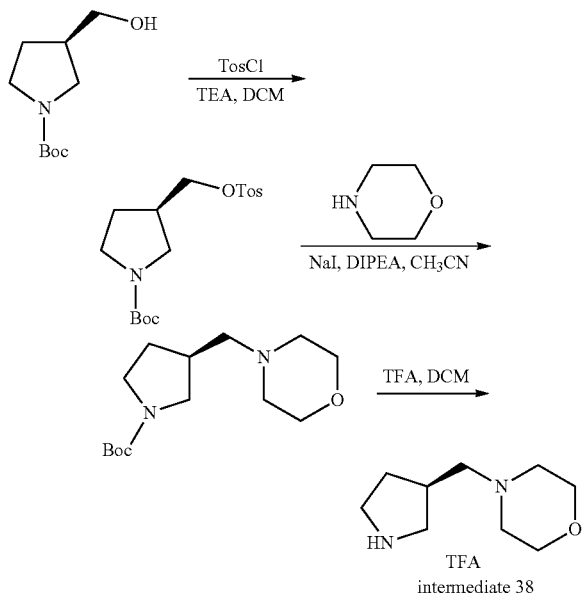

intermediate 38

Step 1: (R)-tert-butyl 3-(tosyloxymethyl)pyrrolidine-1-carboxylate

To a solution of (R)-tert-butyl 3-(hydroxymethyl)pyrrolidine-1-carboxylate (2.8 g, 13.91 mmol) in DCM (50 mL) was added triethylamine (4.21 g, 41.73 mmol) at 0° C. After the mixture was stirred at 0° C. for 30 min, 4-methylbenzene-1-sulfonyl chloride (3.98 g, 20.87 mmol) was added in portions, and the reaction was stirred at room temperature overnight. The mixture was poured into the ice water and extracted with EtOAc (100 mL×2). The organic layers were dried over Na$_2$SO$_4$, filtered and concentrated to give a residue, which was purified by silica gel chromatography (PE:EtOAc=100:1 to 4:1) to give (R)-tert-butyl 3-(tosyloxymethyl)pyrrolidine-1-carboxylate (4.4 g, 88.98% yield) as a white solid. LC-MS: m/z=300 [M+H−56]+.

Step 2: (S)-tert-butyl 3-(morpholinomethyl)pyrrolidine-1-carboxylate

To a solution of (R)-tert-butyl 3-(tosyloxymethyl)pyrrolidine-1-carboxylate (500 mg, 1.41 mmol) in acetonitrile (10 mL) was added DIPEA (545.7 mg 4.23 mmol), sodium iodide (211.4 mg, 1.41mmol) and morpholine (245.1 mg, 2.82 mmol). The reaction was stirred at 80° C. overnight. The mixture was concentrated under reduced pressure and the residue was partitioned with EtOAc and water. The organic layer was dried over Na$_2$SO$_4$, filtered and concentrated to give a residue, which was purified by silica gel chromatography (petroleum ether:ethyl acetate=100:1 to 4:1) to give (S)-tert-butyl 3-(morpholinomethyl)pyrrolidine-1-carboxylate (300 mg, 78.8% yield) as a white solid. LC-MS: m/z=215 [M+H−56]+.

Step 3: (R)-4-(pyrrolidin-3-ylmethyl)morpholine, Trifluoroacetate

To a solution of (S)-tert-butyl 3-(morpholinomethyl)pyrrolidine-1-carboxylate (300 mg, 1.11 mmol) in DCM (5 mL) was added trifluoroacetic acid (2.5 mL) drop-wise at 0° C. The reaction was stirred at room temperature for 1 hr. The mixture was concentrated under reduced pressure to give (R)-4-(pyrrolidin-3-ylmethyl)morpholine trifluoroacetate (300 mg, 97.1% yield) as a yellow syrup, which was directly used to the next reaction without purification. LC-MS: m/z=170 [M+H]+.

The following intermediates were prepared according to procedures similar to that described for Intermediate 38 by using the corresponding amines.

| Intermediate # | Structure | LC-MS |
|---|---|---|
| 39 | ![structure] TFA | 157 [M + H]+ |

Intermediate 40

4-(2-(azetidin-3-yl)ethyl)morpholin-3-one, Trifluoroacetate

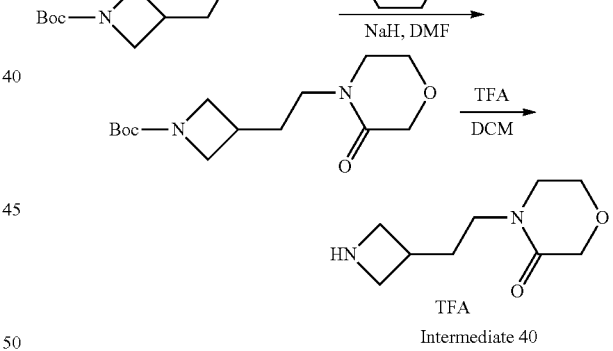

Intermediate 40

Step 1: tert-butyl 3-(2-(3-oxomorpholino)ethyl)azetidine-1-carboxylate

To a solution of morpholin-3-one (156.6 mg, 1.55 mmol) in DMF (8 mL) was added sodium hydride (67.68 mg, 2.82 mmol) in portions at 0° C., and tert-butyl 3-(2-(tosyloxy)ethyl)azetidine-1-carboxylate (500 mg, 1.41 mmol) was then added in portions. The reaction was stirred at room temperature overnight. The reaction mixture was quenched by addition of ice water, and the water layer was extracted with ethyl acetate (50 mL×4). The combined organic layers were dried over anhydrous Na$_2$SO$_4$, filtered and concentrated. The residue was purified by silica gel chromatography (petroleum ether:ethyl acetate=1:1 to 1:2) to give tert-butyl 3-(2-(3-oxomorpholino)ethyl)azetidine-1-carboxylate (300 mg, 75.0% yield) as a colorless oil. LC-MS: m/z=285 [M+H]$^+$.

Step 2: 4-(2-(azetidin-3-yl)ethyl)morpholin-3-one, Trifluoroacetate

A solution of tert-butyl 3-(2-(3-oxomorpholino)ethyl)azetidine-1-carboxylate (300 mg, 1.07 mmol) in trifluoroacetic acid (3 mL) was stirred at 50° C. for 1 hr. The mixture was concentrated under reduced pressure to give 4-(2-(azetidin-3-yl)ethyl)morpholin-3-one trifluoroacetate (420 mg, 95.3% yield) as a brown oil, which was directly used in the next step without purification. LC-MS: m/z=185 [M+H]$^+$.

Intermediate 41

(S)-N-(azetidin-2-ylmethyl)-N-ethylethanamine

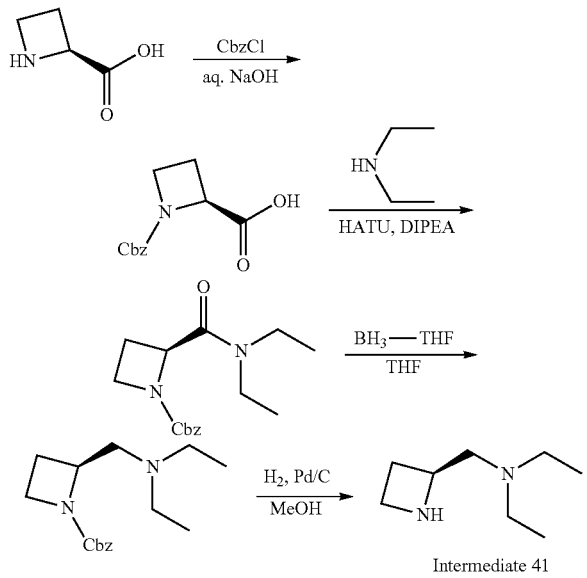

Intermediate 41

Step 1: (S)-1-((benzyloxy)carbonyl)azetidine-2-carboxylic Acid

To a mixture of (S)-azetidine-2-carboxylic acid (1.0 g, 9.89 mmol) in aqueous NaOH solution (2.5 mL, 10 mmol, 4M) was added aqueous sodium hydroxide solution (3.0 mL, 12 mmol, 4 M) drop-wise at 0° C., followed by drop-wise addition of benzyl carbonochloridate (1.53 mL, 10.88 mmol). After the addition was complete, the reaction was stirred at room temperature overnight. The reaction mixture was then washed with diethyl ether (30 mL), and the water layer was acidified with dilute hydrochloric acid (1M). The water layer was then extracted with ethyl acetate (30 mL×3), and the combined ethyl acetate extracts were dried over Na$_2$SO$_4$, filtered and concentrated to give (S)-1-((benzyloxy)carbonyl)azetidine-2-carboxylic acid (2.1 g, 90.2% yield) as a colorless oil. LC-MS: m/z=236 [M+H]$^+$, ee>99% (CHIRALPAK AS-H, 15% ethanol/hexane).

Step 2: (S)-benzyl 2-(diethylcarbamoyl)azetidine-1-carboxylate

To a mixture of (S)-1-((benzyloxy)carbonyl)azetidine-2-carboxylic acid (1.0 g, 4.25 mmol) in DMF (10 mL) was added 2-(7-aza-1H-benzotriazole-1-yl)-1,1,3,3-tetramethyluronium hexafluorophosphate (2.42 g, 6.38 mmol) and ethyldiisopropylamine (2.19 mL, 12.75 mmol) at 0° C. The resulting mixture was stirred for 10 min, and diethylamine (435.3 mg, 5.95 mmol) was added. The reaction was stirred at room temperature overnight, diluted with ethyl acetate (50 mL×3) and washed with water (30 mL) and brine (30 mL). The organic layer was dried over Na$_2$SO$_4$ and concentrated under reduced pressure to give a residue, which was purified by silica gel chromatography (petroleum ether:ethyl acetate=10:1 to 1:1) to give (S)-benzyl 2-(diethylcarbamoyl)azetidine-1-carboxylate (1.04 g, 84.2% yield) as a brown oil. LC-MS: m/z=291 [M+H]$^+$. $^1$H NMR (400 MHz, DMSO) δ 7.32 (m, 5H), 5.00 (m, 3H), 3.90 (m, 3H), 3.26 (m, 4H), 2.55 (m, 1H), 2.01-1.89 (m, 1H), 1.05 (m, 6H)

Step 3: (S)-benzyl 2-((diethylamino)methyl)azetidine-1-carboxylate

To a solution of (S)-benzyl 2-(diethylcarbamoyl)azetidine-1-carboxylate (1.0 g, 3.44 mmol) in THF (anhydrous, 20 mL) was added a solution of borane-tetrahydrofuran complex (9.30 mL, 9.30 mmol, 1M in THF) drop-wise at −10° C. over 30 min. The reaction was stirred at room temperature overnight. The reaction mixture was cooled to 0° C., methanol (10 mL) was added drop-wise, and the resulting mixture was stirred at room temperature for 30 min. The mixture was then concentrated under vacuum to give a yellow reside, which was dissolved in ethanol/water (9 mL/1 mL) and stirred at reflux overnight. The resulting mixture was concentrated under vacuum to give a residue. The residue was purified by silica gel chromatography (DCM:MeOH=100:0 to 60:1) to give (S)-benzyl 2-((diethylamino)methyl)azetidine-1-carboxylate (490 mg, 51.4% yield) as a colorless oil. $^1$H NMR (400 MHz, DMSO) δ 7.53-7.23 (m, 5H), 5.04 (m, 2H), 4.29 (s, 1H), 3.81 (s, 2H), 2.69 (m, 2H), 2.40 (m, 5H), 1.99 (s, 1H), 0.94 (s, 6H); ee=90.5% (AY-H, 15% ethanol/hexane, 0.01 diethylamine).

Step 4: (S)-N-(azetidin-2-ylmethyl)-N-ethylethanamine

To a solution of (S)-benzyl 2-((diethylamino)methyl)azetidine-1-carboxylate (360 mg, 1.30 mmol) in methanol (10 mL) was added three drops of acetic acid. After degassing with N$_2$ three times, Pd/C (36 mg, 10% wt) was added. The resulting mixture was degassed again and stirred at room temperature under a H$_2$ balloon for 4 hrs. The mixture was filtered through Celite. The filtrate was concentrated under reduced pressure to give (S)-N-(azetidin-2-ylmethyl)-N-ethylethanamine (130 mg, 70.1% yield) as a brown oil. LC-MS: m/z=143 [M+H]$^+$. $^1$H NMR (400 MHz, CDCl$_3$) δ 4.22-4.11 (m, 1H), 3.96 (s, 1H), 3.74 (m, 1H), 3.53 (m, 1H), 2.80-2.72 (m, 1H), 2.69-2.51 (m, 5H), 2.40 (m, 1H), 2.14-2.04 (m, 1H), 1.20 (s, 1H), 1.04 (m, 6H).

The following intermediates were prepared according to procedures similar to that described for Intermediate 41 by using the corresponding amines.

| Intermediate # | Structure | LC-MS |
|---|---|---|
| 42 | ![structure] | 141 [M + H]$^+$ |

| Intermediate # | Structure | LC-MS |
|---|---|---|
| 43 | 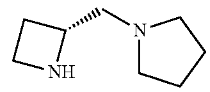 | 141 [M + H]+ |
| 44 | 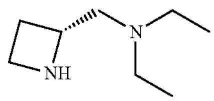 | 143 [M + H]+ |

Intermediate 45

N-ethyl-N-(morpholin-2-ylmethyl)ethanamine, Trifluoroacetate

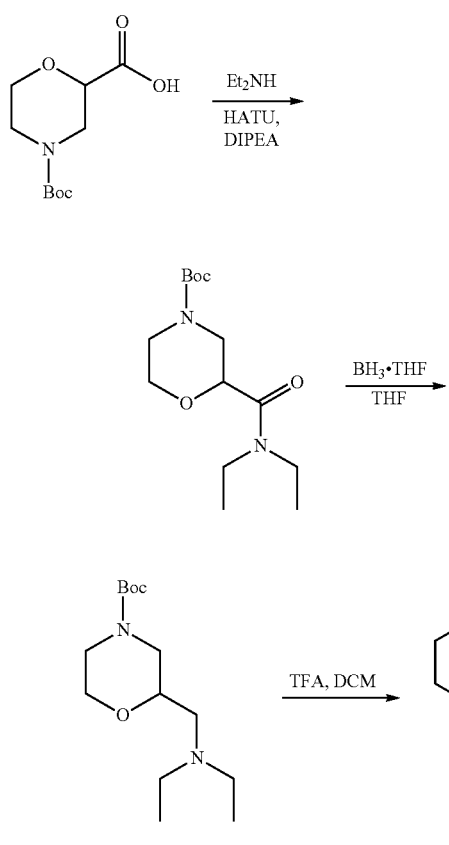

Step 1: tert-butyl 2-(diethylcarbamoyl)morpholine-4-carboxylate

To a solution of 4-(tert-butoxycarbonyl)morpholine-2-carboxylic acid (1.0 g, 4.32 mol) in DMF (10 mL) was added HATU (1.97 g, 5.18 mmol) and DIPEA (1.67 g, 12.96 mmol) at 0° C. The mixture was stirred at 0° C. for 15 min, and diethylamine (442.5 mg, 6.05 mmol) was added. The reaction was stirred at room temperature overnight. The mixture was washed with saturated aqueous lithium chloride solution and brine, dried over anhydrous Na₂SO₄ and concentrated under reduced pressure to give a residue, which was purified by silica gel chromatography (petroleum ether:ethyl acetate=5:1 to 1:1) to give tert-butyl 2-(diethylcarbamoyl)morpholine-4-carboxylate (600 mg, 62.9% yield) as a colorless oil. LC-MS: m/z=287 [M+H]+.

Step 2: tert-butyl 2-((diethylamino)methyl)morpholine-4-carboxylate

To a solution of tert-butyl 2-(diethylcarbamoyl)morpholine-4-carboxylate (600 mg, 2.10 mmol) in THF (anhydrous, 5 mL) was added a solution of borane-tetrahydrofuran complex (7.35 mL, 7.35 mmol, 1M in THF) drop-wise at −10° C. The reaction was stirred at room temperature overnight. The reaction mixture was cooled to 0° C., methanol (5 mL) was added drop-wise, and the resulting mixture was stirred at room temperature for 30 min. The mixture was then concentrated under vacuum to give a yellow reside, which was dissolved in ethanol/water (9 mL/1 mL) and stirred at reflux overnight. The resulting mixture was concentrated under vacuum to give a residue, which was purified by silica gel chromatography (dichloromethane:methanol=200:1 to 50:1) to give tert-butyl 2-((diethylamino)methyl)morpholine-4-carboxylate (250 mg, 43.7% yield) as a colorless oil. LC-MS: m/z=273 [M+H]+.

Step 3: N-ethyl-N-(morpholin-2-ylmethyl)ethanamine, Trifluoroacetate

To a solution of tert-butyl 2-((diethylamino)methyl)morpholine-4-carboxylate (250 mg, 0.92 mmol) in dichloromethane (5 mL) was added TFA (2 mL) drop-wise at 0° C. The mixture was then stirred at room temperature for 2 hrs. The resulting mixture was concentrated under vacuum to give a residue, which was co-evaporated with toluene (5 mL×3) to give N-ethyl-N-(morpholin-2-ylmethyl)ethanamine, trifluoroacetate (310 mg, crude) as a brown oil, which was directly used in the next reaction without purification. LC-MS (ESI) found: 173 [M+H]+.

The following intermediates were prepared according to procedures similar to that described for Intermediate 45 by using 2-(1-(tert-butoxycarbonyl)azetidin-3-yl)acetic acid and 3,3-difluoropyrrolidine as starting materials.

| Intermediate # | Structure | LC-MS |
|---|---|---|
| 46 | 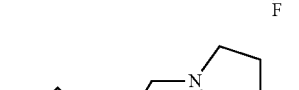 | 191 [M + H]+ |
| 47 | 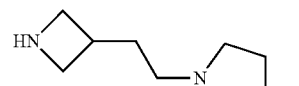 | 171 [M + H]+ |

-continued

| Intermediate # | Structure | LC-MS |
|---|---|---|
| 48 | 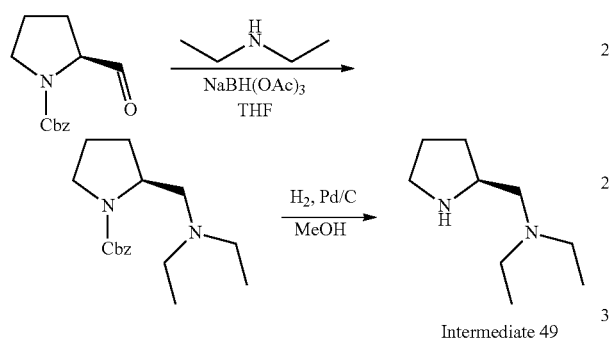 TFA | 171 [M + H]+ |

Intermediate 49

(S)-N-ethyl-N-(pyrrolidin-2-ylmethyl)ethanamine

Step 1: (S)-benzyl 2-((diethylamino)methyl)pyrrolidine-1-carboxylate

To a solution (S)-benzyl 2-formylpyrrolidine-1-carboxylate (600 mg, 2.57 mmol) and diethylamine (281 mg, 3.86 mmol) in THF (10 mL) was added sodium triacetoxyborohydride (1.62 mg, 7.71 mmol) in portions at 0° C. After addition was complete, the mixture was stirred at room temperature overnight. The reaction was quenched with aqueous sodium bicarbonate solution and extracted with ethyl acetate twice. The combined organic layers were washed with brine, dried over Na₂SO₄, filtered and concentrated to give crude product, which was purified by silica gel column (dichloromethane:methanol=100:1 to 50:1) to give (S)-benzyl 2-((diethylamino)methyl)pyrrolidine-1-carboxylate (520 mg, 69.7% yield) as a colorless oil. LC-MS: m/z=291 [M+H]+.

Step 2: (S)-N-ethyl-N-(pyrrolidin-2-ylmethyl)ethanamine

A solution of (S)-benzyl 2-((diethylamino)methyl)pyrrolidine-1-carboxylate (520 mg, 1.79 mmol) in methanol (8 mL) was degassed three times under a N₂ atmosphere and Pd/C (40 mg, 10% wt) was added. The resulting mixture was degassed again and stirred under a H₂ balloon at room temperature overnight. The mixture was filtered, and the filtrate was concentrated to dryness to give (S)-N-ethyl-N-(pyrrolidin-2-ylmethyl)ethanamine (200 mg, 90.8% yield) as a colorless oil. LC-MS: m/z=157 [M+H]+.

Intermediate 50

3-(2-(diethylamino)ethyl)azetidin-3-ol, Trifluoroacetate

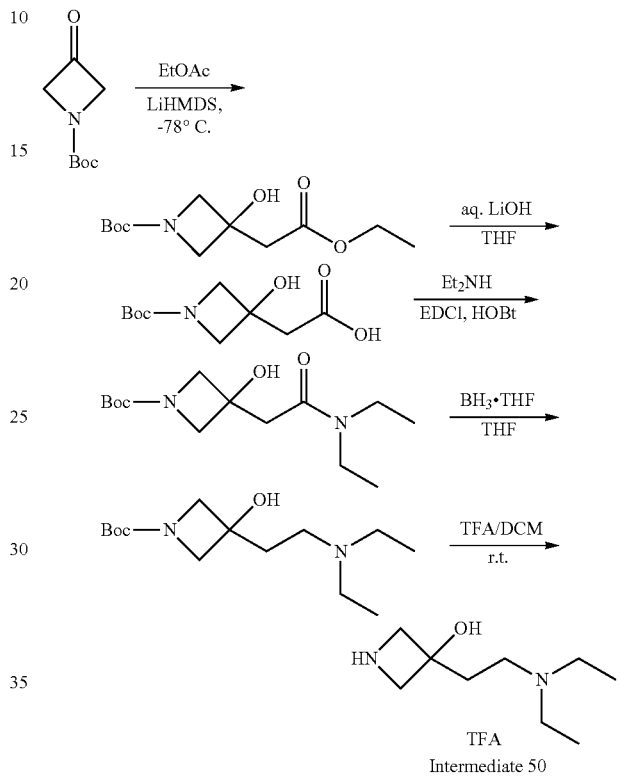

Intermediate 50

Step 1: tert-butyl 3-(2-ethoxy-2-oxoethyl)-3-hydroxyazetidine-1-carboxylate

To a solution of ethyl acetate (2.03 g, 23.12 mmol) in THF (anhydrous, 30 mL) was added lithium bis(trimethylsilyl)amide (17.3 mL, 17.30 mmol) drop-wise at –65° C., and the mixture was stirred at this temperature for 30 min. A solution of tert-butyl 3-oxoazetidine-1-carboxylate (2.00 g, 11.56 mmol) in THF (anhydrous, 10 mL) was added to the above mixture, and the resulting mixture was stirred at –65° C. for 2 hrs and at room temperature for 2 hrs. The reaction quenched with saturated aqueous ammonium chloride solution, diluted with ethyl acetate and washed with brine. The organic layer was dried over Na₂SO₄, filtered and concentrated to give crude product, which was purified by silica gel chromatography (petroleum ether:ethyl acetate=4:1) to give tert-butyl3-(2-ethoxy-2-oxoethyl)-3-hydroxyazetidine-1-carboxylate (1.4 g, 46.8% yield) as a oil. LC-MS: m/z=204 [M+H–56]+.

Step 2: 2-(1-(tert-butoxycarbonyl)-3-hydroxyazetidin-3-yl)acetic acid

To a solution of tert-butyl3-(2-ethoxy-2-oxoethyl)-3-hydroxyazetidine-1-carboxylate (1.4 g, 5.40 mmol) in THF (20 mL) was added aqueous lithium hydroxide solution (8.1 mL, 8.1 mmol) at 0° C. After addition was complete, the reaction was stirred at room temperature for 2 hrs. The mixture was washed with ether and the aqueous layer was acidified by adding 1M dilute hydrochloric acid. The mixture was extracted with chloroform and isopropyl alcohol (3/1) three times. The combined organic layers were dried over Na$_2$SO$_4$, filtered and concentrated to give 2-(1-(tert-butoxycarbonyl)-3-hydroxyazetidin-3-yl)acetic acid (1.1 g, 88.7% yield) as a white solid. LC-MS: m/z=176 [M+H−56]$^+$.

Step 3: tert-butyl 3-(2-(diethylamino)-2-oxoethyl)-3-hydroxyazetidine-1-carboxylate To a solution of 2-(1-(tert-butoxycarbonyl)-3-hydroxyazetidin-3-yl)acetic acid (1.1 g, 4.76 mmol) and diethylamine (416 mg, 5.71 mmol) in dichloromethane (10 mL) was added 1-(3-dimethylaminopropyl)-3-ethylcarbodiimide, hydrochloride (1.09 g, 5.71 mmol) and 1-hydroxybenzotriazole (706 mg, 5.23 mmol) followed by drop-wise addition of ethyldiisopropylamine (920 mg, 7.14 mmol) at 0° C. The reaction was stirred at room temperature. The mixture was diluted with dichloromethane and washed with brine, dried and concentrated to give crude product, which was purified by silica gel chromatography (dichloromethane:methanol=100:1) to give tert-butyl 3-(2-(diethylamino)-2-oxoethyl)-3-hydroxyazetidine-1-carboxylate (920 mg, 72.4% yield) as light yellow oil. LC-MS: m/z=231 [M+H−56]$^+$.

Step 4: tert-butyl 3-(2-(diethylamino)ethyl)-3-hydroxyazetidine-1-carboxylate

To a solution of tert-butyl 3-(2-(diethylamino)-2-oxoethyl)-3-hydroxyazetidine-1-carboxylate (1920 mg, 3.22 mmol) in THF (anhydrous, 10 mL) was added borane-tetrahydrofuran complex (13 mL, 13.00 mmol, 1M) drop-wise at −10° C., and the reaction was stirred at room temperature overnight. The reaction was quenched by drop-wise addition of methanol, and the resulting mixture was concentrated to dryness to give a residue. The residue was dissolved in ethanol/water (9 mL, 8/1 v/v) and stirred at 90° C. for 16 hrs. The mixture was concentrated to dryness and purified by silica gel chromatagraphy (DCM:MeOH=100:1) to give tert-butyl 3-(2-(diethylamino)ethyl)-3-hydroxyazetidine-1-carboxylate (670 mg, 74.2% yield) as light yellow oil. LC-MS: m/z=217 [M+H−56]$^+$.

Step 5: 3-(2-(diethylamino)ethyl)azetidin-3-ol, Trifluoroacetate

To a solution of tert-butyl 3-(2-(diethylamino)ethyl)-3-hydroxyazetidine-1-carboxylate (405 mg, 1.50 mmol) in dichloromethane (6 mL) was added trifluoroacetic acid (2 mL) at 0° C., and the mixture was stirred at room temperature for 1 hr. The mixture was concentrated to dryness and co-evaporated with toluene twice to give 3-(2-(diethylamino)ethyl)azetidin-3-ol, trifluoroacetate (550 mg, 100% yield) as yellow oil, which was used directly in the next reaction without purification. LC-MS: m/z=173 [M+H]$^+$.
Intermediate 51

(R)-N,N-diethyl-2-(pyrrolidin-2-yl)ethanamine

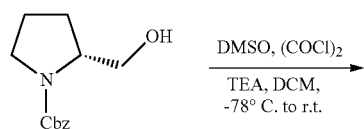

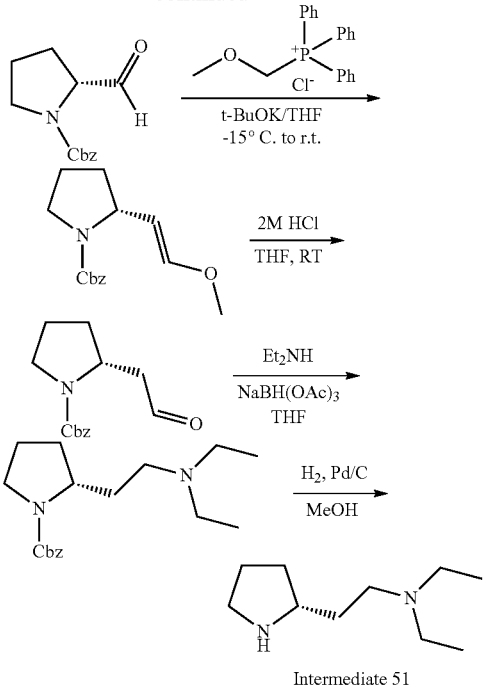

Intermediate 51

Step 1: (R)-benzyl 2-formylpyrrolidine-1-carboxylate

To a solution of (COCl)$_2$ (4.25 mL, 49.57 mmol) in dichloromethane (20 mL) was added a solution of DMSO (7.04 mL, 99.13 mmol) in dichloromethane (20 mL) drop-wise at −78° C. over 1 hr. The mixture was stirred at this temperature for 15 min, and a solution of (R)-benzyl 2-(hydroxymethyl)pyrrolidine-1-carboxylate (8.33 g, 35.40 mmol) in dichloromethane (20 mL) was added drop-wise. The resulting mixture was stirred at −78° C. for 30 min, and a solution of triethylamine (14.27 mL, 102.67 mmol) in dichloromethane (20 mL) was added drop-wise. The reaction mixture was stirred at room temperature for 1 hr and then washed with water (50 mL×2), saturated aqueous sodium bicarbonate (50 mL×2) and brine. The organic layer was dried over Na$_2$SO$_4$ and concentrated under reduced pressure to give a residue, which was purified by silica gel chromatography (petroleum ether:ethyl acetate=20:1 to 1:1) to give (R)-benzyl 2-formylpyrrolidine-1-carboxylate (17.0 g, 84.7% yield) as a brown oil. LC-MS: m/z=234 [M+H]$^+$.
$^1$H NMR (400 MHz, DMSO-d$_6$) δ 9.47 (s, 1H), 7.34 (m, 5H), 5.16-4.98 (m, 2H), 4.33-4.14 (m, 1H), 3.51-3.39 (m, 2H), 2.15-1.64 (m, 4H).

Step 2: (R,E)-benzyl 2-(2-methoxyvinyl)pyrrolidine-1-carboxylate

To a solution of (methoxymethyl)triphenylphosphonium (21.62 g, 63.06 mmol) in THF (anhydrous, 40 mL) was added potassium tert-butanolate (7.08 g, 63.06 mmol) at −15° C. The resulting mixture was stirred at this temperature for 1 hr. Then (R)-benzyl 2-formylpyrrolidine-1-carboxylate (4.9 g, 21.02 mmol) in THF (anhydrous, 20 mL) was added drop-wise. The reaction was stirred at room temperature for 4 hrs. The reaction mixture was then cooled to 0° C., quenched with water, diluted with ethyl acetate (200 mL)

and washed with brine (100 mL). The organic layer was dried over Na$_2$SO$_4$ and concentrated to give (R,E)-benzyl 2-(2-methoxyvinyl)pyrrolidine-1-carboxylate (5.0 g, 90.2% yield) as a brown oil, which was directly used in the next reaction without purification. LC-MS: m/z=262 [M+H]$^+$.

Step 3: (R)-benzyl 2-(2-oxoethyl)pyrrolidine-1-carboxylate

To a solution of (R,E)-benzyl 2-(2-methoxyvinyl)pyrrolidine-1-carboxylate (5.0 g, 19.16 mmol) in THF (anhydrous, 40 mL) was added 2M hydrochloric acid (20 mL), and the reaction was stirred at room temperature for 4 hrs. The reaction mixture was diluted with ethyl acetate (200 mL), and the ethyl acetate solution was washed with brine (100 mL). The organic layer was dried over Na$_2$SO$_4$ and concentrated to give a residue, which was purified by silica gel chromatography (petroleum ether:ethyl acetate=20:1 to 4:1) to give (R)-benzyl 2-(2-oxoethyl)pyrrolidine-1-carboxylate (4.6 g, 84.7% yield) as a brown oil. LC-MS: m/z=248 [M+H]$^+$. $^1$H NMR (400 MHz, CDCl$_3$) δ 9.76 (s, 1H), 7.42-7.30 (m, 5H), 5.14 (m, 2H), 4.34 (s, 1H), 3.46 (m, 2H), 2.53 (m, 1H), 2.16 (m,1H), 1.82 (m, 4H).

Step 4: (R)-benzyl 2-(2-(diethylamino)ethyl)pyrrolidine-1-carboxylate

To a solution of (R)-benzyl 2-(2-oxoethyl)pyrrolidine-1-carboxylate (320 mg, 1.70 mmol) in THF (anhydrous, 10 mL) was added diethylamine (0.26 mL, 2.55 mmol), followed by sodium triacetoxyborohydride (1.08 g, 5.10 mmol) in portions at 0° C. The reaction was stirred at room temperature for 1 hr. The reaction mixture was then quenched with saturated aqueous sodium bicarbonate and diluted with ethyl acetate. The organic layer was washed with brine, dried over Na$_2$SO$_4$ and concentrated to give a residue, which was purified by silica gel chromatography (dichloromethane:methanol=10:0 to 10:1) to give (R)-benzyl 2-(2-(diethylamino)ethyl)pyrrolidine-1-carboxylate (410 mg, 79.3% yield) as a brown oil. LC-MS: m/z=305 [M+H]$^+$. $^1$H NMR (400 MHz, DMSO) δ 7.37 (m, 5H), 5.06 (m, 2H), 3.79 (s, 1H), 3.30-3.22 (m, 1H), 2.33 (m, 6H), 1.87 (m, 4H), 1.65 (s, 1H), 1.45-1.14 (m, 2H), 1.00-0.78 (m, 6H).

Step 5: (R)-N,N-diethyl-2-(pyrrolidin-2-yl)ethanamine

To a solution of (R)-benzyl 2-(2-(diethylamino)ethyl)pyrrolidine-1-carboxylate (380 mg, 1.25 mmol) in degassed methanol (10 mL) was added Pd/C (38 mg, 10% wt) under a N$_2$ atmosphere. The mixture was degassed again and stirred under a H$_2$ balloon for 4 hrs. The mixture was filtered through Celite, and the filtrate was concentrated under reduced pressure to give (R)-N,N-diethyl-2-(pyrrolidin-2-yl)ethanamine (210 mg, 98.8% yield) as a brown oil. LC-MS: m/z=171 [M+H]$^+$.

The following intermediates were prepared according to procedures similar to that described for Intermediate 51 by using the corresponding pyrrolidine isomers.

| Intermediate # | Structure | LC-MS |
| --- | --- | --- |
| 52 | 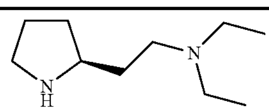 | 171 [M + H]$^+$ |
| 53 |  | 171 [M + H]$^+$ |

Intermediate 54

(R)-N,N-diethyl-2-(pyrrolidin-3-yl)ethanamine Trifluoroacetate

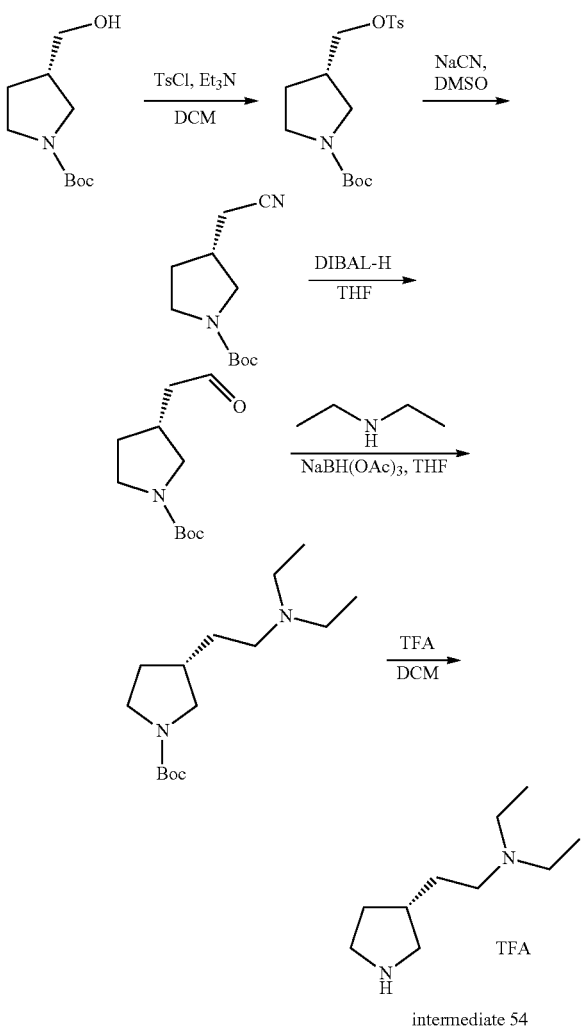

Step 1: tert-butyl (S)-tert-butyl 3-(tosyloxymethyl)pyrrolidine-1-carboxylate To a mixture of (S)-tert-butyl 3-(hydroxymethyl)pyrrolidine-1-carboxylate (3.00 g, 14.9 mmol) and TEA (4.52 g, 44.7 mmol) in DCM (30 mL) was added 4-methylbenzene-1-sulfonyl chloride (4.26 g, 22.4 mmol) under N$_2$ atmosphere. The mixture was stirred at room temperature overnight. The mixture was diluted with DCM and washed with a solution of 1N HCl and saturated aqueous lithium chloride solution and brine successively, dried over Na$_2$SO$_4$ and concentrated under reduced pressure. The residue was purified by silica gel column chromatography (petroleum ether: ethyl acetate=25:1 to 10:1) to give (S)-tert-butyl 3-(tosyloxymethyl)pyrrolidine-1-carboxylate (5.17 g, 97.5% yield) as a colorless oil. LC-MS: m/z=356 [M+H]$^+$.

Step 2: tert-butyl (R)-tert-butyl 3-(cyanomethyl)pyrrolidine-1-carboxylate

To a mixture of (S)-tert-butyl 3-(tosyloxymethyl)pyrrolidine-1-carboxylate (5.17 g, 14.5 mmol) in methylsulfinylmethane (20 mL) was added NaCN (855 mg, 17.5 mmol). The mixture was stirred at 90° C. overnight. The mixture was diluted with EtOAc and washed with saturated aqueous lithium chloride solution and brine successively, dried over Na$_2$SO$_4$ and concentrated under reduced pressure. The residue was purified by silica gel column chromatography (petroleum ether:ethyl acetate=5:1) to give (R)-tert-butyl 3-(cyanomethyl)pyrrolidine-1-carboxylate (2.90 g, 94.8% yield) as a colorless oil. LC-MS: m/z=211 [M+H]$^+$.

Step 3: tert-butyl (R)-tert-butyl 3-(2-oxoethyl)pyrrolidine-1-carboxylate

To a mixture of (R)-tert-butyl 3-(cyanomethyl)pyrrolidine-1-carboxylate (2.30 g, 10.9 mmol) in THF (50 mL) was added dropwise diisobutylaluminum hydride (29.2 mL, 1.5 M) at −65° C. under N$_2$ atmosphere. The mixture was stirred at −65° C. for 2 h. The reaction was quenched by dropwise addition of saturated aqueous ammonium chloride solution and extracted with EtOAc. The combined organic layers were washed with brine, dried over anhydrous Na$_2$SO$_4$ and concentrated under reduced pressure to give (R)-tert-butyl 3-(2-oxoethyl)pyrrolidine-1-carboxylate (1.50 g, 64.4% yield) as a yellow oil. LC-MS: m/z=158 [M+H−56]$^+$.

Step 4: tert-butyl (S)-tert-butyl 3-(2-(diethylamino)ethyl)pyrrolidine-1-carboxylate To a mixture of (R)-tert-butyl 3-(2-oxoethyl)pyrrolidine-1-carboxylate (0.90 g, 4.22 mmol) and diethylamine (463 mg, 6.33 mmol) in THF (20 mL) was added NaBH(OAc)$_3$ (1.79 g, 8.44 mmol). The mixture was stirred at room temperature for 3 h. The mixture was diluted with ethyl acetate and washed with saturated aqueous lithium chloride solution and brine successively, dried over Na$_2$SO$_4$ and concentrated under reduced pressure. The residue was purified by silica gel column chromatography (dichloromethane:methanol=100:1 to 20:1) to give (S)-tert-butyl 3-(2-(diethylamino)ethyl)pyrrolidine-1-carboxylate (423 mg, 37.1% yield) as a colorless oil. LC-MS: m/z 271=[M+H]$^+$.

Step 5: tert-butyl (R)-N,N-diethyl-2-(pyrrolidin-3-yl)ethanamine Trifluoroacetate To a mixture of (S)-tert-butyl 3-(2-(diethylamino)ethyl)pyrrolidine-1-carboxylate (420 mg, 1.55 mmol) in DCM (10 mL) was added TFA (886 mg, 7.77 mmol) dropwise at 0° C. The resulting mixture was stirred room temperature for 2 hrs. The mixture was concentrated under reduced pressure to give (R)-N,N-diethyl-2-(pyrrolidin-3-yl)ethanamine trifluoroacetate (356 mg, 80.7% yield) as a yellow oil, which was directly used to the next reaction without purification. LC-MS: m/z=171 [M+H]$^+$.

The following intermediates were prepared according to procedures similar to that described for Intermediate 54 by using the corresponding amines.

| Intermediate # | Structure | LC-MS |
|---|---|---|
| 55 | 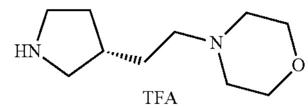 [SMILES: C1C[C@H](CCN2CCOCC2)CN1] | 185 [M + H]$^+$ |
| 56 | 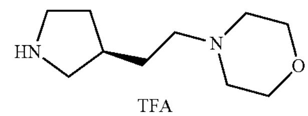 [SMILES: C1C[C@@H](CCN2CCOCC2)CN1] | 185 [M + H]$^+$ |
| 57 | 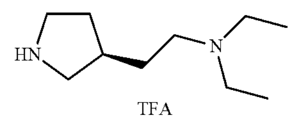 | 171 [M + H]$^+$ |

Intermediate 58

(R)-3-(2-(3,3-difluoroazetidin-1-yl)ethyl)pyrrolidine Trifluoroacetate

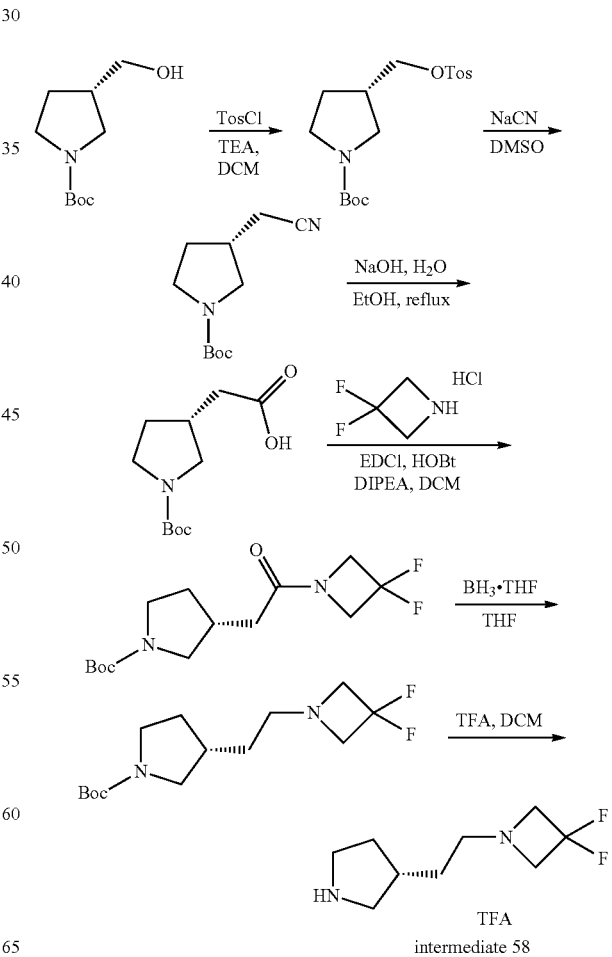

intermediate 58

Step 1: (S)-tert-butyl 3-(tosyloxymethyl)pyrrolidine-1-carboxylate

To a solution of (R)-tert-butyl 3-(hydroxymethyl)pyrrolidine-1-carboxylate (2.0 g, 9.94 mmol) in DCM (50 mL) was added TEA (3.01 g, 29.82 mmol) and 4-methylbenzene-1-sulfonyl chloride (2.84 g, 14.91 mmol) in portions at 0° C. The reaction was stirred at room temperature overnight. The mixture was poured into the ice water and extracted with EtOAc (100 mL×2). The organic layers were dried over Na$_2$SO$_4$, filtered and concentrated. The residue was purified by silica gel column chromatography (petroleum ether:ethyl acetate=100:1 to 4:1) to give (S)-tert-butyl 3-(tosyloxymethyl)pyrrolidine-1-carboxylate (3.3 g, 93.43% yield) as a white solid. LC-MS: m/z=300 [M+H−56]$^+$.

Step 2: (S)-tert-butyl 3-(cyanomethyl)pyrrolidine-1-carboxylate

To a solution of (S)-tert-butyl 3-(tosyloxymethyl)pyrrolidine-1-carboxylate (3.0 g, 8.44 mmol) in DMSO (40 mL) was added NaCN (596 mg, 10.13 mmol) at 100° C. overnight. TLC showed the reaction was completed. The mixture was poured into the ice water and extracted with ethyl acetate (100 mL×2). The organic layers were dried over Na$_2$SO$_4$, filtered and concentrated. The residue was purified by silica gel column chromatography (petroleum ether:ethyl acetate=100:1 to 4:1) to give (R)-tert-butyl 3-(cyanomethyl)pyrrolidine-1-carboxylate (1.6 g, 90.16% yield) as a white solid. LC-MS: m/z 155=[M+H−56]$^+$.

Step 3: (R)-2-(1-(tert-butoxycarbonyl)pyrrolidin-3-yl)acetic acid

To a solution of (R)-tert-butyl 3-(cyanomethyl)pyrrolidine-1-carboxylate (1.6 g, 8.44 mmol) in MeOH (40 mL) was added NaOH solution (30%, 7.6 mL, 10.13 mmol). After the resulting mixture was stirred at 100° C. overnight, solvent was removed. The residue was acidified with aqueous HCl (1 M) to pH 4-5 and extracted with ethyl acetate (100 mL×2). The organic layers were dried over anhydrous Na$_2$SO$_4$, filtered and concentrated. The residue was purified by silica gel column chromatography (petroleum ether:ethyl acetate=100:1~1:1) to give (R)-2-(1-(tert-butoxycarbonyl)pyrrolidin-3-yl)acetic acid (1.6 g, 90.16% yield) as a white solid. LC-MS: m/z=174 [M+H−56]$^+$.

Step 4: (R)-tert-butyl 3-(2-(3,3-difluoroazetidin-1-yl)-2-oxoethyl)pyrrolidine-1-carboxylate To a mixture of (R)-2-(1-(tert-butoxycarbonyl)pyrrolidin-3-yl)acetic acid (690 mg, 3.01 mmol) in dichloromethane (40 mL) was sequentially added 1-(3-dimethylaminopropyl)-3-ethylcarbodiimide hydrochloride (693.3 mg, 3.63 mmol) and 1-hydroxybenzotriazole (593.43 mg, 4.53 mmol), and then DIPEA (1.55 g, 12.04 mmol) was added drop-wise. The mixture was stirred for 10 min and 3,3-difluoroazetidine hydrochloride (464.4 g, 3.6 mmol) was added. The reaction was stirred at room temperature overnight. The reaction was diluted with dichloromethane (50 mL×2) and washed with water (50 mL), brine (50 mL), dried over anhydrous Na$_2$SO$_4$ and concentrated under reduced pressure to give a residue. The residue was purified by silica gel column chromatography (dichloromethane:methanol=100:1 to 50:1 to give (R)-tert-butyl 3-(2-(3,3-difluoroazetidin-1-yl)-2-oxoethyl)pyrrolidine-1-carboxylate (630 mg, 68.79% yield) as a colorless oil. LC-MS: m/z=249 [M+H−56]$^+$.

Step 5: (S)-tert-butyl 3-(2-(3,3-difluoroazetidin-1-yl)ethyl)pyrrolidine-1-carboxylate To a solution of (R)-tert-butyl 3-(2-(3,3-difluoroazetidin-1-yl)-2-oxoethyl)pyrrolidine-1-carboxylate (630 mg, 2.07 mmol) in THF (anhydrous, 50 mL) was added a solution of borane-tetrahydrofuran complex (6.21 mL, 6.21 mmol, 1M in THF) drop-wise at −10° C. over 10 min. The reaction was stirred at room temperature overnight. To the reaction mixture was then added methanol (20 mL) drop-wise at 0° C. After addition was complete, the mixture was stirred at room temperature for 30 min. The mixture was concentrated under vacuum to give a yellow reside, which was dissolved in ethanol/water (9 mL/1 mL) and stirred at reflux overnight. The mixture was concentrated and the residue was purified by silica gel column chromatography (dichloromethane:methanol=100:1 to 40:1) to give (S)-tert-butyl 3-(2-(3,3-difluoroazetidin-1-yl)ethyl)pyrrolidine-1-carboxylate (470 mg, 78.20% yield) as a colorless oil. LC-MS: m/z=235 [M+H−56]$^+$.

Step 6: (R)-3-(2-(3,3-difluoroazetidin-1-yl)ethyl)pyrrolidine trifluoroacetete To a mixture of (S)-tert-butyl 3-(2-(3,3-difluoroazetidin-1-yl)ethyl)pyrrolidine-1-carboxylate (470 mg, 1.62 mmol) in dichloromethane (5 mL) was added trifluoroacetic acid (2.0 mL) drop-wise at 0° C. The reaction was stirred room temperature for 1 hr. The mixture was concentrated under reduced pressure to give (R)-3-(2-(3,3-difluoroazetidin-1-yl)ethyl)pyrrolidine trifluoroacetate (400 mg, 97.1% yield) as a yellow syrup, which was directly used to the next reaction without purification. LC-MS: m/z=191 [M+H]$^+$.

The following intermediates were prepared according to procedures similar to that described for Intermediate 58 by using the corresponding starting materials.

| Intermediate # | Structure | LC-MS |
|---|---|---|
| 59 | 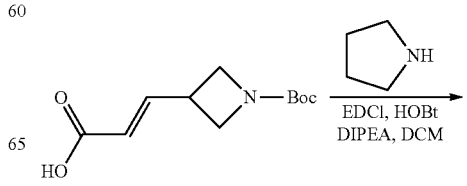 TFA | 191 [M + H]$^+$ |

Intermediate 60

1-(3-(azetidin-3-yl)propyl)pyrrolidine, Trifluoroacetate

-continued

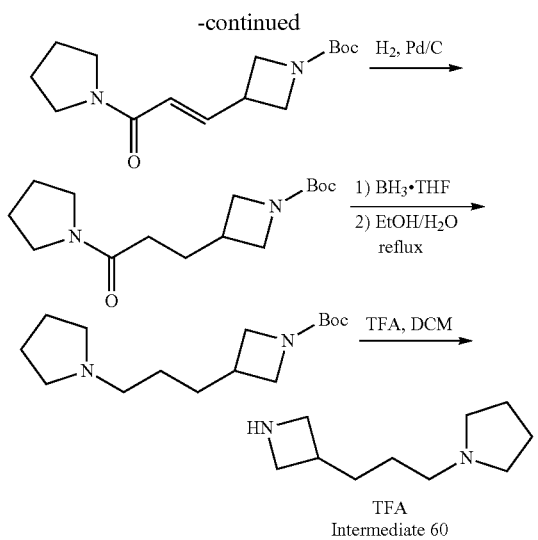

TFA
Intermediate 60

Step 1: (E)-tert-butyl 3-(3-oxo-3-(pyrrolidin-1-yl) prop-1-en-1-yl)azetidine-1-carboxylate To a solution of (E)-3-(1-(tert-butoxycarbonyl)azetidin-3-yl)acrylic acid (1 g, 4.41 mol) in dichloromethane was added DIPEA (3.0 mL, 17.46 mmol) and HOBt (720 mg, 5.29 mmol), followed by addition of EDCI (1.27 g, 6.62 mmol) in portions at 0° C. The reaction was stirred at room temperature for 15 min, and pyrrolidine (0.6 mL, 6.62 mmol) was added. The reaction was stirred at room temperature overnight. The mixture was diluted with dichloromethane, and washed with water and brine. The organic layer was dried over anhydrous $Na_2SO_4$ and concentrated under reduced pressure to give a residue, which was purified by silica gel chromatography (dichloromethane:methanol=100:1 to 10:1) to give (E)-tert-butyl 3-(3-oxo-3-(pyrrolidin-1-yl)prop-1-en-1-yl)azetidine-1-carboxylate (900 mg, 73.1% yield) as a oil. LC-MS: m/z=225 [M+H]$^+$.

Step 2: tert-butyl 3-(3-oxo-3-(pyrrolidin-1-yl)propyl)azetidine-1-carboxylate

A solution of (E)-tert-butyl 3-(3-oxo-3-(pyrrolidin-1-yl)prop-1-en-1-yl)azetidine-1-carboxylate (900 mg, 3.21 mmol) in methanol (10 mL) was degassed three times under a $N_2$ atmosphere, then Pd/C (50 mg, 10% wt) was added. After addition was complete, the mixture was degassed again and stirred under a $H_2$ balloon at room temperature overnight. The resulting mixture was filtered through a pad of Celite, and the filtrate was concentrated under vacuum to give tert-butyl 3-(3-oxo-3-(pyrrolidin-1-yl)propyl)azetidine-1-carboxylate (870 mg, 95.9% yield) as a colorless oil. LC-MS: m/z=227 [M+H−56]$^+$.

Step 3: tert-butyl 3-(3-(pyrrolidin-1-yl)propyl)azetidine-1-carboxylate

To a solution of tert-butyl 3-(3-oxo-3-(pyrrolidin-1-yl)propyl)azetidine-1-carboxylate (890 mg, 3.15 mmol) in THF (anhydrous, 8 mL) was added a solution of borane-tetrahydrofuran complex (8.6 mL, 8.6 mmol, 1M in THF) drop-wise at −10° C. The reaction was stirred at room temperature overnight. The reaction mixture was cooled to 0° C., methanol (10 mL) was added drop-wise, and the resulting mixture was stirred at room temperature for 30 min. The mixture was then concentrated under vacuum to give a yellow reside, which was dissolved in ethanol/water (18 mL/2 mL) and stirred at reflux overnight. The resulting mixture was concentrated under vacuum to give a residue, which was purified by silica gel chromatography (dichloromethane:methanol=100:1 to 20:1) to provide tert-butyl 3-(3-(pyrrolidin-1-yl)propyl)azetidine-1-carboxylate (600 mg, 70.9% yield) as a colorless oil. LC-MS: m/z=213 [M+H−56]$^+$.

Step 4: 1-(3-(azetidin-3-yl)propyl)pyrrolidine, Trifluoroacetate

To a solution of tert-butyl 3-(3-(pyrrolidin-1-yl)propyl)azetidine-1-carboxylate (600 mg, 2.23 mmol) in dichloromethane (20 mL) was added TFA (5 mL) drop-wise at 0° C. The reaction was then stirred at 30° C. for 1 hr. The resulting mixture was concentrated under vacuum to give a residue, which was co-evaporated with toluene (10 mL×3) to give 1-(3-(azetidin-3-yl)propyl)pyrrolidine, trifluoroacetate (700 mg, 100% yield) as a brown oil, which was used directly in the next reaction without purification. LC-MS (ESI) found: 169 [M+H]$^+$.

Intermediate 61

(R)-N-ethyl-N-(pyrrolidin-2-ylmethyl)ethanamine, hydrochloride

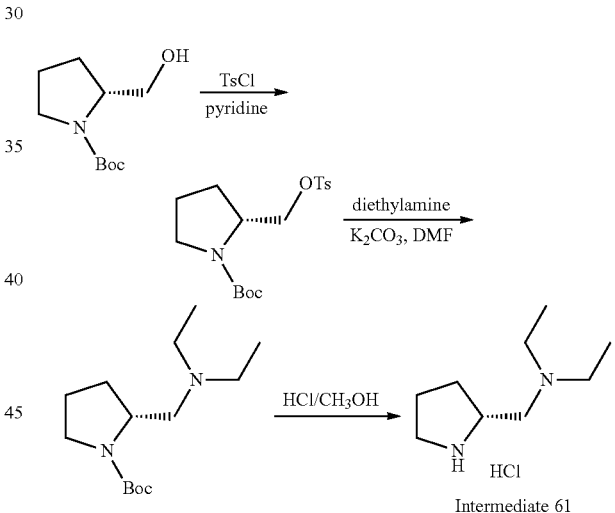

Intermediate 61

Step 1: (R)-tert-butyl 2-((tosyloxy)methyl)pyrrolidine-1-carboxylate

To a solution of (R)-tert-butyl 2-(hydroxymethyl)pyrrolidine-1-carboxylate (5.00 g, 24.8 mmol) in pyridine (20 mL) was added 4-methylbenzene-1-sulfonyl chloride (5.68 g, 29.8 mmol) in portions at 0° C. under a $N_2$ atmosphere. The mixture was stirred at room temperature overnight. The mixture was concentrated to dryness, and the residue was dissolved in ethyl acetate (100 mL). The mixture was washed with brine, dried over $Na_2SO_4$, filtered and concentrated to give crude product, which was purified by silica gel chromatography (petroleum ether/ethyl acetate=10:1-3:1) to give (R)-tert-butyl 2-((tosyloxy)methyl)pyrrolidine-1-carboxylate (7.50 g, 85.2% yield) as a colorless oil. LC-MS: m/z=356 [M+H]$^+$.

Step 2: (R)-tert-butyl 2-((diethylamino)methyl)pyrrolidine-1-carboxylate

To a solution of (R)-tert-butyl 2-((tosyloxy)methyl)pyrrolidine-1-carboxylate (3.00 g, 8.40 mmol) in CH₃CN (30 mL) was added diethylamine (1.20 g, 16.8 mmol) and potassium carbonate (3.50 g, 25.2 mmol). The mixture was stirred at 75° C. for 16 hrs. The mixture was diluted with ethyl acetate and water, and the layers were separated. The organic layer was washed with saturated aqueous lithium chloride solution and brine successively, dried over Na₂SO₄, filtered and concentrated to give crude product, which was purified by silica gel chromatography (dichloromethane:methanol=10:1) to give (R)-tert-butyl 2-((diethylamino)methyl)pyrrolidine-1-carboxylate (390 mg, 18.1% yield) as a yellow oil. LC-MS: m/z=201 [M+H−56]⁺.

Step 3: (R)-N-ethyl-N-(pyrrolidin-2-ylmethyl)ethanamine, hydrochloride

A mixture of (R)-tert-butyl 2-((diethylamino)methyl)pyrrolidine-1-carboxylate (370 mg, 1.44 mmol) in HCl-methanol solution (3 mL) was stirred at room temperature for 1 hr. The mixture was concentrated to dryness and washed with diethyl ether to give (R)-N-ethyl-N-(pyrrolidin-2-ylmethyl)ethanamine, hydrochloride (318 mg, quant. yield) as a white solid. The crude product was used in next step without further purification. LC-MS: m/z=157 [M+H]⁺.

Intermediate 62

3-(3-(diethylamino)propyl)azetidin-3-ol, Trifluoroacetate

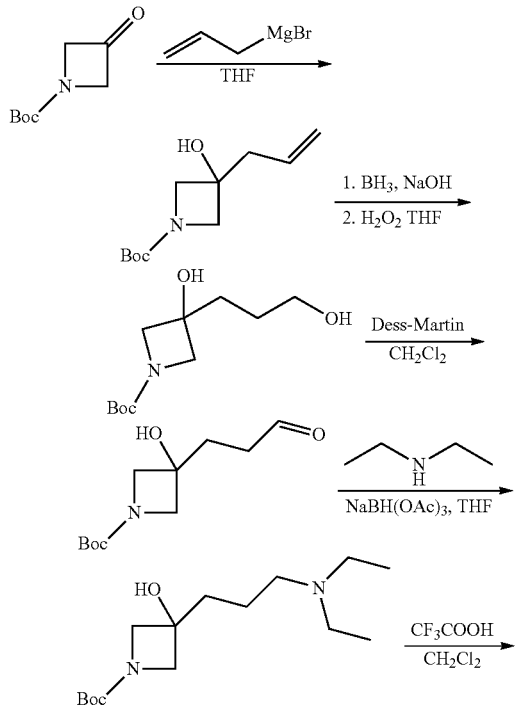

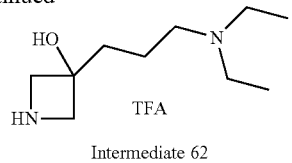

Intermediate 62

Step 1: tert-butyl 3-allyl-3-hydroxyazetidine-1-carboxylate

To a solution of tert-butyl 3-oxoazetidine-1-carboxylate (1.00 g, 5.84 mmol) in dry THF (10 mL) was added allylmagnesium bromide (7.6 mL, 1M) drop-wise at 0° C. under a N₂ atmosphere. The mixture was stirred at room temperature for 2 hrs, then quenched with saturated aqueous ammonium chloride solution and extracted with ethyl acetate twice. The combined organic layers were washed with brine, dried over Na₂SO₄ and concentrated under reduced pressure to give a residue, which was purified by silica gel chromatography (petroleum ether:ethyl acetate=10:1 to 3:1) to give (S)-tert-butyl 2-((((allyloxy)carbonyl)(ethyl)amino)methyl)azetidine-1-carboxylate (1.02 g, 81.6% yield) as a colorless oil. LC-MS: m/z=188 [M+H−56]⁺.

Step 2: tert-butyl 3-hydroxy-3-(3-hydroxypropyl)azetidine-1-carboxylate

To a mixture of tert-butyl 3-allyl-3-hydroxyazetidine-1-carboxylate (1.02 g, 4.78 mmol) in dry THF (50 mL) was added drop-wise a solution of borane-tetrahydrofuran complex in THF (4.78 mL, 1 M) at 0° C. under a N₂ atmosphere. The reaction was stirred at room temperature overnight. Aqueous sodium hydroxide solution (19.1 mL, 95.6 mmol, 5M) was added drop wise to the mixture at 0° C. The mixture was stirred for 30 min at room temperature. Hydrogen peroxide solution (10 mL, 30% wt) was then added to the mixture, and the reaction was stirred at room temperature for 2 hrs. The mixture was diluted with ethyl acetate and washed with water and brine, dried over Na₂SO₄ and concentrated under reduced pressure to give a residue, which was purified by silica gel chromatography (petroleum ether:ethyl acetate=3:1 to 1:1) to give tert-butyl 3-hydroxy-3-(3-hydroxypropyl)azetidine-1-carboxylate (690 mg, 62.7% yield) as a colorless oil. LC-MS: m/z=176 [M+H−56]⁺.

Step 3: tert-butyl 3-hydroxy-3-(3-oxopropyl)azetidine-1-carboxylate

To a mixture of tert-butyl 3-hydroxy-3-(3-hydroxypropyl)azetidine-1-carboxylate (0.50 g, 2.15 mmol) in dry CH₂Cl₂ (20 mL) was added (1,1,1-triacetoxy)-1,1-dihydro-1,2-benziodoxol-3(1H)-one (293 mg, 0.69 mmol) at 0° C. The mixture was stirred at room temperature overnight. The mixture was filtered, and the filtrate was washed with saturated aqueous sodium bicarbonate solution and brine, dried and concentrated under reduced pressure to give tert-butyl 3-hydroxy-3-(3-oxopropyl)azetidine-1-carboxylate (0.55 g, >100%), which was used in next step without further purification. LC-MS: m/z=282 [M+H]⁺.

Step 4: tert-butyl 3-(3-(diethylamino)propyl)-3-hydroxyazetidine-1-carboxylate To a mixture of tert-butyl 3-hydroxy-3-(3-oxopropyl)azetidine-1-carboxylate (0.49 g, 2.15 mmol) in THF (20 mL)

was added diethylamine (235 mg, 2.23 mmol) at 0° C. The mixture was stirred at room temperature 1 hr. Sodium triacetoxyborohydride (906 mg, 4.30 mmol) was added to the mixture in portions at 0° C. The mixture was stirred at room temperature overnight. The mixture was diluted with ethyl acetate and washed with saturated aqueous lithium chloride solution and brine successively, dried over Na$_2$SO$_4$ and concentrated under reduced pressure to give a residue, which was purified by silica gel chromatography (dichloromethane:methanol=50:0 to 20:1) to give tert-butyl 3-(3-(diethylamino)propyl)-3-hydroxyazetidine-1-carboxylate (450 mg, 73.2% yield) as a colorless oil. LC-MS: m/z=287 [M+H]$^+$.

Step 5: 3-(3-(diethylamino)propyl)azetidin-3-ol, Trifluoroacetate

To a solution of tert-butyl 3-(3-(diethylamino)propyl)-3-hydroxyazetidine-1-carboxylate (450 mg, 1.57 mmol) in dichloromethane (10 mL) was added trifluoroacetic acid (10 mL) drop-wise at 0° C. The reaction was stirred room temperature for 2 hrs. The mixture was concentrated under reduced pressure to give 3-(3-(diethylamino)propyl)azetidin-3-ol, trifluoroacetate (440 mg, >100% yield) as a brown oil, which was directly used in the next reaction without purification. LC-MS: m/z=186 [M+H]$^+$.
Intermediate 63

2-(azetidin-3-yl)-1-morpholinoethanone, Trifluoroacetate

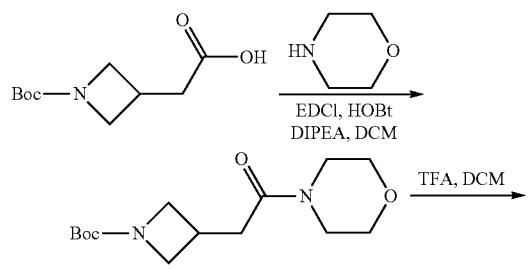

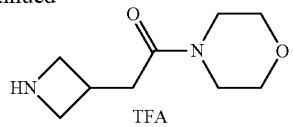

Intermediate 63

Step 1: tert-butyl 3-(2-morpholino-2-oxoethyl)azetidine-1-carboxylate

To a solution of 2-(1-(tert-butoxycarbonyl)azetidin-3-yl) acetic acid (500 mg, 2.32 mmol) in dichloromethane (10 mL) was added 1-(3-dimethylaminopropyl)-3-ethylcarbodiimide, hydrochloride (667.9 mg, 3.48 mmol), 1-hydroxybenzotriazole (376.6 mg, 2.79 mmol) and diisopropylethylamine (1.20 mL, 6.97 mmol) at 0° C. After the mixture was stirred for 10 min, morpholine (0.30 mL, 3.48 mmol) was added. The resulting mixture was stirred at room temperature for 3 hrs. The residue was diluted with dichloromethane, washed with water and brine, dried over anhydrous Na$_2$SO$_4$ and concentrated under reduced pressure. The residue was purified by silica gel chromatography (dichloromethane:methanol=1:0 to 80:1) to give tert-butyl 3-(2-morpholino-2-oxoethyl)azetidine-1-carboxylate (560 mg, 84.7% yield) as a colorless oil. LC-MS: m/z=229 [M+H–56]$^+$.

Step 2: 2-(azetidin-3-yl)-1-morpholinoethanone

To a solution of tert-butyl 3-(2-morpholino-2-oxoethyl)azetidine-1-carboxylate (560 mg, 1.97 mmol) in dichloromethane (3 mL) was added trifluoroacetic acid (1.46 mL, 19.69 mmol). The reaction was stirred at room temperature for 2 hrs. The mixture was concentrated under reduced pressure to give 2-(azetidin-3-yl)-1-morpholinoethanone, trifluoroacetate (360 mg, 99.2% yield) as a brown oil. LC-MS: m/z=185 [M+H]$^+$.

The following intermediates were prepared according to procedures similar to that described for Intermediate 63 by using appropriate starting materials.

| Intermediate # | Structure | LC-MS |
|---|---|---|
| 64 | 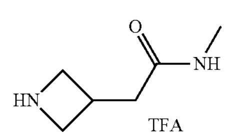 | 129 [M + H]$^+$ |
| 65 | 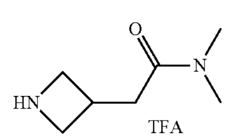 | 143 [M + H]$^+$ |
| 66 | 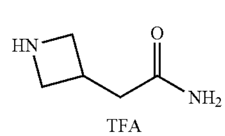 | 115 [M + H]$^+$ |

| Intermediate # | Structure | LC-MS |
|---|---|---|
| 67 | ![structure] HN-azetidine-CH2-C(=O)-NH-CH2CH2-N(Et)2 · TFA | 214 [M + H]+ |
| 68 | TFA · HN-azetidine-CH2CH2-C(=O)-NH-CH2CH2-N(morpholine) | 242 [M + H]+ |

Intermediate 69 azetidin-3-ylmethyl (2-(diethylamino)ethyl)carbamate, Trifluoroacetate

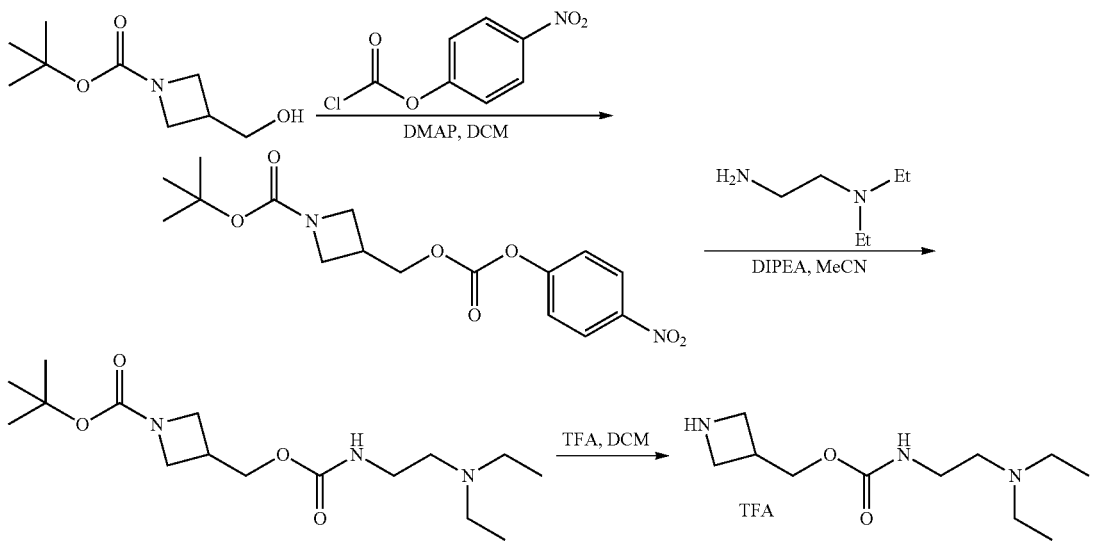

Intermediate 69

Step 1: tert-butyl 3-((((4-nitrophenoxy)carbonyl)oxy)methyl)azetidine-1-carboxylate To a solution of tert-butyl 3-(hydroxymethyl)azetidine-1-carboxylate (1.12g, 6.1 mmol) and DMAP (1.46 g, 12.1 mmol) in anhydrous dichloromethane (20 ml) was added a solution of 4-nitrophenyl chloroformate (2.05 g, 10.2 mmol) in dichloromethane (10 mL) at 0° C. The reaction mixture was allowed to warm to room temperature and stirred overnight. The reaction mixture was washed with aqueous citric acid (10% wt.), and the organic layer was dried over anhydrous $Na_2SO_4$, filtered and concentrated. The residue was purified by silica gel chromatography (petroleum ether: ethyl acetate=15:1 to 8:1) to give tert-butyl 3-((((4-nitrophenoxy)carbonyl)oxy)methyl)azetidine-1-carboxylate (1.51 g, 76.3% yield) as a white solid.

Step 2: tert-butyl 3-((((2-(diethylamino)ethyl)carbamoyl)oxy)methyl)azetidine-1-carboxylate To a solution of N1,N1-diethylethane-1,2-diamine (560 mg, 4.05 mmol) and DIPEA (510 mg, 4.0 mmol) in $CH_3CN$ (8 mL) was added tert-butyl 3-((((4-nitrophenoxy)carbonyl)oxy)methyl)azetidine-1-carboxylate (660 mg, 2.1 mmol) in portions at 0° C. The reaction mixture was allowed to warm to room temperature and was stirred at room temperature for 2 hrs. The solvent was removed under vacuum, and the residue was partitioned with water and ethyl acetate. The aqueous layer was extracted with ethyl acetate. The combined organic layers were dried over anhydrous $Na_2SO_4$ and concentrated. The residue was purified by silica gel chromatography (dichloromethane:methanol=100:0 to 40:1) to give tert-butyl 3-((((2-(diethylamino)ethyl)carbamoyl)oxy)methyl)azetidine-1-carboxylate (520 mg, 78.7% yield) as a light yellow oil LC-MS: m/z=331[M+H]+.

Step 3: azetidin-3-ylmethyl 2-(diethylamino)ethylcarbamate, Trifluoroacetate To a solution of tert-butyl 3-((((2-(diethylamino)ethyl)carbamoyl)oxy)methyl)azetidine-1-carboxylate (510 mg, 1.5 mmol) in dichloromethane (5 mL) was added TFA (1.5 mL) drop-wise at 0° C. The reaction was then stirred at room temperature for 3 hrs. The resulting mixture was concentrated under vacuum to give a residue, which was co-evaporated with toluene (40 mL×3) to give azetidin-3-ylmethyl (2-(diethylamino)ethyl)carbamate, trifluoroacetate (1.05 g, 100% yield) as a brown oil, which was directly used in the next step without purification. LC-MS: m/z=231 [M+H]$^+$.

The following intermediates were prepared according to procedures similar to that described for Intermediate 69 by using the appropriate amines

| Intermediate # | Structure | LC-MS |
|---|---|---|
| 70 | TFA / HN-azetidine-CH2-O-C(O)-NH-CH3 | 144 [M + H]$^+$ |
| 71 | TFA / HN-azetidine-CH2-O-C(O)-N(CH3)2 | 159 [M + H]$^+$ |

Intermediate 72 azetidin-3-yl morpholine-4-carboxylate Trifluoroacetate

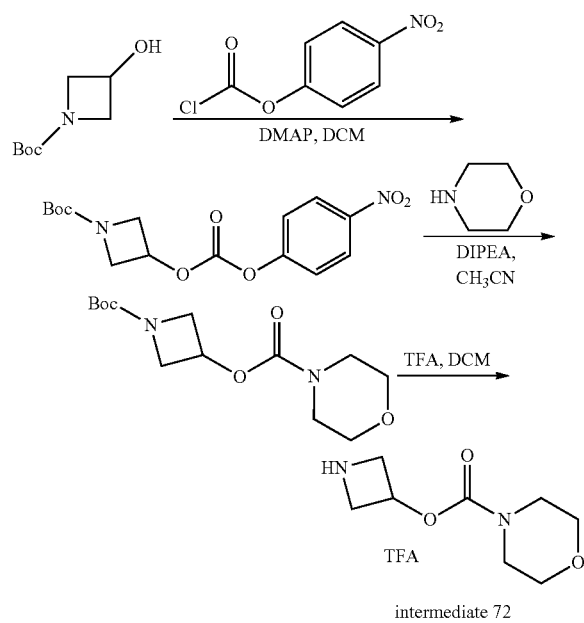

intermediate 72

Step 1: tert-butyl 3-((4-nitrophenoxy)carbonyloxy) azetidine-1-carboxylate

To a stirred solution of tert-butyl 3-hydroxyazetidine-1-carboxylate (0.8 g, 4.62 mmol) and DMAP (1.13 g, 9.24 mmol) in anhydrous DCM (10 mL) was added a solution of 4-nitrophenyl chloroformate (1.58 g, 7.85 mmol) in DCM (5 ml) dropwise at 0° C. The reaction was stirred at room temperature overnight. The mixture was diluted with DCM and washed sequentially with 10% aqueous citric acid solution, saturated aqueous K$_2$CO$_3$ solution and brine. The organic layer was dried over anhydrous Na$_2$SO$_4$ and concentrated. The residue was purified by silica gel column chromatography (petroleum ether:ethyl acetate=50:1 to 20:1) to give tert-butyl 3-((4-nitrophenoxy)carbonyloxy) azetidine-1-carboxylate (1.17 g, 74.9% yield) as a white solid. LC-MS m/z: 324 [M+H−14]$^+$.

Step 2: 1-(tert-butoxycarbonyl)azetidin-3-yl morpholine-4-carboxylate

To a solution of tert-butyl 3-((4-nitrophenoxy)carbonyloxy)azetidine-1-carboxylate (1.17 g, 3.46 mmol) in MeCN (15 mL) was added DIPEA (1.2 mL, 6.92 mmol) and morpholine (0.6 mL, 6.92 mmol) at 0° C. The resulting mixture was stirred at room temperature overnight. The mixture was then concentrated, diluted with DCM, The mixture was then concentrated under vacuum to remove the solvent while keeping the temperature below 40° C. The residue was diluted with DCM and washed with ammonium acetate buffer (pH 4.0, 20 mL×2), 5% aqueous NaHCO$_3$ solution (20 mL) and brine. The organic layer was dried over anhydrous Na$_2$SO$_4$, filtered and concentrated. The residue was purified by silica gel column chromatography (petroleum ether:ethyl acetate=50:1 to 20:1) to give 1-(tert-butoxycarbonyl)azetidin-3-yl morpholine-4-carboxylate (600 mg, 60.6% yield) as a white solid. LC-MS m/z: 231 [M+H−56]$^+$.

Step 3: azetidin-3-yl morpholine-4-carboxylate Trifluoroacetate

To a solution of 1-(tert-butoxycarbonyl)azetidin-3-yl morpholine-4-carboxylate (400 mg, 1.40 mmol) in DCM (4 mL) was added TFA (2 mL) dropwise at 0° C. The reaction was then stirred at room temperature for 1 hr. The resulting mixture was concentrated under vacuum to give a residue, which was co-evaporated with toluene (1 mL×2) to give azetidin-3-yl morpholine-4-carboxylate trifluoroacetate (600 mg, 100% yield) as a brown oil, which was directly used to the next reaction without purification. LC-MS m/z: 187 [M+H]$^+$.

The following intermediates were prepared according to procedures similar to that described for Intermediate 72 by using the appropriate amines

| Intermediate # | Structure | LC-MS |
|---|---|---|
| 73 | TFA / HN-azetidine-O-C(O)-NH2 | 117 [M + H]$^+$ |
| 74 | TFA / HN-azetidine-O-C(O)-NH-CH2CH2-N(Et)2 | 216 [M + H]$^+$ |

| Intermediate # | Structure | LC-MS |
|---|---|---|
| 75 | (azetidin-3-yl N-methylcarbamate, TFA) | 131 [M + H]+ |
| 76 | (azetidin-3-yl N-ethylcarbamate, TFA) | 145 [M + H]+ |
| 77 | (azetidin-3-yl N-isopropylcarbamate, TFA) | 159 [M + H]+ |
| 78 | (azetidin-3-yl N,N-dimethylcarbamate, TFA) | 145 [M + H]+ |
| 79 | (azetidin-3-yl 4-methylpiperazine-1-carboxylate, TFA) | 200 [M + H]+ |
| 80 | (azetidin-3-yl thiomorpholine-1,1-dioxide-4-carboxylate, TFA) | 235 [M + H]+ |
| 81 | (azetidin-3-yl 4-(2,2-difluoroethyl)piperazine-1-carboxylate, TFA) | 250 [M + H]+ |
| 82 | (azetidin-3-yl 4-(2,2,2-trifluoroethyl)piperazine-1-carboxylate, TFA) | 268 [M + H]+ |
| 83 | (azetidin-3-yl N-(2-hydroxy-2-methylpropyl)carbamate, TFA) | 189 [M + H]+ |

Intermediate 84

2-(azetidin-3-yloxy)-N-methylacetamide Trifluoroacetate

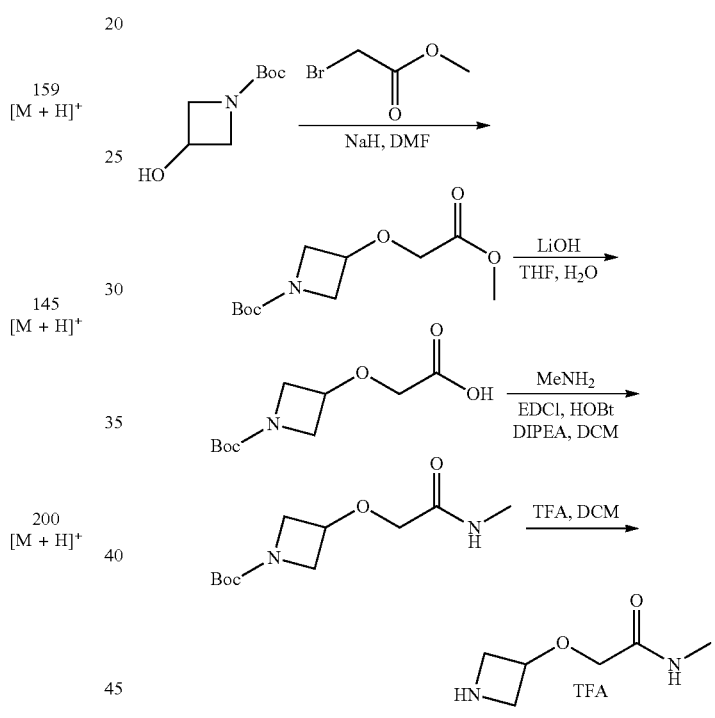

intermediate 84

Step 1: tert-butyl 3-(2-methoxy-2-oxoethoxy)azetidine-1-carboxylate

To a solution of tert-butyl 3-hydroxyazetidine-1-carboxylate (800 mg, 4.62 mmol) in dry THF (20 mL) was added NaH (185 mg, 4.62 mmol, 60 percent) in portions at 0° C. After the mixture was stirred at 0° C. for 20 min, a solution of methyl 2-bromoacetate (702 mg, 4.62 mmol) in THF (10 mL) was added dropwise. After the resulting solution was stirred at rt for 2 hrs, the reaction was quenched by addition of water at 0° C. The mixture was portioned between EtOAc and water. The organic layer was washed with brine, dried over anhydrous Na$_2$SO$_4$ and concentrated. The residue was purified by silica gel column chromatography (petroleum ether:EtOAc=100:1 to 10:1) to give tert-butyl 3-(2-methoxy-2-oxoethoxy)azetidine-1-carboxylate (1.1 g, 97.2% yield) as a colorless oil. LC-MS m/z: 246 [M+H]+.

Step 2: 2-((1-(tert-butoxycarbonyl)azetidin-3-yl)oxy)acetic acid

To a solution of tert-butyl 3-(2-methoxy-2-oxoethoxy)azetidine-1-carboxylate (1.1 g, 4.50 mmol) in THF (10 mL) was added LiOH (216 mg, 9.0 mmol) and water (5mL). The resulting mixture was stirred at room temperature overnight and THF was removed under vacuum. The aqueous residue was acidified to pH 4 by addition of HCl (1 M) and extracted with EtOAc (50 mL×2). The organic layers were dried over anhydrous $Na_2SO_4$ and concentrated to give 2-((1-(tert-butoxycarbonyl)azetidin-3-yl)oxy)acetic acid (600 mg, 57.7% yield) as a colorless oil, which was directly used to the next reaction without purification. LC-MS m/z: 231 [M+H]$^+$.

Step 3: tert-butyl 3-(2-(methylamino)-2-oxoethoxy)azetidine-1-carboxylate

To a solution of 2-((1-(tert-butoxycarbonyl)azetidin-3-yl)oxy)acetic acid (600 mg, 2.60 mmol) in DCM (10 mL) was added HOBt (526.5 mg, 3.90 mmol) followed by addition of EDCI (747.2 mg, 3.90 mmol) in portions at 0° C. DIPEA (1.34 g, 10.4 mmol) was added dropwise. The resulting mixture was stirred at 0° C. for 30 min, and methylamine hydrochloride (351.4 mg, 5.20 mmol) was added at 0° C. The reaction was then stirred at room temperature overnight. The mixture was then diluted with water and extracted with DCM. The organic layers were washed with brine, dried over $Na_2SO_4$, filtered and concentrated. The residue was purified by silica gel column chromatography (petroleum ether:EtOAc=100:1~1:1) to give tert-butyl 3-(2-(methylamino)-2-oxoethoxy)azetidine-1-carboxylate (380 mg, 59.9%) as a colorless oil. LC-MS m/z: 245 [M+H]$^+$.

Step 4: 2-(azetidin-3-yloxy)-N-methylacetamide Trifluoroacetate

To a solution of tert-butyl 3-(2-(methylamino)-2-oxoethoxy)azetidine-1-carboxylate (380 mg, 1.56 mmol) in DCM (5 mL) was added TFA (2 mL) dropwise at 0° C. The reaction was stirred at room temperature for 1 hr. The mixture was concentrated and the residue was coevaporated with toluene (10 mL×2) to give 2-(azetidin-3-yloxy)-N-methylacetamide trifluoroacetate (490 mg, 96.7% yield) as a yellow syrup, which was directly used to the next reaction without purification. LC-MS m/z: 145 [M+H]$^+$.

Intermediate 85

1-(azetidin-3-yl)-3-methylurea Trifluoroacetate

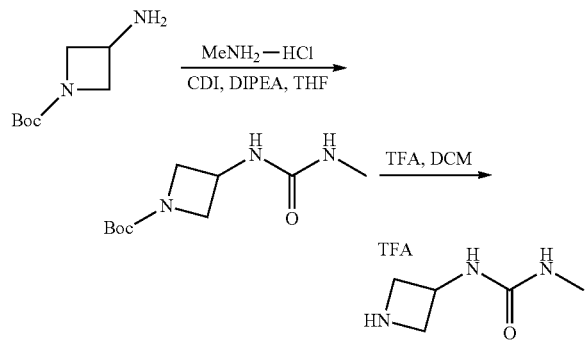

intermediate 85

Step 1: tert-butyl 3-(3-methylureido)azetidine-1-carboxylate

To a solution of tert-butyl 3-aminoazetidine-1-carboxylate (1.05 g, 6.1 mmol) in DCM (30 mL) was added CDI (2 g, 12.3 mmol) and DIPEA (2 ml, 12.3 mmol) at 0° C. After the resulting mixture was stirred at room temperature for 2 hrs, methanamine hydrochloride (1.59 g, 24.4 mmol) and DIPEA (2 ml, 12.3 mmol) were added. The reaction was stirred at room temperature overnight. The reaction mixture was washed with saturated aqueous $NaHCO_3$ solution and brine. The organic layer was dried over anhydrous $Na_2SO_4$, filtered and concentrated. The residue was purified by silica gel column chromatography (petroleum ether:acetone=3:1) to give tert-butyl 3-(3-methylureido)azetidine-1-carboxylate (970 mg, 69.3% yield) as a yellow oil. LC-MS m/z: 174 [M+H−56]$^+$.

Step 2: 1-(azetidin-3-yl)-3-methylurea Trifluoroacetate

To a solution of tert-butyl 3-(3-methylureido)azetidine-1-carboxylate(550 mg, 2.4 mmol) in DCM (3 mL) was added TFA (1 mL) dropwise at 0° C. After the reaction was stirred at room temperature for 3 hrs, the mixture was concentrated under high vacuum and coevaporated with toluene (30 mL×3) to give 1-(azetidin-3-yl)-3-methylurea Trifluoroacetate (1.05 mg, 100% yield) as an oil, which was directly used to the next reaction without purification. LC-MS m/z: 130 [M+H]$^+$.

The following intermediates were prepared according to procedures similar to that described for Intermediate 85 by using the appropriate amines

| Intermediate # | Structure | LC-MS |
|---|---|---|
| 86 | TFA·HN-[azetidine]-NH-C(=O)-N(H)(CH₃) | 144 [M + H]$^+$ |

Intermediate 87

N-(azetidin-3-yl)propionamide Trifluoroacetate

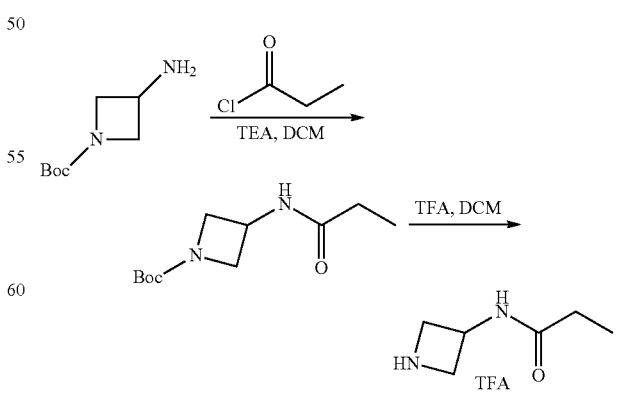

intermediate 87

Step 1: tert-butyl 3-propionamidoazetidine-1-carboxylate

To a mixture of tert-butyl 3-aminoazetidine-1-carboxylate (600 mg, 3.5 mmol) in dry DCM was added propionyl chloride (340 mg, 3.75 mmol) at 0° C. After the resulting mixture was stirred at rt overnight, it was partitioned with DCM and water. The orgainic layer was washed with brine, dried over anhydrous Na$_2$SO$_4$ and concentrated. The residue was purified by silica gel column chromatography (DCM: MeOH=100:1) to give tert-butyl 3-propionamidoazetidine-1-carboxylate (720 mg, 90.2% yield) as a yellow oil. LC-MS m/z: 229 [M+H]$^+$.

Step 2: N-(azetidin-3-yl)propionamide Trifluoroacetate

To a solution of 3-propionamidoazetidine-1-carboxylate (400 mg, 1.75 mmol) in DCM (6 mL) was added TFA (2 mL) dropwise at 0° C. The reaction was then stirred at rt for 2 hrs. The resulting mixture was concentrated under vacuum to give a residue, which was co-evaporated with toluene to give N-(azetidin-3-yl)propionamide trifluoroacetate (810 mg, 100% yield) as a brown oil, which was directly used to the next reaction without purification. LC-MS m/z: 129 [M+H]$^+$.

Intermediate 88 methyl azetidin-3-ylcarbamate Trifluoroacetate

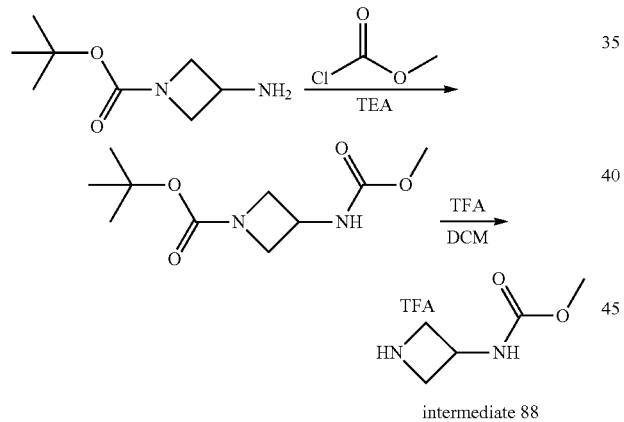

intermediate 88

Step 1: tert-butyl 3-((methoxycarbonyl)amino)azetidine-1-carboxylate

To a mixture of tert-butyl 3-aminoazetidine-1-carboxylate (500 mg, 2.90 mmol) in DCM (150 mL) was added TEA (1.22 mL, 8.71 mmol) followed by dropwise addition of methyl chloroformate (441 mg, 4.35 mmol) at 0° C. The resulting mixture was stirred at room temperature overnight overnight. The mixture was washed with saturated aqueous NaHCO$_3$ solution and brine. The organic layer was dried over Na$_2$SO$_4$, filtered and concentrated. The residue was purified by silica gel column chromatography (petroleum ether:ethyl acetate=20:1 to 5:1) to give tert-butyl 3-((methoxycarbonyl)amino)azetidine-1-carboxylate (450 mg, 67.3% yield) as a yellow oil. LC-MS mz/: 231 [M+H]$^+$.

Step 2: methyl azetidin-3-ylcarbamate Trifluoroacetate

To a mixture of tert-butyl 3-((methoxycarbonyl)amino) azetidine-1-carboxylate (450 mg, 1.95 mmol) in DCM (10 mL) was added TFA (3.5 mL) dropwise at 0° C. The reaction was stirred at room temperature for 3 hrs. The reaction mixture was then concentrated under reduced pressure to give methyl azetidin-3-ylcarbamate trifluoroacatate (250 mg, 100% yield) as a brown oil, which was directly used in the next reaction without purification. LC-MS m/z: 131 [M+H]$^+$.

Intermediate 89

3-(azetidin-3-yl)-N-(2-(diethylamino)ethyl)propanamide Trifluoroacetate

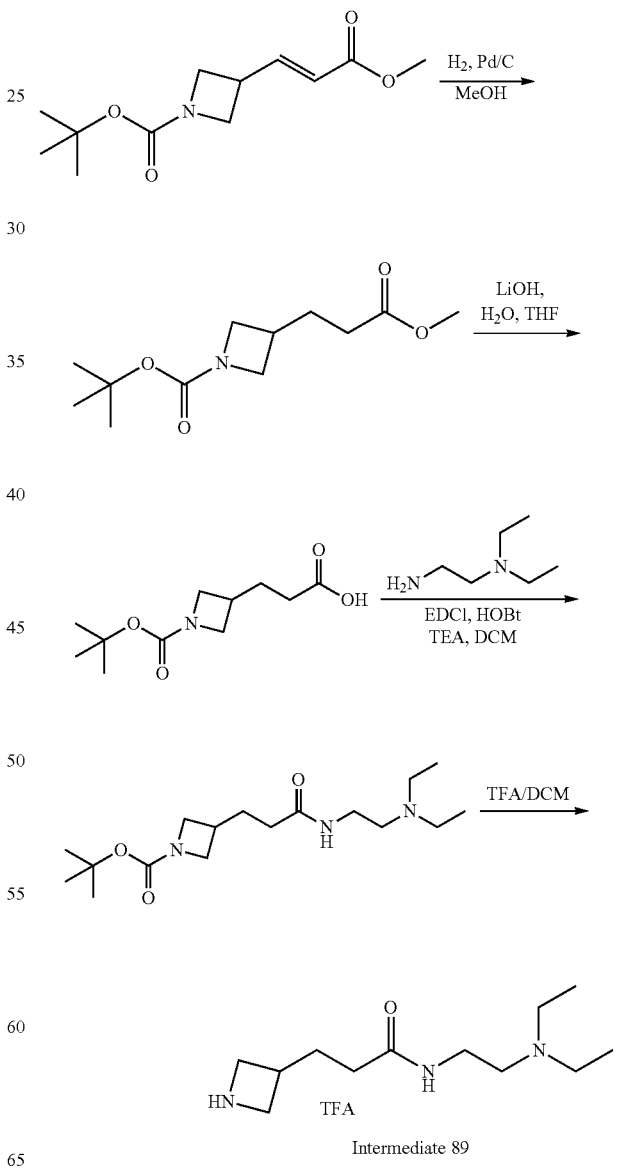

Intermediate 89

Step 1: tert-butyl 3-(3-ethoxy-3-oxopropyl)azetidine-1-carboxylate

A solution of (E)-tert-butyl 3-(3-ethoxy-3-oxoprop-1-enyl)azetidine-1-carboxylate (3.4 g, 13.33 mmol) in methanol (20 mL) was degassed three times with $N_2$ atmosphere, and Pd/C (350 mg, 10% wt) was added. The mixture was degassed again and stirred under a $H_2$ atmosphere at room temperature overnight. The reaction was filtered through Celite, and the filtrate was concentrated to give tert-butyl 3-(3-ethoxy-3-oxopropyl)azetidine-1-carboxylate (3.3 g, 96.1% yield) as a colorness oil. LC-MS: m/z 202 [M+H]$^+$.

Step 2: 3-(1-(tert-butoxycarbonyl)azetidin-3-yl)propanoic acid

To a solution of 3-(3-ethoxy-3-oxopropyl)azetidine-1-carboxylate (3.3 g, 12.8 mmol) in THF/$H_2$O (15 mL/15 mL) was added LiOH (614.3 mg, 25.65 mmol). The reaction was stirred at room temperature overnight. The mixture was concentrated under reduced pressure, diluted with water and extracted with DCM. The combined organic layers were dried over anhydrous $Na_2SO_4$ and concentrated under reduced pressure to give 3-(1-(tert-butoxycarbonyl)azetidin-3-yl)propanoic acid (2.7 g, 92.8% yield) as a colorness oil. LC-MS: m/z 230 [M+H]$^+$.

Step 3: tert-butyl 3-(3-(2-(diethylamino)ethyl-amino)-3-oxopropyl)azetidine-1-carboxylate To a solution of 3-(1-(tert-butoxycarbonyl)azetidin-3-yl)propanoic acid (800 mg, 3.5 mmol) in DCM (10 mL) was added 1-hydroxybenzotriazole (480 mg, 3.5 mmol) followed by addition of 1-(3-dimethylaminopropyl)-3-ethylcarbodiimide hydrochloride (680 mg, 3.5 mmol) in portions and Et$_3$N (1.06 g, 10.5 mmol) at 0° C. The mixture was stirred at 0° C. for 30 min, and $N^1,N^1$-diethylethane-1,2-diamine (609 mg, 5.2 mmol) was added dropwise at 0° C. The reaction was then stirred at room temperature overnight. The reaction mixture was quenched with water and extracted with DCM. The organic layers were washed with brine, dried over $Na_2SO_4$, filtered and concentrated. The residue was purified by silica gel column chromatography (DCM:methanol=30:1) to give tert-butyl 3-(3-(2-(diethylamino)ethylamino)-3-oxopropyl)azetidine-1-carboxylate (630 mg, 55.0% yield) as a brown oil. LC-MS: m/z 328 [M+H]$^+$.

Step 4: 3-(azetidin-3-yl)-N-(2-(diethylamino)ethyl) propanamide Trifluoroacetate To a mixture of tert-butyl 3-(3-(2-(diethylamino)ethyl-amino)-3-oxopropyl)azetidine-1-carboxylate (630 mg, 1.9 mmol) in DCM (2.5 mL) was added trifluoroacetic acid (2.5 mL) dropwise at 0° C. The reaction was stirred room temperature for 2 hr. The mixture was concentrated under reduced pressure to give 3-(azetidin-3-yl)-N-(2-(diethylamino)ethyl)propanamide trifluoroacetate (432 mg, 99.9% yield) as a yellow syrup, which was directly used to the next reaction without purification. LC-MS: m/z 228 [M+H]$^+$.

The following intermediates were prepared according to procedures similar to that described for Intermediate 89 by using the appropriate amine

| Intermediate # | Structure | LC-MS |
|---|---|---|
| 90 | ![structure] | 242 [M + H]$^+$ |

Intermediate 91

4-(2-(azetidin-3-yl)ethyl)-1-methylpiperidine

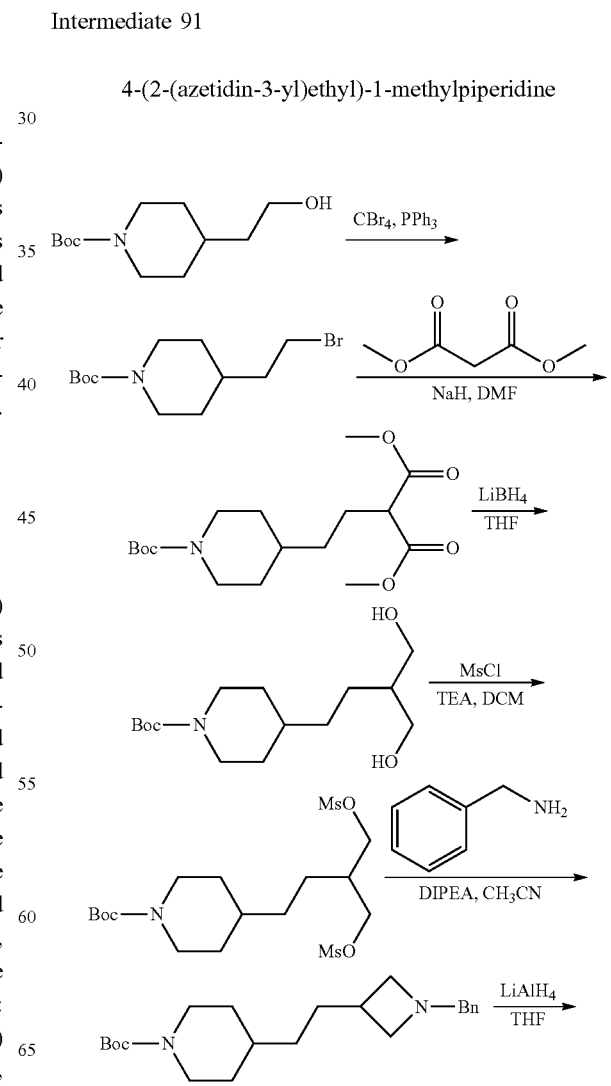

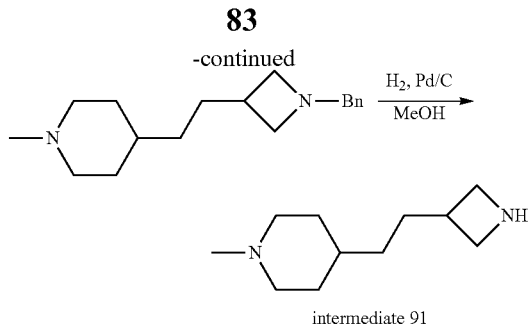

intermediate 91

Step 1: tert-butyl 4-(2-bromoethyl)piperidine-1-carboxylate

To a solution of tert-butyl 4-(2-hydroxyethyl)piperidine-1-carboxylate (15.0 g, 65.5 mmol) and $PPh_3$ (20.6 g, 78.6 mmol) in dry DCM (200 mL) was added a solution of $CBr_4$ (24.9 g, 75.3 mmol) in dry DCM (100 mL) at 0° C. The mixture was stirred at rt overnight. The mixture was concentrated under reduced pressure to give a residue, which was purified by column chromatography on silica gel (petroleum ether:ethyl acetate=100:1~30:1) to give the title compound (16.3 g, 84.5% yield) as a white solid. LC-MS: m/z 239 $[M+H-56]^+$.

Step 2: dimethyl 2-(2-(1-(tert-butoxycarbonyl)piperidin-4-yl)ethyl)malonate

To a solution of dimethyl malonate (9.1 g, 68.4 mmol) in DMF (60 mL) was added NaH (2.04 g, 51.3 mmol, 60% dispersion in mineral oil) in portions at 0° C. After the mixture was stirred at 0° C. for 30 min, a solution of tert-butyl 4-(2-bromoethyl)piperidine-1-carboxylate (5.1 g, 17.1 mmol) in DMF (30 mL) was added dropwise, and the resulting mixture was stirred at 45° C. overnight. The mixture was poured into the ice water and extracted with EtOAc (100 mL×2). The organic layers were washed with aq. LiCl (5%), dried over anhydrous $Na_2SO_4$, filtered and concentrated. The residue was purified by column chromatography on silica gel (petroleum ether:ethyl acetate=30:1 to 10:1) to give dimethyl 2-(2-(1-(tert-butoxycarbonyl)piperidin-4-yl)ethyl)malonate (5.9 g, 95.1% yield) as an oil. LC-MS: m/z 288 $[M+H-56]^+$.

Step 3: tert-butyl 4-(4-hydroxy-3-(hydroxymethyl)butyl)piperidine-1-carboxylate To a solution of methyl dimethyl 2-(2-(1-(tert-butoxycarbonyl)piperidin-4-yl)ethyl)malonate (5.9 g, 17.1 mmol) in THF was added a 2 M solution of $LiBH_4$ (34 mL, 68.0 mmol) in THF dropwise at 0° C. The mixture was warmed to room temperature stirred overnight. The reaction was quenched by with saturated aqueous $NH_4Cl$ and extracted with EtOAc. The combined organic layers were washed with brine, dried over anhydrous $Na_2SO_4$ and concentrated. The residue was purified by silica gel column chromatography (DCM:MeOH=100:1~50:1) to give tert-butyl 4-(4-hydroxy-3-(hydroxymethyl)butyl)piperidine-1-carboxylate (3.4 g, 66.6% yield) as a white solid. LC-MS: m/z 188 $[M+1-100]^+$.

Step 4: tert-butyl 4-(4-((methylsulfonyl)oxy)-3-(((methylsulfonyl)oxy)methyl)butyl)piperidine-1-carboxylate To a solution of tent-butyl 4-(4-hydroxy-3-(hydroxymethyl)butyl)piperidine-1-carboxylate (3.4 g, 11.8 mmol) in DCM (50 mL) was added TEA (5.96 g, 59.1 mmol) and MsCl (3.9 g, 35.5 mmol). The reaction was stirred at room temperature overnight. The mixture was poured into ice water and extracted with EtOAc. The combined organic layers were washed with brine, dried over anhydrous $Na_2SO_4$ and concentrated. The residue was purified by silica gel column chromatography (petroleum ether:ethyl acetate=8:1 to 2:1) to give 4-(4-((methylsulfonyl)oxy)-3-(((methylsulfonyl)oxy)methyl)butyl)piperidine-1-carboxylate (4.8 g, 92.5% yield) as a white solid. LC-MS: m/z 388 $[M+1-56]^+$.

Step 5: tert-butyl 4-(2-(1-benzylazetidin-3-yl)ethyl)piperidine-1-carboxylate To a solution of 4-(4-((methylsulfonyl)oxy)-3-(((methylsulfonyl)oxy)methyl)butyl)piperidine-1-carboxylate (4.8 g, 11.0 mmol) in $CH_3CN$ was added DIPEA (5.7 g, 44.0 mmol) and $BnNH_2$ (2.9 g, 27.5 mmol). The reaction was stirred at reflux for 15 hrs. Solvent was removed and the residue was partitioned with ice-water and EtOAc. The aqueous phase was extracted with EtOAc. The combined organic phases were washed with brine, dried over anhydrous $Na_2SO_4$ and concentrated. The residue was purified by silica gel column chromatography (petroleum ether:acetone=10:1 to 4:1) to give tert-butyl 4-(2-(1-benzylazetidin-3-yl)ethyl)piperidine-1-carboxylate (2.8 g, 70.1% yield) as a yellow oil. LC-MS: m/z 359 $[M+H]^+$.

Step 6: 4-(2-(1-benzylazetidin-3-yl)ethyl)-1-methylpiperidine

To a solution of tert-butyl 4-(2-(1-benzylazetidin-3-yl)ethyl)piperidine-1-carboxylate (1.08 g, 3.0 mmol) a in THF (15 mL) was added $LAlH_4$ (342 mg, 9.1 mmol, in portions at 0° C. The reaction was then stirred at 65° C. overnight. The mixture was quenched with $H_2O$ (0.4 mL), 15% aqueous NaOH (0.4 mL) and $H_2O$ (1.2 mL). The mixture was filtered and the filtrate was concentrated. The residue was purified by silica gel column chromatography (DCM:MeOH=100:1 to 4:1) to give 4-(2-(1-benzylazetidin-3-yl)ethyl)-1-methylpiperidine (280 mg, 31.2% yield) as a brown oil. LC-MS: m/z 273 $[M+H]^+$.

Step 7: 4-(2-(azetidin-3-yl)ethyl)-1-methylpiperidine

A solution of 4-(2-(1-benzylazetidin-3-yl)ethyl)-1-methylpiperidine (280 mg, 0.9 mmol) in MeOH (5 mL) was degassed three times under $N_2$ atmosphere, and $Pd(OH)_2/C$ (50 mg) was added. The mixture was degassed again and stirred under $H_2$ atmosphere at room temperature overnight. The reaction was filtered through Celite, and the filtrate was concentrated to give 4-(2-(azetidin-3-yl)ethyl)-1-methylpiperidine (130 mg, 79.8% yield) as a light yellow solid. LC-MS: m/z 183 $[M+H]^+$.

Intermediate 92

4-(2-(azetidin-3-yl)ethyl)-1-(2,2-difluoroethyl)piperidine

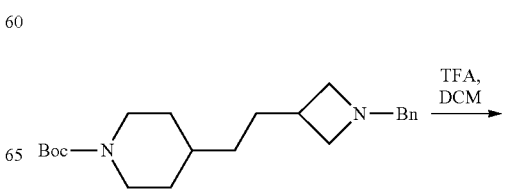

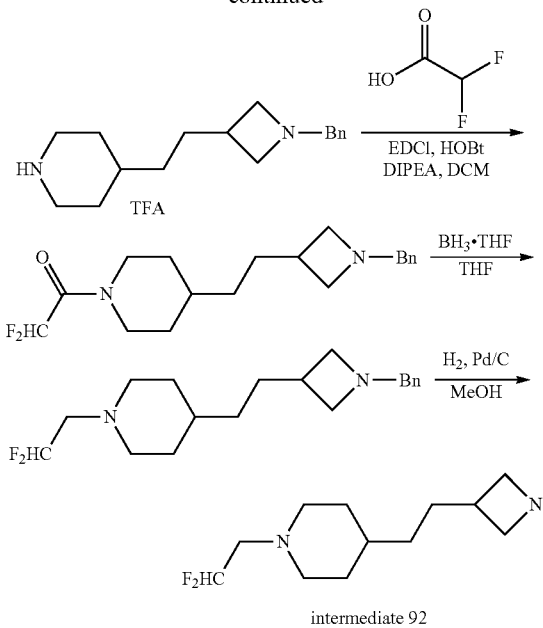

intermediate 92

Step 1: 4-(2-(1-benzylazetidin-3-yl)ethyl)piperidine Trifluoroacetate

To a solution of tert-butyl 4-(2-(1-benzylazetidin-3-yl)ethyl)piperidine-1-carboxylate (1.1 g, 3.0 mmol) in DCM (8 mL) was added TFA (1.8 mL) at 0° C. The reaction was then stirred at rt for 2 hrs. The reaction mixture was concentrated to give 4-(2-(1-benzylazetidin-3-yl)ethyl)piperidine trifluoroacetate (2.1 g,) as a yellow oil. LC-MS: m/z 259 [M+H]$^+$.

Step 2: 1-(4-(2-(1-benzylazetidin-3-yl)ethyl)piperidin-1-yl)-2,2-difluoroethanone To a mixture of 4-(2-(1-benzylazetidin-3-yl)ethyl)piperidine trifluoroacetate (2.1 g) and 2,2-difluoroacetic acid (560 mg, 6.0 mmol) in DCM (10 mL) was added DIPEA (1.7 g, 13.5 mmol) and HOBt (480 mg, 3.6 mmol) at 0° C. Then EDCI (860 mg, 4.5 mmol) was added in portions at 0° C. The resulting mixture was stirred at rt overnight. The resulting mixture was diluted with DCM and washed with water, brine. The organic layer was dried over anhydrous Na$_2$SO$_4$ and concentrated. The residue was purified by column chromatography on silica gel (DCM:methanol=200:0 to 20:1) to give 1-(4-(2-(1-benzylazetidin-3-yl)ethyl)piperidin-1-yl)-2,2-difluoroethanone (610 mg, 59.5% yield) as yellow oil. LC-MS: m/z 337 [M+H]$^+$.

Step 3: 4-(2-(1-benzylazetidin-3-yl)ethyl)-1-(2,2-difluoroethyl)piperidine

To a solution of 1-(4-(2-(1-benzylazetidin-3-yl)ethyl)piperidin-1-yl)-2,2-difluoroethanone (610 mg, 1.7 mmol) in anhydrous THF (10 mL) was added a solution of BH$_3$-THF (5 mL, 5.0 mmol, 1M in THF) dropwise at −10° C. The resulting mixture was stirred at rt overnight. The resulting mixture was cooled to 0-5° C., methanol was added dropwise below 10° C. The mixture was concentrated under vacuum to give a yellow reside, which was dissolved in EtOH/H$_2$O (8 mL/1 mL) and stirred at reflux overnight. The resulting mixture was concentrated under vacuum to give a residue, which was purified by column chromatography on silica gel (DCM:methanol=150:1 to 50:1) to give 4-(2-(1-benzylazetidin-3-yl)ethyl)-1-(2,2-difluoroethyl)piperidine (420mg, 73.5% yield) as a colorless oil. LC-MS: m/z 323 [M+H]$^+$.

Step 4: 4-(2-(azetidin-3-yl)ethyl)-1-(2,2-difluoroethyl)piperidine

A solution of 4-(2-(1-benzylazetidin-3-yl)ethyl)-1-(2,2-difluoroethyl)piperidine (380 mg, 1.1 mmol) in MeOH (8 mL) was degassed three times under N$_2$ atmosphere, and Pd(OH)$_2$/C (50 mg) was added. The mixture was degassed again and stirred under H$_2$ atmosphere at room temperature overnight. The reaction was filtered through Celite, and the filtrate was concentrated to give 4-(2-(azetidin-3-yl)ethyl)-1-(2,2-difluoroethyl)piperidine (250 mg, 89.4% yield) as a light yellow solid. LC-MS: m/z 233 [M+H]$^+$.

Intermediate 93

3-(2-(azetidin-3-yl)ethyl)-1-(2,2-difluoroethyl)azetidine Trifluoroacetate

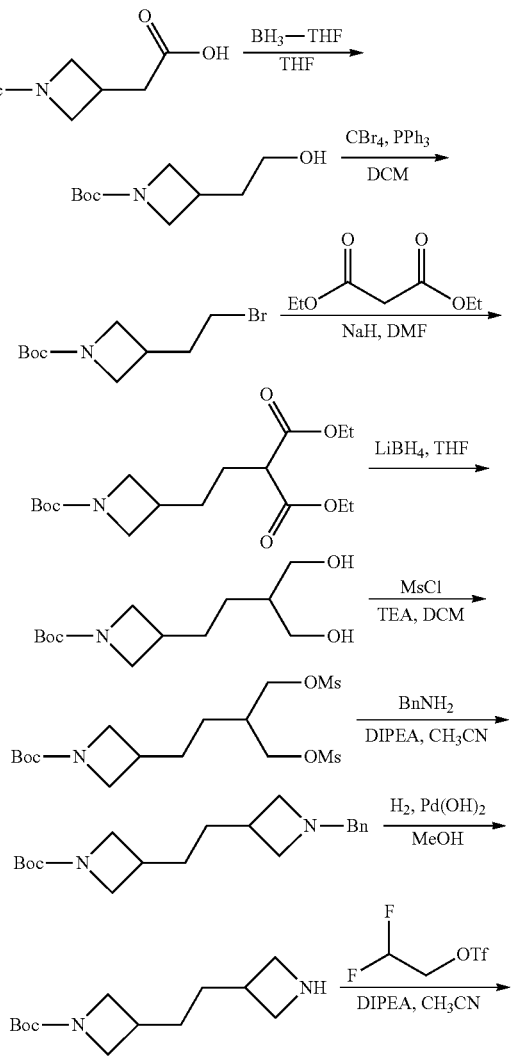

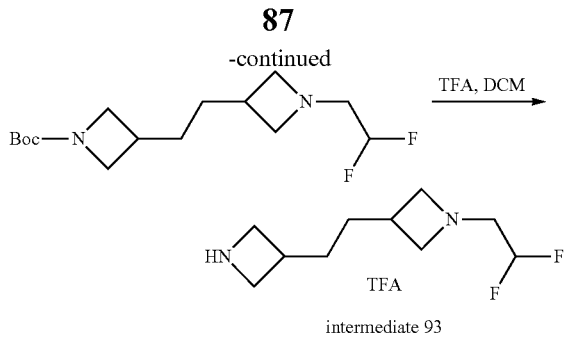

intermediate 93

Step 1: tert-butyl 3-(2-hydroxyethyl)azetidine-1-carboxylate

To a solution of 2-(1-(tert-butoxycarbonyl)azetidin-3-yl)acetic acid (7.5 g, 35 mmol) in THF (100 mL) was added a solution of borane-tetrahydrofuran complex (105 mL, 105 mmol, 1M in THF) dropwise at −10° C. The reaction was stirred at room temperature overnight. To the reaction mixture was then added MeOH (50 mL) dropwise at 0° C. After addition was complete, the mixture was stirred at room temperature for 30 min. The mixture was concentrated under vacuum to give a yellow reside, which was purified by silica gel column chromatography (petroleum ether:EtOAc=100:1 to 1:1) to give tert-butyl 3-(2-hydroxyethyl)azetidine-1-carboxylate (6.6 g, 94.15% yield) as a colorless oil. LC-MS m/z: 146 [M+H−56]+.

Step 2: tert-butyl 3-(2-bromoethyl)azetidine-1-carboxylate

To a solution of tert-butyl 3-(2-hydroxyethyl)azetidine-1-carboxylate (6.1 g, 30.3 mmol) was added a solution of CBr$_4$ (19.8 g, 60.6 mmol) in DCM (100 mL) was added Ph$_3$P (15.7 g, 60.6 mmol) at 0° C. The resulting mixture was stirred at room temperature overnight. The mixture was concentrated and the residue was purified by silica gel column chromatography (petroleum ether:EtOAc=100:1 to 1:1) to give tert-butyl 3-(2-bromoethyl)azetidine-1-carboxylate (5.5 g, 69.4% yield) as a colorless oil. LC-MS m/z: 208 [M+H−56]+.

Step 3: diethyl 2-(2-(1-(tert-butoxycarbonyl)azetidin-3-yl)ethyl)malonate

To a solution of diethyl malonate (4.0 g, 30.3 mmol) in DMF (50 mL) was added NaH (900 mg, 22.7 mmol, 60%) in portions at 0° C. After the mixture was stirred for 10 min, tert-butyl 3-(2-bromoethyl)azetidine-1-carboxylate (2.0 g, 7.6 mmol) was added dropwise 0° C. The resulting mixture was stirred at 45° C. overnight. The mixture was then diluted with water and extracted with DCM. The organic layers were washed with brine, dried over Na$_2$SO$_4$, and concentrated. The residue was purified by silica gel column chromatography (petroleum ether:EtOAc=100:1~1:1) to give diethyl 2-(2-(1-(tert-butoxycarbonyl)azetidin-3-yl)ethyl)malonate (1.8 g, 75.5% yield) as a colorless oil. LC-MS m/z: 344 [M+H]+.

Step 4: tert-butyl 3-(4-hydroxy-3-(hydroxymethyl)butyl)azetidine-1-carboxylate To a solution of diethyl 2-(2-(1-(tert-butoxycarbonyl)azetidin-3-yl)ethyl)malonate (1.8 g, 6 mmol) in THF (30 mL) was added LiBH$_4$ (750 mg, 36 mmol) in portions at −15° C. The mixture was stirred at 45° C. overnight. The mixture was then diluted with aq. NH$_4$Cl solution at 0° C. and extracted with EtOAc. The organic layers were washed with brine, dried over Na$_2$SO$_4$, and concentrated. The residue was purified by silica gel column chromatography (DCM:MeOH=100:1 to 20:1) to give tert-butyl 3-(4-hydroxy-3-(hydroxymethyl)butyl)azetidine-1-carboxylate (1.2 g, 76.9% yield) as a colorless oil. LC-MS m/z: 260 [M+H]+.

Step 5: tert-butyl 3-(4-((methylsulfonyl)oxy)-3-(((methylsulfonyl)oxy)methyl)butyl)azetidine-1-carboxylate To a solution of tert-butyl 3-(4-hydroxy-3-(hydroxymethyl)butyl)azetidine-1-carboxylate (1.2 g, 4.6 mmol) and TEA (2.8 g, 27.6 mmol) in DCM (20 mL) was added methanesulfonyl chloride (2.1 g, 18.5 mmol) dropwise 0° C. The mixture was stirred at room temperature overnight. The mixture was then diluted with water and extracted with DCM. The organic layers were washed with brine, dried over Na$_2$SO$_4$, filtered and concentrated. The residue was purified by silica gel column chromatography (petroleum ether:EtOAc=100:1~1:1) to give tert-butyl 3-(4-((methylsulfonyl)oxy)-3-(((methylsulfonyl)oxy)methyl)butyl)azetidine-1-carboxylate (1.5 g, 78.1% yield) as a colorless oil. LC-MS m/z: 416 [M+H]+.

Step 6: tert-butyl 3-(2-(1-benzylazetidin-3-yl)ethyl)azetidine-1-carboxylate To a solution of benzylamine (775 mg, 7.2 mmol) and DIPEA (1.39 g, 10.8 mmol) in acetonitrile (20 mL) was added tert-butyl 3-(4-((methylsulfonyl)oxy)-3-(((methylsulfonyl)oxy)methyl)butyl)azetidine-1-carboxylate (1.5 g, 3.6 mmol) dropwise at 0° C. The mixture was stirred at 45° C. overnight. The mixture was then concentrated and the residue was diluted with DCM. The organic layer was washed with brine, dried over Na$_2$SO$_4$, filtered and concentrated. The residue was purified by silica gel column chromatography (petroleum ether:EtOAc=100:1~1:1) to give tert-butyl 3-(2-(1-benzylazetidin-3-yl)ethyl)azetidine-1-carboxylate (530 mg, 44.4%) as a colorless oil. LC-MS m/z: 331 [M+H]+.

Step 7: tert-butyl 3-(4-hydroxy-3-(hydroxymethyl)butyl)azetidine-1-carboxylate To a solution of tert-butyl 3-(2-(1-benzylazetidin-3-yl)ethyl)azetidine-1-carboxylate (530 mg, 1.7 mmol) in MeOH (50 mL) was added Pd(OH)$_2$ on activated carbon (200 mg, 10% wt.) and a drop of HOAc. The resulting mixture was degassed and stirred under a H$_2$ atmosphere at room temperature overnight. The mixture was filtered and concentrated under reduced pressure to give tert-butyl 3-(4-hydroxy-3-(hydroxymethyl)butyl)azetidine-1-carboxylate (350 mg, 95.7% yield) as a brown oil, which was directly used in the next reaction without purification. LC-MS m/z: 241 [M+H]+.

Step 8: tert-butyl 3-(2-(1-(2,2-difluoroethyl)azetidin-3-yl)ethyl)azetidine-1-carboxylate To a solution of tert-butyl 3-(4-hydroxy-3-(hydroxymethyl)butyl)azetidine-1-carboxylate (300 mg, 1.3 mmol) and DIPEA (503 mg, 3.9 mmol) in acetonitrile (10 mL) was added 2,2-difluoroethyl trifluoromethanesulfonate (335 mg, 1.56 mmol) dropwise 0° C. The mixture was stirred at reflux overnight. The mixture was then concentrated and the residue was diluted with DCM. The organic layer was washed with brine, dried over Na$_2$SO$_4$, filtered and concentrated. The residue was purified by silica gel column chromatography (petroleum ether:EtOAc=100:1~1:1) to give tert-butyl 3-(2-(1-(2,2-difluoroethyl)azetidin-3-yl)ethyl)azetidine-1-carboxylate (230 mg, 58.2% yield) as a a colorless oil. LC-MS m/z: 304 [M+H]$^+$.

Step 9: 3-(2-(azetidin-3-yl)ethyl)-1-(2,2-difluoroethyl)azetidine Trifluoroacetate To a solution of tert-butyl 3-(2-(1-(2,2-difluoroethyl)azetidin-3-yl)ethyl)azetidine-1-carboxylate (230 mg 0.75 mmol) in DCM (5 mL) was added TFA (2 mL) dropwise at 0° C. The reaction was stirred at room temperature for 1 hr. The mixture was concentrated under reduced pressure and co-evaporated with toluent (10 mL×2) to give 3-(2-(azetidin-3-yl)ethyl)-1-(2,2-difluoroethyl)azetidine trifluoroacetate (350 mg, 99.1% yield) as yellow syrup, which was directly used to the next reaction without purification. LC-MS m/z: 205 [M+H]$^+$.

Intermediate 94

4-(2-(1-(2,2-difluoroethyl)azetidin-3-yl)ethyl)piperidine Trifluoroacetate

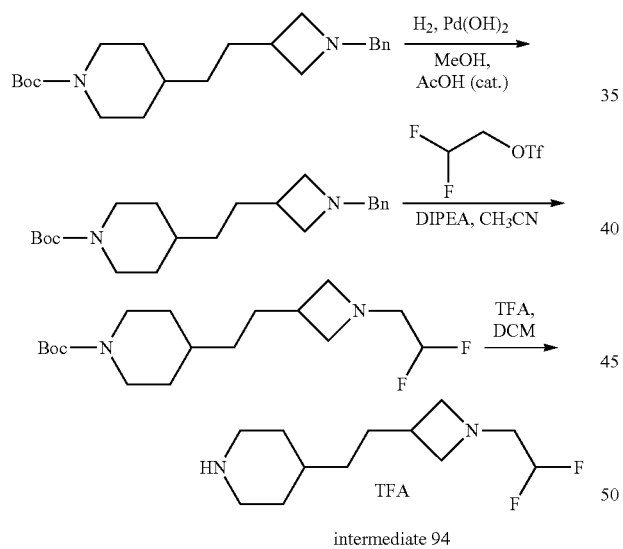

intermediate 94

Step 1: tert-butyl 4-(2-(azetidin-3-yl)ethyl)piperidine-1-carboxylate

To a solution of tert-butyl 4-(2-(1-benzylazetidin-3-yl)ethyl)piperidine-1-carboxylate (400 mg, 1.11 mmol) in MeOH (8 mL) was added Pd(OH)$_2$ on carbon (60 mg, 10% wt) and a drop of HOAc. The resulting mixture was degassed and stirred under a H$_2$ atmosphere at 45° C. for 16 hrs. The mixture was filtered through a pad of Celite, and the filtrate was concentrated to give tert-butyl 4-(2-(azetidin-3-yl)ethyl)piperidine-1-carboxylate (280 mg, 93.4% yield) as a light yellow oil. LC-MS m/z: 269 [M+H]$^+$.

Step 2: tert-butyl 4-(2-(1-(2,2-difluoroethyl)azetidin-3-yl)ethyl)piperidine-1-carboxylate To a solution of tert-butyl 4-(2-(azetidin-3-yl)ethyl)piperidine-1-carboxylate (300 mg, 1.11 mmol) in MeCN (6 mL) was added DIPEA (0.46 mL, 2.79 mmol) and 2,2-difluoroethyl trifluoromethanesulfonate (310 mg, 1.44 mmol) at 0° C. The mixture was stirred at room temperature overnight. The mixture was concentrated and the residue was partitioned between DCM (20 mL) and water (10 mL). The organic layer was dried over anhydrous Na$_2$SO$_4$ and concentrated. The residue was purified by silica gel column chromatography (DCM:MeOH=100:1) to give tert-butyl 4-(2-(1-(2,2-difluoroethyl)azetidin-3-yl)ethyl)piperidine-1-carboxylate (250 mg, 67.3% yield) as a a yellow oil. LC-MS m/z: 333 [M+H]$^+$.

Step 3: 4-(2-(1-(2,2-difluoroethyl)azetidin-3-yl)ethyl)piperidine Trifluoroacetate To a mixture of tert-butyl 4-(2-(1-(2,2-difluoroethyl)azetidin-3-yl)ethyl)piperidine-1-carboxylate (250 mg, 0.75 mmol) in DCM (2 mL) was added TFA (1 mL) dropwise at 0° C. The resulting mixture was stirred at room temperature for 3 hrs. The mixture was concentrated under reduced pressure to give a residue, which was co-evaporated with toluene (3 mL×2) to 4-(2-(1-(2,2-difluoroethyl)azetidin-3-yl)ethyl)piperidine Trifluoroacetate (300 mg, 88.3% yield) as a brown oil. The crude product was directly used in the next reaction without purification. LC-MS m/z: 233 [M+H]$^+$.

Intermediate 95

4-(azetidin-3-ylmethyl)-1-(2,2-difluoroethyl)piperidine

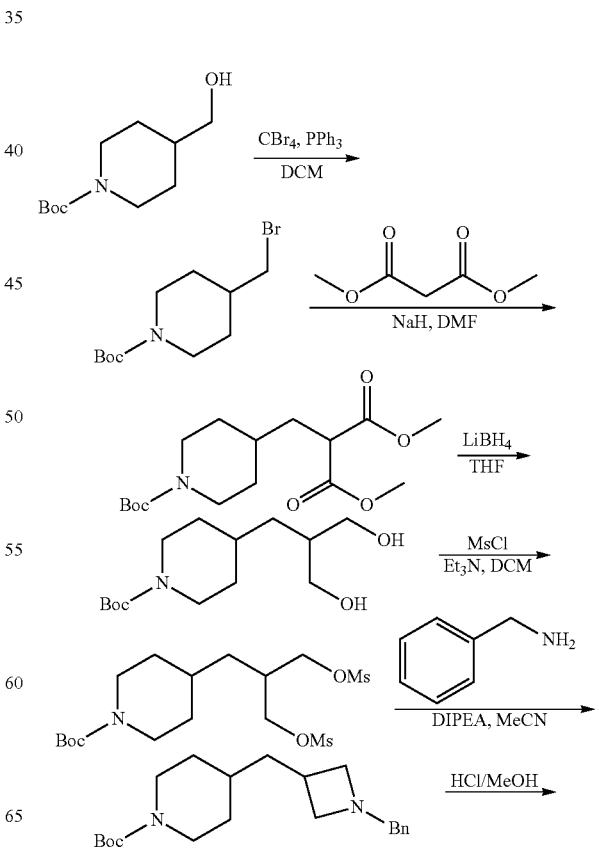

-continued

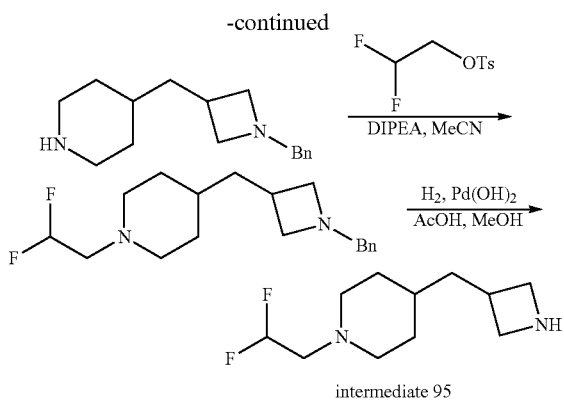

intermediate 95

Step 1: tert-butyl 4-(bromomethyl)piperidine-1-carboxylate

To a solution of tert-butyl 4-(hydroxymethyl)piperidine-1-carboxylate (2.0 g, 9.29 mmol) in DCM (30 mL) was added CBr$_4$ (5.1 g, 15.51 mmol) in one portion. The resulting colorless solution was cooled to 0° C. and PPh$_3$ (4.1 g, 15.51 mmol) was added in one portion. The resulting dark orange solution was first stirred at 0° C. for 1 h and then warmed to rt and stirred overnight. The mixture was washed by H$_2$O (20 mL×2) and the organic layer was dried over anhydrous Na$_2$SO$_4$ and concentrated. The residue was purified by silica gel column chromatography (petroleum ether:EtOAc=20:1) to give tert-butyl 4-(bromomethyl)piperidine-1-carboxylate (1.6 g, 61.9% yield) as a yellow oil. LC-MS m/z: 263 [M+H−15]$^+$.

Step 2: dimethyl 2-((1-(tert-butoxycarbonyl)piperidin-4-yl)methyl)malonate

To a mixture of dimethyl malonate (3.6 mL, 31.98 mmol) in DMF (30 mL) was added sodium hydride (960 mg, 23.99 mmol, 60% dispersion in mineral oil) in portions at 0° C. After the mixture was stirred at 0° C. for 30 min, tert-butyl 4-(bromomethyl)piperidine-1-carboxylate (2.0 g, 8.0 mmol) was added. The resulting mixture was stirred at 50° C. overnight. The mixture was then poured into ice-water and extracted with EtOAc. The combined organic layers were washed with brine, dried and concentrated. The residue was purified via silica gel column chromatography (petroleum ether:EtOAc=20:1) to give dimethyl 2-((1-(tert-butoxycarbonyl)piperidin-4-yl)methyl)malonate (2 g, 84.5% yield) as a colorless oil. LC-MS m/z: 315 [M+H−15]$^+$.

Step 3: 4-(3-hydroxy-2-(hydroxymethyl)propyl) piperidine-1-carboxylate

To a solution of dimethyl 2-((1-(tert-butoxycarbonyl) piperidin-4-yl)methyl)malonate (1.4 g, 4.25 mmol) in dry THF (20 mL) was added LiBH$_4$ (370 mg, 17.0 mmol) in portions at 0° C. under a N$_2$ atmosphere. The resulting mixture was stirred at room temperature overnight. The reaction was quenched by addition of aqueous NH$_4$Cl solution at 0° C. and stirred for 30 min. The mixture was filtered and the filtrate was concentrated under reduced pressure to give tert-butyl 4-(3-hydroxy-2-(hydroxymethyl)propyl)piperidine-1-carboxylate (1.1 g, 94.7% yield) as a yellow oil, which was directly used to next step without purification. LC-MS m/z: 259 [M+H−56]$^+$.

Step 4: 4-(3-(methylsulfonyloxy)-2-((methylsulfonyloxy)methyl)propyl)piperidine-1-carboxylate To a stirred solution of tert-butyl 4-(3-hydroxy-2-(hydroxymethyl)propyl)piperidine-1-carboxylate (1.1 g, 4.02 mmol) and TEA (2.6 mL, 20.12 mmol) in DCM (15 mL) was added methanesulfonyl chloride (0.9 mL, 12.07 mmol) at 0° C. After being stirred overnight at room temperature, the reaction mixture was partitioned between DCM and water. The organic layer was dried over anhydrous MgSO$_4$, and concentrated. The residue was purified by silica gel column chromatography (petroleum ether:EtOAc=20:1) to give tert-butyl 4-(3 -(methylsulfonyloxy)-2-((methylsulfonyloxy)methyl)propyl)piperidine-1-carboxylate (800 mg, 46.3% yield) as a colorless oil. LC-MS m/z: 415 [M−15+H]$^+$.

Step 5: 4-((1-benzylazetidin-3-yl)methyl)piperidine

A solution of tert-butyl 4-(3-(methylsulfonyloxy)-2-((methylsulfonyloxy)methyl)propyl)piperidine-1-carboxylate (700 mg, 1.63 mmol), benzylamine (436 mg, 4.07 mmol) and DIPEA (1.1 mL, 6.52 mmol) in acetonitrile (10.0 mL) was stirred at 80° C. overnight. After cooled to rt, the reaction mixture was diluted with DCM and washed with water. The organic layer was dried over anhydrous MgSO$_4$, filtered and concentrated. The residue was purified by silica gel column chromatography (petroleum ether:EtOAc=10:1) to give tert-butyl 4-((1-benzylazetidin-3-yl)methyl)piperidine-1-carboxylate (450 mg, 90.6% yield) as a colorless oil. LC-MS m/z: 330 [M+H−15]$^+$.

Step 6: 4-((1-benzylazetidin-3-yl)methyl)piperidine

A solution of tert-butyl 4-((1-benzylazetidin-3-yl)methyl) piperidine-1-carboxylate (450 mg, 1.31 mmol) in HCl/MeOH (10 mL, 1 M solution) was stirred at rt overnight. The mixture was then concentrated under reduced pressure to give 4-((1-benzylazetidin-3-yl)methyl)piperidine (320 mg, crude) as a white solid, which was directly used to the next reaction without purification. LC-MS m/z: 230 [M+H−15]$^+$.

Step 7: 4-((1-benzylazetidin-3-yl)methyl)-1-(2,2-difluoroethyl)piperidine

A solution of 4-((1-benzylazetidin-3-yl)methyl)piperidine (320 mg, 1.31 mmol), 2,2-difluoroethyl 4-methylbenzenesulfonate (465 mg, 1.96 mmol) and DIPEA (0.87 mL, 5.24 mmol) in acetonitrile (5 mL) was stirred at room temperature overnight. The reaction mixture was diluted with DCM and washed with water. The organic layer was dried over anhydrous MgSO$_4$, filtered and concentrated. The residue was purified by silica gel column chromatography (petroleum ether:EtOAc=1:1) to give 4-((1-benzylazetidin-3-yl) methyl)-1-(2,2-difluoroethyl)piperidine (150 mg, 37.1% yield) as a colorless oil. LC-MS m/z: 309 [M+H]$^+$.

Step 8: 4-(azetidin-3-ylmethyl)-1-(2,2-difluoroethyl) piperidine

To a solution of 4-((1-benzylazetidin-3-yl)methyl)-1-(2,2-difluoroethyl)piperidine (150 mg, 486.37 mmol) in MeOH (3 mL) was added Pd(OH)$_2$ (15 mg, 10% wt) and a drop of acetic acid. The mixture was degassed with N$_2$ and stirred under H$_2$ atmosphere at room temperature overnight. The reaction was filtered through a pad of Celite, and the filtrate was concentrated to give 4-(azetidin-3-ylmethyl)-1-(2,2-difluoroethyl)piperidine (100 mg, 100% yield) as a light yellow oil. LC-MS m/z: 219 [M+H]$^+$.

Intermediate 96

4-(azetidin-3-ylmethyl)morpholine Trifluoroacetate

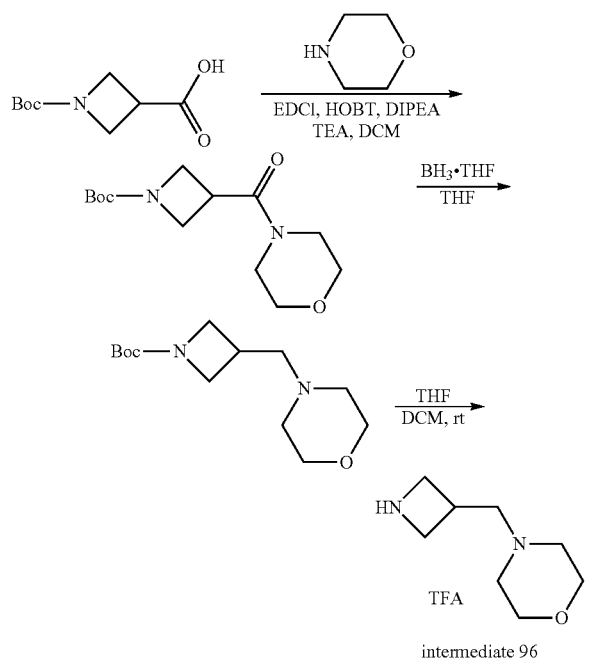

intermediate 96

Step 1:
3-(morpholine-4-carbonyl)-azetidine-1-carboxylic acid tert-butyl ester

To a solution of azetidine-1,3-dicarboxylic acid mono-tert-butyl ester (1 g, 5 mmol) in dry DCM (20 ml) was added EDCI (1.5 g, 7.5 mmol), DIPEA (2.57 g, 20 mmol), HOBt (0.81 g, 6 mmol) and morpholine (0.87 g, 10 mmol) at 0° C. The reaction was stirred at room temperature for 2 hrs. The reaction mixture was diluted with DCM and washed with water and brine. The organic layer was dried over anhydrous Na$_2$SO$_4$ and concentrated. The residue was purified by column chromatography on silica gel (petroleum ether:EtOAc=1:1) to give the titled product (1.15 g, 85.8% yield) as a brown oil. LC-MS m/z: 216 [M+H−56]$^+$.

Step 2: tert-butyl 3-(morpholinomethyl)azetidine-1-carboxylate

To a solution of 3-(morpholine-4-carbonyl)-azetidine-1-carboxylic acid tert-butyl ester (1.28 g, 5 mmol) in dry THF (20 ml) was added borane-tetrahydrofuran complex (15 ml, 15 mmol) at −30° C. The reaction was stirred at rt overnight. MeOH (5 mL) was added to the mixture dropwise at 0° C. and the mixture was stirred at rt for 30 min. The mixture was then concentrated, and the residue was dissolved in EtOH/water (9 mL/1 mL) and stirred at reflux overnight. The mixture was cooled and concentrated. The residue was purified by silica gel column chromatography (DCM:MeOH=1:0 to 60:1) to give the titled product (1.1 g, 90.7% yield) as a colorless oil. LC-MS m/z: 201 [M+H−56]$^+$.

Step 3: 4-(azetidin-3-ylmethyl)-morpholine Trifluoroacetate

To a solution of tent-butyl 3-(morpholinomethyl)azetidine-1-carboxylate (1.1 g, 4.33 mmol) in DCM (20 ml) was added TFA (5 ml) dropwise at 0° C. The reaction was stirred at room temperature for 3 hrs. The mixture was concentrated under vacuum to give a residue, which was co-evaporated with toluene (10 mL×2) to give the titled product (650 mg, 94.4% yield) as a brown oil, which was directly used to the next reaction without purification. LC-MS m/z: 157 [M+H]$^+$.

Intermediate 97

4-(2-(azetidin-3-ylidene)ethyl)morpholine Trifluoroacetate

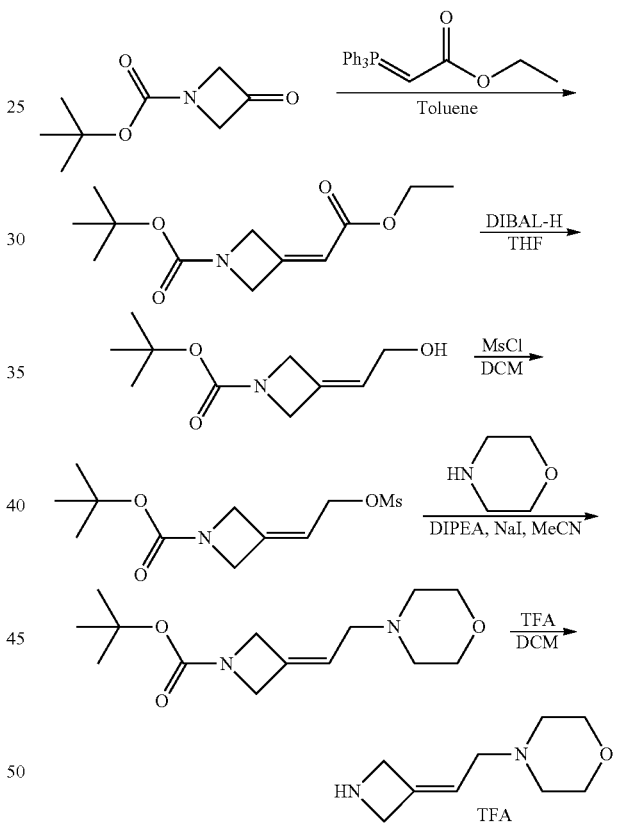

intermediate 97

Step 1: tert-butyl 3-((methoxycarbonyl)amino)azetidine-1-carboxylate

A mixture of tert-butyl 3-oxoazetidine-1-carboxylate (5 g, 29.2 mmol) and ethyl 2-(triphenylphosphoranylidene) acetate (12.21 g, 35.05 mmol) in toluene (50 mL) was stirred at 110° C. for 2 hrs. The solvent was evaporated and the residue was purified by silica gel column chromatography (petroleum ether:EtOAc=100: 1 to 20:1) to give tert-butyl 3-((methoxycarbonyl)amino)azetidine-1-carboxylate (5.2 g, 73.8% yield) as a yellow oil. LC-MS m/z: 243 [M+H]$^+$.

Step 2: tert-butyl 3-(2-hydroxyethylidene)azetidine-1-carboxylate

To a solution of tert-butyl 3-aminoazetidine-1-carboxylate (2 g, 2.90 mmol) in THF (20 mL) was added diisobutyl aluminium hydride (2.9 mL, 2.9 mmol, 1M) dropwised at −75° C. The resulting mixture was stirred at room temperature overnight. The reaction was quenched by addition of MeOH (3 mL). The solvent was evaporated and the residue was purified by silica gel column chromatography (petroleum ether:EtOAc=20:1 to 1:1) to give tert-butyl 3-(2-hydroxyethylidene)azetidine-1-carboxylate (1.05 g, 63.6% yield) as a yellow oil. LC-MS m/z: 144 [M−56+H]⁺.

Step 3: tert-butyl 3-(2-((methylsulfonyl)oxy)ethylidene)azetidine-1-carboxylate To a solution of tert-butyl 3-(2-hydroxyethylidene)azetidine-1-carboxylate (500 mg, 2.51 mmol) in DCM (10 mL) was added TEA (1.02 mL, 7.53 mmol) followed by dropwise addition of a solution of methanesulfonyl chloride (431 mg, 3.76 mmol) at 0° C. The resulting mixture was stirred at room temperature for 2 hrs. The mixture was washed with saturated aqueous NaHCO₃ solution and brine. The organic layer was dried over Na₂SO₄ and concentrated. The residue was purified by silica gel column chromatography (petroleum ether:EtOAc=50:1 to 1:1) to give tert-butyl 3-(2-((methylsulfonyl)oxy)ethylidene)azetidine-1-carboxylate (503 mg, 72.3% yield) as a yellow oil. LC-MS m/z: 223 [M−56+H]⁺.

Step 4: tert-butyl 3-(2-morpholinoethylidene)azetidine-1-carboxylate

To a solution of 3-(2-((methylsulfonyl)oxy)ethylidene)azetidine-1-carboxylate (502 mg, 1.81 mmol) in acetonitrile (20 mL) was added DIPEA (0.98 mL, 5.43 mmol), morpholine (315 mg, 3.62 mmol) and NaI (10 mg, catalytic amount). After the reaction was stirred at 80° C. for 2 hrs, the mixture was concentrated. The residue was partitioned between EtOAc and water. The organic layer was dried over Na₂SO₄ and concentrated. The residue was purified by silica gel chromatography (DCM:MeOH=100:0 to 20:1, v/v) to give tert-butyl 3-(2-morpholinoethylidene)azetidine-1-carboxylate (450 mg, 92.6% yield) as a yellow oil. LC-MS m/z: 214 [M−56+H]⁺.

Step 5: 4-(2-(azetidin-3-ylidene)ethyl)morpholine

To a solution of tert-butyl 3-(2-morpholinoethylidene)azetidine-1-carboxylate (450 mg, 1.68 mmol) in DCM (10 mL) was added TFA (3.5 mL) dropwise at 0° C. The reaction was stirred at room temperature for 3 hrs. The reaction mixture was then concentrated and co-evaporated with toluene (10 mL×2) to give 4-(2-(azetidin-3-ylidene)ethyl)morpholine trifluoroacetate (280 mg, 100% yield) as a brown oil, which was directly used in the next reaction without purification. LC-MS m/z: 169 [M+H]⁺.

The following intermediate was prepared according to procedures similar to that described for Intermediate 97 by using the appropriate starting materials.

| Intermediate # | Structure | LC-MS |
|---|---|---|
| 98 | 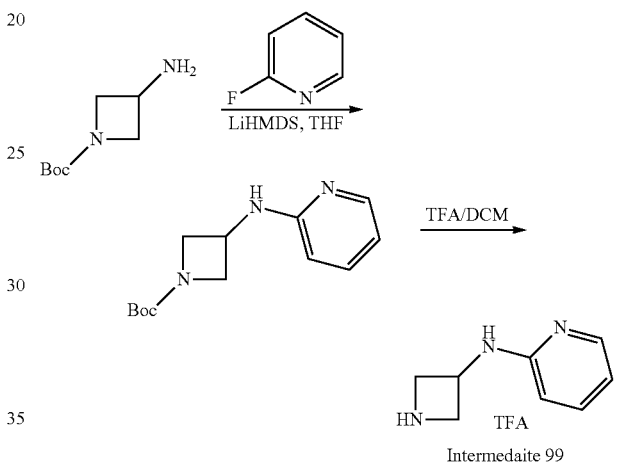 TFA | 232 [M + H]⁺ |

Intermediate 99

N-(azetidin-3-yl)pyridin-2-amine, Trifluoroacetate

Step 1: tert-butyl 3-(pyridin-2-ylamino)azetidine-1-carboxylate

To a solution of 2-fluoropyridine (320 mg, 3.3 mmol.,) and tert-butyl 3-aminoazetidine-1-carboxylate (516 mg, 3.0 mmol.,) in dry THF (10 mL) was added LiHMDS (3.0 mL, 6.0 mmol, 2.0 M solution in THF) at −67° C. The reaction was stirred at room temperature for 1 hour and then at 65° C. overnight. The reaction was diluted with water and extracted with EtOAc (10 mL×2). The organic layers were dried over anhydrous MgSO₄ and concentrated under reduced pressure. The residue was purified by silica gel chromatography (PE:EtOAc=10:1 to 3:1) to give tert-butyl 3-(pyridin-2-ylamino)azetidine-1-carboxylate (350 mg, 46.7% yield) as a light brown oil. LC-MS: m/z=250 [M+H]⁺.

Step 2: N-(azetidin-3-yl)pyridin-2-amine, Trifluoroacetate

To a solution of tert-butyl 3-(pyridin-2-ylamino)azetidine-1-carboxylate (350 mg, 1.4 mmol) in dichloromethane (5 mL) was added TFA (1.6 mL) drop-wise at 0° C. The mixture was then stirred at rt for 3 hrs. The resulting mixture was concentrated under vacuum to give a residue, which was azeotroped with toluene (3 mL×3) to give N-(azetidin-3-yl)

pyridin-2-amine trifluoroacatete (650 mg) as a brown oil, which was directly used to the next reaction without purification. LC-MS: m/z=150 [M+H]$^+$.

Intermediate 100

2-(azetidin-3-yloxy)pyridine Trifluoroacetate

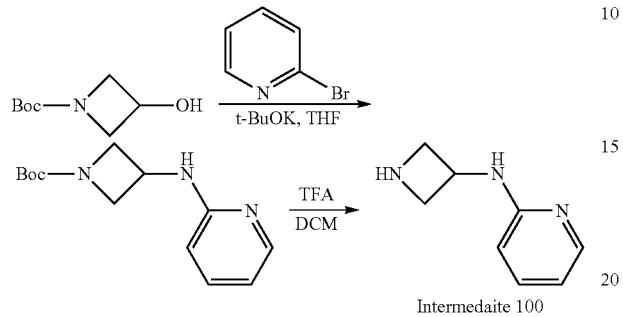

Intermedaite 100

Step 1: tert-butyl 3-(pyridin-2-yloxy)azetidine-1-carboxylate

To a solution of tert-butyl 3-hydroxyazetidine-1-carboxylate (600 mg, 3.5 mmol) in dry THF (10 mL) was added 2-bromopyridine (340 mg, 3.75 mmol) and t-BuOK (1.3 g, 7.0 mmol) at rt. The mixture was stirred at 70° C. for 3 hrs. After the mixture was cooled to rt, water was added slowly, and the mixture was partitioned with EtOAc. The organic layer was washed with brine, dried over anhydrous Na$_2$SO$_4$ and concentrated. The residue was purified by silica gel column chromatography (petroleum ether:EtAOc=50:1 to 10:1) to give tert-butyl 3-(pyridin-2-yloxy)azetidine-1-carboxylate (480 mg, 54.8% yield) as a white solid. LC-MS m/z: 251 [M+H]$^+$.

Step 2: 2-(azetidin-3-yloxy)pyridine Trifluoroacetate

To a solution of tert-butyl 3-(pyridin-2-yloxy)azetidine-1-carboxylate (480 mg, 2.23 mmol) in DCM (6 mL) was added TFA (2 mL) dropwise at 0° C. The reaction was then stirred at rt for 2 hrs. The resulting mixture was concentrated under vacuum to give a residue, which was co-evaporated with toluene to give 2-(azetidin-3-yloxy)pyridine trifluoroacetate (520 mg, 100% yield) as a brown oil, which was directly used to the next reaction without purification. LC-MS m/z: 151 [M+H]$^+$.

Intermediate 101

2-(azetidin-3-ylmethyl)pyridine, Trifluoroacetate

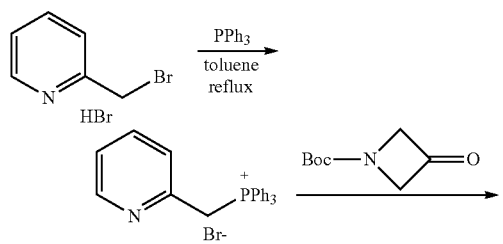

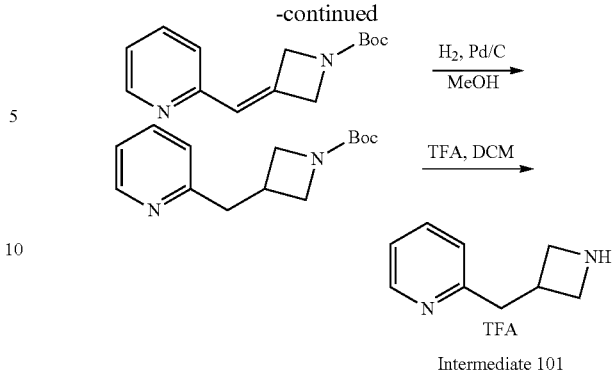

Intermediate 101

Step 1: triphenyl(pyridin-2-ylmethyl)phosphonium bromide

A mixture of 2-(bromomethyl)pyridine hydrobromide (2.0 g, 8.0 mmol) and triphenylphosphine (1.0 mmol) in toluene (20 mL) was stirred at reflux overnight. The reaction mixture was then cooled to room temperature, and the precipitated salt was collected by filtration, washed with cold ethanol and dried to give triphenyl(pyridin-2-ylmethyl)phosphonium bromide (2.6 g, 74.3% yield) as a white solid.

Step 2: tert-butyl 3-(pyridin-2-ylmethylene)azetidine-1-carboxylate

To a cold solution of triphenyl(pyridin-2-ylmethyl)phosphonium bromide (1.5 g, 3.46 mmol) in DMF (10 mL) was added NaH (207.4 mg, 5.18 mmol, 60% suspension in paraffin oil) at 0° C. After the resulting mixture was stirred at 0° C. for 15 minutes, a solution of tert-butyl 3-oxoazetidine-1-carboxylate (800.0 mg, 4.15 mmol) in anhydrous DMF (5 mL) was added and the reaction was stirred at 65° C. overnight. After the reaction was complete, the reaction was quenched with a saturated NH$_4$Cl solution (10 mL) and extracted with EtOAc (50 mL×2). The organic layere were washed with water (20 mL) and brine (15 mL), then dried over anhydrous Na$_2$SO$_4$, filtered and evaporated. This residue was purified by column chromatography on silica gel (PE:EtOAc=5:1) to give tert-butyl 3-(pyridin-2-ylmethylene)azetidine-1-carboxylate (410 mg, 47.8% yield) as a white solid. LC-MS: m/z=248 [M+H]$^+$.

Step 3: tert-butyl 3-(pyridin-2-ylmethyl)azetidine-1-carboxylate

A solution of tert-butyl 3-(pyridin-2-ylmethylene)azetidine-1-carboxylate (410 mg, 1.65 mmol) in methanol (5 mL) was degassed three times with, and Pd/C (50 mg, 10% wt) was added. The mixture was degassed again and stirred under H$_2$ atmosphere at room temperature for 30 min The reaction was filtered through Celite, and the filtrate was concentrated to give tent-butyl 3-(pyridin-2-ylmethyl)azetidine-1-carboxylate (340 mg, 83.1% yield) as a colorless oil. LC-MS: m/z=249 [M+H]$^+$.

Step 4: 2-(azetidin-3-ylmethyl)pyridine

To a mixture of tert-butyl 3-(pyridin-2-ylmethyl)azetidine-1-carboxylate (340 mg, 1.37 mmol) in dichloromethane (1 mL) was added trifluoroacetic acid (1 mL) drop-wise at 0° C. The reaction was stirred at room temperature for 1 hr. The mixture was concentrated under reduced pressure to give 2-(azetidin-3-ylmethyl)pyridine (203 mg, 99.9% yield) as a yellow syrup, which was directly used to the next reaction without purification. LC-MS: m/z=149 [M+H]+.

Intermediate 102

5-(azetidin-3-ylmethyl)-2-methylpyridine Trifluoroacetate

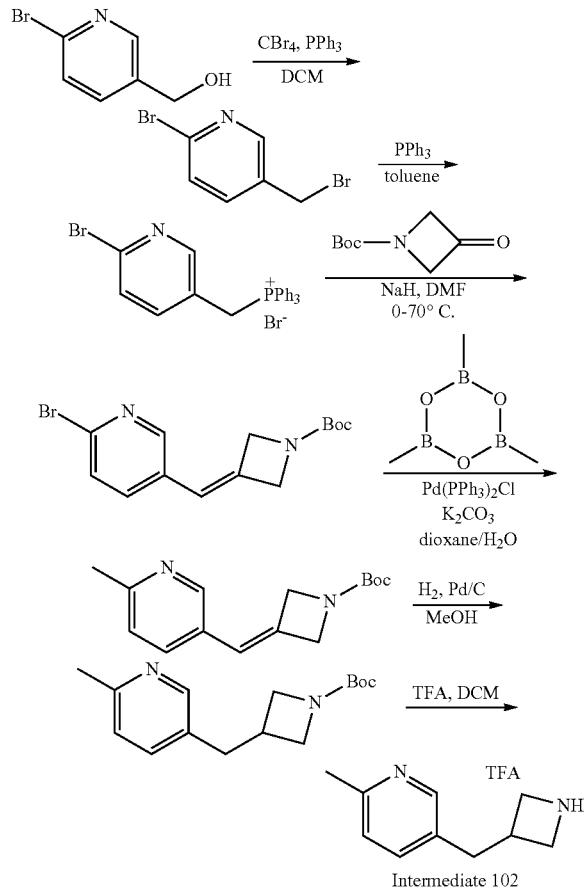

Step 1: 2-bromo-5-(bromomethyl)pyridine

To a solution of (6-bromopyridin-3-yl)methanol (3.0 g, 16.0 mmol) in DCM (60 mL) was added triphenylphosphine (4.82 g, 18.4 mmol). After addition was completed, the mixture was degassed three times under N₂. Then a solution of CBr₄ (5.84 g, 17.6 mmol) in DCM (15 mL) was added dropwise at 0° C., and the reaction was stirred at room temperature overnight. The mixture was concentrated under reduced pressure to give a crude product, which was purified by silica gel column chromatography (petroleum ether:ethyl acetate=50:1 to 15:1) to give 2-bromo-5-(bromomethyl) pyridine (3.46 g, 87.0% yield) as a white solid. LC-MS: m/z 252 [M+H]+.

Step 2: ((6-bromopyridin-3-yl)methyl)triphenylphosphonium bromide

To a solution of 2-bromo-5-(bromomethyl)pyridine (3.7 g, 14.7 mmol) in toluene (30 mL) was added triphenylphos- phine (5.02 g, 19.2 mmol). The reaction mixture was degassed three times under N₂ and stirred at 119° C. for 2 hrs. The mixture was filtrated, and the residue was washed with hexane and filtrated again to give ((6-bromopyridin-3-yl)methyl)triphenylphosphonium bromide (7.3 g, 96.5% yield) as a white solid. LC-MS: m/z 433 [M+H]+.

Step 3: tert-butyl 3-((6-bromopyridin-3-yl)methylene)azetidine-1-carboxylate

To a solution of ((6-bromopyridin-3-yl)methyl)triphenyl- phosphonium bromide (3.3 g, 6.44 mmol) in DMF (60 mL) was added sodium hydride (515 mg, 12.9 mmol, 60% wt in paraffin) in portions at 0° C. After addition was completed, the mixture was stirred at room temperature for 2 hrs. Then a solution of tert-butyl 3-oxoazetidine-1-carboxylate (1.0 g, 5.85 mmol) in DMF (5 mL) was added dropwise at 0° C., and the reaction was stirred at 70° C. overnight. The mixture was cooled to room temperature and diluted with EtOAc. Then the reaction was quenched with saturated aqueous NH₄Cl and extracted with ethyl acetate. The combined organic layers were washed with brine, dried over anhydrous Na₂SO₄ and concentrated under reduced pressure to give a crude product, which was purified by silica gel column chromatography (petroleum ether:ethyl acetate=15:1 to 5:1) to give tert-butyl 3-((6-bromopyridin-3-yl)methylene)azeti- dine-1-carboxylate (789 mg, 41.5% yield) as a white solid. LC-MS: m/z 325 [M+H]+.

Step 4: tert-butyl 3-((6-methylpyridin-3-yl)methylene)azetidine-1-carboxylate

To a solution of 3-((6-bromopyridin-3-yl)methylene)aze- tidine-1-carboxylate (750 mg, 2.31 mmol) in dioxane (18 mL) and H₂O (2 mL) was added K₂CO₃ (956 mg, 6.93 mmol). After addition was completed, the mixture was degassed three times under N₂. Then bis(triphenylphos- phine)palladium(II) chloride (810 mg, 1.16 mmol) and 2,4,6-trimethyl-1,3,5,2,4,6-trioxatriborinane (0.49 mL, 3.47 mmol) was added. The reaction was degassed twice again with N₂ and stirred at 100° C. overnight. The mixture was concentrated under reduced pressure to give a crude product, which was purified by silica gel column chromatography (petroleum ether:ethyl acetate=15:1 to 3:1) to give tert-butyl 3-((6-methylpyridin-3-yl)methylene)azetidine-1-carboxy- late (180 mg, 30.0% yield) as a yellow solid. LC-MS: m/z 261 [M+H]+.

Step 5: tert-butyl 3-((6-methylpyridin-3-yl)methyl) azetidine-1-carboxylatee

A solution of tert-butyl 3-((6-methylpyridin-3-yl)methyl- ene)azetidine-1-carboxylate (220 mg, 0.846 mmol) in methanol (10 mL) was degassed under N₂ atmosphere three times, and Pd/C (130 mg, 5% wt) was added. The mixture was degassed again and stirred under H₂ atmosphere at room temperature overnight. The mixture was filtered through Celite, and the filtrate was concentrated to give tert-butyl 3-((6-methylpyridin-3-yl)methyl)azetidine-1-carboxylatee (203 mg, 91.6% yield) as a colorless oil. LC-MS: m/z 163 [M+H]+.

Step 6: 5-(azetidin-3-ylmethyl)-2-methylpyridine

To a solution of tert-butyl 3-((6-methylpyridin-3-yl) methyl)azetidine-1-carboxylatee (200 mg, 0.763 mmol) in DCM (1 mL) was added trifluoroacetic acid (2 mL) dropwise at 0° C. The reaction was stirred at room temperature for 0.5 hr. The mixture was concentrated under reduced pressure to give 5-(azetidin-3-ylmethyl)-2-methylpyridine trifluoroacetate (350 mg, 100% yield) as a yellow syrup, which was directly used to the next reaction without further purification. LC-MS: m/z 163 [M+1]+.

Intermediate 103

2-(2-(azetidin-3-yl)ethyl)pyridine Trifluoroacetate

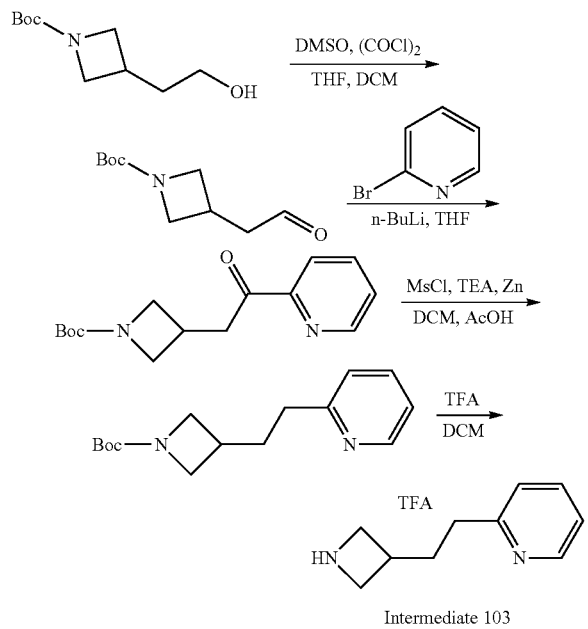

Intermediate 103

Step 1: tert-butyl 3-(2-oxoethyl)azetidine-1-carboxylate

To a mixture of DMSO (3.54 g, 45.23 mmol) in DCM (20 ml) was added oxalyl chloride (3.83 g. 30.2 mmol) at −78° C. After the mixture was stirred at −78° C. for 1 hr, tert-butyl 3-(2-hydroxyethyl)azetidine-1-carboxylate (3 g, 15.08 mmol) and TEA (2.08 g, 20.08 mmol) were added. The resulting mixture was warmed to rt and stirred for 30 min. The reaction mixture was diluted with EtOAc, washed with water and saturated aqueous NaHCO$_3$ solution. The organic layer was dried over anhydrous Na$_2$SO$_4$ and concentrated to give tert-butyl 3-(2-oxoethyl)azetidine-1-carboxylate (3 g, 98.8% yield) as a colorless oil. LC-MS m/z: 144 [M+H−56]+.

Step 2: tert-butyl 3-(2-hydroxy-2-(pyridin-2-yl)ethyl)azetidine-1-carboxylate

To a solution of 2-bromo-pyridine (1 g, 6.33 mmol) in THF (15 mL) was added n-BuLi (4.43 ml, 7.09 mmol) at −78° C. After the mixture was stirred at this temperature for 30 min, tert-butyl 3-(2-oxoethyl)azetidine-1-carboxylate (1.5 g, 7.5 mmol) was added. The reaction was warmed to rt and stirred for 2 hrs. The reaction was quenched by addition of NH$_4$Cl solution and diluted with EtOAc. The organic layer was washed with water, dried over Na$_2$SO$_4$ and concentrated. The residue was purified by silica gel column chromatography (petroleum ether:acetone=1:1) to give tert-butyl 3-(2-hydroxy-2-(pyridin-2-yl)ethyl)azetidine-1-carboxylate (780 m g, 37.3% yield) as a yellow oil. LC-MS m/z: 223 [M+H−56]+.

Step 3: tert-butyl 3-(2-(pyridin-2-yl)ethyl)azetidine-1-carboxylate

To a mixture of tert-butyl 3-(2-hydroxy-2-(pyridin-2-yl)ethyl)azetidine-1-carboxylate (680 mg, 2.44 mmol) in DCM (10 mL) added methanesulfonyl chloride (865 mg, 5.48 mmol) and TEA (493 mg, 4.88 mmol) at 0° C. After the reaction was stirred at room temperature for 2 hrs, the mixture was concentrated. The residue was dissolved in HOAc (8 mL) and Zn powder (957 mg, 14.64 mmol) was added. The reaction was stirred at 40° C. for 3 hrs. The reaction mixture was concentrated and the residue was partitioned between EtOAc and water. The organic layer was dried over anhydrous Na$_2$SO$_4$ and concentrated. The residue was purified by silica gel column chromatography (petroleum ether:EtOAc=5:1) to give tert-butyl 3-(2-(pyridin-2-yl)ethyl)azetidine-1-carboxylate (220 m g, 34.4% yield) as a yellow oil. LC-MS m/z: 207 [M+H−56]+.

Step 4: 2-(2-(azetidin-3-yl)ethyl)pyridine Trifluoroacetate

To a solution of tert-butyl 3-(2-(pyridin-2-yl)ethyl)azetidine-1-carboxylate (850 mg, 2.8 mmol) in DCM (9 ml) was added TFA (3 ml) dropwise at 0° C. The reaction was stirred at room temperature for 2 hrs. The resulting mixture was concentrated and co-evaporated with toluene (10 mL×2) to give 2-(2-(azetidin-3-yl)ethyl)pyridine trifluoroacetate (450 mg, 99.7% yield) as a brown oil, which was directly used to the next reaction without purification. LC-MS m/z: 163 [M+H]+.

Intermediate 104

(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(((allyloxy)carbonyl)(ethyl)amino)ethyl)azetidine-1-carboxylate

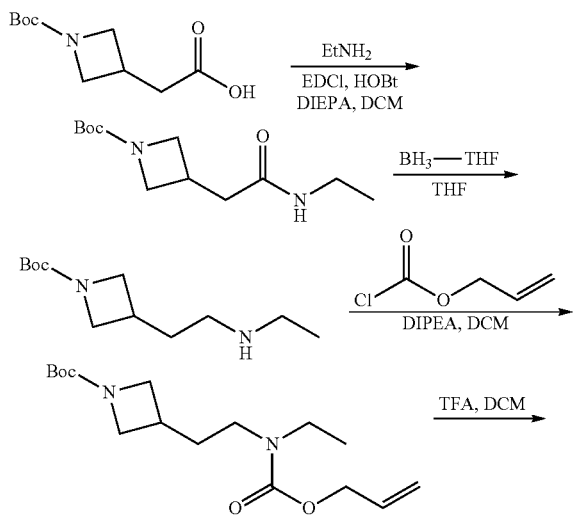

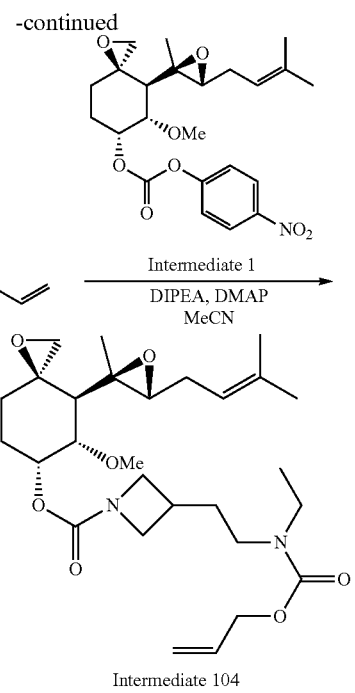

Intermediate 104

Step 1: tert-butyl 3-(2-(ethylamino)-2-oxoethyl)azetidine-1-carboxylate

To a mixture of 2-(1-(tert-butoxycarbonyl)azetidin-3-yl)acetic acid (2 g, 9.29 mmol) in dichloromethane (40 mL) was sequentially added 1-(3-dimethylaminopropyl)-3-ethyl-carbodiimide, hydrochloride (2.67 g, 13.94 mmol) and 1-hydroxybenzotriazole (1.51 g, 11.15 mmol). Ethyldiisopropylamine (6.40 mL, 37.17 mmol) was then added drop-wise. The mixture was stirred for 10 min and ethylamine, hydrochloride (1.14 g, 13.94 mmol) was added. The reaction was stirred at room temperature overnight. The reaction was diluted with dichloromethane (50 mL×2) and washed with water (30 mL) and brine (30 mL), dried over $Na_2SO_4$ and concentrated under reduced pressure to give a residue. The residue was purified by silica gel chromatography (dichloromethane:methanol=100:0 to 80:1) to give tert-butyl 3-(2-(ethylamino)-2-oxoethyl)azetidine-1-carboxylate (1.8 g) as a yellow solid. LC-MS: m/z=187 [M+H−56]$^+$. $^1$H NMR (400 MHz, DMSO) δ 7.86 (s, 1H), 3.90 (s, 2H), 3.50 (s, 2H), 3.04 (m, 2H), 2.80-2.69 (m, 1H), 2.34 (d, J=7.8 Hz, 2H), 1.37 (s, 9H), 0.99 (m, 3H).

Step 2: tert-butyl 3-(2-(ethylamino)ethyl)azetidine-1-carboxylate

To a solution of tert-butyl 3-(2-(ethylamino)-2-oxoethyl)azetidine-1-carboxylate (1.7 g, 7.02 mmol) in THF (anhydrous, 20 mL) was added a solution of borane-tetrahydrofuran complex (24.56 mL, 24.56 mmol, 1M in THF) drop-wise at −10° C. over 30 min. The reaction was stirred at room temperature overnight. To the reaction mixture was then added methanol (10 mL) drop-wise at 0° C. After addition was complete, the mixture was stirred at room temperature for 30 min. The mixture was concentrated under vacuum to give a yellow reside, which was dissolved in ethanol/water (9 mL/1 mL) and stirred at reflux overnight. The mixture was concentrated under vacuum to give a residue, which was purified by silica gel chromatography (dichloromethane:methanol=10:0 to 10:1) to give tert-butyl 3-(2-(ethylamino)ethyl)azetidine-1-carboxylatee (1.0 g) as a colorless oil. LC-MS: m/z=173 [M+H−56]$^+$.

Step 3: tert-butyl 3-(2-(((allyloxy)carbonyl)(ethyl)amino)ethyl)azetidine-1-carboxylate To a solution of tert-butyl 3-(2-(ethylamino)ethyl)azetidine-1-carboxylate (1 g, 4.38 mmol) in dichloromethane (10 mL) was added ethyldiisopropylamine (4.5 mL, 26.3 mmol) followed by drop-wise addition of allyl carbonochloridate (1.40 mL, 13.14 mmol) at 0° C. The reaction was stirred at room temperature for 1 h, and the reaction mixture was then diluted with dichloromethane (40 mL). The dichloromethane solution was washed with water (20 mL) and brine (20 mL), dried over $Na_2SO_4$ and concentrated under reduced pressure to give a residue, which was purified by silica gel chromatography (dichloromethane:methanol=100:0 to 100:1) to give tert-butyl 3-(2-(((allyloxy)carbonyl)(ethyl)amino)ethyl)azetidine-1-carboxylate (1.3 g) as a brown oil. LC-MS: m/z=257 [M+H]$^+$. $^1$H NMR (400 MHz, DMSO) δ 6.00-5.85 (m, 1H), 5.27 (d, J=17.3 Hz, 1H), 5.18 (m, 1H), 4.51 (d, J=4.7 Hz, 2H), 3.88 (s, 2H), 3.46 (s, 2H), 3.25-3.10 (m, 4H), 2.43 (m, 1H), 1.74 (m, 2H), 1.37 (s, 9H), 1.05 (s, 3H).

Step 4: allyl (2-(azetidin-3-yl)ethyl)(ethyl)carbamate, Trifluoroacetate

To a mixture of tert-butyl 3-(2-(((allyloxy)carbonyl)(ethyl)amino)ethyl)azetidine-1-carboxylate (700 mg, 2.24 mmol) in dichloromethane (10 mL) was added trifluoroacetic acid (1.16 mL, 15.69 mmol) drop-wise. The resulting mixture was stirred at 30° C. overnight. The mixture was concentrated under reduced pressure to give allyl (2-(azetidin-3-yl)ethyl)(ethyl)carbamate, trifluoroacetate (420 mg) as a brown oil, which was directly used in the next reaction without purification. LC-MS: m/z=213 [M+H]$^+$. $^1$H NMR (400 MHz, DMSO) δ 5.93 (m, 1H), 5.24 (m, 2H), 4.52 (d, J=4.6 Hz, 2H), 4.03-3.89 (m, 2H), 3.71-3.56 (m, 2H), 3.38-3.01 (m, 4H), 2.80-2.64 (m, 1H), 1.80 (m, 2H), 1.06 (s, 3H).

Step 5: (3R,4S,5S,6R)-5-methoxy-4-((2R,3R)-2-methyl-3-(3-methylbut-2-en-1-yl)oxiran-2-yl)-1-oxaspiro[2.5]octan-6-yl3-(2-(((allyloxy)carbonyl)(ethyl)amino)ethyl)azetidine-1-carboxylate To a mixture of allyl (2-(azetidin-3-yl)ethyl)(ethyl)carbamate (420 mg, 1.98 mmol) in acetonitrile (10 mL) was added ethyldiisopropylamine (0.58 mL, 3.35 mmol) drop-wise at 0° C., and the mixture was stirred at 0° C. for 10 min. Intermediate 1 (500 mg, 1.12 mmol) and 4-dimethylaminopyridine (50 mg) was added. After addition was complete, the reaction was stirred at room temperature overnight under a $N_2$ atmosphere. The mixture was concentrated under vacuum to remove the solvent while keeping the temperature below 40° C. The residue was washed with dichloromethane (50 mL×2), and the combined dichloromethane washes were washed with brine (30 mL), dried over $Na_2SO_4$, filtered and concentrated to yield a yellow oil, which was purified by silica gel chromatography (dichloromethane:methanol=100:0 to 80:1) to give (3R,4S,5S,6R)-5-methoxy-4-((2R,3R)-2-methyl-3-(3-methylbut-2-en-1-yl)oxiran-2-yl)-1-oxaspiro[2.5]octan-6-yl3-(2-(((allyloxy)carbonyl)(ethyl)amino)ethyl)azetidine-1-carboxylate (500 mg) as brown oil. LC-MS: m/z=521 [M+H]$^+$.

The following intermediates were prepared according to procedures similar to that described for Intermediate 104 by using corresponding intermediates.

| Intermediate # | Structure | LC-MS |
|---|---|---|
| 105 | 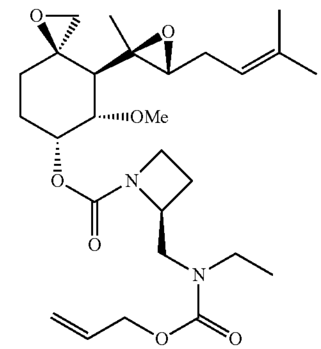 [SMILES: C=CCOC(=O)N(CC)C[C@@H]1CCN1C(=O)O[C@@H]1CC[C@]2(CO2)[C@@H]([C@@]2(C)O[C@@H]2CC=C(C)C)[C@@H]1OC] | 507 [M + H]+ |
| 106 | 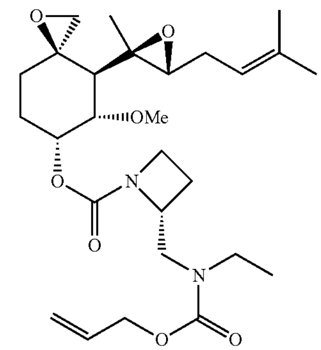 [SMILES: C=CCOC(=O)N(CC)C[C@H]1CCN1C(=O)O[C@@H]1CC[C@]2(CO2)[C@@H]([C@@]2(C)O[C@@H]2CC=C(C)C)[C@@H]1OC] | 507 [M + H]+ |
| 107 | | 535 [M + H]+ |
Intermediate 108
1-allyl 4-(1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl) piperazine-1,4-dicarboxylate
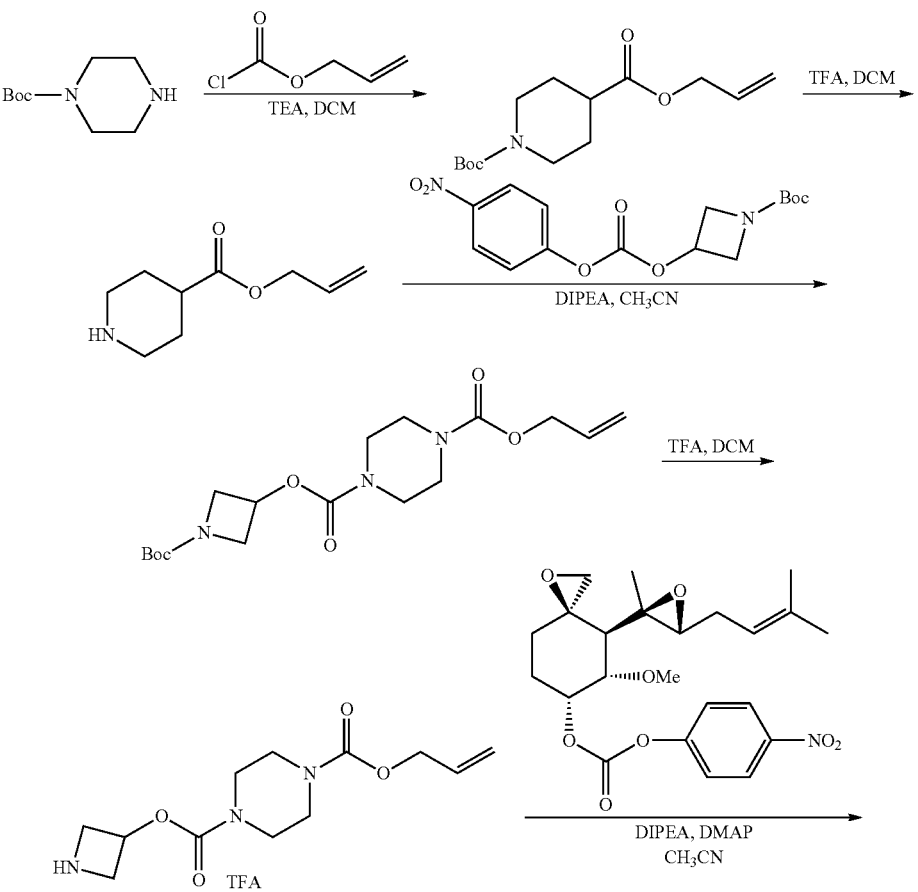

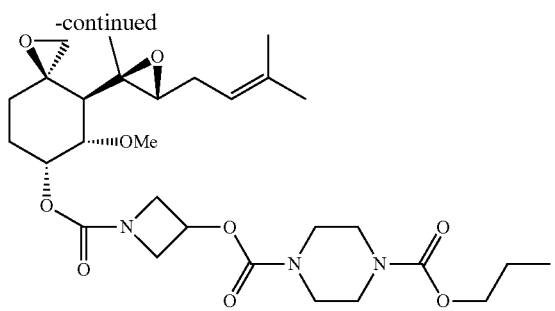

Intermediate 108

Step 1: 1-allyl 4-tert-butyl piperazine-1,4-dicarboxylate

To a solution of tert-butyl piperazine-1-carboxylate (2 g, 10.75 mmol) in DCM (30 mL) was added allyl chloroformate (3.87 g, 32.26 mmol) and DIPEA (9.25 ml, 53.76 mmol) at 0° C. The reaction was stirred at rt overnight. The mixture was washed with water. The organic layer was dried over anhydrous $Na_2SO_4$, filtered and concentrated. The residue was purified by silica gel column chromatography (petroleum ether:acetone=30:1~5:1) to give 1-allyl 4-tert-butyl piperazine-1,4-dicarboxylate (1.5 g, 51.7% yield) as a colourless oil. LC-MS m/z: 215 $[M+H-56]^+$.

Step 2: allyl piperazine-1-carboxylate

To a solution of 1-allyl 4-tert-butyl piperazine-1,4-dicarboxylate (1.5 g, 5.56 mmol) in DCM (9 ml) was added TFA (3 ml) dropwise at 0° C. After the reaction was stirred at rt for 3 hrs, the mixture was concentrated and the residue was co-evaporated with toluene (10 mL×2) to give allyl piperazine-1-carboxylate trifluoroacetate (2.6 g, 100% yield) as a brown oil, which was directly used to the next reaction without purification. LC-MS m/z: 171 $[M+H]^+$.

Step 3: 1-allyl 4-(1-(tert-butoxycarbonyl)azetidin-3-yl) piperazine-1,4-dicarboxylate To a solution of tert-butyl 3-(((4-nitrophenoxy)carbonyl)oxy)azetidine-1-carboxylate (2.6 g, 5.56 mmol) in acetonitrile (20 ml) was added DIPEA (2.9 ml, 16.68 mmol) and allyl piperazine-1-carboxylate (970 mg, 2.87 mmol) at 0° C. The reaction was stirred at reflux overnight. The reaction mixture was then cooled, diluted with DCM, and washed with $NH_4OAc$ buffer (pH=4.0, 20 mL×2) and 5% $NaHCO_3$ solution (20 mL). The organic layer was dried over anhydrous $Na_2SO_4$, filtered and concentrated. The residue was purified by silica gel column chromatography (DCM:MeOH=30:1) to give 1-allyl 4-(1-(tert butoxycarbonyl)azetidin-3-yl) piperazine-1,4-dicarboxylate (470 mg, 44.3% yield) as a colourless oil. LC-MS m/z: 315 $[M+H-56]^+$.

Step 4: 1-allyl 4-azetidin-3-yl piperazine-1,4-dicarboxylate

To a solution of 1-allyl 4-(1-(tert-butoxycarbonyl)azetidin-3-yl) piperazine-1,4-dicarboxylate (430 mg, 1.16 mmol) in DCM (9 ml) was added TFA (3 ml) dropwise at 0° C. The reaction was stirred at room temperture for 3 hrs. The mixture was concentrated and the residue was co-evaporated with toluene (10 mL×2) to give 1-allyl 4-azetidin-3-yl piperazine-1,4-dicarboxylate trifluoroacetate (650 mg, 100% yield) as a brown oil, which was directly used to the next reaction without purification. LC-MS m/z: 271 $[M+H]^+$.

Step 5: 1-allyl 4-(1-((((3R,4S,5S,6R)-5-methoxy-4-((2R,3R)-2-methyl-3-(3-methylbut-2-en-1-yl)oxiran-2-yl)-1-oxaspiro[2.5]octan-6-yl)oxy)carbonyl)azetidin-3-yl)piperazine-1,4-dicarboxylate To a mixture of 1-allyl 4-azetidin-3-yl piperazine-1,4-dicarboxylate (650 mg, 1.16 mmol) in acetonitrile (20 ml) was added DIPEA (0.6 ml, 3.48 mmol), and (3R,4S,5S,6R)-5-methoxy-4-((2R,3R)-2-methyl-3-(3-methylbut-2-en-1-yl)oxiran-2-yl)-1-oxaspiro[2.5]octan-6-yl (4-nitrophenyl) carbonate (500 mg, 1.12 mmol) in portions at 0° C. After addition was completed, the reaction was stirred at room temperture overnight under $N_2$ atmosphere. The mixture was diluted with DCM and washed with $NH_4OAc$ buffer (pH=4.0, 20 mL×2) and 5% $NaHCO_3$ solution (20 mL). The organic layer was dried over anhydrous $Na_2SO_4$, filtered and concentrated. The residue was purified by silica gel column chromatography (DCM:MeOH=20:1 to 10:1) to give the titled product (600 mg, 89.5% yield) as a foam-solid. LC-MS m/z: 578 $[M+H]^+$.

Example 1

(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-morpholinoethyl)azetidine-1-carboxylate

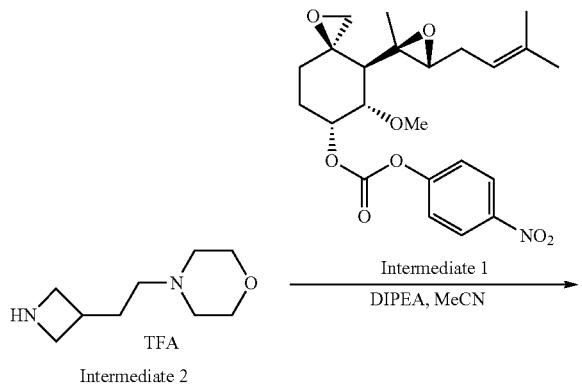

-continued

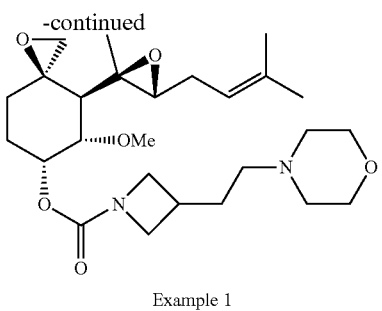

Example 1

To a mixture of 4-(2-(azetidin-3-yl)ethyl)morpholine, trifluoroacetate (2.33 g, 3.7 mmol) in CH₃CN (150 mL) was added DIPEA (2.9 mL, 17 mmol) drop-wise at 0-5° C. The mixture was then stirred at 0-5° C. for 10 min, and carbonate Intermediate 1 (1.3 g, 2.9 mmol) was added to the mixture in portions at 0° C. under a N₂ atmosphere. The reaction mixture was stirred at 25° C. for 16 hrs. TLC (PE:EtOAc=3:1) showed that the reaction was complete. The solvent was removed under vacuum below 40° C. The residue was diluted with DCM (60 mL), and the DCM solution was washed with ammonium acetate buffer (pH~4, 15 mL×2). The combined aqueous layers were back-extracted with DCM (20 mL×2). The combined organic layers were washed with aq. NaHCO₃ solution (15 mL×2, 5% wt), dried over Na₂SO₄ and concentrated. Purification by silica gel column chromatography (DCM:MeOH=100:0~60:1), followed by preparative HPLC (Method A, H₂O (0.1% FA)/CH₃CN) gave the title compound (1.15 g) as a light yellow syrup. LC-MS: m/z=479 [M+H]⁺; ¹H-NMR (400 MHz, CDCl₃) δ 5.43 (br, 1H), 5.13 (t, J=7.6 Hz, 1H), 3.87-4.15 (m, 2H), 3.63-3.65 (m, 4H), 3.52-3.56 (m, 3H), 3.49 (s, 3H), 2.90 (d, J=4.4 Hz, 1H), 2.46-2.54 (m, 3H), 2.19-2.36 (m, 7H), 1.97-2.13 (m, 2H), 1.78-1.89 (m, 5H), 1.73 (s, 3H), 1.62 (s, 3H), 1.13 (s, 3H), 0.99 (d, J=13.6 Hz, 1H).

The following examples were prepared according to procedures similar to that described for Example 1 by using the corresponding intermediates.

| Ex. | Int. | Structure | LC-MS | H-NMR (400 MHz, CDCl₃) |
|---|---|---|---|---|
| 2 | 3 | 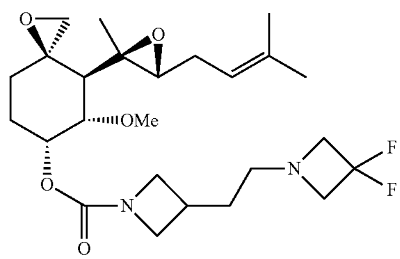 [SMILES: CO[C@@H]1[C@H](OC(=O)N2CC(CCN3CC(F)(F)C3)C2)CC[C@]2(CO2)[C@H]1[C@@]1(C)O[C@@H]1CC=C(C)C] | 485 [M + H]⁺ | 5.44 (s, 1H), 5.11-5.15 (m, 1H), 3.97-4.05 (m, 2H), 3.48-3.60 (m, 7H), 3.38 (s, 3H), 2.91 (d, J = 4.4 Hz, 1H), 2.46-2.53 (m, 5H), 2.25-2.32 (m, 1H), 2.05-2.12 (m, 1H), 1.94-2.02 (m, 1H), 1.84-1.87 (m, 1H), 1.72-1.80 (m, 2H), 1.67 (s, 3H), 1.58 (s, 5H), 1.13 (s, 3H), 0.99 (d, J = 10.8 Hz, 1H) |
| 3 | 4 | 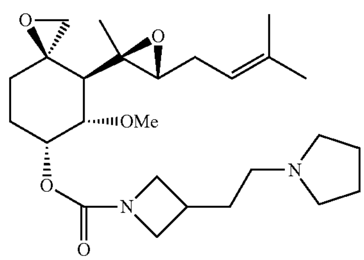 [SMILES: CO[C@@H]1[C@H](OC(=O)N2CC(CCN3CCCC3)C2)CC[C@]2(CO2)[C@H]1[C@@]1(C)O[C@@H]1CC=C(C)C] | 462 [M + H]⁺ | 5.45 (s, 1H), 5.13-5.12 (t, 1H), 4.01-3.97 (m, 2H), 3.57-3.52 (m, 3H), 3.38 (s, 3H), 3.25-3.14 (m, 4H), 2.91-2.90 (m, 3H), 2.52-2.48 (m, 4H), 2.11-2.06 (m, 1H), 2.01-1.96 (m, 10H), 1.84-1.80 (d, J = 16 Hz, 1H), 1.79-1.77 (m, 2H), 1.68 (s, 3H), 1.12 (s, 3H), 1.01-0.97 (d, J = 16 Hz, 1H) |
| 4 | 5 | 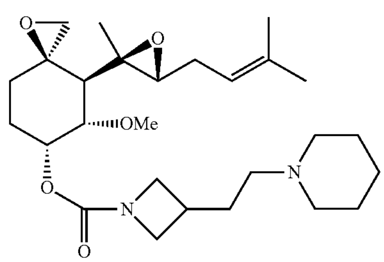 [SMILES: CO[C@@H]1[C@H](OC(=O)N2CC(CCN3CCCCC3)C2)CC[C@]2(CO2)[C@H]1[C@@]1(C)O[C@@H]1CC=C(C)C] | 477 [M + 1]⁺ | 5.53 (s, 1H), 5.20-5.24 (m, 1H), 4.06-4.12 (m, 2H), 3.60-3.69 (m, 3H), 3.46 (s, 3H), 2.51-3.00 (m,10H), 2.34-2.40 (m, 1H), 2.14-2.21 (m, 1H), 1.99-2.11 (m, 3H), 1.92-1.96 (m, 1H), 1.83-1.88 (m, 6H), 1.76 (s, 3H), 1.67 (s, 3H), 1.60 (s, 2H), 1.21 (s, 3H), 1.07 (d, J = 4.0 Hz, 1H) |
| 5 | 6 | 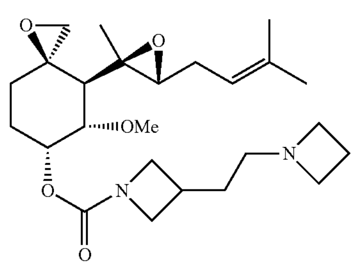 [SMILES: CO[C@@H]1[C@H](OC(=O)N2CC(CCN3CCC3)C2)CC[C@]2(CO2)[C@H]1[C@@]1(C)O[C@@H]1CC=C(C)C] | 449 [M + H]⁺ | 5.28 (s, 1H), 5.19 (m, 1H), 3.92-3.96 (m, 3H), 3.51-3.60 (m, 9H), 3.31 (s, 3H), 2.85 (d, J = 4.4 Hz, 1H), 2.55-2.58 (m, 2H), 2.18 (m, 2H), 1.93-2.05 (m, 4H), 1.95-1.98 (m, 1H), 1.68-1.79 (m, 5H), 1.54-1.60 (m, 4H), 1.57 (m, 3H), 1.08 (d, J = 6.8 Hz, 3H), 1.00 (d, J = 6.8 Hz, 1H) |

-continued

| Ex. | Int. | Structure | LC-MS | H-NMR (400 MHz, CDCl$_3$) |
|---|---|---|---|---|
| 6 | 7 | 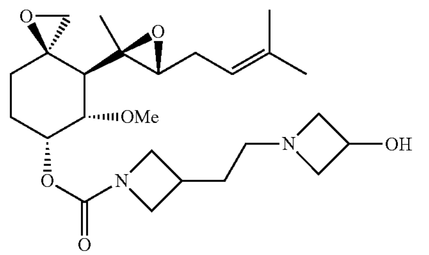 [SMILES: CO[C@@H]1[C@H](OC(=O)N2CC(CCN3CC(O)C3)C2)CC[C@]2(CO2)[C@H]1[C@@]1(C)O[C@@H]1CC=C(C)C] | 465 [M + H]$^+$ | 5.57 (s, 1H), 5.18-5.22 (t, 1H), 4.52 (br, 1H), 3.96-4.32 (m, 6H), 3.63-3.71 (m, 3H), 3.46 (s, 3H), 2.86-3.07 (m, 3H), 2.58-2.63 (m, 3H), 2.33-2.40 (m, 1H), 2.18-2.22 (m, 1H), 2.03-2.08 (m, 1H), 1.81-1.98 (m, 5H), 1.76 (s, 3H), 1.67 (s, 3H), 1.22 (s, 3H), 1.07-1.10 (d, J = 11.2 Hz, 1H) |
| 7 | 8 | 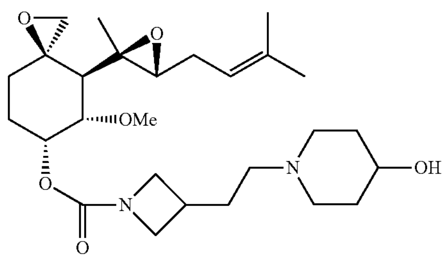 [SMILES: CO[C@@H]1[C@H](OC(=O)N2CC(CCN3CCC(O)CC3)C2)CC[C@]2(CO2)[C@H]1[C@@]1(C)O[C@@H]1CC=C(C)C] | 493 [M + H]$^+$ | 5.44 (s, 1H), 5.14 (t, J = 7.3 Hz, 1H), 3.98 (s, 2H), 3.78-3.50 (m, 4H), 3.39 (d, J = 8.8 Hz, 3H), 2.88 (t, J = 18.0 Hz, 3H), 2.55-2.44 (m, 3H), 2.44-2.20 (m, 5H), 2.09 (dt, J = 14.7, 7.4 Hz, 1H), 1.99 (td, J = 13.5, 4.3 Hz, 3H), 1.90-1.73 (m, 5H), 1.68 (s, 3H), 1.59 (s, 5H), 1.13 (s, 3H), 0.99 (d, J = 13.9 Hz, 1H) |
| 8 | 9 | 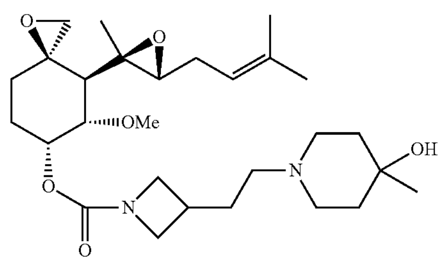 [SMILES: CO[C@@H]1[C@H](OC(=O)N2CC(CCN3CCC(C)(O)CC3)C2)CC[C@]2(CO2)[C@H]1[C@@]1(C)O[C@@H]1CC=C(C)C] | 507 [M + H]$^+$ | 5.44 (s, 1H), 5.14 (s, 1H), 3.98 (s, 2H), 3.54 (d, J = 9.5 Hz, 3H), 3.38 (s, 3H), 2.91 (d, J = 3.7 Hz, 1H), 2.61-2.42 (m, 5H), 2.34-2.25 (m, 2H), 2.13-1.74 (m, 9H), 1.67 (s, 3H), 1.59 (s, 5H), 1.19 (s, 3H), 1.13 (s, 3H), 0.99 (d, J = 13.0 Hz, 1H). |
| 9 | 10 | 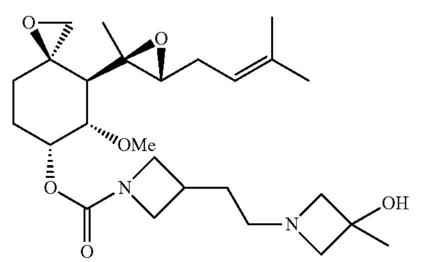 [SMILES: CO[C@@H]1[C@H](OC(=O)N2CC(CCN3CC(C)(O)C3)C2)CC[C@]2(CO2)[C@H]1[C@@]1(C)O[C@@H]1CC=C(C)C] | 479 [M + H]$^+$ | 5.45 (s, 1H), 5.12-5.15 (m, 1H), 3.96 (m, 2H), 3.52-3.56 (m, 3H), 3.39 (s, 3H), 3.24 (s, 2H), 2.91 (d, J = 4.4 Hz, 3H), 2.46-2.51 (m, 3H), 2.28-2.34 (m, 3H), 2.07-2.13 (m, 1H), 1.95-2.03 (m, 1H), 1.76-1.88 (m, 5H), 1.68 (s, 3H), 1.59 (m, 4H), 1.41 (s, 3H), 1.13 (s, 3H), 1.00 (m, 1H) |
| 10 | 11 | 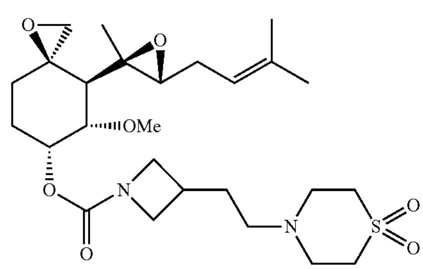 [SMILES: CO[C@@H]1[C@H](OC(=O)N2CC(CCN3CCS(=O)(=O)CC3)C2)CC[C@]2(CO2)[C@H]1[C@@]1(C)O[C@@H]1CC=C(C)C] | 527 [M + H]$^+$ | 5.44 (s, 1H), 5.14 (t, J = 7.5 Hz, 1H), 3.98 (s, 2H), 3.68-3.45 (m, 3H), 3.37 (d, J = 10.8 Hz, 3H), 2.94 (dd, J = 24.2, 5.0 Hz, 9H), 2.48 (dd, J = 10.8, 5.3 Hz, 3H), 2.38 (t, J = 7.2 Hz, 2H), 2.33-2.21 (m, 1H), 2.16-2.04 (m, 1H), 1.98 (td, J = 13.4, 4.4 Hz, 1H), 1.86 (d, J = 11.9 Hz, 1H), 1.81-1.74 (m, 2H), 1.71 (d, J = 6.8 Hz, 2H), 1.68 (s, 3H), 1.59 (s, 3H), 1.13 (s, 3H), 1.00 (d, J = 14.2 Hz, 1H) |

| Ex. | Int. | Structure | LC-MS | H-NMR (400 MHz, CDCl₃) |
|---|---|---|---|---|
| 11 | 12 | 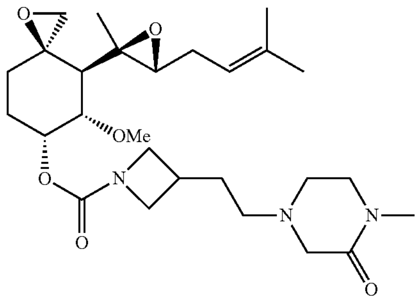 [SMILES: CO[C@@H]1[C@H](OC(=O)N2CC(CCN3CCN(C)C(=O)C3)C2)CC[C@]2(CO2)[C@H]1[C@@]1(C)O[C@@H]1CC=C(C)C] | 506 [M + H]⁺ | 5.44 (d, J = 2.6 Hz, 1H), 5.13 (t, J = 7.5 Hz, 1H), 4.13-3.65 (m, 6H), 3.55 (dd, J = 11.2, 2.7 Hz, 3H), 3.38 (s, 3H), 3.36-3.30 (m, 2H), 3.24-3.11 (m, 2H), 2.91 (s, 4H), 2.83-2.68 (m, 2H), 2.59-2.35 (m, 5H), 2.33-2.25 (m, 1H), 2.09 (dt, J = 14.7, 7.3 Hz, 1H), 2.03-1.93 (m, 1H), 1.90-1.84 (m, 1H), 1.67 (s, 3H), 1.59 (s, 3H), 1.12 (d, J = 6.3 Hz, 3H), 0.99 (dd, J = 10.0, 6.1 Hz, 1H) |
| 12 | 13 | 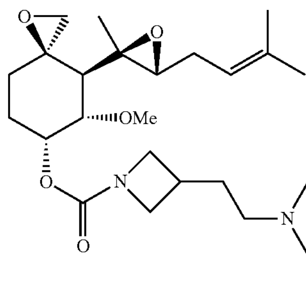 | 492 [M + H]⁺ | 6.08 (s, 1H), 5.44 (s, 1H), 5.13 (m, 1H), 3.99 (m, 2H), 3.71-3.43 (m, 4H), 3.39 (s, 4H), 3.31-3.11 (m, 2H), 2.91 (d, J = 4.2 Hz, 1H), 2.75 (m, 2H), 2.64-2.38 (m, 5H), 2.34-2.24 (m, 1H), 2.18-1.93 (m, 3H), 1.80 (m, 7H), 1.68 (s, 3H), 1.13 (s, 3H), 0.99 (d, J = 12.5 Hz, 1H) |
| 13 | 14 | 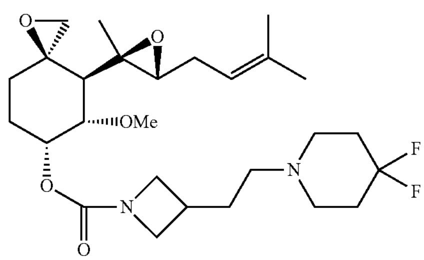 [SMILES: CO[C@@H]1[C@H](OC(=O)N2CC(CCN3CCC(F)(F)CC3)C2)CC[C@]2(CO2)[C@H]1[C@@]1(C)O[C@@H]1CC=C(C)C] | 513 [M + H]⁺ | 5.44 (d, J = 3.0 Hz, 1H), 5.14 (t, J = 7.5 Hz, 1H), 3.98 (s, 2H), 3.69-3.48 (m, 3H), 3.38 (s, 3H), 2.91 (d, J = 4.3 Hz, 1H), 2.60-2.45 (m, 6H), 2.38-2.23 (m, 3H), 2.14-1.90 (m, 6H), 1.90-1.71 (m, 6H), 1.67 (s, 3H), 1.59 (s, 3H), 1.12 (d, J = 6.4 Hz, 3H), 0.99 (d, J = 13.7 Hz, 1H) |
| 14 | 15 | 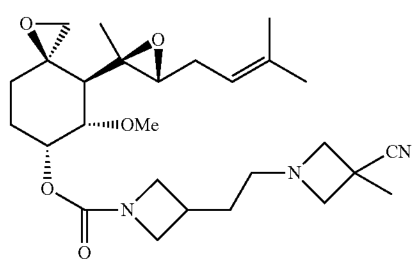 [SMILES: CO[C@@H]1[C@H](OC(=O)N2CC(CCN3CC(C)(C#N)C3)C2)CC[C@]2(CO2)[C@H]1[C@@]1(C)O[C@@H]1CC=C(C)C] | 488 [M + H]⁺ | 5.45 (s, 1H), 5.14 (t, J = 7.5 Hz, 1H), 3.97 (s, 2H), 3.67-3.44 (m, 4H), 3.37 (d, J = 11.6 Hz, 4H), 3.18 (d, J = 18.3 Hz, 2H), 2.91 (t, J = 5.5 Hz, 1H), 2.53-2.45 (m, 3H), 2.31 (dd, J = 14.7, 6.9 Hz, 2H), 2.09 (dd, J = 15.4, 6.7 Hz, 1H), 2.02-1.94 (m, 1H), 1.90-1.70 (m, 4H), 1.67 (s, 3H), 1.59 (s, 8H), 1.14 (s, 3H), 0.99 (d, J = 13.5 Hz, 1H) |
| 15 | 16 | 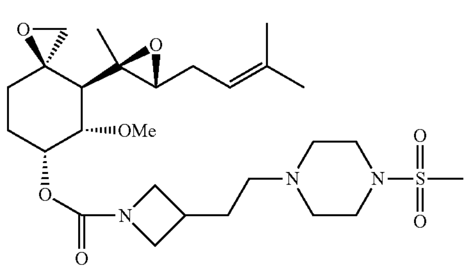 [SMILES: CO[C@@H]1[C@H](OC(=O)N2CC(CCN3CCN(S(C)(=O)=O)CC3)C2)CC[C@]2(CO2)[C@H]1[C@@]1(C)O[C@@H]1CC=C(C)C] | 556 [M + H]⁺ | 5.44 (d, J = 2.9 Hz, 1H), 5.19-5.08 (m, 1H), 3.98 (s, 2H), 3.70-3.46 (m, 3H), 3.38 (s, 3H), 3.21 (d, J = 7.2 Hz, 4H), 2.91 (d, J = 4.3 Hz, 1H), 2.73 (s, 3H), 2.60-2.44 (m, 6H), 2.41-2.21 (m, 3H), 2.10 (dt, J = 14.7, 7.3 Hz, 1H), 1.98 (td, J = 13.5, 4.5 Hz, 1H), 1.91-1.70 (m, 5H), 1.67 (s, 3H), 1.59 (s, 3H), 1.12 (d, J = 6.4 Hz, 3H), 0.99 (dd, J = 10.5, 3.2 Hz, 1H) |

-continued

| Ex. | Int. | Structure | LC-MS | H-NMR (400 MHz, CDCl$_3$) |
|---|---|---|---|---|
| 16 | 17 | 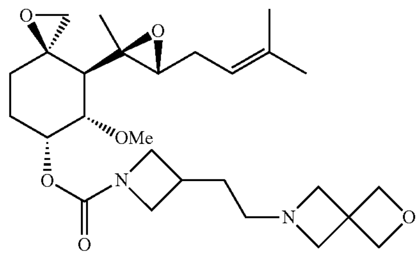 [SMILES: CO[C@@H]1[C@H](OC(=O)N2CC(CCN3CC4(COC4)C3)C2)CC[C@]2(CO2)[C@H]1[C@@]1(C)O[C@@H]1CC=C(C)C] | 491 [M + H]$^+$ | 5.44 (s, 1H), 5.18-5.09 (m, 1H), 4.71-4.47 (m, 4H), 4.02 (m, 3H), 3.63-3.17 (m, 10H), 2.91 (m, 1H), 2.55-2.42 (m, 3H), 2.34-2.23 (m, 2H), 2.09 (m, 1H), 2.03-1.82 (m, 3H), 1.81-1.70 (m, 3H), 1.68 (s, 3H), 1.59 (s, 3H), 1.12 (d, J = 5.3 Hz, 3H), 1.03-0.96 (m, 1H) |
| 17 | 18 | 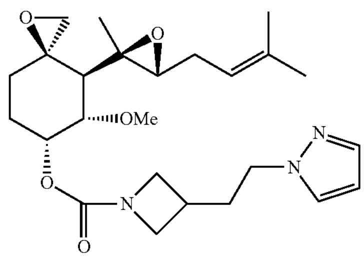 [SMILES: CO[C@@H]1[C@H](OC(=O)N2CC(CCn3cccn3)C2)CC[C@]2(CO2)[C@H]1[C@@]1(C)O[C@@H]1CC=C(C)C] | 460 [M + H]$^+$ | 7.44 (m, 1H), 7.28 (s, 1H), 6.18 (m, 1H), 5.43 (m, 1H), 5.19-5.08 (m, 1H), 4.11-3.88 (m, 4H), 3.53 (m, 1H), 3.43 (m, 1H), 3.37 (s, 3H), 2.91 (d, J = 4.3 Hz, 1H), 2.45 (m, 3H), 2.33-2.24 (m, 1H), 2.09 (m, 3H), 1.96 (m, 1H), 1.83-1.70 (m, 4H), 1.68 (s, 3H), 1.59 (s, 3H), 1.12 (s, 3H), 1.02-0.96 (m, 1H) |
| 18 | 19 | 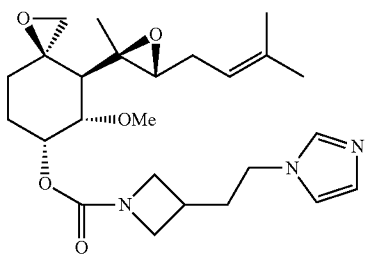 [SMILES: CO[C@@H]1[C@H](OC(=O)N2CC(CCn3ccnc3)C2)CC[C@]2(CO2)[C@H]1[C@@]1(C)O[C@@H]1CC=C(C)C] | 460 [M + H]$^+$ | 7.76 (s, 1H), 7.06 (s, 1H), 6.91 (d, J = 15.2 Hz, 1H), 5.44 (d, J = 2.6 Hz, 1H), 6.14 (m, 1H), 3.98 (m, 4H), 3.73-3.45 (m, 3H), 3.37 (s, 3H), 2.91 (d, J = 4.3 Hz, 1H), 2.49 (m, 2H), 2.29 (m, 1H), 2.08 (m, 3H), 1.97 (m, 1H), 1.88-1.81 (m, 1H), 1.77 (m, 2H), 1.67 (s, 3H), 1.59 (s, 3H), 1.13 (s, 3H), 0.99 (m, 1H) |
| 19 | 20 | 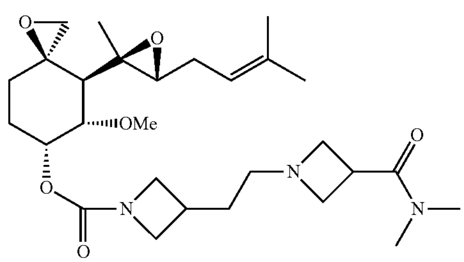 [SMILES: CO[C@@H]1[C@H](OC(=O)N2CC(CCN3CC(C(=O)N(C)C)C3)C2)CC[C@]2(CO2)[C@H]1[C@@]1(C)O[C@@H]1CC=C(C)C] | 520 [M + H]$^+$ | 5.43 (d, J = 2.1 Hz, 1H), 5.14 (m, 1H), 3.97 (m, 2H), 3.57-3.48 (m, 4H), 3.45-3.40 (m, 2H), 3.38 (s, 3H), 3.18-3.11 (m, 2H), 2.91 (d, J = 4.3 Hz, 1H), 2.87 (s, 3H), 2.83 (s, 3H), 2.52-2.43 (m, 3H), 2.35-2.24 (m, 3H), 2.14-1.92 (m, 4H), 1.88-1.73 (m, 3H), 1.67 (s, 3H), 1.59 (s, 3H), 1.13 (s, 3H), 0.99 (m, 1H) |
| 20 | 21 | 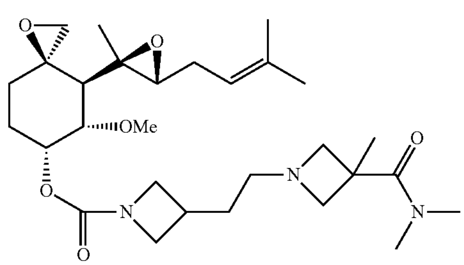 [SMILES: CO[C@@H]1[C@H](OC(=O)N2CC(CCN3CC(C)(C(=O)N(C)C)C3)C2)CC[C@]2(CO2)[C@H]1[C@@]1(C)O[C@@H]1CC=C(C)C] | 534 [M + H]$^+$ | 5.43 (s, 1H), 5.14 (t, J = 7.5 Hz, 1H), 3.98 (m, 2H), 3.54 (m, 5H), 3.38 (s, 3H), 2.91 (d, J = 4.3 Hz, 1H), 2.87 (s, 3H), 2.75 (s, 3H), 2.59-2.43 (m, 4H), 2.23-2.35 (m, 1H), 2.14-2.03 (m, 2H), 1.96 (m, 3H), 1.74-1.87 (m, 4H), 1.68 (s, 4H), 1.60 (m, 6H), 1.13 (s, 3H), 0.99 (d, J = 13.5 Hz, 1H) |
| 21 | 22 | 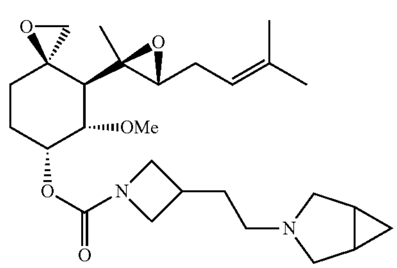 [SMILES: CO[C@@H]1[C@H](OC(=O)N2CC(CCN3CC4CC4C3)C2)CC[C@]2(CO2)[C@H]1[C@@]1(C)O[C@@H]1CC=C(C)C] | 475 [M + H]$^+$ | 5.50 (d, J = 3.1 Hz, 1H), 5.23-5.19 (m, 1H), 4.01 (s, 2H), 3.62-3.58 (m, 3H), 3.45 (s, 3H), 3.06-2.87 (m, 3H), 2.65-2.49 (m, 3H), 2.39-2.32 (m, 5H), 2.20-2.12 (m, 2H), 2.08-2.01 (m, 1H), 1.97-1.88 (m, 3H), 1.74-1.69 (m, 5H), 1.65 (s, 3H), 1.35-1.29 (m, 2H), 1.10-1.02 (m, 1H), 0.66-0.30 (m, 1H) |

| Ex. | Int. | Structure | LC-MS | H-NMR (400 MHz, CDCl₃) |
|---|---|---|---|---|
| 22 | 23 | 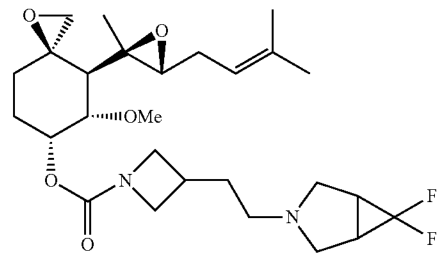 [SMILES: CO[C@@H]1[C@H](OC(=O)N2CC(CCN3CC4C(C3)C4(F)F)C2)CC[C@]2(CO2)[C@H]1[C@@]1(C)O[C@@H]1CC=C(C)C] | 511 [M + H]⁺ | 5.44 (s, 1H), 5.11-5.15 (m, 1H), 3.96-4.00 (m, 5H), 3.52-3.55 (m, 3H), 3.37 (s, 3H), 2.90-2.91 (d, J = 4.4 Hz, 1H), 2.82-2.85 (m, 2H), 2.46-2.51 (m, 5H), 2.27-2.32 (m, 3H), 2.05-2.12 (m, 1H), 1.93-1.98 (m, 1H), 1.74-1.85 (m, 4H), 1.67 (s, 3H), 1.58 (s, 3H), 1.12 (s, 3H), 0.97-1.00 (dd, J = 12, 2 Hz, 1H) |
| 23 | 24 | 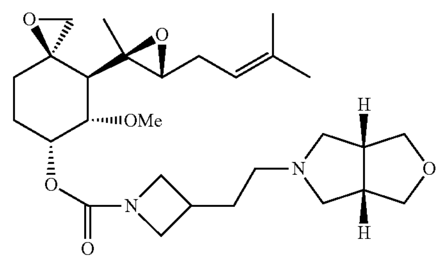 [SMILES: CO[C@@H]1[C@H](OC(=O)N2CC(CCN3C[C@H]4COC[C@H]4C3)C2)CC[C@]2(CO2)[C@H]1[C@@]1(C)O[C@@H]1CC=C(C)C] | 505 [M + H]⁺ | 5.44 (s, 1H), 5.14 (s, 1H), 3.97 (s, 2H), 3.67 (d, J = 5.1 Hz, 2H), 3.54 (dd, J = 11.1, 2.6 Hz, 4H), 3.42 (s, 1H), 3.38 (s, 3H), 2.91 (d, J = 4.3 Hz, 1H), 2.80 (s, 3H), 2.58-2.45 (m, 3H), 2.28 (d, J = 6.4 Hz, 5H), 2.09 (dt, J = 14.6, 7.3 Hz, 1H), 1.98 (td, J = 13.6, 4.5 Hz, 1H), 1.89-1.73 (m, 5H), 1.67 (s, 3H), 1.59 (s, 3H), 1.18 (s, 1H), 1.13 (s, 3H), 0.99 (d, J = 13.9 Hz, 1H) |
| 24 | 25 | 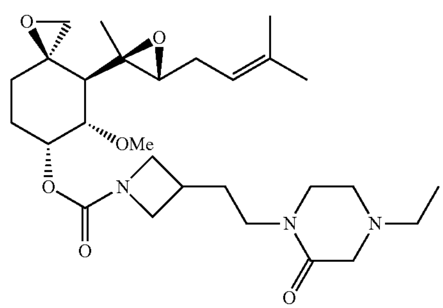 [SMILES: CCN1CCN(CCC2CN(C(=O)O[C@@H]3CC[C@]4(CO4)[C@@H]([C@@]4(C)O[C@@H]4CC=C(C)C)[C@@H]3OC)C2)C(=O)C1] | 520 [M + H]⁺ | 5.50 (s, 1H), 5.21 (m, 1H), 4.05 (m, 2H), 3.80-3.57 (m, 3H), 3.45 (s, 3H), 3.38-3.20 (m, 3H), 3.15-3.09 (m, 2H), 2.98 (d, J = 4.3 Hz, 1H), 2.68 (m, 2H), 2.61-2.51 (m, 3H), 2.46 (m, 2H), 2.35 (m, 1H), 2.16 (m, 1H), 2.06 (m, 1H), 1.95-1.79 (m, 5H), 1.74 (s, 3H), 1.65 (m, 4H), 1.20 (s, 3H), 1.11 (m, 3H), 1.05 (d, J = 13.4 Hz, 1H) |
| 25 | 26 | 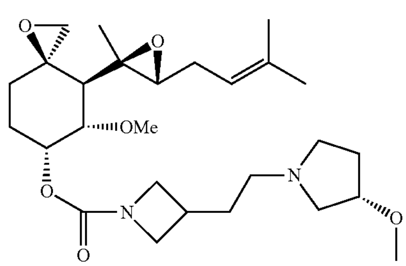 [SMILES: CO[C@H]1CCN(CCC2CN(C(=O)O[C@@H]3CC[C@]4(CO4)[C@@H]([C@@]4(C)O[C@@H]4CC=C(C)C)[C@@H]3OC)C2)C1] | 493 [M + H]⁺ | 5.43 (d, J = 2.9 Hz, 1H), 5.14 (dd, J = 10.4, 4.6 Hz, 1H), 3.97 (s, 2H), 3.88 (d, J = 6.0 Hz, 1H), 3.71-3.45 (m, 3H), 3.38 (s, 3H), 3.22 (s, 3H), 2.91 (d, J = 4.3 Hz, 1H), 2.85-2.22 (m, 10H), 2.12-1.95 (m, 3H), 1.88-1.73 (m, 6H), 1.67 (s, 3H), 1.59 (s, 3H), 1.13 (s, 3H), 0.99 (d, J = 13.9 Hz, 1H) |
| 26 | 27 | 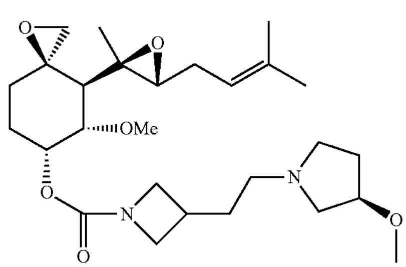 [SMILES: CO[C@@H]1CCN(CCC2CN(C(=O)O[C@@H]3CC[C@]4(CO4)[C@@H]([C@@]4(C)O[C@@H]4CC=C(C)C)[C@@H]3OC)C2)C1] | 493 [M + H]⁺ | 5.43 (d, J = 3.0 Hz, 1H), 5.14 (t, J = 7.5 Hz, 1H), 4.12-3.91 (m, 2H), 3.88 (s, 1H), 3.75-3.44 (m, 3H), 3.37 (d, J = 11.4 Hz, 3H), 3.21 (d, J = 8.7 Hz, 3H), 2.91 (d, J = 4.3 Hz, 1H), 2.73-2.40 (m, 7H), 2.35-2.24 (m, 1H), 2.15-1.93 (m, 4H), 1.90-1.72 (m, 7H), 1.67 (s, 3H), 1.59 (s, 3H), 1.12 (d, J = 6.3 Hz, 3H), 0.99 (d, J = 13.7 Hz, 1H) |

| Ex. | Int. | Structure | LC-MS | H-NMR (400 MHz, CDCl₃) |
|---|---|---|---|---|
| 27 | 28 | 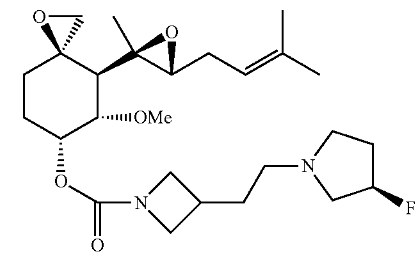 [SMILES: CO[C@@H]1[C@H](OC(=O)N2CC(CCN3CC[C@@H](F)C3)C2)CC[C@]2(CO2)[C@H]1[C@@]1(C)O[C@@H]1CC=C(C)C] | 481 [M + H]⁺ | 5.43 (d, J = 3.1 Hz, 1H), 5.21-5.02 (m, 2H), 3.98 (s, 2H), 3.54 (dd, J = 11.2, 2.7 Hz, 3H), 3.38 (s, 3H), 2.86 (dd, J = 38.0, 6.0 Hz, 4H), 2.66-2.35 (m, 6H), 2.33-2.23 (m, 1H), 2.13-1.93 (m, 4H), 1.89-1.72 (m, 6H), 1.67 (s, 3H), 1.59 (s, 3H), 1.13 (s, 3H), 1.03-0.95 (m, 1H) |
| 28 | 29 | 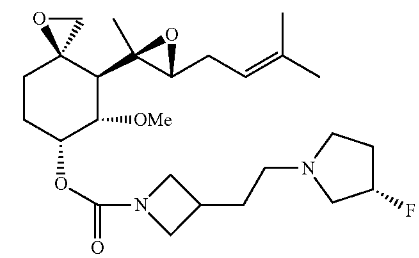 [SMILES: CO[C@@H]1[C@H](OC(=O)N2CC(CCN3CC[C@H](F)C3)C2)CC[C@]2(CO2)[C@H]1[C@@]1(C)O[C@@H]1CC=C(C)C] | 481 [M + H]⁺ | 5.44 (s, 1H), 5.16-5.11 (m, 1H), 3.99 (t, J = 8.1 Hz, 2H), 3.54 (dd, J = 11.2, 2.6 Hz, 3H), 3.38 (s, 3H), 2.91 (d, J = 4.3 Hz, 4H), 2.75-2.43 (m, 5H), 2.37-2.00 (m, 5H), 1.99-1.82 (m, 4H), 1.83-1.70 (m, 3H), 1.68 (s, 3H), 1.59 (s, 3H), 1.12 (d, J = 5.8 Hz, 3H), 0.99 (d, J = 14.0 Hz, 1H) |
| 29 | 30 | 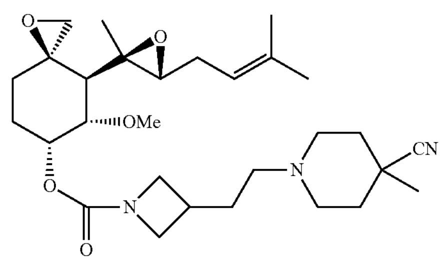 | 505 [M + H]⁺ | 5.41 (d, J = 26.4 Hz, 1H), 5.13 (t, J = 7.4 Hz, 1H), 4.01 (d, J = 16.3 Hz, 2H), 3.71-3.47 (m, 3H), 3.43-3.33 (m, 3H), 3.25 (s, 2H), 2.91 (d, J = 4.3 Hz, 1H), 2.78-2.41 (m, 7H), 2.37-2.23 (m, 1H), 2.10 (dt, J = 14.7, 7.3 Hz, 1H), 2.04-1.69 (m, 10H), 1.68 (s, 3H), 1.59 (s, 3H), 1.38 (s, 3H), 1.15 (d, J = 14.6 Hz, 3H), 0.99 (d, J = 13.7 Hz, 1H) |
| 30 | 31 | 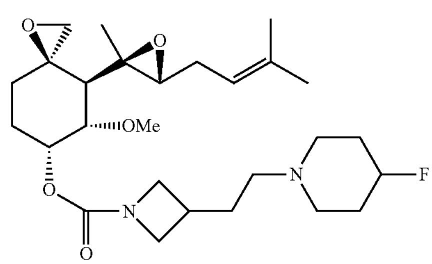 [SMILES: CO[C@@H]1[C@H](OC(=O)N2CC(CCN3CCC(F)CC3)C2)CC[C@]2(CO2)[C@H]1[C@@]1(C)O[C@@H]1CC=C(C)C] | 495 [M + H]⁺ | 5.44 (d, J = 3.0 Hz, 1H), 5.13 (m, 1H), 4.65 (d, J = 48.8 Hz, 1H), 3.97 (m, 2H), 3.54 (m, 3H), 3.38 (s, 3H), 2.91 (d, J = 4.3 Hz, 1H), 2.61-2.44 (m, 5H), 2.41-2.16 (m, 4H), 2.15-1.94 (m, 3H), 1.80 (m, 8H), 1.67 (s, 3H), 1.55 (m, 4H), 1.13 (s, 3H), 0.99 (m, 1H) |
| 31 | 32 | 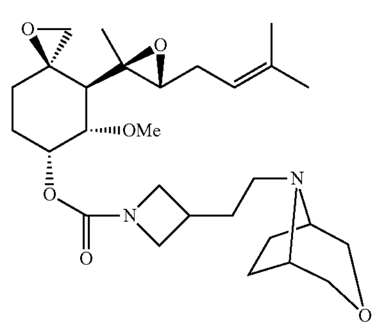 [SMILES: CO[C@@H]1[C@H](OC(=O)N2CC(CCN3C4CCC3COC4)C2)CC[C@]2(CO2)[C@H]1[C@@]1(C)O[C@@H]1CC=C(C)C] | 505 [M + H]⁺ | 5.44 (d, J = 2.6 Hz, 1H), 5.14 (t, J = 7.5 Hz, 1H), 4.18-3.89 (m, 4H), 3.72-3.48 (m, 7H), 3.42-3.33 (m, 3H), 2.91 (d, J = 4.3 Hz, 1H), 2.54 (ddd, J = 38.3, 33.5, 16.1 Hz, 5H), 2.35-2.22 (m, 1H), 2.14-1.82 (m, 9H), 1.81-1.71 (m, 2H), 1.68 (s, 3H), 1.59 (s, 3H), 1.13 (s, 3H), 1.03-0.95 (m, 1H) |

-continued

| Ex. | Int. | Structure | LC-MS | H-NMR (400 MHz, CDCl₃) |
|---|---|---|---|---|
| 32 | 33 | 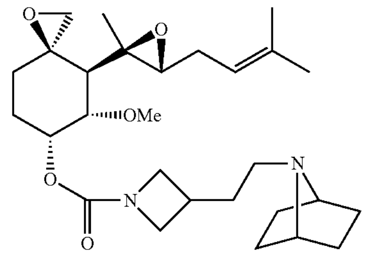 [SMILES: CO[C@@H]1[C@H](OC(=O)N2CC(CCN3C4CCC3CC4)C2)CC[C@]2(CO2)[C@H]1[C@@]1(C)O[C@@H]1CC=C(C)C] | 489 [M + H]⁺ | 5.44 (s, 1H), 5.14 (t, J = 7.4 Hz, 1H), 3.95 (d, J = 25.5 Hz, 4H), 3.54 (dd, J = 11.2, 2.4 Hz, 3H), 3.38 (s, 3H), 2.87 (dd, J = 28.4, 7.3 Hz, 2H), 2.49 (dd, J = 10.9, 5.3 Hz, 2H), 2.28 (d, J = 6.4 Hz, 3H), 2.15-1.73 (m, 9H), 1.63 (d, J = 34.9 Hz, 11H), 1.18 (s, 1H), 1.12 (s, 3H), 0.99 (d, J = 13.9 Hz, 1H) |
| 33 | 34 | 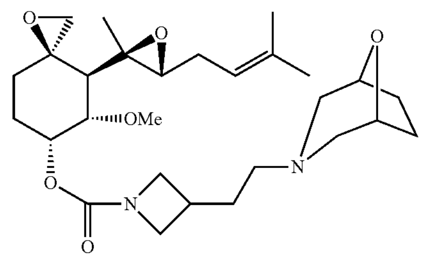 [SMILES: CO[C@@H]1[C@H](OC(=O)N2CC(CCN3CC4CCC(C3)O4)C2)CC[C@]2(CO2)[C@H]1[C@@]1(C)O[C@@H]1CC=C(C)C] | 505 [M + H]⁺ | 5.44 (d, J = 3.0 Hz, 1H), 5.14 (s, 1H), 4.21 (s, 2H), 3.96 (s, 2H), 3.54 (dd, J = 11.2, 2.7 Hz, 3H), 3.38 (s, 3H), 2.91 (d, J = 4.3 Hz, 1H), 2.48 (dd, J = 12.3, 5.4 Hz, 5H), 2.34-2.05 (m, 6H), 2.02-1.94 (m, 1H), 1.87-1.74 (m, 6H), 1.67 (s, 3H), 1.60 (d, J = 9.3 Hz, 6H), 1.13 (s, 3H), 0.99 (dd, J = 10.4, 3.4 Hz, 1H) |
| 34 | 35 | 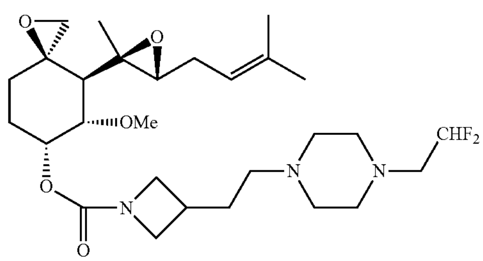 [SMILES: CO[C@@H]1[C@H](OC(=O)N2CC(CCN3CCN(CC(F)F)CC3)C2)CC[C@]2(CO2)[C@H]1[C@@]1(C)O[C@@H]1CC=C(C)C] | 542 [M + H]⁺ | 6.05-5.63 (m, 1H), 5.43 (d, J = 3.2 Hz, 1H), 5.12-5.16 (m, 1H), 3.95 (s, 2H), 3.52-3.56 (m, 3H), 3.38 (s, 3H), 2.91 (d, J = 4.4 Hz, 1H), 2.63-2.72 (m, 3H), 2.57 (s, 3H), 2.41-2.52 (m, 6H), 2.25-2.30 (m, 3H), 2.07-2.13 (m, 1H), 1.94-1.98 (m, 1H), 1.74-1.84 (m, 5H), 1.67 (s, 3H), 1.55 (s, 3H), 1.13 (s, 3H), 0.99 (dd, J = 10.4, 3.4 Hz, 1H) |
| 35 | 36 | 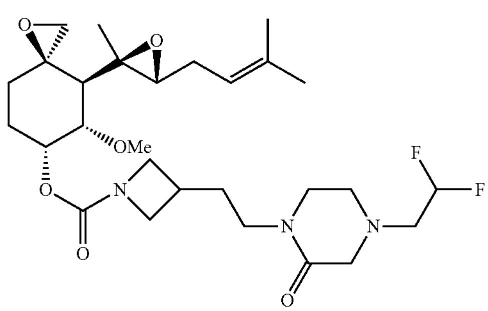 [SMILES: CO[C@@H]1[C@H](OC(=O)N2CC(CCN3CCN(CC(F)F)CC3=O)C2)CC[C@]2(CO2)[C@H]1[C@@]1(C)O[C@@H]1CC=C(C)C] | 556 [M + H]⁺ | 5.88 (m, 1H), 5.50 (s, 1H), 5.21 (m, 1H), 4.11 (m, 2H), 3.79-3.56 (m, 3H), 3.45 (s, 3H), 3.38-3.22 (m, 5H), 2.98 (d, J = 4.3 Hz, 1H), 2.88-2.74 (m, 4H), 2.62-2.49 (m, 3H), 2.40-2.30 (m, 1H), 2.16 (m, 1H), 2.06 (m, 1H), 1.95-1.78 (m, 5H), 1.74 (s, 3H), 1.66 (s, 3H), 1.31-1.23 (m, 1H), 1.20 (s, 3H), 1.05 (d, J = 12.5 Hz, 1H) |
| 36 | 37 | 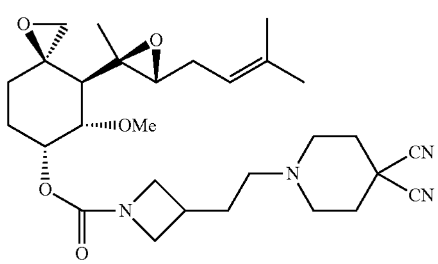 [SMILES: CO[C@@H]1[C@H](OC(=O)N2CC(CCN3CCC(C#N)(C#N)CC3)C2)CC[C@]2(CO2)[C@H]1[C@@]1(C)O[C@@H]1CC=C(C)C] | 527 [M + H]⁺ | 5.45 (s, 1H), 5.12 (m, 1H), 3.98 (s, 2H), 3.68-3.44 (m, 3H), 3.38 (s, 3H), 2.91 (d, J = 4.3 Hz, 1H), 2.66-2.43 (m, 6H), 2.30 (m, 3H), 2.13 (m, 4H), 2.09-1.91 (m, 2H), 1.86 (m, 1H), 1.76 (m, 3H), 1.68 (s, 3H), 1.59 (s, 3H), 1.54 (s, 2H), 1.13 (s, 3H), 0.99 (d, J = 13.6 Hz, 1H) |

-continued

| Ex. | Int. | Structure | LC-MS | H-NMR (400 MHz, CDCl₃) |
|---|---|---|---|---|
| 37 | 38 | 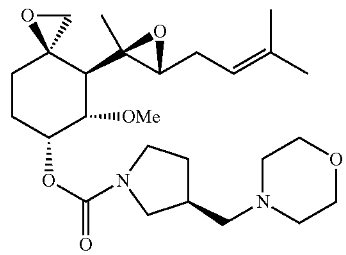 [SMILES: CO[C@@H]1[C@H](OC(=O)N2CC[C@@H](CN3CCOCC3)C2)CC[C@]2(CO2)[C@H]1[C@@]1(C)O[C@@H]1CC=C(C)C] | 479 [M + H]⁺ | 5.51 (s, 1H), 5.14 (t, J = 7.4 Hz, 1H), 3.68 (dd, J = 10.0, 5.0 Hz, 5H), 3.61-3.51 (m, 3H), 3.51-3.42 (m, 1H), 3.39 (s, 3H), 3.23 (ddd, J = 26.5, 16.5, 8.7 Hz, 1H), 3.03-2.83 (m, 2H), 2.52 (dt, J = 14.6, 5.5 Hz, 5H), 2.40 (s, 2H), 2.36-2.21 (m, 2H), 2.15-1.91 (m, 3H), 1.91-1.69 (m, 3H), 1.68 (s, 3H), 1.59-1.54 (m, 3H), 1.14 (s, 3H), 1.01 (d, J = 13.7 Hz, 1H) |
| 38 | 39 | 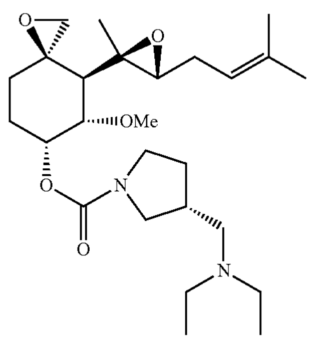 [SMILES: CCN(CC)C[C@H]1CCN(C(=O)O[C@@H]2CC[C@]3(CO3)[C@@H]([C@@]3(C)O[C@@H]3CC=C(C)C)[C@@H]2OC)C1] | 465 [M + H]⁺ | 5.50 (s, 1H), 5.14 (t, J = 7.1 Hz, 1H), 3.63 (ddd, J = 17.8, 10.7, 7.2 Hz, 1H), 3.55 (dd, J = 11.3, 2.2 Hz, 1H), 3.42 (s, 2H), 3.39 (d, J = 2.3 Hz, 3H), 3.32-3.16 (m, 1H), 3.05 (dt, J = 20.9, 8.4 Hz, 5H), 2.94-2.85 (m, 2H), 2.58 (ddd, J = 37.5, 22.8, 6.1 Hz, 3H), 2.35-2.21 (m, 1H), 2.18-1.97 (m, 3H), 1.90-1.73 (m, 3H), 1.68 (s, 3H), 1.59 (s, 3H), 1.28-1.16 (m, 6H), 1.13 (s, 3H), 1.01 (d, J = 14.1 Hz, 1H) |
| 39 | 40 | 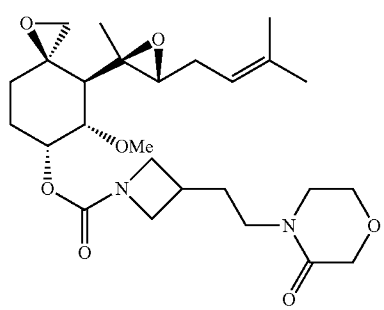 [SMILES: CO[C@@H]1[C@H](OC(=O)N2CC(CCN3CCOCC3=O)C2)CC[C@]2(CO2)[C@H]1[C@@]1(C)O[C@@H]1CC=C(C)C] | 493 [M + H]⁺ | 5.45 (d, J = 2.9 Hz, 1H), 5.18-5.09 (m, 1H), 4.04 (d, J = 38.3 Hz, 4H), 3.82 (t, 2H), 3.69-3.51 (m, 3H), 3.39 (s, 3H), 3.32-3.18 (m, 3H), 2.91 (d, J = 4.3 Hz, 1H), 2.53-2.44 (m, 3H), 2.35-2.22 (m, 1H), 2.14-1.94 (m, 2H), 1.87-1.73 (m, 5H), 1.68 (s, 3H), 1.58 (d, J = 3.8 Hz, 4H), 1.13 (s, 3H), 0.98 (d, J = 11.7 Hz, 1H) |
| 40 | 41 | 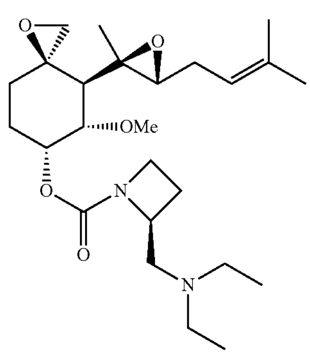 [SMILES: CCN(CC)C[C@@H]1CCN1C(=O)O[C@@H]1CC[C@]2(CO2)[C@@H]([C@@]2(C)O[C@@H]2CC=C(C)C)[C@@H]1OC] | 451 [M + 1]⁺ | 5.43 (s, 1H), 5.13 (m, 1H), 4.51 (s, 1H), 3.82 (s, 2H), 3.66-3.33 (m, 9H), 2.91 (m, 5H), 2.49 (m, 3H), 2.34-2.20 (m, 1H), 2.16-2.04 (m, 2H), 1.96 (m, 2H), 1.78 (m, 2H), 1.67 (s, 3H), 1.58 (s, 3H), 1.18 (m, 6H), 1.02 (d, J = 13.8 Hz, 1H) |

-continued

| Ex. | Int. | Structure | LC-MS | H-NMR (400 MHz, CDCl₃) |
|---|---|---|---|---|
| 41 | 42 | 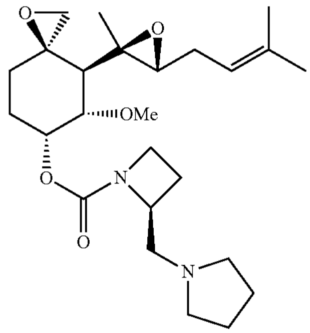 [SMILES: CO[C@@H]1[C@H](OC(=O)N2CC[C@H]2CN2CCCC2)CC[C@]2(CO2)[C@H]1[C@@]1(C)O[C@@H]1CC=C(C)C] | 449 [M + H]⁺ | 5.39 (s, 1H), 5.10-5.23 (m, 1H), 4.51-4.54 (m, 1H), 3.83 (s, 2H), 3.53-3.56 (m, 1H), 3.36 (s, 3H), 3.25-3.31 (m, 6H), 2.90 (d, J = 4.0 Hz, 1H), 2.39-2.50 (m, 3H), 2.18-2.28 (m, 2H), 2.06-2.13 (m, 1H), 2.13-2.21 (m, 1H), 1.96 (s, 6H), 1.73-1.81 (m, 2H), 1.67 (s, 3H), 1.58 (s, 3H), 1.12 (s, 3H), 1.02 (d, J = 13.6 Hz, 1H) |
| 42 | 43 | 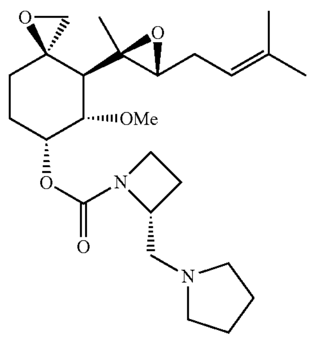 [SMILES: CO[C@@H]1[C@H](OC(=O)N2CC[C@@H]2CN2CCCC2)CC[C@]2(CO2)[C@H]1[C@@]1(C)O[C@@H]1CC=C(C)C] | 449 [M + H]⁺ | 5.33 (s, 1H), 5.11 (s, 1H), 4.58 (s, 1H), 3.87 (s, 2H), 3.67 (m, 1H), 3.57 (d, J = 11.0 Hz, 1H), 3.32 (m, 8H), 2.89 (d, J = 3.1 Hz, 1H), 2.54 (m, 3H), 2.19 (m, 3H), 1.97 (s, 6H), 1.81-1.78 (m, 2H), 1.66 (s, 3H), 1.58 (s, 3H), 1.13 (d, J = 12.8 Hz, 3H), 1.00 (d, J = 13.0 Hz, 1H) |
| 43 | 44 | 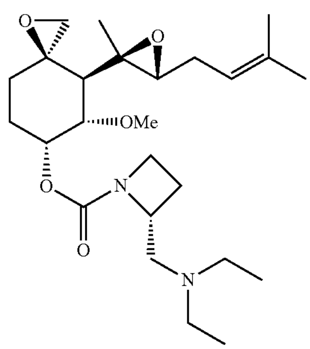 [SMILES: CCN(CC)C[C@H]1CCN1C(=O)O[C@@H]1CC[C@]2(CO2)[C@@H]([C@@]2(C)O[C@@H]2CC=C(C)C)[C@@H]1OC] | 451 [M + H]⁺ | 5.34 (s, 1H), 5.13 (m, 1H), 4.77 (s, 0.7H), 4.48 (s, 0.3H), 3.85 (m, 2H), 3.56-3.57 (d, J = 11.2 Hz, 1H), 3.29-3.49 (m, 4H), 2.95-3.14 (m, 5H), 2.89-2.90 (d, J = 3.6 Hz, 1H), 2.51-2.63 (m, 3H), 1.73-2.13 (m, 7H), 1.66 (s, 3H), 1.57 (s, 3H), 1.18 (m, 6H), 1.12 (s, 3H), 0.96-1.02 (d, J = 13.6 Hz, 1H) |
| 44 | 45 | 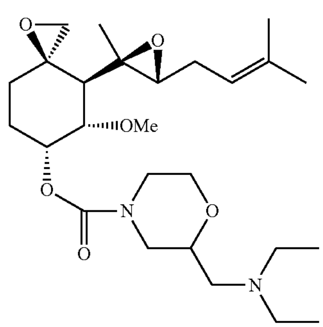 [SMILES: CCN(CC)CC1CN(C(=O)O[C@@H]2CC[C@]3(CO3)[C@@H]([C@@]3(C)O[C@@H]3CC=C(C)C)[C@@H]2OC)CCO1] | 481 [M + H]⁺ | 5.53 (s, 1H), 5.14-5.13 (d, J = 4 Hz, 1H), 3.96-3.92 (d, J = 16 Hz, 1H), 3.82-3.79 (m, 2H), 3.59-3.58 (d, J = 4 Hz, 1H), 3.56-3.49 (m, 1H), 3.38 (s, 3H), 3.09-3.07 (m, 5H), 2.93-2.92 (m, 3H), 2.60-2.50 (m, 4H), 2.28-2.26 (m, 1H), 2.11-1.78 (m, 6H), 1.67 (s, 3H), 1.58 (s, 3H), 1.23-1.19 (m, 6H), 1.13 (s, 3H), 1.04-1.01 (d, J = 12 Hz, 1H) |

| Ex. | Int. | Structure | LC-MS | H-NMR (400 MHz, CDCl$_3$) |
|---|---|---|---|---|
| 45 | 46 | 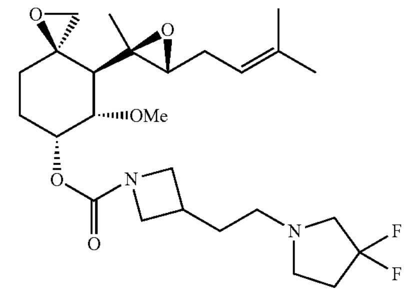 [SMILES: CO[C@@H]1[C@H](OC(=O)N2CC(CCN3CCC(F)(F)C3)C2)CC[C@]2(CO2)[C@H]1[C@@]1(C)O[C@@H]1CC=C(C)C] | 499 [M + H]$^+$ | 5.43 (s, 1H), 5.14-5.16 (m, 1H), 3.85-4.01 (m, 2H), 3.42-3.65 (m, 3H), 3.40 (s, 3H), 2.90 (d, J = 4.0 Hz, 1H), 2.80 (t, J = 13.2 Hz, 2H), 2.62-2.66 (m, 2H), 2.42-2.60 (m, 3H), 1.91-2.39 (m, 7H), 1.62-1.96 (m, 8H), 1.61 (s, 3H), 1.18 (s, 3H), 0.98-1.03 (m, 1H) |
| 46 | 47 | 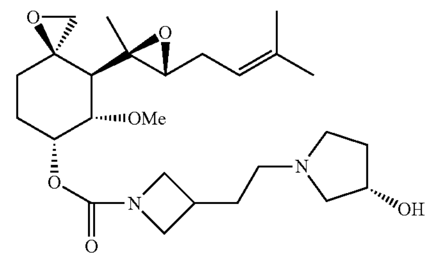 [SMILES: CO[C@@H]1[C@H](OC(=O)N2CC(CCN3CC[C@H](O)C3)C2)CC[C@]2(CO2)[C@H]1[C@@]1(C)O[C@@H]1CC=C(C)C] | 479 [M + H]+ | 5.45 (s, 1H), 5.12 (s, 1H), 4.49 (s, 1H), 4.07-3.97 (m, 2H), 3.61-3.50 (m, 4H), 3.45-3.36 (m, 4H), 3.23 (d, J = 21.6 Hz, 1H), 3.05-2.86 (m, 4H), 2.50 (dd, J = 12.7, 5.4 Hz, 3H), 2.27 (dd, J = 14.2, 6.8 Hz, 2H), 2.13-1.94 (m, 5H), 1.78 (d, J = 11.3 Hz, 3H), 1.68 (s, 3H), 1.59 (s, 3H), 1.12 (s, 3H), 0.99 (d, J = 13.7 Hz, 1H) |
| 47 | 48 | 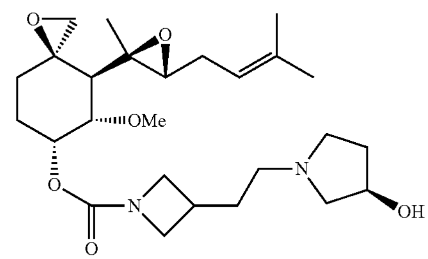 [SMILES: CO[C@@H]1[C@H](OC(=O)N2CC(CCN3CC[C@@H](O)C3)C2)CC[C@]2(CO2)[C@H]1[C@@]1(C)O[C@@H]1CC=C(C)C] | 479 [M + 1]$^+$ | 5.45 (s, 1H), 5.13 (t, J = 7.4 Hz, 1H), 4.30 (s, 1H), 3.98 (s, 2H), 3.72-3.46 (m, 3H), 3.44-3.32 (m, 3H), 2.91 (d, J = 4.3 Hz, 2H), 2.74 (d, J = 40.5 Hz, 1H), 2.62-2.44 (m, 5H), 2.37-2.22 (m, 2H), 2.12 (ddd, J = 22.5, 14.6, 6.6 Hz, 3H), 2.02-1.91 (m, 3H), 1.84-1.74 (m, 5H), 1.68 (s, 3H), 1.59 (s, 3H), 1.12 (d, J = 6.8 Hz, 3H), 0.99 (d, J = 13.7 Hz, 1H) |
| 48 | 49 | 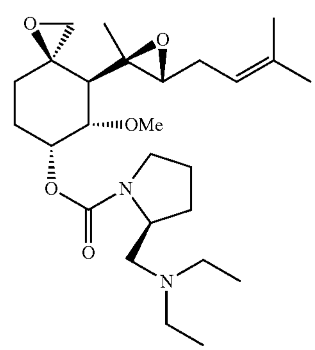 [SMILES: CCN(CC)C[C@@H]1CCCN1C(=O)O[C@@H]1CC[C@]2(CO2)[C@@H]([C@@]2(C)O[C@@H]2CC=C(C)C)[C@@H]1OC] | 465 [M + H]$^+$ | 5.48 (s, 1H), 5.13 (t, J = 7.2 Hz, 1H), 4.11 (s, 1H), 3.56 (dd, J = 2.8 Hz, 1H), 3.39 (s, 4H), 3.05-3.21 (m, 6H), 2.92 (d, J = 2.8 Hz, 1H), 2.77 (t, J = 7.5 Hz, 2H), 2.49 (m, 2H), 2.27 (m, 1H), 1.97-2.13 (m, 4H), 1.77-1.95 (m, 5H), 1.67 (s, 3H), 1.59 (s, 3H), 1.26 (m, 6H), 1.18 (s, 1H), 1.14 (s, 3H), 1.03 (m, 1H) |
| 49 | 50 | 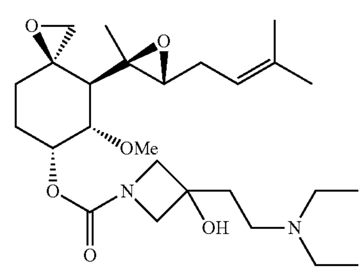 [SMILES: CCN(CC)CCC1(O)CN(C(=O)O[C@@H]2CC[C@]3(CO3)[C@@H]([C@@]3(C)O[C@@H]3CC=C(C)C)[C@@H]2OC)C1] | 481 [M + H]$^+$ | 5.23 (s, 1H), 5.12-5.16 (m, 1H), 3.75-3.87 (m, 4H), 3.53-3.56 (m, 1H), 3.38 (s, 3H), 2.91 (d, J = 4.4 Hz, 1H), 2.47-2.75 (m, 6H), 2.25-2.31 (m, 2H), 2.08-2.12 (m, 1H), 1.72-2.00 (m, 7H), 1.67 (s, 3H), 1.59 (s, 3H), 1.18 (s, 1H), 1.13 (s, 3H), 0.97-1.06 (m, 6H) |

| Ex. | Int. | Structure | LC-MS | H-NMR (400 MHz, CDCl₃) |
|---|---|---|---|---|
| 50 | 51 | 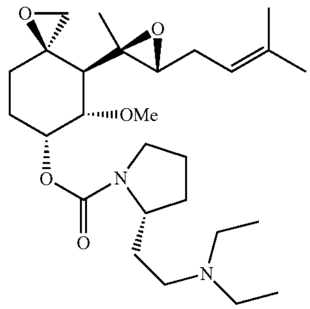 [SMILES: CCN(CC)CC[C@H]1CCCN1C(=O)O[C@@H]1CC[C@]2(CO2)[C@@H]([C@@]2(C)O[C@@H]2CC=C(C)C)[C@@H]1OC] | 479 [M + H]⁺ | 5.59 (s, 1H), 5.22 (m, 1H), 3.85 (m, 1H), 3.71-3.60 (m, 1H), 3.53-3.28 (m, 5H), 3.01 (m, 2H), 2.60 (m, 6H), 2.40 (m, 2H), 2.24-1.82 (m, 9H), 1.76 (s, 3H), 1.67 (s, 3H), 1.57 (m, 1H), 1.30-1.00 (m, 10H), 0.90 (m, 1H) |
| 51 | 52 | 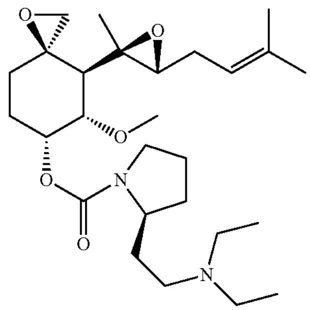 [SMILES: CCN(CC)CC[C@@H]1CCCN1C(=O)O[C@@H]1CC[C@]2(CO2)[C@@H]([C@@]2(C)O[C@@H]2CC=C(C)C)[C@@H]1OC] | 479 [M + H]⁺ | 5.44 (d, J = 21.1 Hz, 1H), 5.14 (s, 1H), 3.98-3.50 (m, 2H), 3.46-3.18 (m, 5H), 2.97 (d, J = 35.9 Hz, 6H), 2.38 (d, J = 88.5 Hz, 2H), 1.92 (dd, J = 94.4, 36.3 Hz, 9H), 1.67 (s, 3H), 1.59 (s, 3H), 1.10 (dd, J = 62.2, 21.2 Hz, 10H) |
| 52 | 53 | 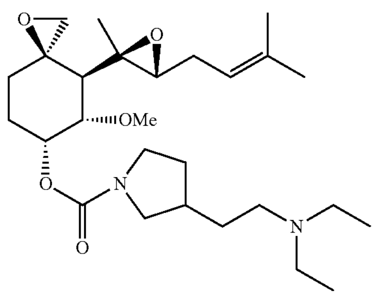 [SMILES: CCN(CC)CCC1CCN(C(=O)O[C@@H]2CC[C@]3(CO3)[C@@H]([C@@]3(C)O[C@@H]3CC=C(C)C)[C@@H]2OC)C1] | 479 [M + H]⁺ | 5.50 (s, 1H), 5.14 (t, J = 7.4 Hz, 1H), 3.61-3.44 (m, 2H), 3.37 (d, J = 22.4 Hz, 3H), 3.20 (ddd, J = 28.4, 21.0, 12.5 Hz, 1H), 2.99-2.75 (m, 2H), 2.74-2.17 (m, 9H), 2.17-1.72 (m, 7H), 1.67 (s, 3H), 1.59 (s, 3H), 1.54-1.33 (m, 3H), 1.24 (d, J = 44.3 Hz, 1H), 1.14 (s, 3H), 1.07-0.87 (m, 6H) |
| 53 | 54 | 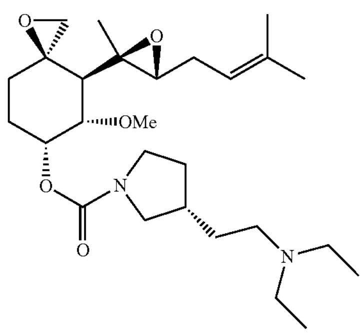 [SMILES: CCN(CC)CC[C@H]1CCN(C(=O)O[C@@H]2CC[C@]3(CO3)[C@@H]([C@@]3(C)O[C@@H]3CC=C(C)C)[C@@H]2OC)C1] | 479 [M + H]⁺ | 5.49 (s, 1H), 5.14 (t, J = 7.5 Hz, 1H), 3.54 (t, J = 9.0 Hz, 2H), 3.49-3.37 (m, 4H), 3.32 (dd, J = 10.1, 5.6 Hz, 1H), 3.23 (dd, J = 10.3, 6.8 Hz, 1H), 2.96-2.83 (m, 2H), 2.52-2.41 (m, 6H), 2.31 (ddd, J = 21.1, 14.1, 6.6 Hz, 3H), 2.14-1.71 (m, 7H), 1.67 (s, 3H), 1.59 (s, 3H), 1.52 (s, 5H), 1.14 (s, 3H), 1.06-0.88 (m, 7H) |
| 54 | 55 | 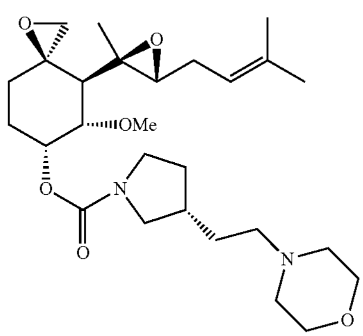 [SMILES: CO[C@@H]1[C@H](OC(=O)N2CC[C@H](CCN3CCOCC3)C2)CC[C@]2(CO2)[C@H]1[C@@]1(C)O[C@@H]1CC=C(C)C] | 493 [M + H]⁺ | 5.50 (s, 1H), 5.14 (t, J = 7.0 Hz, 1H), 3.70-3.60 (m, 4H), 3.59-3.51 (m, 2H), 3.50-3.36 (m, 4H), 3.32 (dd, J = 10.2, 5.2 Hz, 1H), 3.28-3.18 (m, 1H), 2.98-2.83 (m, 2H), 2.53-2.45 (m, 2H), 2.36 (s, 3H), 2.29 (dt, J = 8.7, 6.9 Hz, 3H), 2.08 (dt, J = 14.8, 6.2 Hz, 2H), 2.03-1.84 (m, 3H), 1.80 (t, J = 13.3 Hz, 2H), 1.67 (s, 3H), 1.59 (s, 3H), 1.56-1.48 (m, 4H), 1.14 (s, 3H), 1.07-0.94 (m, 1H) |

| Ex. | Int. | Structure | LC-MS | H-NMR (400 MHz, CDCl₃) |
|---|---|---|---|---|
| 55 | 56 | 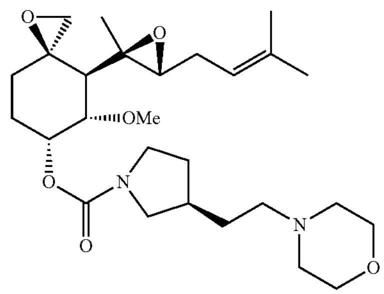 [SMILES: CO[C@@H]1[C@H](OC(=O)N2CC[C@@H](CCN3CCOCC3)C2)CC[C@]2(CO2)[C@H]1[C@@]1(C)O[C@@H]1CC=C(C)C] | 493 [M + H]⁺ | 5.51 (s, 1H), 5.14 (t, J = 7.4 Hz, 1H), 3.68 (dd, J = 10.0, 5.0 Hz, 5H), 3.61-3.51 (m, 3H), 3.51-3.42 (m, 1H), 3.39 (s, 3H), 3.23 (ddd, J = 26.5, 16.5, 8.7 Hz, 1H), 3.03-2.83 (m, 2H), 2.52 (dt, J = 14.6, 5.5 Hz, 5H), 2.40 (s, 2H), 2.36-2.21 (m, 2H), 2.15-1.91 (m, 3H), 1.91-1.69 (m, 3H), 1.68 (s, 3H), 1.59-1.54 (m, 3H), 1.14 (s, 3H), 1.01 (d, J = 13.7 Hz, 1H) |
| 56 | 57 | 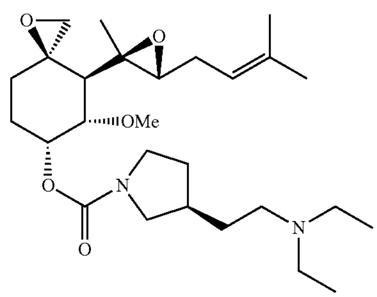 [SMILES: CCN(CC)CC[C@@H]1CCN(C(=O)O[C@@H]2CC[C@]3(CO3)[C@@H]([C@@]3(C)O[C@@H]3CC=C(C)C)[C@@H]2OC)C1] | 479 [M + H]⁺ | 5.58 (s, 1H), 5.23 (d, J = 4.1 Hz, 1H), 3.73-3.53 (m, 3H), 3.46 (t, J = 7.1 Hz, 3H), 3.36-3.27 (m, 1H), 3.09-2.97 (m, 6H), 2.95-2.83 (m, 2H), 2.59 (ddd, J = 12.2, 10.4, 5.3 Hz, 2H), 2.42-2.31 (m, 1H), 2.21-2.12 (m, 2H), 2.08 (ddd, J = 15.3, 10.0, 6.9 Hz, 2H), 1.96 (d, J = 13.9 Hz, 1H), 1.86 (ddd, J = 17.6, 11.8, 3.9 Hz, 3H), 1.76 (s, 4H), 1.67 (s, 3H), 1.63-1.48 (m, 1H), 1.28 (t, J = 7.3 Hz, 6H), 1.22 (d, J = 2.5 Hz, 3H), 1.14-1.04 (m, 1H) |
| 57 | 58 | 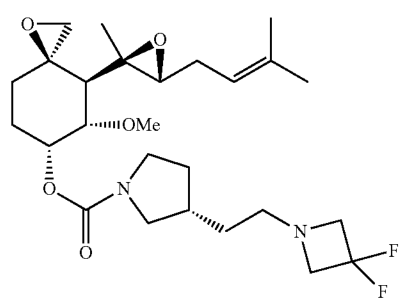 [SMILES: CO[C@@H]1[C@H](OC(=O)N2CC[C@H](CCN3CC(F)(F)C3)C2)CC[C@]2(CO2)[C@H]1[C@@]1(C)O[C@@H]1CC=C(C)C] | 499 [M + H]⁺ | 5.50 (s, 1H), 5.14 (t, J = 7.3 Hz, 1H), 3.59-3.44 (m, 6H), 3.40 (d, J = 5.5 Hz, 3H), 3.35-3.28 (m, 1H), 2.97-2.80 (m, 2H), 2.54-2.43 (m, 4H), 2.33-2.23 (m, 1H), 2.16-2.05 (m, 2H), 2.05-1.84 (m, 4H), 1.83-1.71 (m, 2H), 1.67 (s, 3H), 1.59 (s, 3H), 1.48-1.33 (m, 3H), 1.14 (s, 3H), 1.01 (dd, J = 13.5, 2.3 Hz, 1H) |
| 58 | 59 | 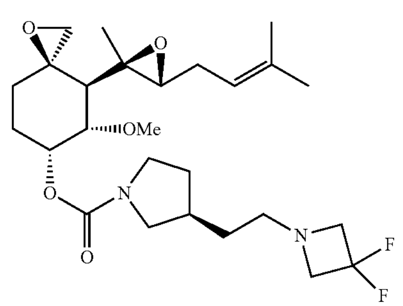 [SMILES: CO[C@@H]1[C@H](OC(=O)N2CC[C@@H](CCN3CC(F)(F)C3)C2)CC[C@]2(CO2)[C@H]1[C@@]1(C)O[C@@H]1CC=C(C)C] | 499 [M + H]⁺ | 5.50 (s, 1H), 4.14 (t, J = 6.9 Hz, 1H), 3.62-3.52 (m, 2H), 3.47 (dd, J = 15.3, 8.6 Hz, 5H), 3.39 (s, 3H), 3.29-3.11 (m, 1H), 2.92 (t, J = 4.0 Hz, 1H), 2.88-2.71 (m, 1H), 2.57-2.42 (m, 4H), 2.33-2.22 (m, 1H), 2.16-2.05 (m, 2H), 2.03-1.84 (m, 3H), 1.78 (dd, J = 27.8, 12.4 Hz, 2H), 1.67 (s, 3H), 1.59 (s, 3H), 1.49-1.31 (m, 3H), 1.14 (d, J = 2.2 Hz, 3H), 1.00 (dd, J = 13.5, 2.3 Hz, 1H) |

| Ex. | Int. | Structure | LC-MS | H-NMR (400 MHz, CDCl₃) |
|---|---|---|---|---|
| 59 | 60 | 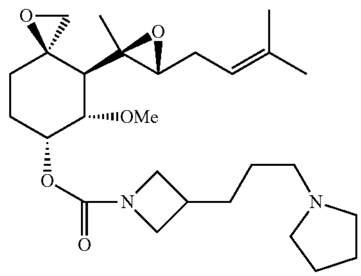 | 447 [M + H]⁺ | 5.53 (s, 1H), 5.20-5.24 (m, 1H), 4.04 (s, 3H), 3.55-3.69 (m, 3H), 3.46 (s, 3H), 3.23-3.33 (m, 3H), 2.92-3.06 (m, 3H), 2.55-2.62 (m, 3H), 2.34-2.41 (m, 1H), 2.13-2.21 (m, 1H), 2.04-2.10 (m, 5H), 1.83-1.96 (m, 3H), 1.76 (s, 3H), 1.60-1.72 (m, 6H), 1.21 (s, 3H), 1.07 (d, J = 13.6 Hz, 1H) |
| 60 | 61 | 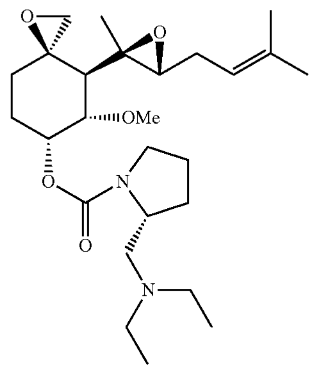 [SMILES: CCN(CC)C[C@H]1CCCN1C(=O)O[C@@H]1CC[C@]2(CO2)[C@@H]([C@@]2(C)O[C@@H]2CC=C(C)C)[C@@H]1OC] | 465 [M + H]⁺ | 5.47 (s, 1H), 5.30 (d, J = 18.2 Hz, 1H), 5.12 (d, J = 8.4 Hz, 1H), 4.25-4.02 (m, 1H), 3.69-3.46 (m, 1H), 3.44-3.26 (m, 5H), 3.18-2.97 (m, 5H), 2.91 (dd, J = 8.9, 4.1 Hz, 1H), 2.83-2.67 (m, 1H), 2.55-2.41 (m, 2H), 2.27-1.79 (m, 10H), 1.67 (s, 3H), 1.58 (s, 3H), 1.21 (t, J = 7.4 Hz, 6H), 1.13 (s, 3H), 1.02 (d, J = 7.1 Hz, 1H) |
| 61 | 62 | 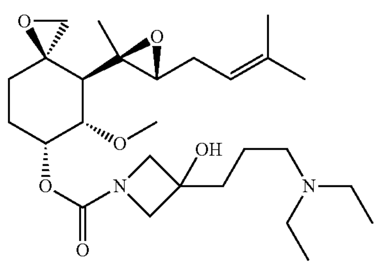 [SMILES: CCN(CC)CCCC1(O)CN(C(=O)O[C@@H]2CC[C@]3(CO3)[C@@H]([C@@]3(C)O[C@@H]3CC=C(C)C)[C@@H]2OC)C1] | 495 [M + H]⁺ | 5.43 (s, 1H), 5.14 (dd, J = 10.4, 4.6 Hz, 1H), 3.78 (d, J = 25.8 Hz, 4H), 3.55 (dd, J = 11.1, 2.7 Hz, 1H), 3.37 (s, 3H), 2.91 (d, J = 4.3 Hz, 1H), 2.53-2.41 (m, 6H), 2.40-2.34 (m, 2H), 2.29 (dt, J = 13.5, 6.6 Hz, 1H), 2.09 (dt, J = 14.8, 7.3 Hz, 1H), 2.04-1.92 (m, 1H), 1.84 (dd, J = 23.8, 10.8 Hz, 4H), 1.78-1.72 (m, 1H), 1.67 (s, 3H), 1.59 (s, 6H), 1.14 (s, 3H), 0.97 (t, J = 7.2 Hz, 6H) |
| 62 | 63 | 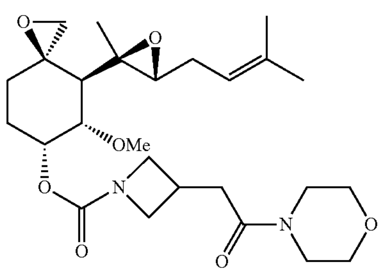 [SMILES: CO[C@@H]1[C@H](OC(=O)N2CC(CC(=O)N3CCOCC3)C2)CC[C@]2(CO2)[C@H]1[C@@]1(C)O[C@@H]1CC=C(C)C] | 493 [M + H]⁺ | 5.41 (s, 1H), 5.12 (m, 1H), 4.17-4.02 (m, 1H), 3.99-3.91 (m, 1H), 3.85-3.77 (m, 1H), 3.71-3.64 (m, 4H), 3.58 (m, 1H), 3.42 (m, 8H), 2.92 (d, J = 4.2 Hz, 1H), 2.84-2.67 (m, 2H), 2.56-2.43 (m, 3H), 2.27 (m, 1H), 2.08 (m, 2H), 1.87 (m, 3H), 1.68 (s, 3H), 1.58 (s, 3H), 1.12 (m, 3H), 1.02 (d, J = 11.9 Hz, 1H) |
| 63 | 64 | 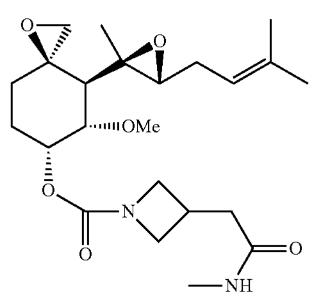 [SMILES: CNC(=O)CC1CN(C(=O)O[C@@H]2CC[C@]3(CO3)[C@@H]([C@@]3(C)O[C@@H]3CC=C(C)C)[C@@H]2OC)C1] | 437 [M + H]⁺ | 5.89-5.48 (m, 2H), 5.14 (t, J = 7.5 Hz, 1H), 4.07-4.03 (m, 2H), 3.69-3.50 (m, 3H), 3.39 (s, 3H), 2.91 (t, J = 4.3 Hz, 2H), 2.72 (d, J = 4.7 Hz, 3H), 2.51-2.39 (m, 4H), 2.36-2.24 (m, 1H), 2.12-2.10 (m, 1H), 2.05-1.92 (m, 1H), 1.84-1.78 (m, 3H), 1.68 (s, 3H), 1.59 (s, 3H), 1.13 (s, 3H), 1.02-0.94 (m, 1H) |

| Ex. | Int. | Structure | LC-MS | H-NMR (400 MHz, CDCl$_3$) |
|---|---|---|---|---|
| 64 | 65 | 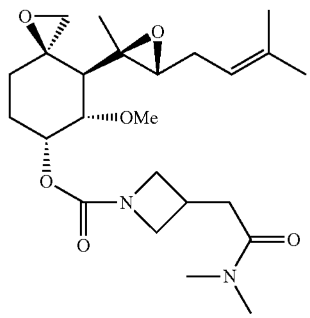 [SMILES: CO[C@@H]1[C@H](OC(=O)N2CC(CC(=O)N(C)C)C2)CC[C@]2(CO2)[C@H]1[C@@]1(C)O[C@@H]1CC=C(C)C] | 451 [M + H]$^+$ | 5.52 (s, 1H), 5.24-5.16 (m, 1H), 4.16 (t, J = 8.5 Hz, 2H), 3.75-3.53 (m, 3H), 3.46 (s, 3H), 3.06-2.89 (m, 8H), 2.77-2.61 (m, 2H), 2.60-2.46 (m, 2H), 2.42-2.27 (m, 1H), 2.21-1.99 (m, 2H), 1.94-1.78 (m, 3H), 1.75 (s, 3H), 1.66 (s, 3H), 1.19 (s, 3H), 1.04 (d, J = 13.0 Hz, 1H) |
| 65 | 66 | 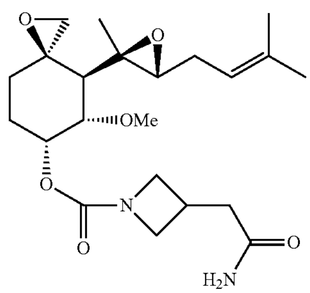 [SMILES: CO[C@@H]1[C@H](OC(=O)N2CC(CC(N)=O)C2)CC[C@]2(CO2)[C@H]1[C@@]1(C)O[C@@H]1CC=C(C)C] | 423 [M + H]$^+$ | 5.87-5.90 (m, 0.55H), 5.47 (s, 1H), 5.24 (s, 1H), 5.10-5.14 (m, 1H), 4.04-4.10 (m, 2H), 3.52-3.66 (m, 3H), 3.39 (s, 3H), 2.84-2.92 (m, 2H), 2.47-2.50 (m, 4H), 2.24-2.27 (m, 1H), 1.95-2.13 (m, 2H), 1.72-1.87 (m, 3H), 1.67 (s, 3H), 1.58 (s, 3H), 1.13 (s, 3H), 0.95-1.00 (m, 1H) |
| 66 | 67 | 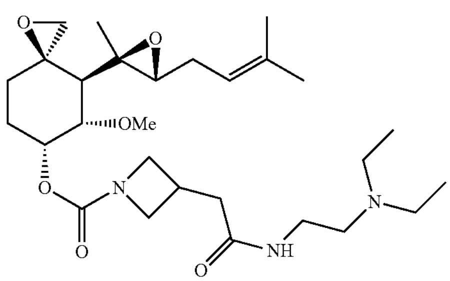 [SMILES: CCN(CC)CCNC(=O)CC1CN(C(=O)O[C@@H]2CC[C@]3(CO3)[C@@H]([C@@]3(C)O[C@@H]3CC=C(C)C)[C@@H]2OC)C1] | 522 [M + H]$^+$ | 6.17 (s, 1H), 5.45 (s, 1H), 5.20-5.10 (m, 1H), 4.05 (t, J = 8.3 Hz, 2H), 3.78-3.49 (m, 3H), 3.39 (s, 3H), 3.21 (d, J = 5.0 Hz, 2H), 2.91 (d, J = 4.3 Hz, 2H), 2.51-2.42 (m, 9H), 2.29 (dt, J = 13.4, 6.6 Hz, 1H), 2.15-1.94 (m, 2H), 1.88-1.71 (m, 4H), 1.68 (s, 3H), 1.59 (s, 3H), 1.13 (s, 3H), 1.03-0.88 (m, 7H) |
| 67 | 68 | 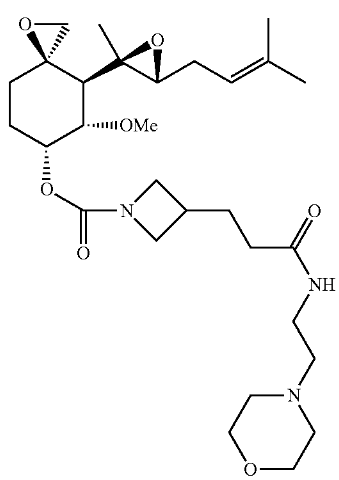 [SMILES: CO[C@@H]1[C@H](OC(=O)N2CC(CCC(=O)NCCN3CCOCC3)C2)CC[C@]2(CO2)[C@H]1[C@@]1(C)O[C@@H]1CC=C(C)C] | 550 [M + H]$^+$ | 6.40 (s, 1H), 5.44 (s, 1H), 5.17-5.10 (m, 1H), 3.96 (s, 2H), 3.72 (m, 4H), 3.54 (dd, J = 11.2, 2.6 Hz, 2H), 3.38 (s, 3H), 3.34 (d, J = 5.5 Hz, 2H), 2.91 (d, J = 4.3 Hz, 1H), 2.59-2.45 (m, 9H), 2.33-2.25 (m, 1H), 2.10 (m, 3H), 2.07-1.92 (m, 2H), 1.91-1.83 (m, 3H), 1.82-1.73 (m, 2H), 1.68 (s, 3H), 1.59 (s, 3H), 1.12 (s, 3H), 0.99 (dd, J = 10.5, 3.4 Hz, 1H) |

| Ex. | Int. | Structure | LC-MS | H-NMR (400 MHz, CDCl₃) |
|---|---|---|---|---|
| 68 | 69 | 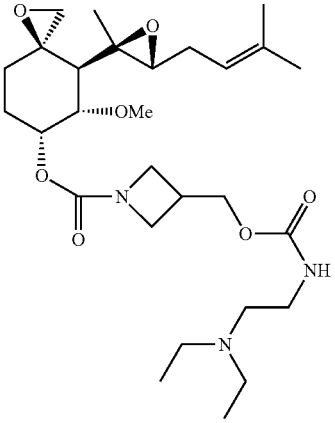 | 523 [M + H]⁺ | 5.48 (s, 1H), 5.12-5.23 (m, 1H), 3.66-4.13 (m, 6H), 3.52-3.56 (m, 1H), 3.39 (m, 3H), 3.14-3.18 (m, 1H), 2.91 (d, J = 4.4 Hz, 1H), 2.77-2.80 (m, 1H), 2.46-2.50 (m, 8H), 2.26-2.33 (m, 1H), 1.95-2.12 (m, 2H), 1.72-1.88 (m, 3H), 1.67 (s, 3H), 1.59 (s, 4H), 1.59 (s, 3H), 1.29 (s, 3H), 0.92-1.01 (m, 7H) |
| 69 | 70 | 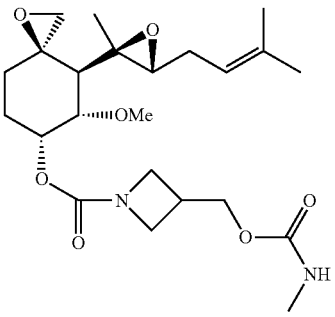 [SMILES: CNC(=O)OCC1CN(C(=O)O[C@@H]2CC[C@]3(CO3)[C@@H]([C@@]3(C)O[C@@H]3CC=C(C)C)[C@@H]2OC)C1] | 453 [M + H]⁺ | 5.46 (s, 1H), 5.12-5.15 (m, 1H), 3.70-4.15 (m, 6H), 3.53 (dd, J = 2.8, 2.4 Hz, 1H), 3.39 (s, 3H), 2.91 (d, J = 4.0 Hz, 1H), 2.72-2.76 (m, 4H), 2.46-2.50 (m, 2H), 2.27-2.31 (m, 1H), 1.95-2.10 (m, 2H), 1.77-1.84 (m, 3H), 1.68 (s, 3H), 1.59 (s, 3H), 1.12 (s, 3H), 0.96-1.02 (m, 1H) |
| 70 | 71 | 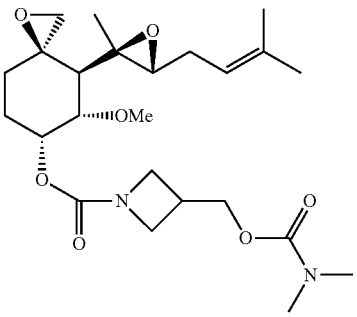 [SMILES: CO[C@@H]1[C@H](OC(=O)N2CC(COC(=O)N(C)C)C2)CC[C@]2(CO2)[C@H]1[C@@]1(C)O[C@@H]1CC=C(C)C] | 467 [M + H]⁺ | 5.50 (s, 1H), 5.27-5.13 (m, 1H), 4.26-3.97 (m, 4H), 3.76 (s, 2H), 3.61 (dd, J = 11.2, 2.7 Hz, 1H), 3.45 (s, 3H), 2.98 (d, J = 4.3 Hz, 1H), 2.90 (t, J = 10.4 Hz, 7H), 2.61-2.50 (m, 2H), 2.41-2.30 (m, 1H), 2.16 (dt, J = 14.7, 7.4 Hz, 1H), 2.11-1.99 (m, 1H), 1.93 (dd, J = 14.4, 2.5 Hz, 1H), 1.88-1.77 (m, 2H), 1.74 (s, 3H), 1.66 (s, 3H), 1.20 (s, 3H), 1.11-1.03 (m, 1H) |
| 71 | 72 | 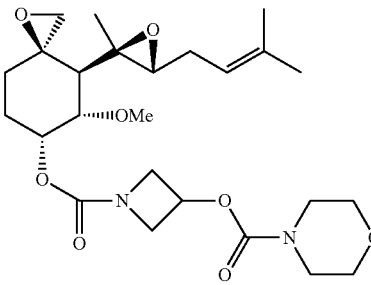 | 495 [M + H]⁺ | 5.47 (s, 1H), 5.14 (t, J = 7.5 Hz, 1H), 5.05 (dq, J = 6.7, 4.2 Hz, 1H), 4.30-4.13 (m, 2H), 3.91 (d, J = 21.4 Hz, 2H), 3.61 (d, J = 4.2 Hz, 4H), 3.54 (dd, J = 11.2, 2.7 Hz, 1H), 3.46-3.35 (m, 7H), 2.91 (d, J = 4.3 Hz, 1H), 2.52-2.43 (m, 2H), 2.32-2.21 (m, 1H), 2.08 (dt, J = 26.6, 9.6 Hz, 1H), 2.01-1.93 (m, 1H), 1.85-1.74 (m, 3H), 1.68 (s, 3H), 1.59 (s, 3H), 1.12 (d, J = 5.9 Hz, 3H), 0.99 (d, J = 13.7 Hz, 1H) |

| Ex. | Int. | Structure | LC-MS | H-NMR (400 MHz, CDCl₃) |
|---|---|---|---|---|
| 72 | 73 | 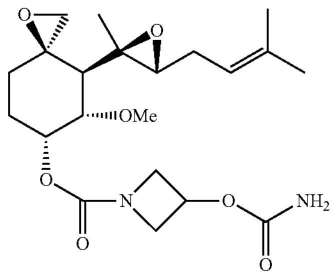 [SMILES: CO[C@@H]1[C@H](OC(=O)N2CC(OC(N)=O)C2)CC[C@]2(CO2)[C@H]1[C@@]1(C)O[C@@H]1CC=C(C)C] | 425 [M + H]⁺ | 5.46 (d, J = 2.8 Hz, 1H), 5.11-5.16 (m, 1H), 5.02-5.08 (m, 1H), 4.66 (s, 1H), 4.16-4.23 (m, 2H), 3.87-3.94 (m, 2H), 3.52-3.56 (m, 2H), 3.38 (s, 3H), 2.91 (d, J = 4.4 Hz, 1H), 2.46-2.51 (m, 2H), 2.25-2.32 (m, 1H), 2.05-2.12 (m, 1H), 1.93-2.01 (m, 1H), 1.75-1.88 (m, 3H), 1.67 (s, 3H), 1.58 (s, 3H), 1.12 (s, 3H), 0.97-1.02 (m, 1H) |
| 73 | 74 | 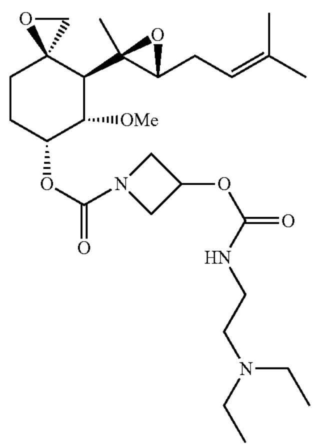 [SMILES: CCN(CC)CCNC(=O)OC1CN(C(=O)O[C@@H]2CC[C@]3(CO3)[C@@H]([C@@]3(C)O[C@@H]3CC=C(C)C)[C@@H]2OC)C1] | 524 [M + H]⁺ | 5.81 (br, 1H), 5.52 (s, 1H), 5.18 (d, J = 8.2 Hz, 1H), 5.01-5.06 (m, 1H), 4.23-4.25 (m, 2H), 3.88-4.01 (m, 2H), 3.52-3.56 (m, 1H), 3.45 (s, 3H), 3.29 (br, 2H), 2.96 (d, J = 4.4 Hz, 1H), 2.67 (br, 5H), 2.53-2.57 (m, 3H), 2.32-2.37 (m, 1H), 2.15-2.18 (m, 1H), 2.01-2.04 (m, 1H), 1.81-1.89 (m, 3H), 1.73 (s, 3H), 1.65 (s, 3H), 1.11 (s, 3H), 0.97-1.05 (m, 7H) |
| 74 | 75 | 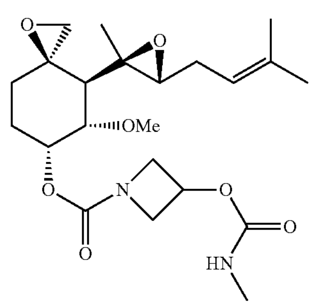 [SMILES: CNC(=O)OC1CN(C(=O)O[C@@H]2CC[C@]3(CO3)[C@@H]([C@@]3(C)O[C@@H]3CC=C(C)C)[C@@H]2OC)C1] | 439 [M + H]⁺ | 5.46 (s, 1H), 5.21-5.23 (m, 1H), 5.09-5.15 (m, 1H), 4.70 (s, 1H), 4.17-4.19 (m, 2H), 3.91-3.98 (m, 2H), 3.58-3.62 (m, 1H), 3.39 (s, 3H), 2.97 (d, J = 4.4 Hz, 1H), 2.79 (d, J = 4.8 Hz, 3H), 2.53-2.57 (m, 2H), 2.25-2.31 (m, 1H), 2.07-2.13 (m, 1H), 1.94-2.01 (m, 1H), 1.79-1.93 (m, 3H), 1.74 (s, 3H), 1.64 (s, 3H), 1.19 (s, 3H), 1.03-1.08 (m, 1H) |
| 75 | 76 | 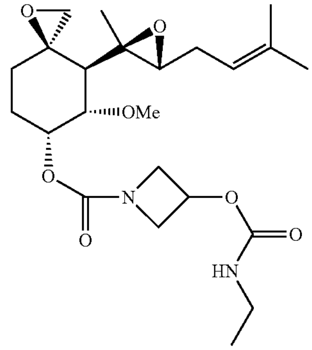 [SMILES: CCNC(=O)OC1CN(C(=O)O[C@@H]2CC[C@]3(CO3)[C@@H]([C@@]3(C)O[C@@H]3CC=C(C)C)[C@@H]2OC)C1] | 453 [M + H]⁺ | 5.52 (s, 1H), 5.21 (t, J = 7.5 Hz, 1H), 5.12 (s, 1H), 4.24 (s, 2H), 3.96 (d, J = 23.1 Hz, 2H), 3.61 (dd, J = 11.2, 2.6 Hz, 1H), 3.46 (s, 3H), 3.27-3.18 (m, 2H), 2.98 (d, J = 4.3 Hz, 1H), 2.54 (t, J = 5.2 Hz, 2H), 2.38-2.30 (m, 1H), 2.17 (dd, J = 14.8, 7.4 Hz, 1H), 2.02 (dd, J = 13.5, 4.5 Hz, 1H), 1.87 (dd, J = 23.4, 6.8 Hz, 3H), 1.70 (d, J = 34.8 Hz, 6H), 1.17 (dd, J = 15.9, 8.7 Hz, 6H), 1.10-1.03 (m, 1H) |

| Ex. | Int. | Structure | LC-MS | H-NMR (400 MHz, CDCl₃) |
|---|---|---|---|---|
| 76 | 77 | 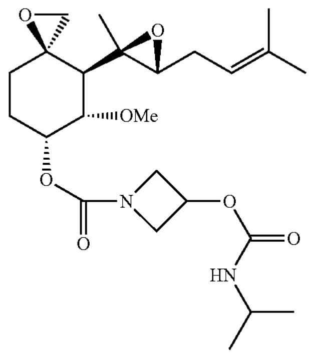 [SMILES: CO[C@@H]1[C@H](OC(=O)N2CC(OC(=O)NC(C)C)C2)CC[C@]2(CO2)[C@H]1[C@@]1(C)O[C@@H]1CC=C(C)C] | 467 [M + H]⁺ | 5.52 (s, 1H), 5.21 (m, 1H), 5.11 (s, 1H), 4.64 (s, 1H), 4.24 (s, 2H), 3.98 m, 2H), 3.85-3.76 (m, 1H), 3.61 (m, 1H), 3.46 (s, 3H), 2.98 (d, J = 4.3 Hz, 1H), 2.55 (m, 2H), 2.41-2.31 (m, 1H), 2.16 (m, 1H), 2.04 (m, 1H), 1.96-1.78 (m, 3H), 1.74 (s, 3H), 1.66 (s, 3H), 1.21-1.14 (m, 9H), 1.06 (d, J = 13.6 Hz, 1H) |
| 77 | 78 | 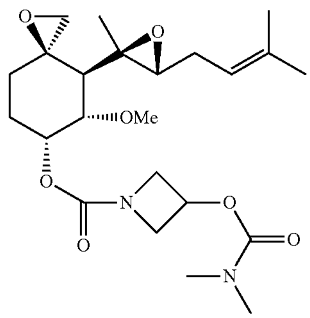 [SMILES: CO[C@@H]1[C@H](OC(=O)N2CC(OC(=O)N(C)C)C2)CC[C@]2(CO2)[C@H]1[C@@]1(C)O[C@@H]1CC=C(C)C] | 453 [M + H]⁺ | 5.52 (s, 1H), 5.21 (m, 1H), 5.09 (m, 1H), 4.41-4.20 (m, 2H), 3.98 (d, J = 26.5 Hz, 2H), 3.61 (dd, J = 11.2, 2.6 Hz, 1H), 3.46 (s, 3H), 2.96 (m, 7H), 2.55 (m, 2H), 2.40-2.30 (m, 1H), 2.16 (m, 1H), 2.09-2.00 (m, 1H), 1.96-1.79 (m, 3H), 1.75 (s, 3H), 1.65 (s, 3H), 1.20 (s, 3H), 1.60 (dd, J = 10.5, 3.3 Hz, 1H) |
| 78 | 79 | 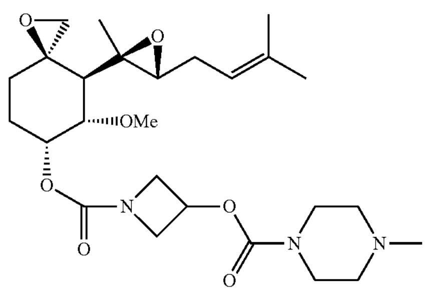 [SMILES: CO[C@@H]1[C@H](OC(=O)N2CC(OC(=O)N3CCN(C)CC3)C2)CC[C@]2(CO2)[C@H]1[C@@]1(C)O[C@@H]1CC=C(C)C] | 508 [M + H]⁺ | 5.48 (s, 1H), 5.13 (t, J = 7.4 Hz, 1H), 5.03 (s, 1H), 4.20 (dd, J = 9.7, 6.3 Hz, 2H), 3.99-3.65 (m, 6H), 3.55 (dd, J = 11.3, 2.7 Hz, 1H), 3.39 (d, J = 4.6 Hz, 3H), 2.91 (d, J = 4.3 Hz, 1H), 2.77 (dd, J = 16.3, 5.3 Hz, 3H), 2.58-2.45 (m, 5H), 2.31-2.23 (m, 1H), 2.09 (dt, J = 14.9, 7.4 Hz, 1H), 2.00-1.93 (m, 1H), 1.85-1.73 (m, 4H), 1.68 (s, 3H), 1.59 (s, 3H), 1.12 (d, J = 5.0 Hz, 3H), 0.99 (d, J = 13.8 Hz, 1H) |
| 79 | 80 | 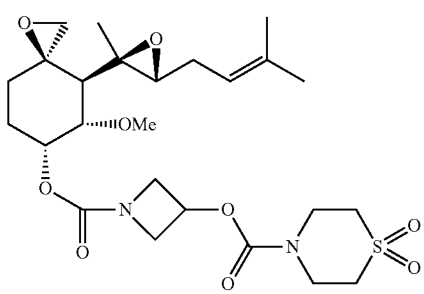 [SMILES: CO[C@@H]1[C@H](OC(=O)N2CC(OC(=O)N3CCS(=O)(=O)CC3)C2)CC[C@]2(CO2)[C@H]1[C@@]1(C)O[C@@H]1CC=C(C)C] | 543 [M + H]⁺ | 5.48 (s, 1H), 5.17-5.02 (m, 2H), 4.21 (s, 2H), 3.95 (s, 6H), 3.55 (dd, J = 11.3, 2.7 Hz, 1H), 3.39 (d, J = 4.2 Hz, 3H), 2.99 (s, 4H), 2.91 (d, J = 4.3 Hz, 1H), 2.47 (d, J = 4.3 Hz, 1H), 2.34-2.21 (m, 1H), 2.19-2.05 (m, 1H), 1.97 (dd, J = 13.4, 9.1 Hz, 1H), 1.85-1.74 (m, 4H), 1.68 (s, 3H), 1.59 (s, 3H), 1.12 (d, J = 5.5 Hz, 3H), 0.99 (d, J = 13.4 Hz, 1H) |

| Ex. | Int. | Structure | LC-MS | H-NMR (400 MHz, CDCl₃) |
|---|---|---|---|---|
| 80 | 81 | 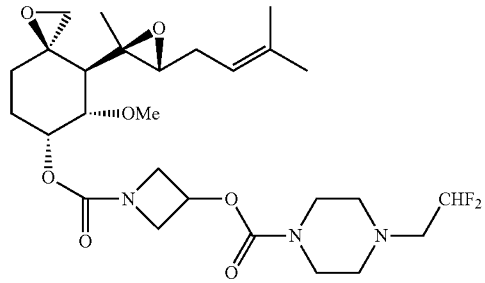 [SMILES: CO[C@@H]1[C@H](OC(=O)N2CC(OC(=O)N3CCN(CC(F)F)CC3)C2)CC[C@]2(CO2)[C@H]1[C@@]1(C)O[C@@H]1CC=C(C)C] | 558 [M + H]⁺ | 5.86 (t, J = 54.5 Hz, 1H), 5.46 (s, 1H), 5.18-5.10 (m, 1H), 5.07-4.98 (m, 1H), 4.35-4.10 (m, 2H), 3.91 (d, J = 23.6 Hz, 2H), 3.63-3.40 (m, 5H), 3.39 (s, 3H), 2.91 (d, J = 4.3 Hz, 1H), 2.74 (s, 2H), 2.65-2.44 (m, 6H), 2.28 (dt, J = 13.5, 6.6 Hz, 1H), 2.09 (dt, J = 14.6, 7.2 Hz, 1H), 1.97 (td, J = 13.5, 4.6 Hz, 1H), 1.87-1.73 (m, 3H), 1.68 (s, 3H), 1.59 (s, 3H), 1.12 (d, J = 5.8 Hz, 3H), 0.99 (d, J = 13.8 Hz, 1H) |
| 81 | 82 | 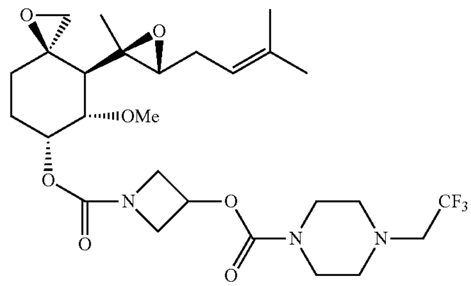 [SMILES: CO[C@@H]1[C@H](OC(=O)N2CC(OC(=O)N3CCN(CC(F)(F)F)CC3)C2)CC[C@]2(CO2)[C@H]1[C@@]1(C)O[C@@H]1CC=C(C)C] | 576 [M + H]⁺ | 5.46 (s, 1H), 5.12-5.16 (m, 1H), 5.01-5.06 (m, 1H), 4.18 (m, 2H), 3.88-3.95 (m, 2H), 3.54 (dd, J = 2.8, 2.4 Hz, 6H), 3.88-3.95 (m, 7H) 2.90-2.98 (m, 3H), 2.61 (m, 4H), 2.46-2.50 (m, 2H), 2.25-2.30 (m, 1H), 2.07-2.13 (m, 1H), 1.93-2.01 (m, 1H), 1.76-1.87 (m, 3H), 1.68 (s, 3H), 1.59 (s, 3H), 1.12 (s, 3H), 1.00 (d, J = 2.4 Hz, 1H) |
| 82 | 83 | 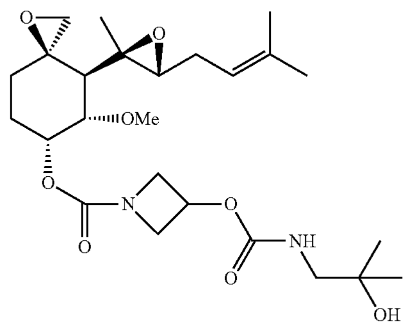 [SMILES: CO[C@@H]1[C@H](OC(=O)N2CC(OC(=O)NCC(C)(C)O)C2)CC[C@]2(CO2)[C@H]1[C@@]1(C)O[C@@H]1CC=C(C)C] | 497 [M + H]⁺ | 5.46 (s, 1H), 5.20-5.01 (m, 3H), 4.32-4.11 (m, 2H), 3.87 (t, J = 26.8 Hz, 2H), 3.56-3.49 (m, 1H), 3.39 (d, J = 2.4 Hz, 3H), 3.11 (d, J = 6.2 Hz, 2H), 2.91 (d, J = 4.3 Hz, 1H), 2.48 (dd, J = 12.8, 5.3 Hz, 2H), 2.33-2.21 (m, 1H), 2.14-1.91 (m, 2H), 1.89-1.73 (m, 3H), 1.68 (s, 3H), 1.59 (s, 3H), 1.17 (s, 6H), 1.13 (s, 3H), 1.03-0.96 (m, 1H) |
| 83 | 84 | 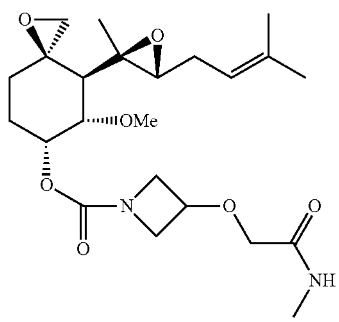 [SMILES: CNC(=O)COC1CN(C(=O)O[C@@H]2CC[C@]3(CO3)[C@@H]([C@@]3(C)O[C@@H]3CC=C(C)C)[C@@H]2OC)C1] | 453 [M + H]⁺ | 6.59 (s, 1H), 5.54 (d, J = 2.5 Hz, 1H), 5.20 (dt, J = 17.9, 6.1 Hz, 1H), 4.39-4.26 (m, 1H), 4.15 (s, 2H), 4.05-3.80 (m, 4H), 3.62 (dd, J = 11.2, 2.7 Hz, 1H), 3.46 (s, 3H), 2.99 (d, J = 4.3 Hz, 1H), 2.89 (d, J = 5.0 Hz, 3H), 2.60-2.49 (m, 2H), 2.43-2.28 (m, 1H), 2.16 (dt, J = 14.7, 7.3 Hz, 1H), 2.03 (dd, J = 13.7, 4.8 Hz, 1H), 1.96-1.78 (m, 3H), 1.75 (s, 3H), 1.66 (s, 3H), 1.20 (s, 3H), 1.11-1.02 (m, 1H) |
| 84 | 85 | 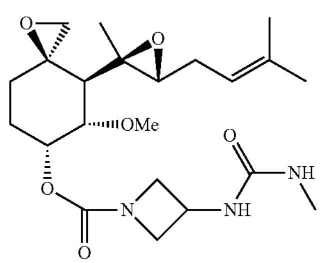 [SMILES: CNC(=O)NC1CN(C(=O)O[C@@H]2CC[C@]3(CO3)[C@@H]([C@@]3(C)O[C@@H]3CC=C(C)C)[C@@H]2OC)C1] | 438 [M + H]⁺ | 5.49 (s, 1H), 5.13 (t, J = 7.5 Hz, 1H), 4.70 (s, 1H), 4.51 (s, 1H), 4.18 (dd, J = 20.4, 12.1 Hz, 2H), 3.74-3.51 (m, 3H), 3.40 (s, 3H), 2.90 (d, J = 4.2 Hz, 1H), 2.70 (d, J = 4.8 Hz, 3H), 2.51 (dd, J = 16.8, 5.2 Hz, 2H), 2.29 (d, J = 7.4 Hz, 1H), 2.14-1.93 (m, 2H), 1.80 (d, J = 11.5 Hz, 2H), 1.68 (s, 3H), 1.59 |

| Ex. | Int. | Structure | LC-MS | H-NMR (400 MHz, CDCl₃) |
|---|---|---|---|---|
| | | | | (s, 3H), 1.13 (s, 3H), 0.99 (d, J = 12.5 Hz, 1H) |
| 85 | 86 | 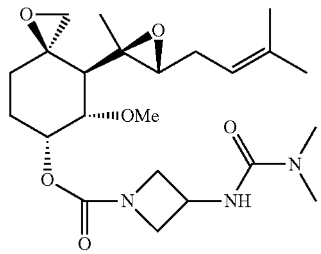 | 438 [M + H]⁺ | 5.54 (s, 1H), 5.21 (t, J = 7.5 Hz, 1H), 4.58 (s, 1H), 4.27 (dd, J = 19.4, 10.9 Hz, 2H), 3.85 (s, 1H), 3.73 (dd, J = 9.1, 5.2 Hz, 1H), 3.61 (dd, J = 11.3, 2.6 Hz, 1H), 3.47 (s, 3H), 2.98 (d, J = 4.3 Hz, 1H), 2.93 (s, 6H), 2.54 (dd, J = 5.3, 3.0 Hz, 2H), 2.34 (dd, J = 14.1, 7.0 Hz, 1H), 2.17 (dd, J = 14.8, 7.3 Hz, 1H), 2.10-2.02 (m, 1H), 1.92-1.82 (m, 3H), 1.75 (s, 3H), 1.66 (s, 3H), 1.19 (s, 3H), 1.05 (d, J = 13.9 Hz, 1H) |
| 86 | 87 | 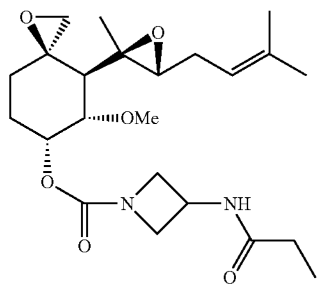 [SMILES: CCC(=O)NC1CN(C(=O)O[C@@H]2CC[C@]3(CO3)[C@@H]([C@@]3(C)O[C@@H]3CC=C(C)C)[C@@H]2OC)C1] | 437 [M + H]⁺ | 6.24 (s, 1H), 5.54 (s, 1H), 5.21 (m, 1H), 4.68 (s, 1H), 4.27 (m, 2H), 3.85 (s, 1H), 3.75 (m, 1H), 3.62 (dd, J = 11.3, 2.6 Hz, 1H), 3.46 (s, 3H), 2.98 (d, J = 4.3 Hz, 1H), 2.56 (dd, J = 8.7 Hz, 5.3 Hz, 2H), 2.30 (m, 1H), 2.20 (m, 3H), 2.03 (m, 1H), 1.85 (m, 3H), 1.75 (s, 3H), 1.66 (s, 3H), 1.17 (m, 6H), 1.11-1.00 (m, 1H) |
| 87 | 88 | 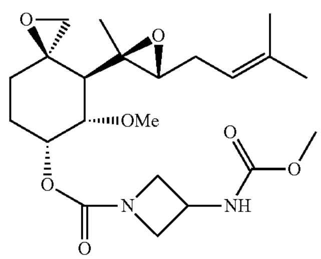 [SMILES: COC(=O)NC1CN(C(=O)O[C@@H]2CC[C@]3(CO3)[C@@H]([C@@]3(C)O[C@@H]3CC=C(C)C)[C@@H]2OC)C1] | 439 [M + H]⁺ | 5.52 (s, 1H), 5.20 (dd, J = 16.1, 8.6 Hz, 1H), 4.32 (dd, J = 60.1, 45.3 Hz, 3H), 3.94-3.74 (m, 2H), 3.68 (s, 3H), 3.61 (dd, J = 11.2, 2.6 Hz, 1H), 3.45 (s, 3H), 2.98 (d, J = 4.3 Hz, 1H), 2.59-2.50 (m, 2H), 2.42-2.30 (m, 1H), 2.16 (dt, J = 14.7, 7.3 Hz, 1H), 2.04 (td, J = 13.5, 4.5 Hz, 1H), 1.94-1.81 (m, 3H), 1.75 (s, 3H), 1.66 (s, 3H), 1.20 (s, 3H), 1.06 (d, J = 13.7 Hz, 1H) |
| 88 | 89 | 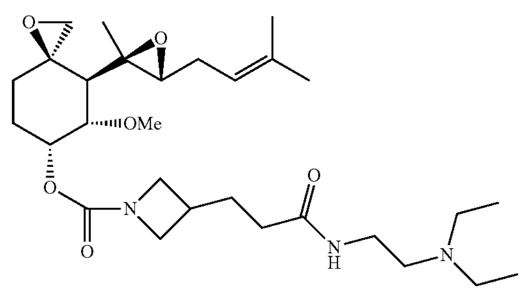 [SMILES: CCN(CC)CCNC(=O)CCC1CN(C(=O)O[C@@H]2CC[C@]3(CO3)[C@@H]([C@@]3(C)O[C@@H]3CC=C(C)C)[C@@H]2OC)C1] | 536 [M + H]⁺ | 5.43 (d, J = 3.1 Hz, 1H), 5.16-5.12 (m, 1H), 3.96 (s, 2H), 3.55-3.52 (m, 2H), 3.38 (s, 3H), 3.27-3.25 (m, 2H), 2.91 (d, J = 4.3 Hz, 1H), 2.56-2.46 (m, 9H), 2.35-2.23 (m, 1H), 2.16-2.03 (m, 3H), 2.03-1.91 (m, 2H), 1.86 (d, J = 7.6 Hz, 3H), 1.81-1.78 (m, 3H), 1.67 (s, 3H), 1.59 (s, 3H), 1.13 (s, 3H), 0.99 (t, J = 7.2 Hz, 7H) |
| 89 | 90 | 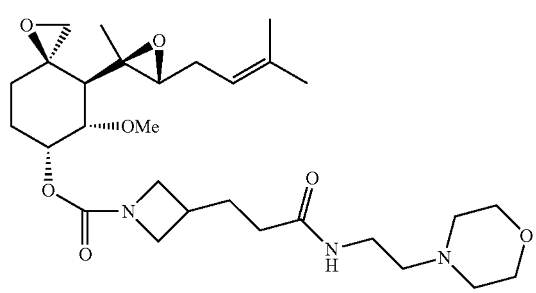 [SMILES: CO[C@@H]1[C@H](OC(=O)N2CC(CCC(=O)NCCN3CCOCC3)C2)CC[C@]2(CO2)[C@H]1[C@@]1(C)O[C@@H]1CC=C(C)C] | 550 [M + H]⁺ | 6.40 (s, 1H), 5.44 (s, 1H), 5.17-5.09 (m, 1H), 3.96 (s, 2H), 3.69 (d, J = 25.2 Hz, 4H), 3.54 (dd, J = 11.2, 2.6 Hz, 2H), 3.37 (d, J = 5.3 Hz, 3H), 3.34 (d, J = 5.5 Hz, 2H), 2.91 (d, J = 4.3 Hz, 1H), 2.62-2.41 (m, 9H), 2.33-2.24 (m, 1H), 2.10 (dd, J = 14.7, 7.2 Hz, 3H), 2.06-1.90 (m, 2H), 1.91-1.82 (m, 3H), 1.81-1.70 (m, 2H), 1.68 (s, 3H), 1.59 (s, 3H), 1.12 (d, J = 6.3 Hz, |

| Ex. | Int. | Structure | LC-MS | H-NMR (400 MHz, CDCl$_3$) |
|---|---|---|---|---|
| | | | | 3H), 0.99 (dd, J = 10.5, 3.4 Hz, 1H) |
| 90 | 91 | 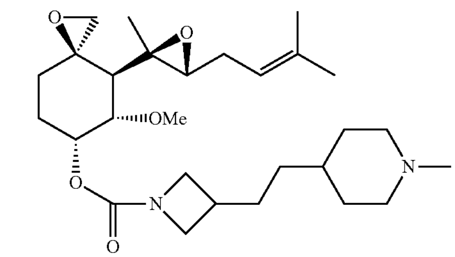 [SMILES: CO[C@@H]1[C@H](OC(=O)N2CC(CCC3CCN(C)CC3)C2)CC[C@]2(CO2)[C@H]1[C@@]1(C)O[C@@H]1CC=C(C)C] | 491 [M + H]$^+$ | 5.44 (s, 1H), 5.12-5.16 (m, 1H), 3.96 (s, 2H), 3.51-3.60 (m, 3H), 3.28-3.48 (m, 7H), 2.91 (d, J = 4.0 Hz, 1H), 2.61 (s, 3H), 2.41-2.52 (m, 4H), 2.28-2.30 (m, 1H), 1.93-2.12 (m, 2H), 1.75-1.84 (m, 5H), 1.67 (s, 3H), 1.50-1.62 (m, 6H), 1.34 (s, 1H), 1.13-1.18 (m, 5H), 0.97 (d, J = 4.0 Hz, 1H) |
| 91 | 92 | 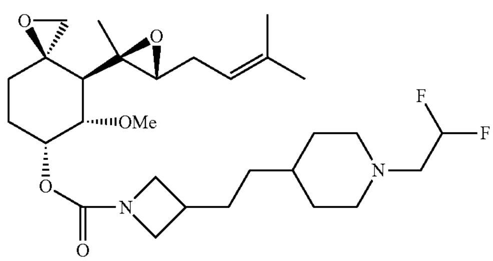 [SMILES: CO[C@@H]1[C@H](OC(=O)N2CC(CCC3CCN(CC(F)F)CC3)C2)CC[C@]2(CO2)[C@H]1[C@@]1(C)O[C@@H]1CC=C(C)C] | 541 [M + H]$^+$ | 6.01-5.87 (m, 1H), 5.86 (s, 1H), 5.38-5.31 (m, 1H), 5.12-5.14 (m, 1H), 3.95 (s, 2H), 3.47-3.56 (m, 3H), 3.38 (s, 3H), 2.90-2.93 (m, 3H), 2.66-2.74 (m, 8H), 2.39-2.51 (m, 3H), 2.27-2.30 (m, 1H), 2.07-2.16 (m, 3H), 1.94-2.02 (m, 6H), 1.81-1.88 (m, 3H), 1.67 (s, 3H), 1.60 (s, 4H), 1.48-1.54 (m, 2H), 1.13 (s, 3H), 1.07-1.11 (m, 1H), 0.99 (d, J = 13.8 Hz, 1H) |
| 92 | 93 | 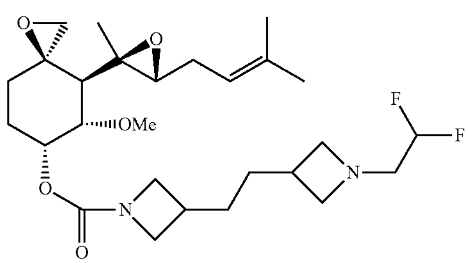 [SMILES: CO[C@@H]1[C@H](OC(=O)N2CC(CCC3CN(CC(F)F)C3)C2)CC[C@]2(CO2)[C@H]1[C@@]1(C)O[C@@H]1CC=C(C)C] | 513 [M + H]$^+$ | 5.86-5.39 (m, 2H), 5.14 (t, J = 7.5 Hz, 1H), 3.95 (s, 2H), 3.52 (ddd, J = 23.4, 10.1, 5.2 Hz, 5H), 3.39 (d, J = 3.8 Hz, 3H), 2.92 (t, J = 6.1 Hz, 1H), 2.81 (dd, J = 16.4, 10.0 Hz, 2H), 2.77-2.63 (m, 2H), 2.53-2.34 (m, 4H), 2.34-2.22 (m, 1H), 2.09 (dt, J = 14.8, 7.3 Hz, 1H), 2.02-1.69 (m, 5H), 1.67 (s, 3H), 1.59 (s, 3H), 1.42 (s, 3H), 1.13 (s, 3H), 0.99 (d, J = 13.8 Hz, 1H) |
| 93 | 94 | 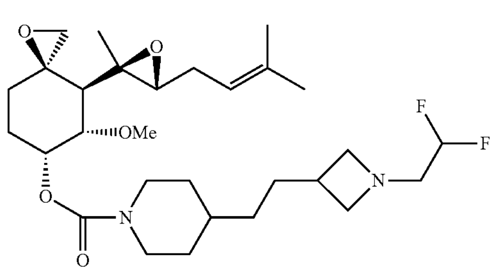 [SMILES: CO[C@@H]1[C@H](OC(=O)N2CCC(CCC3CN(CC(F)F)C3)CC2)CC[C@]2(CO2)[C@H]1[C@@]1(C)O[C@@H]1CC=C(C)C] | 541 [M + H]$^+$ | 5.60-5.83 (m, 1H), 5.47 (s, 1H), 5.14 (t, J = 1.2 Hz, 1H), 3.95-4.07 (m, 2H), 3.51-3.58 (m, 3H), 3.37 (s, 3H), 2.69-2.93 (m, 7H), 2.46-2.52 (m, 3H), 2.27-2.31 (m, 1H), 2.11-2.18 (m, 1H), 1.71-2.01 (m, 4H), 1.67 (s, 3H), 1.60 (s, 5H), 1.42-1.48 (m, 2H), 1.24-1.35 (m, 1H), 0.95-1.16 (m, 8H) |

| Ex. | Int. | Structure | LC-MS | H-NMR (400 MHz, CDCl₃) |
|---|---|---|---|---|
| 94 | 95 | 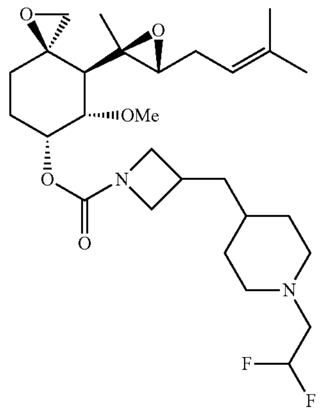 [SMILES: CO[C@@H]1[C@H](OC(=O)N2CC(CC3CCN(CC(F)F)CC3)C2)CC[C@]2(CO2)[C@H]1[C@@]1(C)O[C@@H]1CC=C(C)C] | 527 [M + H]⁺ | 5.68 (tt, J = 56.0, 4.4 Hz, 1H), 5.50 (s, 1H), 5.25-5.16 (m, 1H), 4.04 (s, 2H), 3.74-3.50 (m, 3H), 3.45 (s, 3H), 2.98 (d, J = 4.3 Hz, 1H), 2.91 (d, J = 11.7 Hz, 2H), 2.70 (td, J = 15.1, 4.3 Hz, 2H), 2.65-2.57 (m, 1H), 2.55 (d, J = 6.4 Hz, 1H), 2.53 (d, J = 4.3 Hz, 1H), 2.40-2.30 (m, 1H), 2.15 (dt, J = 17.4, 9.3 Hz, 3H), 2.08-2.00 (m, 1H), 1.97-1.89 (m, 1H), 1.83 (dd, J = 26.8, 11.6 Hz, 2H), 1.74 (s, 3H), 1.66 (s, 4H), 1.57 (s, 2H), 1.26 (dd, J = 16.3, 7.3 Hz, 4H), 1.20 (s, 3H), 1.06 (dd, J = 10.2, 3.1 Hz, 1H) |
| 95 | 96 | 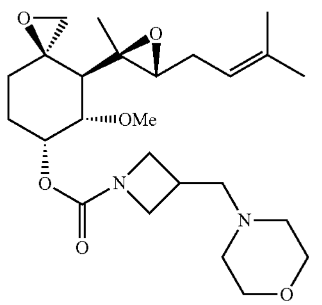 [SMILES: CO[C@@H]1[C@H](OC(=O)N2CC(CN3CCOCC3)C2)CC[C@]2(CO2)[C@H]1[C@@]1(C)O[C@@H]1CC=C(C)C] | 465 [M + H]⁺ | 5.45 (d, J = 3.0 Hz, 1H), 5.17-5.09 (m, 1H), 4.09-3.91 (m, 2H), 3.71-3.46 (m, 7H), 3.39 (s, 3H), 2.91 (d, J = 4.3 Hz, 1H), 2.74-2.64 (m, 1H), 2.57-2.43 (m, 4H), 2.41-2.20 (m, 5H), 2.09 (dt, J = 14.8, 7.4 Hz, 1H), 2.02-1.92 (m, 1H), 1.89-1.72 (m, 3H), 1.67 (s, 3H), 1.59 (s, 3H), 11.5 (d, J = 16.1 Hz, 3H), 1.04-0.94 (m, 1H) |
| 96 | 97 | 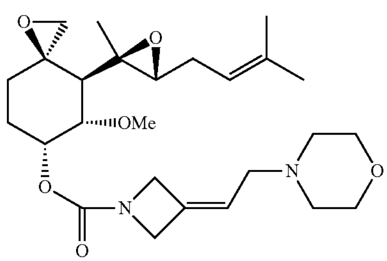 [SMILES: CO[C@@H]1[C@H](OC(=O)N2CC(=CCN3CCOCC3)C2)CC[C@]2(CO2)[C@H]1[C@@]1(C)O[C@@H]1CC=C(C)C] | 477 [M + H]⁺ | 5.53 (d, J = 3.0 Hz, 1H), 5.41 (s, 1H), 5.25-5.18 (m, 1H), 4.52 (s, 4H), 3.75-3.67 (m, 4H), 3.62 (dd, J = 11.2, 2.7 Hz, 1H), 3.46 (s, 3H), 2.99 (d, J = 4.3 Hz, 1H), 2.84 (d, J = 6.9 Hz, 2H), 2.61-2.51 (m, 2H), 2.49-2.31 (m, 5H), 2.17 (dt, J = 14.7, 7.3 Hz, 1H), 2.06 (td, J = 13.5, 4.4 Hz, 1H), 1.95 (ddd, J = 14.0, 6.5, 4.0 Hz, 1H), 1.89-1.79 (m, 2H), 1.75 (s, 3H), 1.66 (s, 3H), 1.21 (s, 3H), 1.13-1.03 (m, 1H) |
| 97 | 98 | 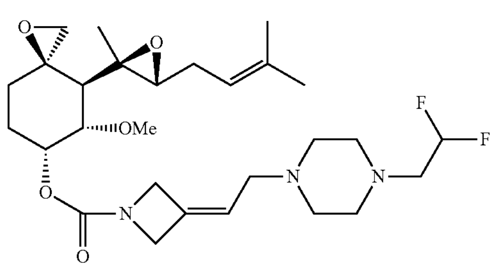 [SMILES: CO[C@@H]1[C@H](OC(=O)N2CC(=CCN3CCN(CC(F)F)CC3)C2)CC[C@]2(CO2)[C@H]1[C@@]1(C)O[C@@H]1CC=C(C)C] | 540 [M + H]⁺ | 5.87 (tt, J = 56.0, 4.3 Hz, 1H), 5.53 (d, J = 3.1 Hz, 1H), 5.41 (s, 1H), 5.25-5.15 (m, 1H), 4.51 (s, 4H), 3.68-3.55 (m, 1H), 3.44 (d, J = 24.5 Hz, 3H), 2.99 (d, J = 4.3 Hz, 1H), 2.84 (d, J = 6.6 Hz, 2H), 2.75 (td, J = 15.0, 4.3 Hz, 2H), 2.69-2.40 (m, 9H), 2.40-2.31 (m, 1H), 2.17 (dt, J = 14.6, 7.2 Hz, 1H), 2.06 (td, J = 13.7, 4.3 Hz, 1H), 1.99-1.92 (m, 1H), 1.90-1.80 (m, 2H), 1.75 (s, 4H), 1.66 (s, 3H), 1.23 (d, J = 29.3 Hz, 3H), 1.08 (d, J = 12.4 Hz, 1H) |

-continued

| Ex. | Int. | Structure | LC-MS | H-NMR (400 MHz, CDCl₃) |
|---|---|---|---|---|
| 98 | 99 | 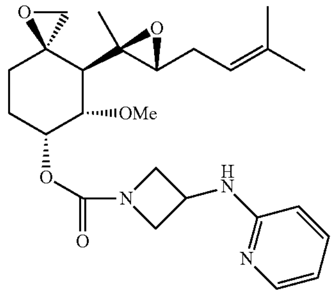 [SMILES: CO[C@@H]1[C@H](OC(=O)N2CC(Nc3ccccn3)C2)CC[C@]2(CO2)[C@H]1[C@@]1(C)O[C@@H]1CC=C(C)C] | 458 [M + H]⁺ | 8.01-8.03 (m, 1H), 7.35-7.39 (m, 1H), 6.55-6.58 (m, 1H), 6.31 (s, 1H), 5.46 (s, 1H), 5.13 (t, J = 7.8 Hz, 1H), 4.81-4.82 (m, 1H), 4.26-4.61 (s, 3H), 3.70-3.80 (m, 2H), 3.55 (dd, J = 6.4 Hz, 1H), 3.40 (s, 3H), 2.91 (d, J = 4.4 Hz, 1H), 2.46-2.50 (m, 2H), 2.27-2.30 (m, 1H), 1.95-2.12 (m, 2H), 1.83-1.88 (m, 1H), 1.76-1.81 (m, 2H), 1.67 (s, 3H), 1.61 (s, 3H), 1.13 (s, 3H), 0.99 (d, J = 13.8 Hz, 1H) |
| 99 | 100 | 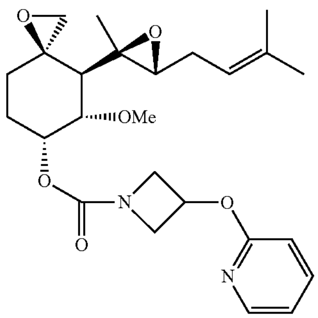 [SMILES: CO[C@@H]1[C@H](OC(=O)N2CC(Oc3ccccn3)C2)CC[C@]2(CO2)[C@H]1[C@@]1(C)O[C@@H]1CC=C(C)C] | 459 [M + H]⁺ | 8.10 (d, J = 3.8 Hz, 1H), 7.60 (ddd, J = 9.0, 7.2, 2.0 Hz, 1H), 6.90 (ddd, J = 7.1, 5.1, 0.9 Hz, 1H), 6.78 (d, J = 8.0 Hz, 1H), 5.53 (d, J = 3.1 Hz, 1H), 5.37-5.33 (m, 1H), 5.20 (t, J = 7.4 Hz, 1H), 4.36 (s, 2H), 4.05 (s, 2H), 3.62 (dd, J = 11.2, 2.7 Hz, 1H), 3.46 (s, 3H), 2.98 (d, J = 4.3 Hz, 1H), 2.68-2.47 (m, 2H), 2.36-2.34 (m, 1H), 2.17-2.02 (m, 2H), 1.98-1.82 (m, 3H), 1.74 (s, 3H), 1.65 (s, 3H), 1.20 (s, 3H), 1.06 (d, J = 13.8 Hz, 1H) |
| 100 | 101 | 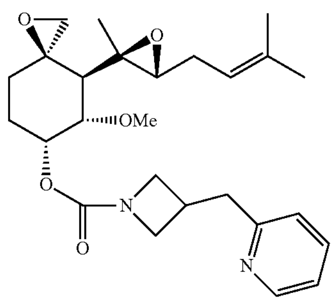 [SMILES: CO[C@@H]1[C@H](OC(=O)N2CC(Cc3ccccn3)C2)CC[C@]2(CO2)[C@H]1[C@@]1(C)O[C@@H]1CC=C(C)C] | 457 [M + H]⁺ | 8.64-8.25 (m, 1H), 7.55-7.51 (m, 1H), 7.08-7.05 (m, 2H), 5.44 (d, J = 3.2 Hz, 1H), 5.15-5.12 (m, 1H), 4.14-3.89 (m, 2H), 3.80-3.61 (m, 2H), 3.56-3.53 (m, 1H), 3.40 (s, 3H), 3.02 (s, 3H), 2.90 (d, J = 4.3 Hz, 1H), 2.51-2.42 (m, 2H), 2.33-2.21 (m, 1H), 2.13-2.07 (m, 1H), 2.03-1.92 (m, 1H), 1.91-1.69 (m, 3H), 1.67 (s, 3H), 1.58 (s, 3H), 1.13 (s, 3H), 1.02-0.94 (m, 1H) |
| 101 | 102 | 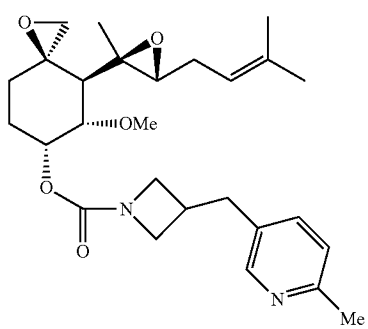 [SMILES: CO[C@@H]1[C@H](OC(=O)N2CC(Cc3ccc(C)nc3)C2)CC[C@]2(CO2)[C@H]1[C@@]1(C)O[C@@H]1CC=C(C)C] | 471 [M + 1]⁺ | 8.24 (d, J = 2.0 Hz, 1H), 7.30 (d, J = 6.0 Hz, 1H), 7.02 (d, J = 7.6 Hz, 1H), 5.44 (s, 1H), 5.12-5.15 (m, 1H), 3.92-4.01 (m, 2H), 3.52-3.61 (m, 3H), 3.39 (s, 3H), 2.90 (d, J = 4.4 Hz, 1H), 2.76-2.80 (m, 3H), 2.45-2.49 (m, 5H), 2.25-2.31 (m, 1H), 2.05-2.12 (m, 1H), 1.92-2.00 (m, 1H), 1.71-1.87 (m, 3H), 1.67 (s, 3H), 1.58 (s, 3H), 1.13 (s, 3H), 0.98 (d, J = 12.8 Hz, 1H) |

| Ex. | Int. | Structure | LC-MS | H-NMR (400 MHz, CDCl₃) |
|---|---|---|---|---|
| 102 | 103 | (structure) | 471 [M + H]⁺ | 8.46 (d, J = 4.2 Hz, 1H), 7.57 (t, J = 7.3 Hz, 1H), 7.16-7.03 (m, 2H), 5.43 (d, J = 3.1 Hz, 1H), 5.13 (d, J = 7.1 Hz, 1H), 3.95 (t, J = 8.3 Hz, 2H), 3.52 (dd, J = 8.2, 5.8 Hz, 2H), 3.38 (s, 3H), 2.91 (d, J = 4.3 Hz, 1H), 2.69 (d, J = 6.5 Hz, 2H), 2.54-2.43 (m, 3H), 2.28 (dd, J = 14.0, 7.0 Hz, 2H), 2.10 (dd, J = 14.7, 7.4 Hz, 1H), 1.98 (dd, J = 15.2, 7.8 Hz, 3H), 1.88-1.73 (m, 3H), 1.67 (s, 3H), 1.59 (s, 3H), 1.13 (s, 3H), 1.02-0.94 (m, 1H) |

Following the above procedures, the following compounds are prepared:

| Example No. | Structure |
|---|---|
| 103 | (structure) |
| 104 | (structure) |
| 105 | (structure) |

-continued
| Example No. | Structure |
|---|---|
| 106 | 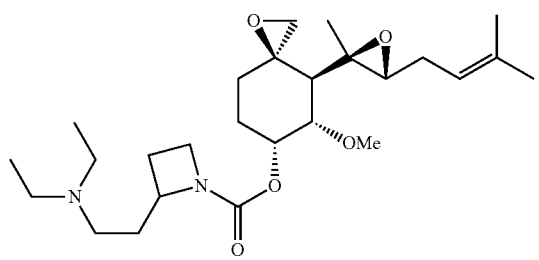 [SMILES: CCN(CC)CCC1CCN1C(=O)O[C@@H]1CC[C@]2(CO2)[C@@H]([C@@]2(C)O[C@@H]2CC=C(C)C)[C@@H]1OC] |
| 107 | 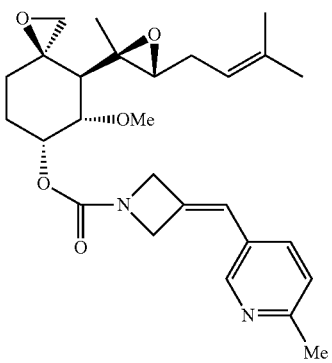 [SMILES: CO[C@@H]1[C@H](OC(=O)N2CC(=Cc3ccc(C)nc3)C2)CC[C@]2(CO2)[C@H]1[C@@]1(C)O[C@@H]1CC=C(C)C] |
| 108 | 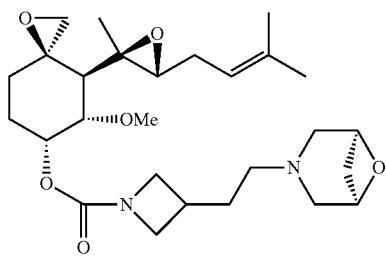 [SMILES: CO[C@@H]1[C@H](OC(=O)N2CC(CCN3C[C@H]4C[C@@H](C3)O4)C2)CC[C@]2(CO2)[C@H]1[C@@]1(C)O[C@@H]1CC=C(C)C] |
| 109 | 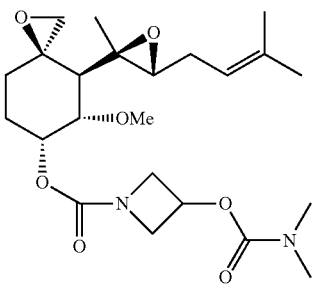 [SMILES: CO[C@@H]1[C@H](OC(=O)N2CC(OC(=O)N(C)C)C2)CC[C@]2(CO2)[C@H]1[C@@]1(C)O[C@@H]1CC=C(C)C] |
| 110 | 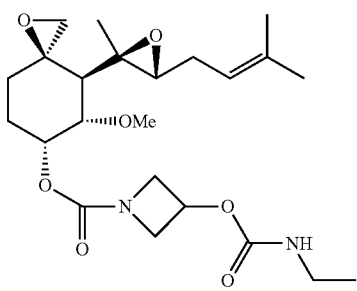 [SMILES: CCNC(=O)OC1CN(C(=O)O[C@@H]2CC[C@]3(CO3)[C@@H]([C@@]3(C)O[C@@H]3CC=C(C)C)[C@@H]2OC)C1] |

| Example No. | Structure |
|---|---|
| 111 | 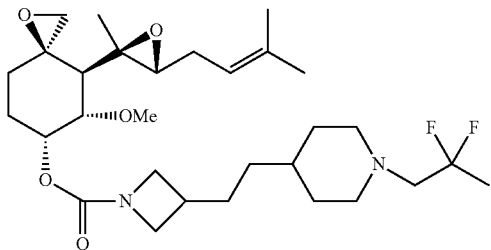 [SMILES: CO[C@@H]1[C@H](OC(=O)N2CC(CCC3CCN(CC(C)(F)F)CC3)C2)CC[C@]2(CO2)[C@H]1[C@@]1(C)O[C@@H]1CC=C(C)C] |
| 112 | 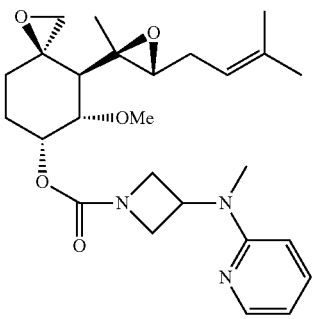 |
| 113 | 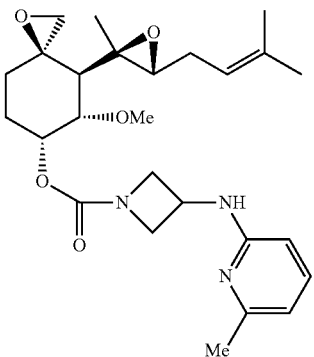 [SMILES: CO[C@@H]1[C@H](OC(=O)N2CC(Nc3cccc(C)n3)C2)CC[C@]2(CO2)[C@H]1[C@@]1(C)O[C@@H]1CC=C(C)C] |
| 114 | 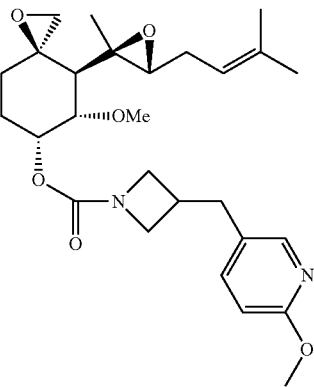 [SMILES: COc1ccc(CC2CN(C(=O)O[C@@H]3CC[C@]4(CO4)[C@@H]([C@@]4(C)O[C@@H]4CC=C(C)C)[C@@H]3OC)C2)cn1] |

| Example No. | Structure |
|---|---|
| 115 | 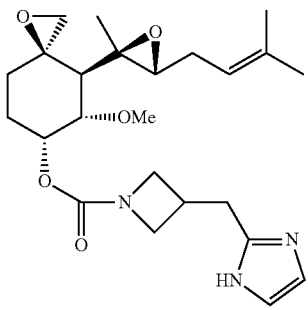 [SMILES: CO[C@@H]1[C@H](OC(=O)N2CC(Cc3ncc[nH]3)C2)CC[C@]2(CO2)[C@H]1[C@@]1(C)O[C@@H]1CC=C(C)C] |
| 116 | 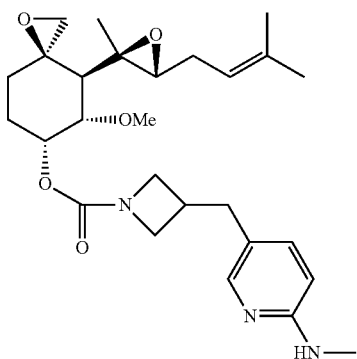 [SMILES: CNc1ccc(CC2CN(C(=O)O[C@@H]3CC[C@]4(CO4)[C@@H]([C@@]4(C)O[C@@H]4CC=C(C)C)[C@@H]3OC)C2)cn1] |
| 117 | 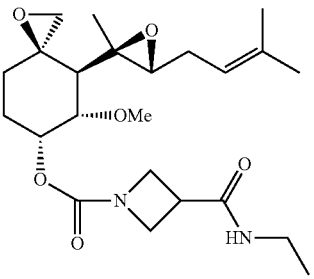 [SMILES: CCNC(=O)C1CN(C(=O)O[C@@H]2CC[C@]3(CO3)[C@@H]([C@@]3(C)O[C@@H]3CC=C(C)C)[C@@H]2OC)C1] |
| 118 | 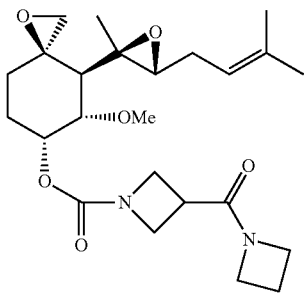 [SMILES: CO[C@@H]1[C@H](OC(=O)N2CC(C(=O)N3CCC3)C2)CC[C@]2(CO2)[C@H]1[C@@]1(C)O[C@@H]1CC=C(C)C] |
| 119 | 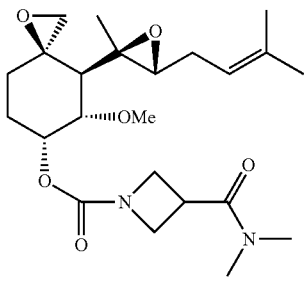 [SMILES: CO[C@@H]1[C@H](OC(=O)N2CC(C(=O)N(C)C)C2)CC[C@]2(CO2)[C@H]1[C@@]1(C)O[C@@H]1CC=C(C)C] |

| Example No. | Structure |
|---|---|
| 120 | 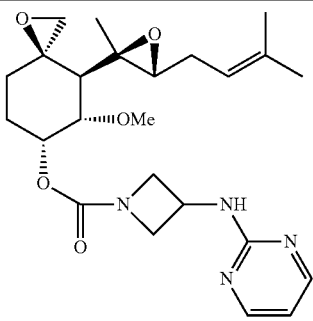 |

Example 121

(3R,4S,5S,6R)-5-methoxy-4-((2R,3R)-2-methyl-3-(3-methylbut-2-en-1-yl)oxiran-2-yl)-1-oxaspiro[2.5]octan-6-yl3-(2-(ethylamino)ethyl)azetidine-1-carboxylate

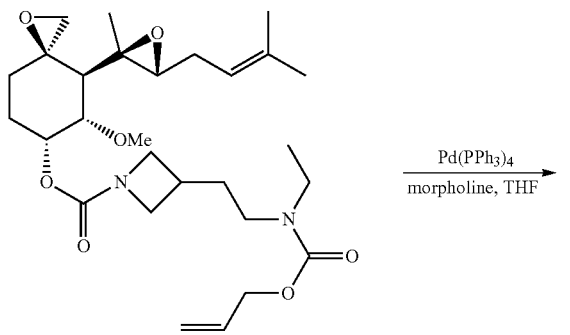

Intermediate 104

Example 121

To a $N_2$ degassed (3×) solution of (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(((allyloxy)carbonyl)(ethyl)amino)ethyl)azetidine-1-carboxylate (500mg, 0.96 mmol) in THF (10 mL) was added morpholine (0.84 mL, 9.60 mmol) and tetrakis(triphenylphosphine)palladium (11.10 mg, 0.0096 mmol). The reaction was then stirred at room temperature under a $N_2$ atmosphere overnight. The reaction mixture was diluted with ethyl acetate (40 mL×2) and then washed with water (20 mL) and brine (20 mL). The organic layer was dried over $Na_2SO_4$, filtered and concentrated under reduced pressure to give a residue, which was purified by silica gel chromatography (dichloromethane:methanol=10:0 to 8:1) and preparative HPLC (Method A, $H_2O$ (0.1% FA)/$CH_3CN$) to give (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(ethylamino)ethyl)azetidine-1-carboxylate (60 mg, 14.3% yield) as a colorless oil. LC-MS: m/z=437 [M+H]$^+$. $^1$H NMR (400 MHz, CDCl$_3$) δ 5.44 (s, 1H), 5.13 (s, 1H), 3.99 (m, 3H), 3.54 (m, 3H), 3.38 (s, 3H), 2.99-2.87 (m, 3H), 2.78 (s, 2H), 2.62-2.43 (m, 3H), 2.30 (m, 1H), 2.01 (m, 4H), 1.84 (m, 1H), 1.78 (m, 2H), 1.67 (s, 3H), 1.59 (s, 3H), 1.27 (m, 3H), 1.13 (s, 3H), 0.99 (d, J=14.3 Hz, 1H).

The following examples were prepared according to procedures similar to that described for Example 121 by using the corresponding intermediates.

| Example | Intermediate | Structure | LC-MS | H-NMR (400 MHz, CDCl$_3$) |
|---|---|---|---|---|
| 122 | 105 | 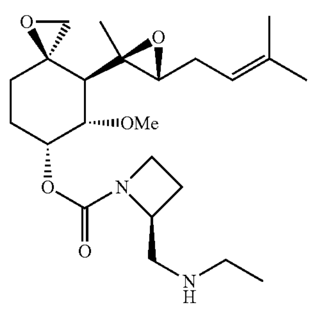 [SMILES: CCNC[C@@H]1CCN1C(=O)O[C@@H]1CC[C@]2(CO2)[C@@H]([C@@]2(C)O[C@@H]2CC=C(C)C)[C@@H]1OC] | 423 [M + H]$^+$ | 5.44 (d, J = 2.5 Hz, 1H), 5.13 (m, 1H), 4.71 (m, 1H), 3.86 (m, 2H), 3.56 (m, 1H), 3.39 (s, 4H), 3.14-2.96 (m, 2H), 2.91 (m, 2H), 2.49 (m, 2H), 2.31 (m, 2H), 2.14-1.92 (m, 3H), 1.75 (m, 3H), 1.68 (s, 3H), 1.59 (s, 3H), 1.27 (m, 3H), 1.13 (s, 3H), 1.08-0.95 (m, 1H) |

-continued

| Example | Intermediate | Structure | LC-MS | H-NMR (400 MHz, CDCl$_3$) |
|---|---|---|---|---|
| 123 | 106 | 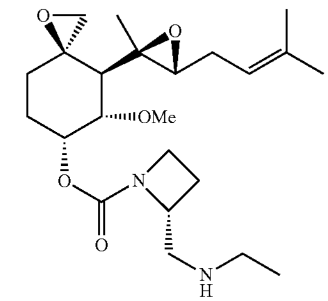 [SMILES: CCNC[C@H]1CCN1C(=O)O[C@@H]1CC[C@]2(CO2)[C@@H]([C@@]2(C)O[C@@H]2CC=C(C)C)[C@@H]1OC] | 423 [M + H]$^+$ | 5.34 (d, J = 66.0 Hz, 1H), 5.11 (s, 1H), 4.95-4.51 (m, 1H), 3.89 (ddd, J = 46.7, 29.9, 18.0 Hz, 2H), 3.61 (ddd, J = 25.8, 10.9, 4.1 Hz, 1H), 3.37 (s, 3H), 3.31-3.01 (m, 4H), 2.95-2.78 (m, 2H), 2.58-2.28 (m, 3H), 2.02 (ddt, J = 61.8, 57.8, 23.8 Hz, 5H), 1.77 (t, J = 13.6 Hz, 1H), 1.67 (s, 3H), 1.58 (s, 3H), 1.30-1.17 (m, 3H), 1.11 (s, 3H), 1.03-0.92 (m, 1H) |
| 124 | 107 | 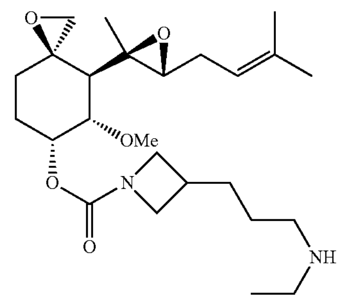 [SMILES: CCNCCCC1CN(C(=O)O[C@@H]2CC[C@]3(CO3)[C@@H]([C@@]3(C)O[C@@H]3CC=C(C)C)[C@@H]2OC)C1] | 451 [M + H]$^+$ | 5.45 (s, 1H), 5.12 (d, J = 7.1 Hz, 1H), 3.96 (s, 2H), 3.54 (dd, J = 11.3, 2.2 Hz, 3H), 3.39 (s, 3H), 2.91 (d, J = 4.2 Hz, 3H), 2.82 (s, 2H), 2.53 (s, 1H), 2.48 (d, J = 4.2 Hz, 2H), 2.35-2.23 (m, 1H), 2.14-2.02 (m, 1H), 1.98 (dd, J = 13.5, 4.4 Hz, 1H), 1.89-1.71 (m, 3H), 1.68 (s, 4H), 1.59 (s, 7H), 1.25 (t, J = 7.2 Hz, 3H), 1.13-1.05 (m, 2H), 0.99 (d, J = 13.5 Hz, 1H) |
| 125 | 108 | 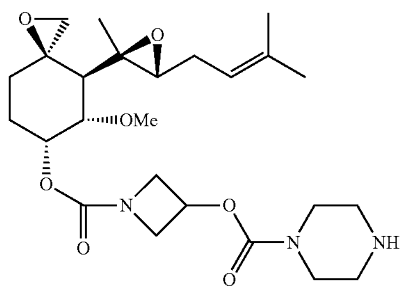 [SMILES: CO[C@@H]1[C@H](OC(=O)N2CC(OC(=O)N3CCNCC3)C2)CC[C@]2(CO2)[C@H]1[C@@]1(C)O[C@@H]1CC=C(C)C] | 493 [M + H]$^+$ | 5.53 (s, 1H), 5.24-5.09 (m, 2H), 4.40-4.21 (m, 2H), 3.98 (d, J = 27.2 Hz, 2H), 3.61 (dd, J = 11.2, 2.7 Hz, 1H), 3.46 (s, 4H), 2.98 (d, J = 4.3 Hz, 1H), 2.91-2.75 (m, 4H), 2.55 (dd, J = 10.3, 5.3 Hz, 2H), 2.34 (dd, J = 14.2, 7.1 Hz, 1H), 2.20-2.00 (m, 2H), 1.87 (dd, J = 23.2, 6.7 Hz, 3H), 1.75 (s, 3H), 1.66 (s, 3H), 1.62 (s, 3H), 1.20 (s, 3H), 1.06 (d, J = 13.6 Hz, 1H) |

Example 126

(3R,4S,5S,6R)-4-((2R,3R)-3-isopentyl-2-methyloxiran-2-yl)-5-methoxy-1-oxaspiro[2.5]octan-6-yl3-(2-(3,3-difluoroazetidin-1-yl)ethyl)azetidine-1-carboxylate

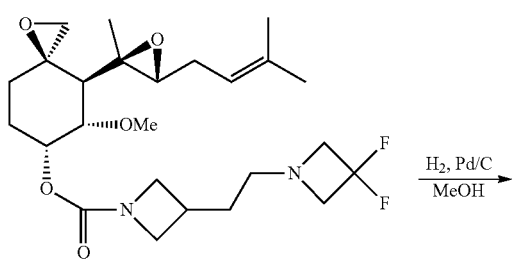

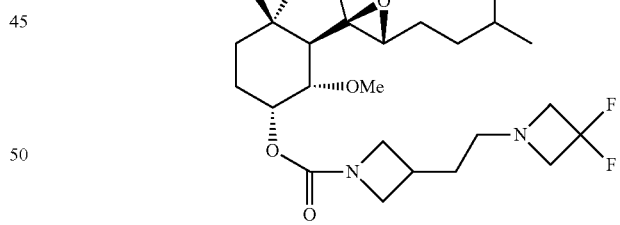

Example 126

A solution of (3R,4S,5S,6R)-5-methoxy-4-((2R,3R)-2-methyl-3-(3-methylbut-2-en-1-yl)oxiran-2-yl)-1-oxaspiro [2.5]octan-6-yl 3-(2-(3,3-difluoroazetidin-1-yl)ethyl)azetidine-1-carboxylate (500 mg, 1.03 mmol) in methanol (10 mL) was degassed three times with N$_2$ atmosphere, and Pd/C (50 mg, 10% wt) was added. The mixture was degassed again and stirred under H$_2$ atmosphere at room temperature for 1 hr. The reaction mixture was filtered through Celite, and the filtrate was concentrated to give a residue, which was purified by preparative HPLC (Method A, H$_2$O (0.1% FA)/CH$_3$CN) to give (3R,4S,5S,6R)-4-((2R,3R)-3-isopentyl-2-methyloxiran-2-yl)-5-methoxy-1-oxaspiro[2.5]octan- 6-yl 3-(2-(3,3-difluoroazetidin-1-yl)ethyl)azetidine-1-carboxylate (185.0 mg, 36.8% yield) as a colorless oil. LC-MS: m/z=487 [M+H]+. 1H NMR (400 MHz, CDCl3) δ 5.44 (d, J=4.0 Hz, 1H), 3.97-4.02 (m, 2H), 3.39-3.56 (m, 8H), 3.38 (m, 3H), 2.82 (d, J=4.4 Hz, 1H), 2.41-2.53 (m, 5H), 1.94-2.02 (m, 1H), 1.74-1.89 (m, 3H), 1.55-1.62 (m, 3H), 1.32-1.42 (m, 2H), 1.21-1.28 (m, 1H), 1.14 (s, 3H), 0.99-1.04 (m, 1H), 0.84 (d, J=1.2 Hz, 3H), 0.82 (d, J=1.2 Hz, 3H).

Example 127

(3R,4S,5S,6R)-4-((2R,3R)-3-isopentyl-2-methyloxiran-2-yl)-5-methoxy-1-oxaspiro[2.5]octan-6-yl 3-(2-morpholinoethyl)azetidine-1-carboxylate

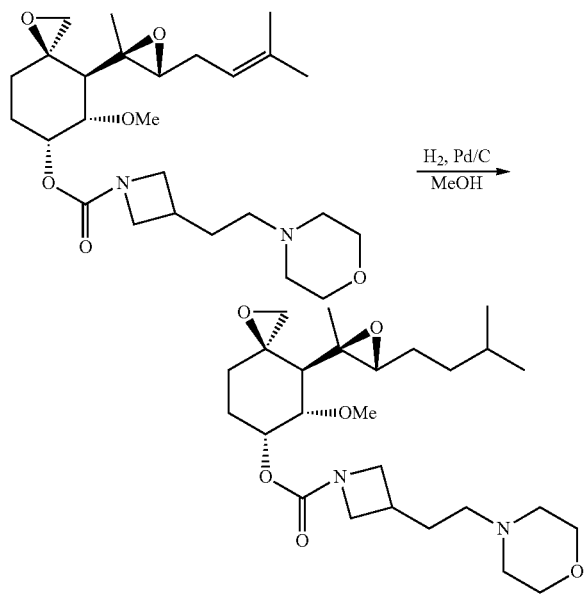

Example 127

A solution of (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-morpholinoethyl)azetidine-1-carboxylate (400 mg, 0.84 mmol) in methanol (10 mL) was degassed with N2 three times, and Pd/C (130 mg, 10% wt) was added. The mixture was degassed again and stirred under H2 atmosphere at room temperature overnight. The reaction mixture was filtered through Celite, and the filtrate was concentrated to give a residue, which was purified by preparative HPLC (Method A, H2O (0.1% FA)/CH3CN) to give (3R,4S,5S,6R)-4-((2R,3R)-3-isopentyl-2-methyloxiran-2-yl)-5-methoxy-1-oxaspiro[2.5]octan-6-yl 3-(2-morpholinoethyl)azetidine-1-carboxylate (250 mg, 62.5% yield) as a coreless oil. LC-MS: m/z=481 [M+H]+. 1H NMR (400 MHz, CDCl3) δ 5.49 (s, 1H), 4.00-4.19 (m, 2H), 3.59-3.71 (m, 7H), 3.45 (s, 3H), 2.87 (d, J=4.4 Hz, 1H), 2.51-2.58 (m, 3H), 2.41 (s, 4H), 2.24-2.28 (m, 2H), 1.77-2.05 (m, 6H), 1.56-1.63 (m, 4H), 1.24-1.45 (m, 4H), 1.06-1.17 (m, 1H), 0.93-0.97 (m, 6H).

Example 128

(3R,4S,5S,6R)-4-((2R,3R)-3-isopentyl-2-methyloxiran-2-yl)-5-methoxy-1-oxaspiro[2.5]octan-6-yl3-(2-(1-(2,2-difluoroethyl)piperidin-4-yl)ethyl)azetidine-1-carboxylate

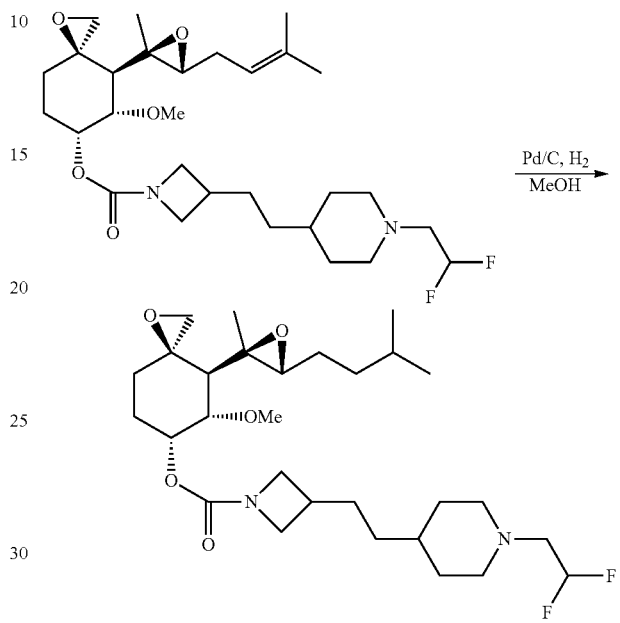

Example 128

A solution of (3R,4S,5 S,6R)-5 -methoxy-4-((2R,3R)-2-methyl-3 -(3-methylbut-2-enyl)oxiran-2-yl)-1-oxaspiro[2.5]octan-6-yl 3-(2-(1-(2,2-difluoroethyl)piperidin-4-yl)ethyl)azetidine-1-carboxylate (400 mg, 0.74 mmol) in MeOH (10 mL) was degassed under N2 atmosphere three times, and Pd/C (60 mg, 10% wt) was added. The mixture was degassed again and stirred under a H2 atmosphere at room temperature overnight. The mixture was filtered through Celite, and the filtrate was concentrated to give the crude, which was purified by preparative HPLC (Method A, H2O (0.1% FA)/CH3CN) to give (3R,4S,5S,6R)-4-((2R,3R)-3-isopentyl-2-methyloxiran-2-yl)-5-methoxy-1-oxaspiro[2.5] octan-6-yl 3-(2-(1-(2,2-difluoroethyl)piperidin-4-yl)ethyl)azetidine-1-carboxylate (250 mg, 62.5% yield) as a coreless oil. LC-MS m/z: 543 [M+H]+. 1H NMR (400 MHz, CDCl3) δ 5.73-6.02 (m, 1H), 5.51 (s, 1H), 4.01-4.07 (m, 2H), 3.57-3.63 (m, 3H), 3.45 (s, 2H), 3.38 (s, 1H), 2.88-2.93 (m, 3H), 2.67-2.75 (m, 2H), 2.45-2.58 (m, 3H), 2.01-2.17 (m, 3H), 1.84-1.94 (m, 3H), 1.57-1.67 (m, 4H), 1.06-1.50 (m, 14H), 0.91-0.95 (m, 6H).

Biological Example A

Compounds are tested for their capacity to inhibit recombinant human MetAP2 activity using the following assay.

Flag tagged Human recombinant MetAP2 expressed and isolated for use as the enzyme source. 10 mM stock solutions of compounds were prepared in 100% DMSO and further diluted in 100% DMSO required concentration to 1 mM stocks. The stock compound solutions and DMSO vehicle controls were diluted to target final compound concentrations using assay buffer to a final concentration of 50 mM HEPES containing 100 mM NaCl, pH adjusted to 7.5. The MAS peptide was formulated to a 7.5 mM stock in distilled water and prior to use further diluted 1:4. Amino acid oxidase was prepared as a stock solution (6.2 mg/ml) and prior to use further diluted 1:49.6 in distilled water. A 250 µM solution of $MnCl_2$ was prepared in advance of thawing an aliquot of MetAP2 enzyme. 40 µl of enzyme was mixed with 100 µl of $MnCl_2$ then further diluted in assay buffer to a final concentration of 16 µg/ml. To test for compound effect on MetAP2 enzyme activity, 5 µl of test compound, 10 µl of MAS substrate/amino acid oxidase mixture, 10 µl of MetAP2 was added to test wells in a 384 well black plate with blank wells containing no enzyme, replaced with 10 µl of assay buffer. All compounds were tested in duplicate on two occasions on the same day. The final in well concentrations of the assay were: 1% DMSO, 0.272 µg/ml MetAP2, 10 µM MnCl2, 50.0 µg/ml (0.225 U/ml) amino acid oxidase, and 0.75 mM MAS.

The plate was sealed with a TopSeal A cover and mixed briefly on an orbital mixer at 900 rpm. The plate was incubated for a further 25 minutes at 25° C. A 5× stock of Amplex buffer was prepared (0.25M sodium phosphate, pH 7.4) and stored at 4° C. When preparing for use the stock was diluted with distilled water Amplex Ultraread stock solution was prepared at 2.57 mg/ml in 100% DMSO and stored in 50 µl aliquots at −20° C. 20 µl of 505 U/ml. Horse radish peroxidase was diluted in 990 ml of Amplex buffer, 100 µl of this was combined with 50 µl of Amplex Ultrared in 4850 ml of 1× Amplex buffer to generate sufficient detection reagent for a 384 well plate. 25 µl detection reagent was added to each well of the test plate, which was re-sealed and mixed briefly on an orbital shaker. The plate was transferred to an Envision Multi-label reader and RFU measured corresponding to excitation 531 nm and emission 595 nm At the end of the MetAP2 incubation 25 µl Amplex/HRP mixture per well was added and the plate read plate on a plate reader.

The $IC_{50}$ is defined as the concentration at which a given compound achieves 50% inhibition of control.

Compounds of the disclosure demonstrated activity in the assay of this Example as indicated in the following tables, wherein A represents an $IC_{50}$ of <0.05 µM and B represents an $IC_{50}$ between 0.05 µM and 0.5 µM.

TABLE 1

| Example No. | Compound Name | MetAP2 $IC_{50}$ (µM) |
|---|---|---|
| 103 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(diethylamino)ethyl)azetidine-1-carboxylate | A |
| 104 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(diethylamino)propyl)azetidine-1-carboxylate | B |
| 105 | (3R,4S,5S,6R)-5-methoxy-4-((2R,3R)-2-methyl-3-(3-methylbut-2-enyl)oxiran-2-yl)-1-oxaspiro[2.5]octan-6-yl 2-((diethylamino)methyl)azetidine-1-carboxylate | B |
| 1 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholinoethyl)azetidine-1-carboxylate | A |
| 2 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3,3-difluoroazetidin-1-yl)ethyl)azetidine-1-carboxylate | B |
| 8 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-hydroxy-4-methylpiperidin-1-yl)ethyl)azetidine-1-carboxylate | A |
| 7 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-hydroxypiperidin-1-yl)ethyl)azetidine-1-carboxylate | A |
| 6 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-hydroxyazetidin-1-yl)ethyl)azetidine-1-carboxylate formate | A |
| 60 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)pyrrolidine-1-carboxylate formate | B |
| 9 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-hydroxy-3-methylazetidin-1-yl)ethyl)azetidine-1-carboxylate formate | A |
| 4 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(piperidin-1-yl)ethyl)azetidine-1-carboxylate formate | A |
| 3 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(pyrrolidin-1-yl)ethyl)azetidine-1-carboxylate formate | A |
| 43 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)azetidine-1-carboxylate formate | B |
| 40 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)azetidine-1-carboxylate formate | A |
| 48 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)pyrrolidine-1-carboxylate formate | B |
| 59 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(pyrrolidin-1-yl)propyl)azetidine-1-carboxylate formate | A |

TABLE 1-continued

| Example No. | Compound Name | MetAP2 IC$_{50}$ (μM) |
|---|---|---|
| 41 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(pyrrolidin-1-ylmethyl)azetidine-1-carboxylate formate | B |
| 44 | (3R,4S,5S,6R)-5-methoxy-4-((2R,3R)-2-methyl-3-(3-methylbut-2-enyl)oxiran-2-yl)-1-oxaspiro[2.5]octan-6-yl 2-((diethylamino)methyl)morpholine-4-carboxylate formate | B |
| 51 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(2-(diethylamino)ethyl)pyrrolidine-1-carboxylate formate | B |
| 38 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-((diethylamino)methyl)pyrrolidine-1-carboxylate formate | B |
| 121 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(ethylamino)ethyl)azetidine-1-carboxylate formate | A |
| 42 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(pyrrolidin-1-ylmethyl)azetidine-1-carboxylate formate | B |
| 50 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(2-(diethylamino)ethyl)pyrrolidine-1-carboxylate formate | B |
| 49 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(diethylamino)ethyl)-3-hydroxyazetidine-1-carboxylate | A |
| 124 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(ethylamino)propyl)azetidine-1-carboxylate formate | A |
| 122 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((ethylamino)methyl)azetidine-1-carboxylate | A |
| 52 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-(diethylamino)ethyl)pyrrolidine-1-carboxylate | A |
| 123 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((ethylamino)methyl)azetidine-1-carboxylate formate | A |
| 5 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(azetidin-1-yl)ethyl)azetidine-1-carboxylate | A |
| 61 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(diethylamino)propyl)-3-hydroxyazetidine-1-carboxylate | A |
| 65 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-amino-2-oxoethyl)azetidine-1-carboxylate | A |
| 63 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(methylamino)-2-oxoethyl)azetidine-1-carboxylate | A |
| 68 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((((2-(diethylamino)ethyl)carbamoyl)oxy)methyl)azetidine-1-carboxylate | A |
| 73 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(((2-(diethylamino)ethyl)carbamoyl)oxy)azetidine-1-carboxylate | A |
| 62 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholino-2-oxoethyl)azetidine-1-carboxylate formate | A |
| 39 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-oxomorpholino)ethyl)azetidine-1-carboxylate | B |
| 66 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(2-(diethylamino)ethylamino)-2-oxoethyl)azetidine-1-carboxylate | A |
| 95 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(morpholinomethyl)azetidine-1-carboxylate | B |
| 74 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(methylcarbamoyloxy)azetidine-1-carboxylate | A |
| 72 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(carbamoyloxy)azetidine-1-carboxylate | A |
| 69 | (3R,4S,5S,6R)-5-methoxy-4-((2R,3R)-2-methyl-3-(3-methylbut-2-enyl)oxiran-2-yl)-1-oxaspiro[2.5]octan-6-yl 3-((methylcarbamoyloxy)methyl)azetidine-1-carboxylate | B |

TABLE 1-continued

| Example No. | Compound Name | MetAP2 IC$_{50}$ (μM) |
|---|---|---|
| 98 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(pyridin-2-ylamino)azetidine-1-carboxylate | B |
| 100 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(pyridin-2-ylmethyl)azetidine-1-carboxylate | B |
| 37 | (S)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(morpholinomethyl)pyrrolidine-1-carboxylate formate | B |
| 127 | (3R,4S,5S,6R)-4-((2R,3R)-3-isopentyl-2-methyloxiran-2-yl)-5-methoxy-1-oxaspiro[2.5]octan-6-yl 3-(2-morpholinoethyl)azetidine-1-carboxylate | B |
| 45 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3,3-difluoropyrrolidin-1-yl)ethyl)azetidine-1-carboxylate | B |
| 101 | (3R,4S,5S,6R)-5-methoxy-4-((2R,3R)-2-methyl-3-(3-methylbut-2-enyl)oxiran-2-yl)-1-oxaspiro[2.5]octan-6-yl 3-((6-methylpyridin-3-yl)methyl)azetidine-1-carboxylate | B |
| 54 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-morpholinoethyl)pyrrolidine-1-carboxylate | A |
| 53 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-(diethylamino)ethyl)pyrrolidine-1-carboxylate | A |
| 34 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-(2,2-difluoroethyl)piperazin-1-yl)ethyl)azetidine-1-carboxylate | B |
| 88 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(2-(diethylamino)ethylamino)-3-oxopropyl)azetidine-1-carboxylate formate | A |
| 55 | (R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-morpholinoethyl)pyrrolidine-1-carboxylate | B |
| 56 | (S)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(diethylamino)ethyl)pyrrolidine-1-carboxylate | A |
| 57 | (R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(3,3-difluoroazetidin-1-yl)ethyl)pyrrolidine-1-carboxylate | B |
| 58 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-(3,3-difluoropyrrolidin-1-yl)ethyl)pyrrolidine-1-carboxylate | B |
| 22 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(6,6-difluoro-3-azabicyclo[3.1.0]hexan-3-yl)ethyl)azetidine-1-carboxylate formate | A |
| 90 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1-methylpiperidin-4-yl)ethyl)azetidine-1-carboxylate formate | B |
| 91 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1-(2,2-difluoroethyl)piperidin-4-yl)ethyl)azetidine-1-carboxylate formate | B |
| 10 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-thiomorpholinoethyl)azetidine 2,2-dioxide-1-carboxylate | B |
| 84 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-methylureido)azetidine-1-carboxylate | A |
| 81 | 1-(((3R,4S,5S,6R)-5-methoxy-4-((2R,3R)-2-methyl-3-(3-methylbut-2-enyfloxiran-2-yl)-1-oxaspiro[2.5]octan-6-yloxy)carbonyl)azetidin-3-yl 4-(2,2,2-trifluoroethyl)piperazine-1-carboxylate | B |
| 71 | 1-(((3R,4S,5S,6R)-5-methoxy-4-((2R,3R)-2-methyl-3-(3-methylbut-2-enyl)oxiran-2-yl)-1-oxaspiro[2.5]octan-6-yloxy)carbonyl)azetidin-3-yl morpholine-4-carboxylate formate | B |
| 78 | 1-(((3R,4S,5S,6R)-5-methoxy-4-((2R,3R)-2-methyl-3-(3-methylbut-2-enyl)oxiran-2-yl)-1-oxaspiro[2.5]octan-6-yloxy)carbonyl)azetidin-3-yl 4-methylpiperazine-1-carboxylate | B |
| 82 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-hydroxy-2-methylpropylcarbamoyloxy)azetidine-1-carboxylate | B |
| 11 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-methyl-3-oxopiperazin-1-yl)ethyl)azetidine-1-carboxylate formate | B |
| 67 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(2-morpholinoethylamino)-3-oxopropyl)azetidine-1-carboxylate | B |

TABLE 1-continued

| Example No. | Compound Name | MetAP2 IC$_{50}$ (μM) |
|---|---|---|
| 16 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(2-oxa-6-azaspiro[3.3]heptan-6-yl)ethyl)azetidine-1-carboxylate | A |
| 17 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1H-pyrazol-1-yl)ethyl)azetidine-1-carboxylate | B |
| 19 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-(dimethylcarbamoyl)azetidin-1-yl)ethyl)azetidine-1-carboxylate | B |
| 13 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4,4-difluoropiperidin-1-yl)ethyl)azetidine-1-carboxylate | B |
| 14 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-cyano-3-methylazetidin-1-yl)ethyl)azetidine-1-carboxylate | B |
| 33 | (4S,5S,6R)-5-methoxy-4-((2R,3R)-2-methyl-3-(3-methylbut-2-enyl)oxiran-2-yl)-1-oxaspiro[2.5]octan-6-yl 3-(2-(8-oxa-3-azabicyclo[3.2.1]octan-3-yl)ethyl)azetidine-1-carboxylate | B |
| 31 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((1R,5S)-3-oxa-8-azabicyclo[3.2.1]octan-8-yl)ethyl)azetidine-1-carboxylate | B |
| 20 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-(dimethylcarbamoyl)-3-methylazetidin-1-yl)ethyl)azetidine-1-carboxylate | B |
| compound A | [(3R,6R,7S,8S)-7-methoxy-8-[(2R,3R)-2-methyl-3-(3-methylbut-2-enyl)oxiran-2-yl]-2-oxaspiro[2.5]octan-6-yl] (E)-3-[4-[2-(dimethylamino)ethoxy]phenyl]prop-2-enoate | B |

Biological Example B

Study Summary Mouse DIO:

The objective of this study design was to investigate the efficacy of disclosed compounds in a 10 day DIO mouse model. Effects on body weight, food intake, hematology and blood chemistry were the primary readouts of this study design. Male, Diet Induced Obese (DIO) C57BL/6 mice, 19-21 weeks of age (13-15 weeks on high fat diet) were ordered from a certified vendor and upon receipt were housed on irradiated corncob bedding in micro-isolator cages on a 12-hour light-dark cycle (0700-1900) at 68-74° F. and 30-70% humidity. Mice were fed Research Diets D12492 (60% Kcal fat, 20% Kcal carbohydrate and 20% protein) and provided water ad libitum. DIO mice were received and housed in the facility for approximately two weeks prior to the start of test article administration. On Day −4 or −3, mice were randomized into study groups based on body weight and body weights were continued to be recorded daily for the duration of the study. Daily food intake was assessed starting on Study Day −2 by weighing of the food with hopper together to avoid loss of food in transfer.

Compounds were formulated into a 100% DMSO stock (at 9 mg/mL) prior to the start, and further diluted into the target working concentration using the vehicle of 10% DMSO in water. Prior to test article administration, starting on Day −3 a dosing acclimation occured with all animals receiving a subcutaneous injection of vehicle (10% DMSO) only for 3 days. Starting on Day 1, test compounds or vehicle were administered based on individual body weight, subcutaneously, once a day for 10 days. All mice were sacrificed on Day 11, 24 hours following the final dosing on Day 10. After sacrifice, whole blood was collected and analyzed for hematology and blood chemistry parameters.

Study Summary Rat DIO:

The objective of this study design is to investigate the efficacy of disclosed compounds in an 11 day rat DIO model used to screen compounds for pharmacologic efficacy on endpoints related to obesity and metabolism. Effects on body weight, food intake, hematology and blood chemistries were the primary readouts of this study design. Male Sprague Dawley rats, approximately 8 weeks of age, were ordered from a certified vendor and housed on irradiated corncob bedding in micro-isolator cages, on a 12-hour light-dark cycle (0700-1900) at 68-74° F. and 30-70% humidity. Rats were fed Research Diets D12451 (45% High Fat) and provided water ad libitum. Rats were received and housed in the facility for at least two or three weeks prior to start of test article administration. On Day −4 or −3, rats were randomized into study groups based on body weight and body weights were continued to be recorded daily for the duration of the study. Daily food intake was assessed starting on Study Day −2 by weighing the hopper including the food to avoid loss of food in transfer.

Compounds were formulated into a 100% DMSO stock (at 9 mg/mL) prior to the start, and further diluted into the target working concentration using the vehicle of 10% DMSO in water. Prior to test article administration, starting on Day −3 a dosing acclimation occured with all animals receiving a subcutaneous injection of vehicle (10% DMSO) only for 3 days. Starting on Day 1, test compounds or vehicle were administered based on individual body weight, subcutaneously, once a day for 11 days. All animals were sacrificed on Day 11, approximately 2 hours following the final dosing on Day 11. After sacrifice, whole blood was collected and analyzed for hematology and blood chemistry parameters.

Compounds were tested vs. vehicle at various doses (1.0, 0.5, 0.3, 0.1, 0.03 mpk sc (mg per kg animal weight delivered subcutaneously), and the results are shown in Table 2 below.

TABLE 2

| Ex. | Compound Name | 1.0 mpk sc¹ (%) | 0.3 mpk sc¹ (%) | 0.1 mpk sc¹ (%) | 0.03 mpk sc¹ (%) | 0.3 mpk sc² (%) | 0.5 mpk sc² (%) | 1.0 mpk sc² (%) |
|---|---|---|---|---|---|---|---|---|
| 103 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(diethylamino)ethyl)azetidine-1-carboxylate | 15.8 | 6.7 | 5.1 | | | 2.57 | 4.7 |
| 104 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(diethylamino)propyl)azetidine-1-carboxylate | 10.9 | 6.4 | 8.3 | −0.9 | 1.2 | | 9.9 |
| 106 | (3R,4S,5S,6R)-5-methoxy-4-((2R,3R)-2-methyl-3-(3-methylbut-2-enyl)oxiran-2-yl)-1-oxaspiro[2.5]octan-6-yl 2-((diethylamino)methyl)azetidine-1-carboxylate | 20.2 | 10.8 | 2 | | | 4.82 | |
| 106 | (3R,4S,5S,6R)-5-methoxy-4-((2R,3R)-2-methyl-3-(3-methylbut-2-enyl)oxiran-2-yl)-1-oxaspiro[2.5]octan-6-yl 2-(2-(diethylamino)ethyl)azetidine-1-carboxylate | 8.1 | 0.8 | | | | | |
| 1 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholinoethyl)azetidine-1-carboxylate | | 16.8 | | | 5.7 | | 7.7 |
| 2 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3,3-difluoroazetidin-1-yl)ethyl)azetidine-1-carboxylate | 24.2 | 19.7 | 14.2 | | 5.7 | | 6.4 |
| 8 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-hydroxy-4-methylpiperidin-1-yl)ethyl)azetidine-1-carboxylate | 17.3 | 4.9 | | | | | |
| 7 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-hydroxypiperidin-1-yl)ethyl)azetidine-1-carboxylate | | 1.8 | | | | | |
| 6 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-hydroxyazetidin-1-yl)ethyl)azetidine-1-carboxylate formate | | 11.8 | | | 0.8 | | 4.6 |
| 60 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)pyrrolidine-1-carboxylate formate | | 6.3 | | | 1.95 | | 7.79 |
| 9 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-hydroxy-3-methylazetidin-1-yl)ethyl)azetidine-1-carboxylate formate | | 7.4 | | | 5.5 | | 4.8 |
| 4 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(piperidin-1-yl)ethyl)azetidine-1-carboxylate formate | | 4.1 | | | | | |
| 3 | (3R,4S,5S,6R)-5-methoxy-4-((2R,3R)-2-methyl-3-(3-methylbut-2-enyl)oxiran-2-yl)-1- | | 5.9 | | | | | |

TABLE 2-continued

| Ex. | Compound Name | 1.0 mpk sc[1] (%) | 0.3 mpk sc[1] (%) | 0.1 mpk sc[1] (%) | 0.03 mpk sc[1] (%) | 0.3 mpk sc[2] (%) | 0.5 mpk sc[2] (%) | 1.0 mpk sc[2] (%) |
|---|---|---|---|---|---|---|---|---|
| | oxaspiro[2.5]octan-6-yl 3-(2-(pyrrolidin-1-yl)ethyl)azetiine-1-carboxylate formate | | | | | | | |
| 43 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)azetidine-1-carboxylate formate | | 2.7 | | | 0.35 | | 2.9 |
| 40 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)azetidine-1-carboxylate formate | | 6 | | | 0.08 | | 4.73 |
| 48 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((diethylamino)methyl)pyrrolidine-1-carboxylate formate | | 7.2 | | | 0.65 | | 7.88 |
| 59 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(pyrrolidin-1-yl)propyl)azetidine-1-carboxylate formate | | 9.1 | | | | | |
| 41 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(pyrrolidin-1-ylmethyl)azetidine-1-carboxylate formate | | 4.4 | | | | | |
| 44 | (3R,4S,5S,6R)-5-methoxy-4-((2R,3R)-2-methyl-3-(3-methylbut-2-enyl)oxiran-2-yl)-1-oxaspiro[2.5]octan-6-yl 2-((diethylamino)methyl)morpholine-4-carboxylate formate | | 2.1 | | | | | |
| 51 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(2-(diethylamino)ethyl)pyrrolidine-1-carboxylate formate | | 4.3 | | | | | |
| 38 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-((diethylamino)methyl)pyrrolidine-1-carboxylate formate | | 6.7 | | | | | |
| 121 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(ethylamino)ethyl)azetidine-1-carboxylate formate | 12.6 | 7.5 | | | 5 | | |
| 42 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(pyrrolidin-1-ylmethyl)azetidine-1-carboxylate formate | | 5.3 | | | | | |
| 50 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-(2-(diethylamino)ethyl)pyrrolidine-1-carboxylate formate | | 2.6 | | | | | |
| 49 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(diethylamino)ethyl)-3-hydroxyazetidine-1-carboxylate | | 4.1 | | | | | |
| 124 | (3R,4S,5S,6R)-5-methoxy-4-((2R,3R)-2-methyl-3-(3-methylbut- | | 4.9 | | | | | |

TABLE 2-continued

| Ex. | Compound Name | 1.0 mpk sc[1] (%) | 0.3 mpk sc[1] (%) | 0.1 mpk sc[1] (%) | 0.03 mpk sc[1] (%) | 0.3 mpk sc[2] (%) | 0.5 mpk sc[2] (%) | 1.0 mpk sc[2] (%) |
|---|---|---|---|---|---|---|---|---|
| | 2-enyl)oxiran-2-yl)-1-oxaspiro[2.5]octan-6-yl 3-(3-(ethylamino)propyl)azetidine-1-carboxylate formate | | | | | | | |
| 122 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((ethylamino)methyl)azetidine-1-carboxylate | | 3.2 | | | | | |
| 52 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-(diethylamino)ethyl)pyrrolidine-1-carboxylate | | 8.3 | | | 4 | | |
| 123 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 2-((ethylamino)methyl)azetidine-1-carboxylate formate | 9.7 | | | | 1 | | 5.4 |
| 5 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(azetidin-1-yl)ethyl)azetidine-1-carboxylate | | 4.3 | | | | | |
| 65 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-amino-2-oxoethyl)azetidine-1-carboxylate | | 2.6 | | | | | |
| 63 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(methylamino)-2-oxoethyl)azetidine-1-carboxylate | | 0.5 | | | | | |
| 68 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-((((2-(diethylamino)ethyl)carbamoyl)oxy)methyl)azetidine-1-carboxylate | | 0 | | | | | |
| 73 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(((2-(diethylamino)ethyl)carbamoyl)oxy)azetidine-1-carboxylate | | 7.4 | | | | | |
| 62 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholino-2-oxoethyl)azetidine-1-carboxylate formate | | 7.4 | | | | | |
| 39 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-oxomorpholino)ethyl)azetidine-1-carboxylate | | 1.7 | | | | | |
| 66 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(2-(diethylamino)ethylamino)-2-oxoethyl)azetidine-1-carboxylate | | 7.6 | | | | | |
| 95 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(morpholinomethyl)azetidine-1-carboxylate | | 14.7 | | | 3 | | |

TABLE 2-continued

| Ex. | Compound Name | 1.0 mpk sc$^1$ (%) | 0.3 mpk sc$^1$ (%) | 0.1 mpk sc$^1$ (%) | 0.03 mpk sc$^1$ (%) | 0.3 mpk sc$^2$ (%) | 0.5 mpk sc$^2$ (%) | 1.0 mpk sc$^2$ (%) |
|---|---|---|---|---|---|---|---|---|
| 74 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(methylcarbamoyloxy)azetidine-1-carboxylate | | 12.3 | | | 7.9 | | 6 |
| 72 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(carbamoyloxy)azetidine-1-carboxylate | | 0.8 | | | | | |
| 69 | (3R,4S,5S,6R)-5-methoxy-4-((2R,3R)-2-methyl-3-(3-methylbut-2-enyl)oxiran-2-yl)-1-oxaspiro[2.5]octan-6-yl 3-((methylcarbamoyloxy)methyl)azetidine-1-carboxylate | | 12.7 | | | 2.1 | | |
| 98 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(pyridin-2-ylamino)azetidine-1-carboxylate | | 12.6 | | | 1.2 | | |
| 100 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(pyridin-2-ylmethyl)azetidine-1-carboxylate | | 9.8 | | | 5.5 | | |
| 126 | (3R,4S,5S,6R)-4-((2R,3R)-3-isopentyl-2-methyloxiran-2-yl)-5-methoxy-1-oxaspiro[2.5]octan-6-yl 3-(2-(3,3-difluoroazetidin-1-yl)ethyl)azetidine-1-carboxylate | | 13.2 | | | 7.4 | | 9.1 |
| 37 | (S)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(morpholinomethyl)pyrrolidine-1-carboxylate | | 11.1 | | | 5.3 | | |
| 127 | (3R,4S,5S,6R)-4-((2R,3R)-3-isopentyl-2-methyloxiran-2-yl)-5-methoxy-1-oxaspiro[2.5]octan-6-yl 3-(2-morpholinoethyl)azetidine-1-carboxylate | | 15.2 | | | 6.1 | | 10.7 |
| 45 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3,3-difluoropyrrolidin-1-yl)ethyl)azetidine-1-carboxylate | | 16.8 | | | 5.2 | | |
| 101 | (3R,4S,5S,6R)-5-methoxy-4-((2R,3R)-2-methyl-3-(3-methylbut-2-enyl)oxiran-2-yl)-1-oxaspiro[2.5]octan-6-yl 3-((6-methylpyridin-3-yl)methyl)azetidine-1-carboxylate | | 15.6 | | | 3.9 | | |
| 54 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-morpholinoethyl)pyrrolidine-1-carboxylate | | 16.4 | | | 7.3 | | |
| 53 | (S)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-(diethylamino)ethyl)pyrrolidine-1-carboxylate | | 10.9 | | | 3 | | |
| 34 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(4-(2,2-difluoroethyl)piperazin-1-yl)ethyl)azetidine-1-carboxylate | | 9.3 | | | 5.1 | | |
| 88 | (3R,4S,5S,6R)-5-methoxy-4-((2R,3R)-2-methyl-3-(3-methylbut-2-enyl)oxiran-2-yl)-1- | | 9 | | | 4.4 | | |

TABLE 2-continued

| Ex. | Compound Name | 1.0 mpk sc¹ (%) | 0.3 mpk sc¹ (%) | 0.1 mpk sc¹ (%) | 0.03 mpk sc¹ (%) | 0.3 mpk sc² (%) | 0.5 mpk sc² (%) | 1.0 mpk sc² (%) |
|---|---|---|---|---|---|---|---|---|
| | oxaspiro[2.5]octan-6-yl 3-(3-(2-(diethylamino)ethylamino)-3-oxopropyl)azetidine-1-carboxylate formate | | | | | | | |
| 55 | (R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-morpholinoethyl)pyrrolidine-1-carboxylate | | 12.2 | | | 7.5 | | |
| 56 | (S)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(diethylamino)ethyl)pyrrolidine-1-carboxylate | | 7.2 | | | | | |
| 57 | (R)-(3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(3,3-difluoroazetidin-1-yl)ethyl)pyrrolidine-1-carboxylate | | 17.4 | | | 5.3 | | |
| 58 | (R)-((3R,4S,5S,6R)-5-methoxy-4-((2R,3R)-2-methyl-3-(3-methylbut-2-enyl)oxiran-2-yl)-1-oxaspiro[2.5]octan-6-yl) 3-(2-(3,3-difluoroazetidin-1-yl)ethyl)pyrrolidine-1-carboxylate | | 15.8 | | | | | |
| 22 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(6,6-difluoro-3-azabicyclo[3.1.0]hexan-3-yl)ethyl)azetidine-1-carboxylate formate | | 14 | | | | | |
| 90 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1-methylpiperidin-4-yl)ethyl)azetidine-1-carboxylate formate | | 13.5 | | | | | |
| 91 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1-(2,2-difluoroethyl)piperidin-4-yl)ethyl)azetidine-1-carboxylate formate | | 29.7 | | | 17.2 | | |
| 10 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-thiomorpholinoethyl)azetidine 2,2-dioxide-1-carboxylate | | 1.8 | | | | | |
| 84 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-methylureido)azetidine-1-carboxylate | | 0.8 | | | | | |
| 81 | 1-(((3R,4S,5S,6R)-5-methoxy-4-((2R,3R)-2-methyl-3-(3-methylbut-2-enyl)oxiran-2-yl)-1-oxaspiro[2.5]octan-6-yloxy)carbonyl)azetidin-3-yl 4-(2,2,2-trifluoroethyl)piperazine-1-carboxylate | | 16.9 | | | | | |
| 71 | 1-(((3R,4S,5S,6R)-5-methoxy-4-((2R,3R)-2-methyl-3-(3-methylbut-2-enyl)oxiran-2-yl)-1-oxaspiro[2.5]octan-6-yloxy)carbonyl)azetidin-3-yl morpholine-4-carboxylate formate | | 8.9 | | | 10.3 | | 10.3 |
| 78 | 1-(((3R,4S,5S,6R)-5-methoxy-4-((2R,3R)-2-methyl-3-(3-methylbut-2-enyl)oxiran-2-yl)-1- | | 10.7 | | | 1.2 | | |

TABLE 2-continued

| Ex. | Compound Name | 1.0 mpk sc[1] (%) | 0.3 mpk sc[1] (%) | 0.1 mpk sc[1] (%) | 0.03 mpk sc[1] (%) | 0.3 mpk sc[2] (%) | 0.5 mpk sc[2] (%) | 1.0 mpk sc[2] (%) |
|---|---|---|---|---|---|---|---|---|
| | oxaspiro[2.5]octan-6-yloxy)carbonyl)azetidin-3-yl 4-methylpiperazine-1-carboxylate | | | | | | | |
| 79 | 1-(((3R,4S,5S,6R)-5-methoxy-4-((2R,3R)-2-methyl-3-(3-methylbut-2-enyl)oxiran-2-yl)-1-oxaspiro[2.5]octan-6-yloxy)carbonyl)azetidin-3-yl thiomorpholine 2,2-dioxide-4-carboxylate formate | | 0.1 | | | | | |
| 82 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-hydroxy-2-methylpropylcarbamoyloxy)azetidine-1-carboxylate | | −0.7 | | | | | |
| 80 | 1-(((3R,4S,5S,6R)-5-methoxy-4-((2R,3R)-2-methyl-3-(3-methylbut-2-enyl)oxiran-2-yl)-1-oxaspiro[2.5]octan-6-yloxy)carbonyl)azetidin-3-yl 4-(2,2-difluoroethyl)piperazine-1-carboxylate | | 16.5 | | | 7.3 | | |
| 11 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-methyl-3-oxopiperazin-1-yl)ethyl)azetidine-1-carboxylate formate | | 2 | | | | | |
| 67 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(3-(2-morpholinoethylamino)-3-oxopropyl)azetidine-1-carboxylate | | 2.8 | | | | | |
| 16 | (3R,4S,5S,6R)-5-methoxy-4-((2R,3R)-2-methyl-3-(3-methylbut-2-en-1-yl)oxiran-2-yl)-1-oxaspiro[2.5]octan-6-yl 3-(2-(2-oxa-6-azaspiro[3.3]heptan-6-yl)ethyl)azetidine-1-carboxylate | | 3.1 | | | | | |
| 17 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1H-pyrazol-1-yl)ethyl)azetidine-1-carboxylate | | 12.6 | | | 5.1 | | |
| 19 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-(dimethylcarbamoyl)azetidin-1-yl)ethyl)azetidine-1-carboxylate | | 6.7 | | | | | |
| 15 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-(methylsulfonyl)piperazin-1-yl)ethyl)azetidine-1-carboxylate | | 0.1 | | | | | |
| 13 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4,4-difluoropiperidin-1-yl)ethyl)azetidine-1-carboxylate | | 18.2 | | | | | |
| 14 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-cyano-3-methylazetidin-1-yl)ethyl)azetidine-1-carboxylate | | 12.5 | | | | | |
| 33 | (4S,5S,6R)-5-methoxy-4-((2R,3R)-2-methyl-3-(3-methylbut-2-enyl)oxiran-2-yl)-1-oxaspiro[2.5]octan-6-yl 3-(2-(8- | | 15.9 | | | | | |

TABLE 2-continued

| Ex. | Compound Name | 1.0 mpk sc¹ (%) | 0.3 mpk sc¹ (%) | 0.1 mpk sc¹ (%) | 0.03 mpk sc¹ (%) | 0.3 mpk sc² (%) | 0.5 mpk sc² (%) | 1.0 mpk sc² (%) |
|---|---|---|---|---|---|---|---|---|
| | oxa-3-azabicyclo[3.2.1]octan-3-yl)ethyl)azetidine-1-carboxylate | | | | | | | |
| 31 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((1R,5S)-3-oxa-8-azabicyclo[3.2.1]octan-8-yl)ethyl)azetidine-1-carboxylate | 4.2 | | | | | | |
| 20 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-(dimethylcarbamoyl)-3-methylazetidin-1-yl)ethyl)azetidine-1-carboxylate | 2.1 | | | | | | |
| 18 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1H-imidazol-1-yl)ethyl)azetidine-1-carboxylate | 3 | | | | | | |
| 25 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((S)-3-methoxypyrrolidin-1-yl)ethyl)azetidine-1-carboxylate | 4.8 | | | | | | |
| 46 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((S)-3-hydroxypyrrolidin-1-yl)ethyl)azetidine-1-carboxylate formate | 5.2 | | | | | | |
| 47 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((R)-3-hydroxypyrrolidin-1-yl)ethyl)azetidine-1-carboxylate | 5.6 | | | | | | |
| 28 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((S)-3-fluoropyrrolidin-1-yl)ethyl)azetidine-1-carboxylate | 12.7 | | | | | | |
| 12 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(3-oxopiperazin-1-yl)ethyl)azetidine-1-carboxylate | 1.1 | | | | | | |
| 29 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-cyano-4-methylpiperidin-1-yl)ethyl)azetidine-1-carboxylate | 10.7 | | | | | | |
| 26 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((R)-3-methoxypyrrolidin-1-yl)ethyl)azetidine-1-carboxylate | 4.1 | | | | | | |
| 27 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((R)-3-fluoropyrrolidin-1-yl)ethyl)azetidine-1-carboxylate | 13.3 | | | | | | |
| 36 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4,4-dicyanopiperidin-1-yl)ethyl)azetidine-1-carboxylate | 11.2 | | | | | | |

TABLE 2-continued

| Ex. | Compound Name | 1.0 mpk sc[1] (%) | 0.3 mpk sc[1] (%) | 0.1 mpk sc[1] (%) | 0.03 mpk sc[1] (%) | 0.3 mpk sc[2] (%) | 0.5 mpk sc[2] (%) | 1.0 mpk sc[2] (%) |
|---|---|---|---|---|---|---|---|---|
| 30 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-fluoropiperidin-1-yl)ethyl)azetidine-1-carboxylate | 9.1 | | | | | | |
| 32 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-((1S,4S)-7-azabicyclo[2.2.1]heptan-7-yl)ethyl)azetidine-1-carboxylate | 0.5 | | | | | | |
| 92 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(1-(2,2-difluoroethyl)azetidin-3-yl)ethyl)azetidine-1-carboxylate | 20.7 | | | | | | |
| 99 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(pyridin-2-yloxy)azetidine-1-carboxylate | 22.9 | | | | | | |
| 76 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(isopropylcarbamoyloxy)azetidine-1-carboxylate | 15.4 | | | | | | |
| 77 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(dimethylcarbamoyloxy)azetidine-1-carboxylate | 16.3 | | | | | | |
| 128 | (3R,4S,5S,6R)-4-((2R,3R)-3-isopentyl-2-methyloxiran-2-yl)-5-methoxy-1-oxaspiro[2.5]octan-6-yl 3-(2-(1-(2,2-difluoroethyl)piperidin-4-yl)ethyl)azetidine-1-carboxylate | 15.2 | | | | | | |
| 94 | (3R,4S,5S,6R)-5-methoxy-4-((2R,3R)-2-methyl-3-(3-methylbut-2-enyl)oxiran-2-yl)-1-oxaspiro[2.5]octan-6-yl 3-((1-(2,2-difluoroethyl)piperidin-4-yl)methyl)azetidine-1-carboxylate | 22.5 | | | | | | |
| 35 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-(2,2-difluoroethyl)-2-oxopiperazin-1-yl)ethyl)azetidine-1-carboxylate | 21.3 | | | | | | |
| 87 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(methoxycarbonylamino)azetidine-1-carboxylate | 10.9 | | | | | | |
| 96 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholinoethylidene)azetidine-1-carboxylate | 18.6 | | | | | | |
| 75 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(ethylcarbamoyloxy)azetidine-1-carboxylate | 12.8 | | | | | | |
| 97 | (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-(4-(2,2-difluoroethyl)piperazin-1- | 21.3 | | | | | | |

TABLE 2-continued

| Ex. | Compound Name | 1.0 mpk sc[1] (%) | 0.3 mpk sc[1] (%) | 0.1 mpk sc[1] (%) | 0.03 mpk sc[1] (%) | 0.3 mpk sc[2] (%) | 0.5 mpk sc[2] (%) | 1.0 mpk sc[2] (%) |
|---|---|---|---|---|---|---|---|---|
| 70 | yl)ethylidene)azetidine-1-carboxylate (3R,4S,5S,6R)-5-methoxy-4-((2R,3R)-2-methyl-3-(3-methylbut-2-enyl)oxiran-2-yl)-1-oxaspiro[2.5]octan-6-yl 3-((dimethylcarbamoyloxy)methyl)azetidine-1-carboxylate | | | 14.5 | | | | |
| Comp A | [(3R,6R,7S,8S)-7-methoxy-8-[(2R,3R)-2-methyl-3-(3-methylbut-2-enyl)oxiran-2-yl]-2-oxaspiro[2.5]octan-6-yl] (E)-3-[4-[2-(dimethylamino)ethoxy]phenyl]prop-2-enoate | | | 18.0 | | 20.0 | | |

[1] DIO Mouse 10-day weight loss vs vehicle at indicated dose.
[2] DIO Rat 11-day weight loss vs vehicle at indicated dose.

Biological Example C

Study Summary HT-1080:

The human fibrosarcoma cell line HT-1080 were grown to almost complete confluence in T75 tissue culture flasks in preparation for the experiment. The cells were trypsinised and re-suspended in complete medium using DMEM plus 9% FBS including penicillin/streptomycin supplements. 500 cells in a total volume of 25 µl were seeded into black walled 384 well plates and returned to a CO2 incubator over-night. Compounds and standards were prepared at 333.3× actual test concentration in neat DMSO. 10 point dose response curves of test compounds were generated by 1:3 serial dilutions, 2 µl of DMSO stock was transferred to 109 µl complete medium. This was further diluted 1:6 in complete medium, with 5 µl of the resulting solution added to the incubated 384 well plate. The assay had a final DMSO concentration of 0.3%, a level which was identified as being non-cytotoxic to the cells. For experimental blanks at the start of the experiment, CellTiter-Glo was added to a satellite plate of cells (identical to the experimental plate), when adding compounds on Day 1. The average of these wells is used as the blanks in the calculation template. Following 72 hours incubation with compounds and standard the plate was removed from the incubator and allowed to equilibrate at room temperature for at least 30 minutes. CellTiter-Glo was thawed and subsequently 30 µl added to columns 2-23. The plate was covered with a clear Perkin Elmer Topseal and placed on a plate shaker for 10-20 mins to aid homogenous mixing. Luminescence per well was determined using an EnVision 2104 Multilabel Reader (PerkinElmer) or other suitable reader. The compound blank value recorded on Day 1 is subtracted from all other data. Data is expressed as % inhibition of mean DMSO control response and the $EC_{50}$ is calculated as 50% maximum response. The $EC_{50}$ values are determined from a sigmoidal 4 parameter curve fit using XLfit in conjunction with Activity Base (IDBS; Guildford, Surrey, UK). The bottom of the curve is fixed to 0% inhibition.

Study Summary Rat Embryofetal:

The objective of this study design was to evaluate the potential effects of disclosed compounds on embryo/fetal development when given subcutaneously to pregnant rats once every three days during the critical period of organogenesis (Gestation Days 6-18). Female, Sprague Dawley rats, approximately 10 weeks of age, time bred, were ordered from a certified vendor and housed individually housed in stainless steel cages suspended over flush pans, on a 12-hour light-dark cycle (0700-1900) at 20-26° C. and 30-70% humidity. Rats were fed a standard rodent chow and provided water ad libitum. Rats were received and housed in the facility for a period of approximately 1 to 2 days.

Compounds were formulated using 100% DMSO mixed in Sterile Water for Injection, resulting in 2% DMSO solution in water. If necessary, due to limited solubility of a test article, a higher percentage of DMSO solution in water was used. Groups of 8 mated and presumed pregnant female rats were given subcutaneous doses of vehicle or test article, once every three days, beginning on Gestation Day 6 and ending on Gestation Day 18 (Days 6, 9, 12, 15, and 18), maintained two more days, and then euthanized and necropsied on Gestation Day 20. Body weights was recorded for all animals on Gestation Days 5 (purpose of randomization), 6, 9, 12, 15, 18, and 20 (scheduled euthanasia). Food consumption by weight was recorded on Gestation Days 6, 9, 12, 15, 18, and 20 (scheduled termination).

At necropsy, the dams were examined visually for external abnormalities including palpable masses. The abdominal, thoracic, and cranial cavities and their contents were examined for abnormalities and findings will be recorded. The reproductive tract were examined to record the number of ovarian corpora lutea, the number and location of uterine implantation sites noting the position of the cervix, and the number of early resorptions, late resorptions, live fetuses, and dead fetuses. For dead fetuses and late resorptions, crown-to-rump length and weight were recorded, if possible, and the fetus was discarded. For viable fetuses, weight, sex, and grossly visible external abnormalities were recorded. Fetuses with external findings involving the head had a fresh visceral evaluation performed on the head to confirm the external finding, if applicable.

The results are summarized in Table 3, below, wherein A represents an $EC_{50}$ of <0.30 nM and B represents an $EC_{50}$ between 0.30 nM and 1.3 nM.

TABLE 3

| Example | HT-1080 EC50 (nM) | Rat Embryofetal @6 mpk |
|---|---|---|
| 103 | A | Positive |
| 104 | A | Positive |
| 1 | A | Negative |
| 2 | A | Negative |

TABLE 3-continued

| Example | HT-1080 EC50 (nM) | Rat Embryofetal @6 mpk |
|---|---|---|
| 6 | A | Positive |
| 9 | A | Positive |
| 74 | A | Negative |
| 101 | B | Positive |
| 88 | B | Positive |
| 22 | B | Negative |
| 91 | B | Positive |
| 81 | B | Positive |
| 71 | A | Negative |
| 78 | B | Positive |
| compound A | B | Positive |

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound represented by:

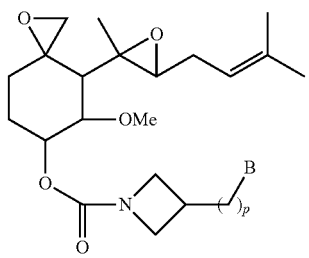

wherein:
p is 2;
B is $R^iR^jN$—; wherein $R^i$ and $R^j$ taken together with the nitrogen to which they are attached form a 4-9 membered monocyclic, bridged bicyclic, fused bicyclic or spirocyclic heterocyclic ring, which may have an additional heteroatom selected from the group consisting of N, O, and $S(O)_w$ (wherein w is 0, 1 or 2);

wherein
the 4-9 membered monocyclic, bridged bicyclic, fused bicyclic or spirocyclic heterocyclic ring may be optionally substituted on carbon by one, two, or more substituents selected from the group consisting of halogen, hydroxyl, oxo, cyano, $C_{1-6}$alkyl, $C_{1-6}$alkoxy, and $R^aR^bN$-carbonyl-; wherein said $C_{1-6}$alkyl may optionally be substituted by one, two, or more substituents selected from the group consisting of fluorine and hydroxyl;

wherein if said 4-9 membered monocyclic, bridged bicyclic, fused bicyclic or spirocyclic heterocyclic ring contains a —NH moiety, that nitrogen may be optionally substituted by a substituent selected from the group consisting of $C_{1-6}$alkyl and $C_{1-6}$alkyl-$S(O)_2$—; wherein $C_{1-6}$alkyl and $C_{1-6}$alkyl-$S(O)_2$— may optionally be substituted by one or more fluorines;

$R^a$ and $R^b$ are independently selected, for each occurrence, from the group consisting of hydrogen and $C_{1-3}$alkyl; wherein $C_{1-3}$alkyl may optionally be substituted by one or more substituents selected from halogen, cyano, oxo and hydroxyl;

or a pharmaceutically acceptable salt or stereoisomer thereof.

2. The compound of claim 1, wherein B is:

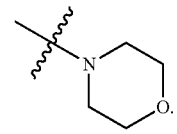

3. The compound of claim 1, wherein the compound is represented by:

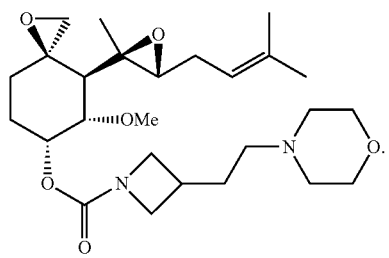 [SMILES: CO[C@@H]1[C@H](OC(=O)N2CC(CCN3CCOCC3)C2)CC[C@]2(CO2)[C@H]1[C@@]1(C)O[C@@H]1CC=C(C)C]

4. A compound selected from the group consisting of (3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholinoethyl)azetidine-1-carboxylate and a pharmaceutically acceptable salt or stereoisomer thereof.

5. A pharmaceutically acceptable composition comprising a compound of claim 1, and a pharmaceutically acceptable excipient.

6. A pharmaceutically acceptable composition comprising:
(3R,4S,5S,6R)-5-methoxy-4-((2R,3R)-2-methyl-3-(3-methylbut-2-enyl)oxiran-2-yl)-1-oxaspiro[2.5]octan-6-yl 3-(2-morpholinoethyl)azetidine-1-carboxylate or pharmaceutically acceptable salt thereof; and
a pharmaceutically acceptable excipient.

7. The composition of claim 5, wherein the composition is formulated as a unit dose.

8. The composition of claim 5, wherein the composition is formulated for subcutaneous administration.

9. The composition of claim 5, wherein the composition is formulated for intravenous administration.

\* \* \* \* \*